US008546643B2

(12) United States Patent
Bentzon et al.

(10) Patent No.: US 8,546,643 B2
(45) Date of Patent: Oct. 1, 2013

(54) PIG MODEL FOR ATHEROSCLEROSIS

(75) Inventors: Jacob Fog Bentzon, Horsens (DK); Charlotte Brandt Sørensen, Højbjerg (DK); Peter Michael Kragh, Trondheim (NO); Jacob Giehm Mikkelsen, Silkeborg (DK); Erling Falk, Harlev (DK); Lars Axel Bolund, Skødstrup (DK); Thomas Juhl Corydon, Risskov (DK)

(73) Assignee: Aarhus Universitet (DK)

( * ) Notice: Subject to any disclaimer, the term of this patent is extended or adjusted under 35 U.S.C. 154(b) by 693 days.

(21) Appl. No.: 12/529,955

(22) PCT Filed: Mar. 6, 2008

(86) PCT No.: PCT/DK2008/050055
§ 371 (c)(1),
(2), (4) Date: Jan. 7, 2010

(87) PCT Pub. No.: WO2008/106982
PCT Pub. Date: Sep. 12, 2008

(65) Prior Publication Data
US 2010/0138939 A1    Jun. 3, 2010

(30) Foreign Application Priority Data

Mar. 7, 2007  (DK) ................................ 2007 00348

(51) Int. Cl.
*A01K 97/00* (2006.01)
*A01K 67/027* (2006.01)
*C12N 15/00* (2006.01)

(52) U.S. Cl.
USPC ............ 800/9; 800/3; 800/8; 800/17; 800/21; 800/24

(58) Field of Classification Search
None
See application file for complete search history.

(56) References Cited

U.S. PATENT DOCUMENTS

| 6,271,436 | B1 | 8/2001 | Piedrahita et al. | |
|---|---|---|---|---|
| 6,498,285 | B1 | 12/2002 | Ebert | |
| 7,300,754 | B2 * | 11/2007 | Abi Fadel et al. | 435/6.11 |
| 2003/0208785 | A1 | 11/2003 | Tzang et al. | |
| 2009/0119787 | A1 * | 5/2009 | Du et al. | 800/17 |
| 2010/0154069 | A1 * | 6/2010 | Mikkelsen et al. | 800/9 |

FOREIGN PATENT DOCUMENTS

| EP | 1 475 436 | 11/2004 |
|---|---|---|
| WO | WO 01/35734 | 5/2001 |
| WO | WO 2005/032245 | 4/2005 |
| WO | WO2006/111757 A2 | 10/2006 |

OTHER PUBLICATIONS

Lagace et al. J Clin Invest 2006;116:2995-3005.*
Kolber-Simonds et al. PNAS 2004;101:7335-40.*
Al-Mashhadi et al. Sci Transl Med 2013;5(166ra 1):1-10 and supplemental materials.*
Lai et al., 2002, "Production of alpha-1,3-galactosyltransferase knockout pigs by nuclear transfer cloning", Science, 295, pp. 1089-1092.
Yamada et al., 2006, "GalT knockout pig to baboon xenotransplantation", International Congress Series, 1292, pp. 123-127.
Abifadel M et al.(2003), Mutations in PCSK9 cause autosomal dominant hypercholesterolemia, Nature Genetics vol. 34, No. 2, pp. 154-156.
Andersen et al. (Nov. 2002), Mechanisms underlying targeted gene correction using chimeric RNA/DNA and single-stranded DNA oligonucleotides, J Mol Med, vol. 80, p. 770-781.
Benjannet et al., (2004), NARC-1/PCSK9 and its natural mutants, The Journal of biol. chem., vol. 279, No. 47, pp. 48865-48875.
Booth et al. (2001), Simplification of Bovine Somatic Cell Nuclear Transfer by Application of a Zona-Free Manipulation Technique, Cloning and Stem Cells, vol. 3, No. 3, p. 139-150.
Brown et al. (Sep. 1983), Lipcoprotein Receptors in the Liver: Control signals for plasma cholesterol traffic, J Clin Invest, vol. 72, p. 743-747.
Christidis et al. (Sep. 2006), The Effect of Apolipoprotein E Polymorphism on the Response to Lipid-Lowering Treatment With Atorvastain or Fenofibrate, J. Cardiovasc. Pharmacol. Ther., vol. 11, No. 3, p. 211-221.
Chu et al. (Jul. 5, 2005), Detection of Carotid Atherosclerotic Plaque Ulceration, Calcification, and Thrombosis by Multicontrast Weighted Magnetic Resonance Imaging, Circulation, vol. 112, p. e3-e4.
Chung et al. (Jan. 1997), Characterization of the chicken b-globin insulator, Proc. Natl. Acad. Sci. USA, vol. 94, p. 575-580.
Dobrinsky et al. (1996), Development of a Culture Medium (BECM-3) for Porcine Embryos: Effect of Bovine Serum Albumin and Fetal Bovine Serum on Embryo Development, Biol Reprod, vol. 55, p. 1069-1074.
Du et al. (2005), High overall In Vitro Efficiency of Porcine Handmade Cloning (HMC) Combining Partial Zona Digestion and Oocyte Trisection with Sequential Culture, Cloning and Stem Cells, vol. 7, No. 3, p. 199-204.
Esaki et al. (2004), Cryopreservation of Porcine Embryos Derived from In Vitro-Matured Oocytes, Biology of Reproduction, vol. 71, p. 432-437.
Feltrin et al. (2006), In Vitro Bovine Embryo Development After Nuclear Transfer by Handmade Cloning Using a Modified Wow Culture System, Reprod Fertil Dev 18(2), p. 126.

(Continued)

*Primary Examiner* — Q. Janice Li
(74) *Attorney, Agent, or Firm* — McLane, Graf, Raulerson & Middleton, PA

(57) ABSTRACT

The present invention relates to a genetically modified pig as a model for studying atherosclerosis. The modified pig model displays one or more phenotypes associated with atherosclerosis. Disclosed is also a modified pig comprising a mutation in the endogenous ApoE gene or part thereof, LDL gene or part thereof, LDL receptor gene, or transcriptional or translational product or part thereof. The invention further relates to methods for producing the modified pig; and methods for evaluating the effect of a therapeutical treatment of atherosclerosis; methods for screening the efficacy of a pharmaceutical composition; and a method for treatment of a human being suffering from atherosclerosis are disclosed.

19 Claims, 15 Drawing Sheets

(56) References Cited

OTHER PUBLICATIONS

Feussner et al.. (1992), Severe type III hyperlipoproteinemia associated with unusual apoilpoprotein E1 phenotype and epsilon 1 /'null' genotype, Eur. J. Clin. Invest, vol. 22, p. 599-608.
Gerrity et al. (Jul. 2001), Diabetes-Induced Accelerated Atherosclerosis in Swine, Diabetes, vol. 50, p. 1654-1665.
Greeve et al. (1993), Apolipoprotein B mRNA editing in 12 different mammalian species: hepatic expression is reflected in low concentrations of apoB-containing plasma lipoproteins. J. Lipid. Res., vol. 34, p. 1367-1383.
Gupta et al. (Dec. 22, 2006), Lipid-induced Extension of Apolipoprotein E Helix 4 Correlates with Low Density Liproprotein Receptor Binding Ability, J. Biol. Chem , vol. 281, No. 51, p. 39294-39299.
Hansson GK (Apr. 21, 2005), Inflammation, Atherosclerosis, and Coronary Artery Disease, N. Engl J. Med., vol. 352, No. 16, p. 1685-1695.
Hasler-Rapacz et al. (1998), Identification of a Mutation in the Low Density Lipoprotein Receptor Gene Associated With Recessive Familial Hypercholesterolemia in Swine, Am. J. Med. Genet., vol. 76, No. 5, p. 379-386.
Holvoet et al. (1998), LDL Hypercholesterolemia Is Accociated With Accumulation of Oxidized LDL, Atherosclerotic Plaque Growth, and Compensatory Vessel Enlargement in Coronary Arteries of Miniature Pigs, Arterioscler Thromb Vasc Biol, vol. 18, p. 415-422.
Hoshino et al. (2005), Development Competence of Somatic Cell Nuclear Transfer Embryos Reconstructed from Oocytes Matured in Vitro with Follicle Shells in Miniature Pig, Cloning and Stem Cells, vol. 7, No. 1, p. 17-27.
Ishibashi et al. (May 1994), Massive Xanthomatosis and Atherosclerosis in Cholesterol-fed Low Density Lipoprotein Receptor-negative Mice, J Clin Invest, vol. 93, p. 1885-1893.
Ivics et al. (Nov. 1997),Molecular Reconstruction of Sleeping Beauty, a Tc1-like Transposon from Fish, and Its Transposition in Human Cells, Cell, vol. 91, p. 501-510.
Kikuchi et al. (1999), Development Competence, after Transfer to Recipients, of Porcine Oocytes Matured, Fertilized, and Cultured In Vitro, Biology of Reproduction, vol. 60, p. 336-340.
Kikuchi et al. (2002), Successful Piglet Production after Transfer of Blastocysts Produced by a Modified In Vitro System, Biology of Reproduction, vol. 66, p. 1033-1041.
Kohli et al. (2004), Facile methods for generating human somatic cell gene knockouts using recombinant adeno-associated viruses, Nucleic Acids Research, vol. 32, No. 1, e3.
Kragh et al. (2004), Production of Transgenic Porchine Blastocysts by Handmade Cloning, Reprod. Fert. Dev. 16. p. 290.
Kragh et al. (2004), Production of transgenic porcine blastocysts by hand-made cloning, Repord. Fert. Dev. 16. p. 315-318.
Kragh et al. (2005), Efficient in vitro production of porcine blastocysts by handmade cloning with a combined electrical and chemical activation, Thenogenology 64, p. 1536-1545.
Law et al. (2004), The performance of blood pressure and other cariovascular risk factors as screening tests for ischaemic heart disease and stroke, J Med Screen, vol. 11, No. 1, p. 3-7.
Leber et al. (2005), Quantification of Obstructive and Nonobstructive Coronary Lesions by 64-Slice Computed Tomography: A Comparative Study With Quantitative Coronary Angiography and Intravascular Ultrasound, J Am Coll Cardiol, vol. 46, No. 1, p. 147-154.
Lohse et al. (1992), Familial apolipoprotein E deficiency and type III hyperlipoproteinemia due to a premature stop codon in the apolipoprotein E gene, J Lipid Res, vol. 33, No. 11, p. 1583-1590.
MacKay et al. (2004), The Atlas of Heart Disease and Stroke, WHO and CDC, ISBN 92 4 156276 8, p. 46, 48, 50, 52, 54.
Mazur et al. (Mar. 2006), A novel porcine model atherosclerosis, Faseb Journal vol. 20 No. 4, p. A207.
Miao et al. (Jun. 2000), Inclusion of the Hepatic Locus Control Region, an Intron, and Untranslated Region Increases and Stabilizes Hepatic Factor IX Gene Expression in Vivo but Not in Vitro, Mol Ther, vol. 1, No. 6, p. 522-532.

Moriyama et al. (1992), Apolipoprotein E1 Lys-146--> Glu with type III hyperlipoproteinemia, Biochim. Biophys. Acta, vol. 1128, No. 1, p. 58-64.
Mullick et al. (Feb. 2007), Apolipoprotein E3- and Nitric Oxide-Dependent Modulation of Endothelial Cell Inflammatory Responses, Arterioscler Thromb Vasc. Biol., vol. 27, No. 2, p. 339-345.
Needleman SB et al. (1970), A General Method Applicable to the Search for Similarities in the Amino Acid Sequence of Two Proteins, J. Mol. Biol. 48, p. 443-453.
Nickerson et al. (2000), Sequence Diversity and Large-Scale Typing of SNPs in the Human Apolipoprotein E Gene, Genome Res, vol. 10, No. 10, p. 1532-1545.
Oback et al. (2003), Cloned Cattle Derived from a Novel Zona-Free Embryo Reconstruction System, Cloning and Stem Cells, vol. 5, No. 1, p. 3-12.
Olarte et al. (Nov. 2006), Apolipoprotein E epsilon4 and Age at Onset of Sporadic and Familial Alzheimer Disease in Caribbean Hispanics, Arch. Neurol., vol. 63, p. 1586-1590.
Palinski et al.(Apr. 1, 1994), ApoE-deficient mice are a model of lipoprotein oxidation in atherogenisis, Arteriosclerosis and Thrombosis vol. 14, No. 4, p. 605-616.
Panpepinto et al. (1978), The Yucatan minature pig as a laboratory animal, Lab Anim Sci., vol. 28, No. 3, p. 308-313.
Park et al (2004), Post-transcriptional regulation of low density lipoprotein receptor protein by proprotein convertase subtilisin/kexin type 9a in mouse liver, The journal of biol. chem. vol. 279, No. 48. pp. 50630-50638.
Peura et al. (1998), The Effect of Recipient Oocyte Volume on Nuclear Transfer in Cattle, Molecular Reproduction and Development, vol. 50, p. 185-191.
Peura et al. (2003), A Comparison of Established and New Apporaches in Ovine and Bovine Nuclear Transfer, Cloning and Stem Cells, vol. 5, No. 4, 257-277.
Ramsoondar et al. (1998), Isolation and genetic characterization of the porcine apolpoprotein E gene, Anim. Genet., vol. 29, p. 43-47.
Rapacz et al. (1998), Animal Models: The Pig, In: Lusis et al. eds. Genetic factors in atherosclerosis: Approaches and model systems, Karger, p. 139-169.
Ratcliffe et al., (1971) The domestic pig: A model for experimental atherosclerosis, Atherosclerosis vol. 13, 1971, p. 133-136.
Reed et al. (Jan. 1992), In Vitro Culture of Pig Embryos, Theriogeneology, vol. 37, No. 1, p. 95-109.
Rohlmann et al. (Feb. 1998), Inducible Inactivation of Hepatic LRP Gene by Cre-mediated Recombination Confirms Role of LRP in Clearance of Chylomicron Remnants, J Clin Invest, vol. 101, No. 3, p. 689-695.
Schuler et al. (Jul. 1992), Regular Physical Exercise and Low-Fat Diet. Effects on Progression of Coronary Artery Disease, Circulation, vol. 86, No. 1, p. 1-11.
Sherrer et al. (2004), Fertilization and blastocyst development in oocytes obtained from prepubertal and adult pigs, J Anim Sci, vol. 82, p. 102-108.
Smith et al. (1981), Comparison of Biosequences, Advances in Applied Mathematics 2, p. 482-489.
Sørensen et al. (2005), Site-specific strand bias in gene correction using single-stranded oligonucleotides, J Mol Med, vol. 83, p. 39-49.
Umov et al. (Jun. 2005), Highly efficient endogenous human gene correction using designed zinc-finger nucleases, Nature, vol. 435, p. 646-651.
Utermann et al. (1979), Polymorphism of apolipoprotein E. III. Effect of a single polymorphic gene locus on plasma lipid levels in man, Clin. Genet., vol. 15, p. 63-72.
Vajta et al. (1997), Survival and development of bovine blastocysts produced in vitro after assisted hatching, vitrification and in-straw direct rehydration, Journal of Reproduction and Fertility, vol. 111, p. 65-70.
Vajta et al. (2004), Production of a healthy calf by somatic cell nuclear transfer without micromanipulators and carbon dioxide incubators using the Handmade Cloning (HMC) and the Submarine Incubation System (SIS), Theriogenology, vol. 62, p. 1465-1472.
Vajta et. al (2003), Handmade Somatic Cell Cloning Cattle: Analysis of Factors Contributing to High Efficiency In Vitro, Biology of Reproduction, vol. 68, p. 571-578.

Vajta G. (2000), Oocyte and Embryo Vitrification, Annual ESDAR Conference 1999, p. 45-48.

Verbeuren (2006) Experimental models of thrombosis and atherosclerosis, Therapie vol. 61, No. 5 pp. 379-387.

Vodicka et al. (May 1, 2005) The miniature pig as an animal model in biomedical research, Ann. N.Y. Acad Sci. vol. 1049, p. 161-171.

Wu et al. (2004), Birth of Piglets by in vitro fertilization of zona-free porcine oocytes, Theriogenology, vol. 62, p. 1544-1556.

Yant et al. (2004), Mutational Analysis of the N-Terminal DNA-Binding Domain of Sleeping Beauty Transposase: Critical Residues for DNA Binding and Hyperactivity in Mammalian Cells, Mol. Cell. Biol., vol. 24, No. 20, p. 9239-9247.

Yant et al. (Dec. 2003), Nonhomologous-End-Joining Factors Regulate DNA Repair Fidelity during Sleeping Beauty Element Transposition in Mammalian Cells, Mol. Cell. Biol., vol. 23, No. 23, p. 8505-8518.

Yant et al. (May 2000), Somatic integration and long-term transgene expression in normal and haemophilic mice using DNA transposon system, Nature Genetics, vol. 24, p. 35-41.

Yoshioka et al. (2002), Birth of Piglets Derived from Porcine Zygotes Cultured in a Chemically Defined Medium, Biology of Reproduction, vol. 66, p. 112-119.

Zhang et al. (Jun. 22, 2007), Binding of Proprotein Convertase Subtilisin/Kexin Type 9 to Epidermal Growth Factor-like Repeat A of Low Density Lipoprotein Receptor Decreases Receptor Recycling and Increases Degradation, J. Biol. Chem., vol. 282, No. 25, p. 18602-18612.

Zhang et al. (Oct. 16, 1992), Spontaneous hypercholesterolemia and arterial lesions in mice lacking apolipoprotein E, Science, vol. 258, p. 468-471.

Book et al. (1974), The Fetal Neonatal Pig in Biomedical Research, Journal of Animal Science, vol. 38, No. 5, p. 997-1002.

* cited by examiner

A

B

PIG MODEL FOR ATHEROSCLEROSIS

CROSS-REFERENCE TO RELATED APPLICATIONS

This application is the U.S. National Stage of International Application No. PCT/DK2008/050055, filed on Mar. 6, 2008, published in English. This application claims priority under 35 U.S.C. §119 or 365 to DK PA 2007 00348, filed Mar. 7, 2007. The entire teachings of the above applications are incorporated herein by reference.

INCORPORATION-BY-REFERENCE OF MATERIAL SUBMITTED IN ASCII TEXT FILE

This application incorporates by reference the Sequence Listing contained in the following ASCII text file:

a) File name 48651003000SequenceListing.txt; created Oct. 24, 2012, 172 KB in size.

FIELD OF INVENTION

The present invention relates to a genetically modified pig as a model for studying atherosclerosis, wherein the pig model expresses at least one phenotype associated with said disease. The invention further relates to methods by which the genetically modified pig is produced. In addition, methods for evaluating the response of a therapeutical treatment of atherosclerosis, for screening the efficacy of a pharmaceutical composition, and a method for treatment of human being suffering from atherosclerosis are disclosed.

BACKGROUND OF INVENTION

Transgenic, non-human animals can be used to understand the action of a single gene or genes in the context of the whole animal and the interrelated phenomena of gene activation, expression, and interaction. The technology has also led to the production of models for various diseases in humans and other animals which contributes significantly to an increased understanding of genetic mechanisms and of genes associated with specific diseases.

Traditionally, smaller animals such as mice have been used as disease models for human diseases and have been found to be suitable as models for certain diseases. However, their value as animal models for many human diseases is quite limited due to differences in mice compared to humans. Larger transgenic animals are much more suitable than mice for the study of many of the effects and treatments of most human diseases because of their greater similarity to humans in many aspects. Particularly, pigs are believed to be valuable as disease models for human diseases.

Atherosclerosis is by far the most frequent cause of coronary artery disease (angina pectoris, myocardial infarction and sudden death), carotid artery disease (stroke), and peripheral arterial disease. Atherosclerosis is referred to as 'hardening of the arteries' which is caused by the formation of numerous plaques within the arteries.

It is a chronic inflammatory disease, fueled by high plasma levels of cholesterol-rich lipoproteins, that leads to the development of atherosclerotic plaques of inflammatory cells, debris, and smooth muscle cells in large and medium-sized arteries[1]. These lesions by themselves rarely cause symptoms. The mechanical process wherein plaques burst open, known as plaque ruptures, causes the devastating consequences of atherosclerosis. By this process the thrombogenic core of the plaque is exposed to the haemostatic system of the circulating blood and this may elicit an acute flow-limiting superimposed thrombus.

In most cases of atherosclerosis the genetic component is complex, but in some cases the inheritance of the disease is monogenic. These cases are mostly due to mutations in genes coding for proteins involved in lipoprotein trafficking, and the most severe in humans are caused by homozygous null mutations in the low-density lipoprotein (LDL) receptor (homozygous familial hypercholesterolemia). Even though the disease process in homozygous LDL 10 receptor deficiency is immensely aggressive leading to severe coronary atherosclerosis in childhood, the disease is deemed qualitatively no different from that seen in more slowly developing atherosclerosis. Thus, monogenic causes of atherosclerosis can be used as tools to model atherosclerosis and atherosclerotic complications in genetically modified animal models. Apolipoprotein E (ApoE) and LDL-receptor deficient mice with severe hypercholesterolemia and rapid development of atherosclerosis were created in the early 1990s by homologous recombination in embryonic stem cells[6,7]. These mouse models have been instrumental in understanding many aspects of plaque development, but they are limited as models for human atherosclerosis because they lack measurable coronary atherosclerosis and do not develop the most feared complication of atherosclerosis, i.e. atherosclerotic plaque rupture and superimposed thrombosis. In addition—because of their small size—these animals have not aided research on bioimaging of atherosclerosis and percutaneous coronary intervention.

Similarities in cardiovascular structure and coronary artery distribution with humans make swine an attractive species to explore cardiovascular function and diseases. On conventional diets (~3% fat, w/w), pigs have low plasma cholesterol levels (~2 mmol/l), but many strains of pigs are susceptible to hypercholesterolemia and moderate atherosclerosis when fed a diet high in saturated fat and cholesterol, including miniature Yucatan[8] and Yorkshire farm pigs[9]. Yucatan minipigs are of particular interest as models of human atherosclerosis because their adult weight compares well with that of humans (60-80 kg for males and 50-70 kg for females[10]) and thus equipment for imaging and percutaneous coronary intervention can be used directly.

The most pronounced lesions to date have been described in a progeny of large farm pigs identified in Wisconsin that harbor a single-nucleotide missense mutation in the LDL receptor gene that reduces affinity of the receptor to its ligands[11]. A colony of these pigs is now maintained in France by Professor Ludovic Drouet, INRA, Jouy en Josas. The pigs develop atherosclerosis in coronary arteries with many aspects of human atherosclerosis including plaque ruptures and superimposed thrombosis. However, hypercholesterolemia is modest on a normal pig diet (total cholesterol 5-8 mM) and atherosclerosis develops only slowly over several years. By the time these pigs have developed atherosclerosis, they are by far too large for most scientific purposes.

Even though considerable advances in anti-atherosclerotic pharmacological therapy have been achieved in the past decades, atherosclerosis remains one of the leading causes of death and severe disability in Denmark and worldwide[2]. There are at least three parts to an explanation for that.

First, the conventional population-based risk factor approach recommended in official guidelines is unable to identify those who need treatment on the level of the individual[3]. Thus, even though we have access to effective preventive treatment we are unable to identify those to treat. This problem could be solved by diagnostic imaging of atherosclerosis, which is becoming theoretically possible with the advent of new high-resolution imaging technology[4,5]. However, to develop tracers/contrast agents and imaging sequences that are able to visualize atherosclerotic plaques and atherosclerotic disease activity, we need a human-sized animal model of the disease that can be examined in patient CT, MR and PET-scanners.

Second, anti-atherosclerotic therapy is effective in preventing atherosclerosis in the long-term, but there is a lack of medical therapy that is effective at rapidly decreasing the risk of thrombotic complications in persons that have established severe atherosclerosis. E.g. in those persons that have identified themselves by presenting symptoms of atherosclerosis and in which maximal treatment is instigated, future events might still occur. Today, the major obstacle of developing such medicine is the lack of an animal model in which plaque rupture and arterial thrombosis occurs.

Third, the best treatment for coronary events today is primary percutaneous coronary intervention with placement of a stent, but these procedures are subject to complications including stent thrombosis and in-stent restenosis. Most research within this important area is carried out in non-diseased coronary pig arteries, but this approach has obvious limitations.

For these reasons, a human-sized pig model with severe human-like atherosclerosis, including plaque ruptures and thrombotic complications, is needed more than ever.

Even though the genes responsible for inherited atherosclerosis or involved in the development of disease have been identified in humans it does not follow that animals transgenic for such mutations display a phenotype comparable to that of the human disease. However, the present invention has surprisingly shown that the genetically modified pig models according to the present invention display the atherosclerosis phenotype.

SUMMARY OF INVENTION

The present invention concerns a genetically modified pig model which allows for the study of atherosclerosis.

Thus, one aspect of the present invention relates to a genetically modified pig as a model for studying atherosclerosis, wherein the pig model expresses at least one phenotype associated with said disease and/or a modified pig comprising at least one mutation in the i) endogenous ApoE gene or part thereof and/or LDL gene or part thereof, and/or ii) endogenous ApoE gene or part thereof and/or iii) endogenous LDL receptor gene or part thereof, transcriptional and/or translational product or part thereof and/or a modified pig comprising at least one human and/or porcine proprotein convertase subtilisin/kexin type 9 (PCSK9) gene or part thereof, transcriptional and/or translational product or part thereof.

Embodiments for the present invention comprises, mini-pigs for example selected from the group consisting of Goettingen, Yucatan, Bama Xiang Zhu, Wuzhishan and Xi Shuang Banna, including any combination thereof. However, another embodiment relates to pigs that are not a mini-pig, such as the species of Sus domesticus, for example where the pig is selected from the group consisting of Landrace, Yorkshire, Hampshire, Duroc, Chinese Meishan, Berkshire and Piêtrain, including any combination thereof. In a preferred embodiment the pig is a Yucatan minipig.

Embodiments of the present invention comprise the modified pig, wherein the pig comprises at least one mutation in a ApoE and/or LDL gene or part thereof, transcriptional and/or translational product or part thereof. In another embodiment the modified pig comprises at least one mutation in an endogenous ApoE gene or part thereof, transcriptional and/or translational product or part thereof. In a further embodiment the modified pig comprises at least one mutation in an endogenous LDL gene or part thereof, transcriptional and/or translational product or part thereof. In yet another embodiment the at least one mutation is introduced into the endogenous porcine ApoE or LDL gene by homologous recombination or alternatively by random integration. In yet a further embodiment the at least one mutation is introduced into the endogenous porcine ApoE or LDL gene, transcriptional and/or translational product or part thereof by siRNA. A further embodiment relates to the modified pig, wherein said pig comprises at least one human and/or porcine PCSK9 gene or part thereof, transcriptional and/or translational product or part thereof.

A second aspect of the present invention relates to a genetically modified porcine blastocyst derived from the genetically modified pig model as disclosed herein and/or a modified porcine blastocyst comprising at least one mutation in the i) endogenous ApoE gene or part thereof and/or LDL gene or part thereof, and/or ii) endogenous ApoE gene or part thereof and/or iii) endogenous LDL receptor gene or part thereof, transcriptional and/or translational product or part thereof and/or a modified blastocyst comprising at least one human and/or porcine PCSK9 gene or part thereof, transcriptional and/or translational product or part thereof.

A third aspect of the present invention relates to a genetically modified porcine embryo derived from the genetically modified pig model as disclosed herein and/or a modified porcine embryo comprising at least one mutation in the i) endogenous ApoE gene or part thereof and/or LDL gene or part thereof, and/or ii) endogenous ApoE gene or part thereof and/or iii) endogenous LDL receptor gene or part thereof, transcriptional and/or translational product or part thereof and/or a modified embryo comprising at least one human and/or porcine PCSK9 gene or part thereof, transcriptional and/or translational product or part thereof.

A fourth aspect of the present invention relates to a genetically modified porcine fetus derived from the genetically modified pig model as disclosed herein and/or a modified porcine fetus comprising at least one mutation in the i) endogenous ApoE gene or part thereof and/or LDL gene or part thereof, and/or ii) endogenous ApoE gene or part thereof and/or iii) endogenous LDL receptor gene or part thereof, transcriptional and/or translational product or part thereof and/or a modified fetus comprising at least one human and/or porcine PCSK9 gene or part thereof, transcriptional and/or translational product or part thereof.

A fifth aspect of the present invention relates to a genetically modified porcine donor cell derived from the genetically modified pig model as disclosed herein and/or a modified porcine donor cell comprising at least one mutation in the i) endogenous ApoE gene or part thereof and/or LDL gene or part thereof, and/or ii) endogenous ApoE gene or part thereof and/or iii) endogenous LDL receptor gene or part thereof, transcriptional and/or translational product or part thereof and/or a modified donor cell comprising at least one human and/or porcine PCSK9 gene or part thereof, transcriptional and/or translational product or part thereof.

In one embodiment of the present invention the at least one phenotype of the modified pig or pig derived from a modified porcine blastocyst, embryo, fetus and/or donor cell is hypercholesterolemia. The hypercholesterolemia is characterized by an at least 10% increase in total cholesterol level in the plasma as compared to a standard level of the pig. In another embodiment of the present invention the at least one phenotype of the modified pig or pig derived from a modified porcine blastocyst, embryo, fetus and/or donor cell is atherosclerosis. The atherosclerosis is for example determined by intravascular ultrasound, PET scanning, CT scanning and/or MR scanning.

A sixth aspect of the present invention relates to the genetically modified pig as described herein, porcine blastocyst, embryo, fetus and/or donor cell obtainable by nuclear transfer comprising the steps of
  i) establishing at least one oocyte having at least a part of a modified zona pellucida,
  ii) separating the oocyte into at least two parts obtaining an oocyte having a nucleus and at least one cytoplast,
  iii) establishing a donor cell or cell nucleus with desired genetic properties,
  iv) fusing at least one cytoplast with the donor cell or membrane surrounded cell nucleus,
  v) obtaining a reconstructed embryo,
  vi) activating the reconstructed embryo to form an embryo; culturing said embryo; and
  vii) transferring said cultured embryo to a host mammal such that the embryo develops into a genetically modified fetus.
wherein said genetically modified embryo obtainable by nuclear transfer comprises steps i) to v) and/or vi),
wherein said genetically modified blastocyst obtainable by nuclear transfer comprises steps i) to vi) and/or vii),
wherein said genetically modified fetus obtainable by nuclear transfer comprises steps i) to vii).

A seventh aspect of the present invention pertains to a method for producing a transgenic pig as a model for atherosclerosis, porcine blastocyst, embryo, fetus and/or donor cell comprising:
  i) establishing at least one oocyte
  ii) separating the oocyte into at least three parts obtaining at least one cytoplast,
  iii) establishing a donor cell or cell nucleus having desired genetic properties,
  iv) fusing at least one cytoplast with the donor cell or membrane surrounded cell nucleus,
  v) obtaining a reconstructed embryo,
  vi) activating the reconstructed embryo to form an embryo;
  vii) culturing said embryo; and
  viii) transferring said cultured embryo to a host mammal such that the embryo develops into a genetically modified fetus,
wherein said genetically modified embryo obtainable by nuclear transfer comprises steps i) to v) and/or vi),
wherein said genetically modified blastocyst obtainable by nuclear transfer comprises steps i) to vi) and/or vii),
wherein said genetically modified fetus obtainable by nuclear transfer comprises steps i) to vii).

Embodiments of the sixth and seventh aspects comprise one or more of the features as defined in any of the preceding claims, wherein the method for activation of the reconstructed embryo is selected from the group of methods consisting of electric pulse, chemically induced shock, increasing intracellular levels of divalent cations and reducing phosphorylation. Further embodiments of the second and third aspects comprise one or more of the features as defined above, wherein steps iv) and vi) are performed sequentially or simultaneously, and embodiments comprising one or more of the features, wherein the embryo is cultured in vitro. Such embryo may be cultured in sequential culture. The embryo, for example at the blastocyst stage, is cryopreserved prior to transfer to a host mammal.

For the methods of the present invention embodiments cover pigs, mini-pigs for example selected from the group consisting of Goettingen, Yucatan, Bama Xiang Zhu, Wuzhishan and Xi Shuang Banna, including any combination thereof. However, another embodiment relates to pigs that are not a mini-pig, such as the species of Sus scrofa domesticus, for example where the pig is selected from the group consisting of Landrace, Yorkshire, Hampshire, Duroc, Chinese Meishan, Berkshire and Piêtrain, including any combination thereof. In a preferred embodiment is the Yucatan minipig.

A further aspect of the present invention pertains to method for evaluating the effect of a therapeutical treatment of atherosclerosis, said method comprising the steps of i) providing the pig model as disclosed herein, ii) treating said pig model with a pharmaceutical composition exerting an effect on said phenotype, and iii) evaluating the effect observed.

In one embodiment the method further comprises a step of advising on medical treatment based on the afore-mentioned observed effects.

Yet a further aspect of the present invention relates to a method for screening the efficacy of a pharmaceutical composition for atherosclerosis, said method comprising the steps of i) providing the pig model as disclosed herein, ii) expressing in said pig model said genetic determinant and exerting said phenotype for said disease, iii) administering to said pig model a pharmaceutical composition the efficacy of which is to be evaluated, and iv) evaluating the effect, if any, of the pharmaceutical composition on the phenotype exerted by the genetic determinant when expressed in the pig model.

Furthermore the present invention in another aspect relates to a method for treatment of a human being suffering from atherosclerosis, said method comprising the initial steps of i) providing the pig model as disclosed herein, ii) expressing in said pig model said genetic determinant and exerting said phenotype for said disease, iii) administering to said pig model a pharmaceutical composition the efficacy of which is to be evaluated, and iv) evaluating the effect observed, and v) treating said human being suffering from atherosclerosis based on the effects observed in the pig model.

DETAILED DESCRIPTION OF THE INVENTION

Figure 1:
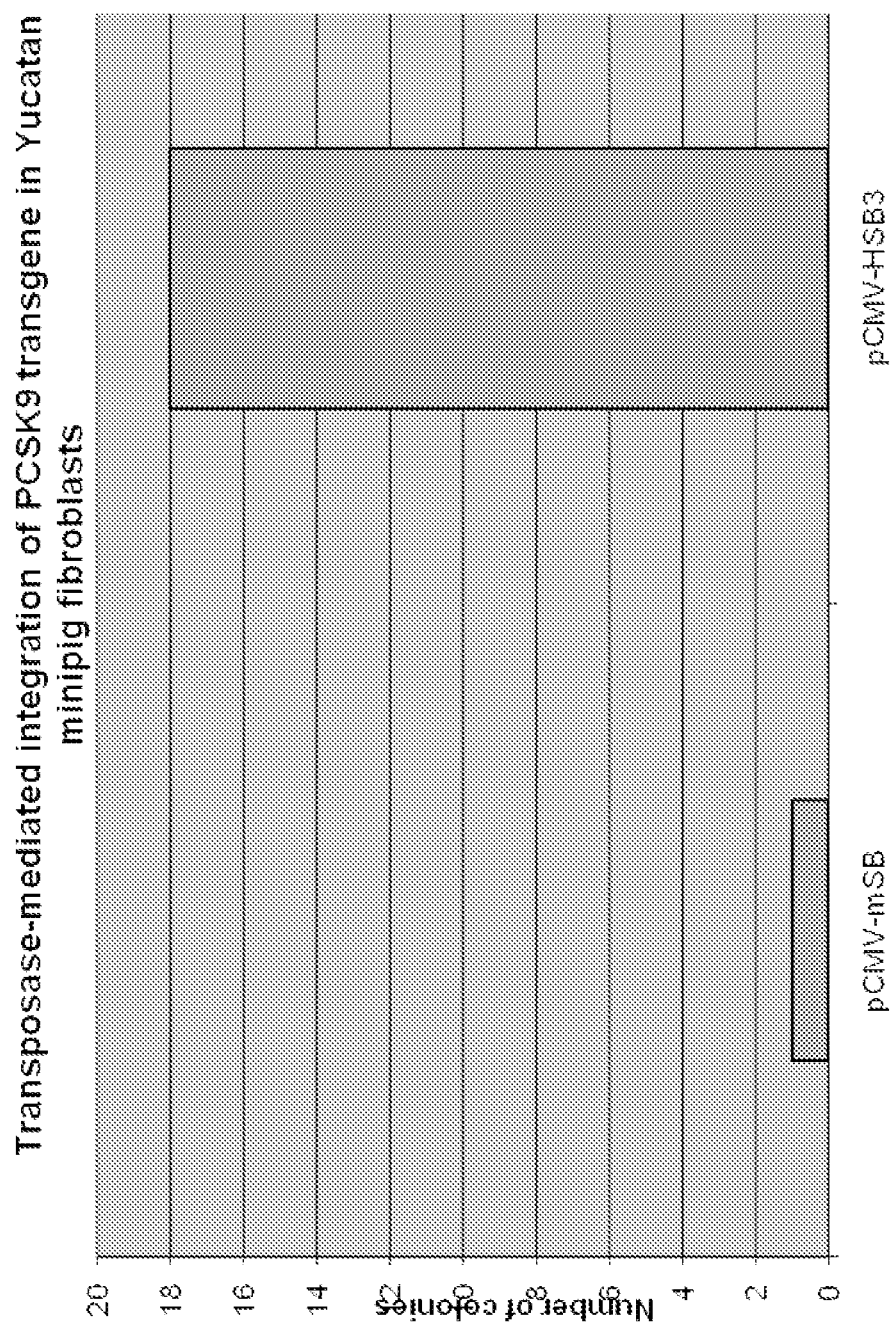
FIG. 1 shows the number of resistant clones after co-transfection of pSBT-HCRapoE-hAAT-PCSK9-bpA with pCMV-mSB (Left) and pCMV-HSB3 (Right).

The present invention pertains to a genetically modified pig model, blastocysts, donor cells and/or fetuses for studying atherosclerosis wherein the pig model expresses at least one phenotype associated with atherosclerosis.

It will be appreciated that the invention does not comprise processes for modifying the genetic identity of pigs which are likely to cause them suffering without any substantial medical benefit to man or animal, or animals resulting from such processes.

The present invention also relates to genetically modified pig embryos obtainable by the methods described herein.

The methods for producing the pig model for studying atherosclerosis described herein do not encompass a surgical step performed on the pig.

The term 'endogenous' is used herein to specify a particular gene present naturally in the genome of a particular target cell (for example cells of a pig).

The term "genetic determinant" is used herein to refer to a single-stranded or double-stranded "polynucleotide molecule" or "nucleic acid" comprising a structural gene of interest. The "genetic determinant" encodes a protein not ordinarily made in appreciable amounts in the target cells. Thus, "genetic determinants" include nucleic acids which are not ordinarily found in the genome of the target cell. "Genetic determinants" also include nucleic acids which are ordinarily found within the genome of the target cell, but is in a form which allows for the expression of proteins which are not ordinarily expressed in the target cells in appreciable amounts. Alternatively, "genetic determinants" may encode a variant or mutant form of a naturally-occurring protein.

The terms "polynucleotide" and "nucleic acid" are used interchangeably, and, when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The terms 'transgenic' pig and 'genetically modified' pig are used in identical meaning herein.

The present invention pertains to a modified pig model for studying atherosclerosis, wherein the pig model expresses at least one phenotype associated with atherosclerosis.

Pigs

The present invention relates to a modified pig as a model for studying atherosclerosis, wherein the pig model expresses at least one phenotype associated with atherosclerosis. The pig of the present invention may be any pig.

The pig is evolutionary close to humans as compared to for example rodentia. Furthermore, the pig has been widely used in bio-medical research because of the similarities between human and porcine physiology (Douglas, 1972; Book & Bustad, 1974).

In one embodiment the pig is a wild pig. In another embodiment the pig is the domestic pig, *Sus scrofa*, such as *S. domesticus*. In yet another embodiment the invention relates to mini pigs, as well as to inbred pigs. The pig can be selected e.g. from the group consisting of Landrace, Yorkshire, Hampshire, Duroc, Chinese Meishan, Berkshire and Pietrain, such as the group consisting of Landrace, Yorkshire, Hampshire and Duroc, for example the group consisting of Landrace, Duroc and Chinese Meishan, such as the group consisting of Berkshire, Pietrain, Landrace and Chinese Meishan, for example the group consisting of Landrace and Chinese Meishan. In one embodiment, the pig is not a mini-pig. In another embodiment the pig of the present invention is an inbred pig.

In another embodiment of the present invention the pig is a mini-pig and the mini-pig is preferably selected from the group consisting of Goettingen, Yucatan, Bama Xiang Zhu, Wuzhishan and Xi Shuang Banna. Thus, the present invention relates to any of Goettingen, Yucatan, Bama Xiang Zhu, Wuzhishan and Xi Shuang Banna separately, or in any combination. In a preferred embodiment of the invention the Yucatan mini pig is used.

Due to its size and weight of about 200 kg the domestic pig is not easily handled in a laboratory setting. A preferred alternative to the domestic pig is the Goettingen (Göttingen) mini-pig that weighs about 30 kg. However, alternatives to the Goettingen minipig is the Yucatan minipig, Preferred embodiments of the present invention comprises Goettingen mini pig, or the Yucatan minipig.

Genetically Modified

The genetic modifications are introduced in the somatic cell prior to cell nuclear transfer. However, the genetic modification may in another embodiment be introduced during the cell nuclear transfer process, for example by addition of transgenes at different steps of the hand made cloning (HMC) procedure that will then find their way to the genome of the embryo.

The genetic modifications comprise random integration of a disease causing gene, mutated gene, into the genome of the somatic cell. It could also be random integration of a normal non-mutated gene that will cause a disease when expressed in a specific tissue or at a specific expression level.

However, the invention also pertains to modified pigs, embryos, donor cells, blastocysts and/or fetuses obtained by transfer of mRNA and/or protein of the genes disclosed herein. Thus, the modification of the pig is in one embodiment does not lead to integration of a transgene into the genome of the pig, embryo, blastocyst and/or fetus.

The introduced gene or transgene, transcriptional and/or translational product or part thereof may originate from any species, including bacteria, pig, human, mouse, rat, yeast, invertebrates, or plants. Regulatory sequences of the transgene may drive ubiquitous or inducible or tissue- and/or time-specific expression and may also originate from any species including pig, human, mouse, rat, yeast, invertebrates, or plants.

Importantly, the genetic modification in the somatic cell may be targeted to a specific region in the porcine genome by homologous recombination of a targeting construct or by gene editing procedures. This could be inactivation (e.g. knock-out) of specific genes that will cause a disease or phenotype.

Homologous recombination occurs between two homologous DNA molecules. It is also called DNA crossover. By homologous recombination, one DNA segment can replace another DNA segment with a similar sequence. The process involve breakage and reunion between the homologous regions of DNA, which is mediated by specialized enzymes. The technique allows replacing one allele with an engineered construct without affecting any other locus in the genome. Using homologous recombination it is possible to direct the insertion of a transgene to a specific known locus of the host cells genome. Knowing the DNA sequence of the target locus, it is possible to replace any gene with a genetically modified DNA construct, thereby either replacing or deleting the target sequence. The technique comprises discovering and isolating the normal gene and then determining its function by replacing it in vivo with a defective copy. This procedure is known as 'gene knock-out', which allows for specific gene targeting by taking advantage of homologous recombination. Cloned copies of the target gene are altered to make them nonfunctional and are then introduced into ES cells where they recombine with the homologous gene in the cell's genome, replacing the normal gene with a nonfunctional copy.

Homologous recombination can similarly be exploited to generate fusion genes or insertion of point mutations in a 'knock-in' strategy, in which a targeting vector, comprising a relevant exon of the target locus fused with the cDNA sequence of chromosomal translocation-fusion partner, is transfected into embryonic stem cells, whereby the recombinant sequence is fused to an endogenous gene to generate fusion a gene.

Another applicable technique to exploits the phenomenon called RNA interference (RNAi), in which 21 nucleotide small interfering RNAs (siRNA) can elicit an effective degradation of specific mRNAs. RNA interference constitutes a new level of gene regulation in eukaryotic cells. It is based on the fact that presence of double stranded RNA in a cell eliminates the expression of a gene of the same sequence, whereas expression of other unrelated genes is left undisturbed. The siRNA stimulates the cellular machinery to cut up other single-stranded RNA having the same sequence as the siRNA. In a preferred embodiment of the present invention, siRNAs are directed towards porcine ApoE, and/or porcine LDL. In one embodiment, the siRNA may be selected from the siRNA sequences, described herein.

The genetic modifications introduced into the porcine genome prior or during the HMC procedure could also be epigenetic modifications (e.g. methylation of DNA or methylation or acetylation/deacetylation of histones) by incubating somatic cells, oocytes or reconstructed HMC embryos with chemical components such as tricostatin or compounds with similar effect.

The present invention relates to a modified pig, blastocyst, embryo, fetus and/or donor cell comprising a genetic determinant in the form of at least one mutation in an endogenous, and thus porcine, ApoE gene or part thereof, and/or at least one mutation in an endogenous, and thus porcine, LDL gene or part thereof, and/or in the form of an overexpressed human and/or porcine PCSK9 gene or part thereof, separately or in combination as described in detail herein.

The present invention also relates to porcine embryos, blastocysts and/or fetuses derived from a modified pig expressing at least one phenotype associated with atherosclerosis.

It is within the scope of the present invention that the modified pig, blastocyst, embryo, fetus and/or donor cell comprises at least one mutation, such as 2, 3, 4, 5, 6, 7, 8, 9, 10 or 15 mutations in the ApoE gene and/or the LDL gene.

In one embodiment of the present invention the modified pig according to the present invention is mutated in the ApoE gene or part thereof, transcriptional and/or translational product or part thereof (Sus scrofa ApoE gene and protein, SEQ ID NO: 1, SEQ ID NO: 2) and/or the LDL gene or part thereof, transcriptional and/or translational product or part thereof (Sus scrofa LDL gene and protein, SEQ ID NO: 3, SEQ ID NO: 4). The genes are mutated so that the function of the gene is disrupted. It is appreciated that a mutation and/or disrupted function of the gene will result in a reduction in the amount of the transcriptional product or part thereof and/or translational product or part thereof of said gene compared to the amount of transcriptional and/or translational product of the gene in question, here the ApoE gene and/or the LDL gene.

However, in another embodiment the transgenic pig is transgenic for a combination of mutations, for example at least one mutation in the porcine endogenous ApoE gene and/or at least one mutation in the porcine endogenous LDL gene.

The mutations introduced into the endogenous porcine ApoE gene and/or the endogenous porcine LDL gene or part thereof may be introduced by any method known to the person skilled in the art. In one embodiment the at least one mutation is introduced by knock out through homologous recombination. However, in another preferred embodiment the at least one mutation is in the form of a reduction in the amount of transcriptional and/or translational product or part thereof of the endogenous ApoE and/or endogenous LDL gene compared to the amount of transcriptional and/or translational product or part thereof of a wild type ApoE gene and/or a LDL gene. A preferred method for reducing the amount of ApoE and/or LDL transcriptional and/or translational product or part thereof is by use of small interfering RNAs (siRNA) directed against the transcriptional products or part thereof of the ApoE gene and/or LDL gene. In a preferred embodiment the transcriptional product or part thereof of the LDL gene is targeted. Non-limiting targets for small interfering RNAs knock down of LDL receptors are shown in Table 1. Each of the targets may be chosen separately, or in any combination. In a preferred embodiment the target is T8. In another embodiment the preferred target is T9.

TABLE 1

Targets for shRNA directed LDL receptor knockdown

| First base in pig cDNA AF065990 sequence | Sequence |
|---|---|
| T1 | 763 | tgtcaaagcggcgagtgca (SEQ ID NO: 5) |
| T2 | 889 | tcccatatctgcaatgacc (SEQ ID NO: 6) |
| T3 | 1150 | accctggaccgtagtgagt (SEQ ID NO: 7) |
| T4 | 1308 | tgacaccattattggcgaa (SEQ ID NO: 8) |
| T5 | 1309 | gacaccattattggcgaag (SEQ ID NO: 9) |
| T6 | 1439 | agactctcttccaagagaa (SEQ ID NO: 10) |
| T7 | 1553 | tgaacggagtggacgtcta (SEQ ID NO: 11) |

TABLE 1-continued

Targets for shRNA directed LDL receptor knockdown

| First base in pig cDNA AF065990 sequence | Sequence |
|---|---|
| T8 | 1814 | tcacaggctcggacataca (SEQ ID NO: 12) |
| T9 | 858 | ccaacgagtgtctggacaa (SEQ ID NO: 13) |
| T10 | 1109 | cctacctcttcttcaccaa (SEQ ID NO: 14) |

One or more mutations of the ApoE and/or LDL gene may be in coding region of the ApoE and/or the LDL gene, however, one or more mutations of the ApoE and/or the LDL gene may also be determined in at least one regulatory sequence of the ApoE and/or LDL gene. By regulatory sequence is meant sequences that regulate the transcriptional and translational process, for example, promoters, enhancers, sequences that affect polyadenylation, translational or transcriptional start, splicing of transcriptional products. The promoters and enhancers that control the transcription of protein-encoding genes are composed of multiple genetic elements. The cellular machinery is able to gather and integrate the regulatory information conveyed by each element, allowing different genes to evolve distinct, often complex patterns of transcriptional regulation. The ApoE and/or LDL gene may alternatively be mutated in one or more of its exons.

In one embodiment the endogenous porcine ApoE gene of the genetically modified pig, embryo, blastocyst, donor cell and/or fetus of the present invention is mutated in one or more of its exons, thus disrupting gene function of ApoE. Thus, any of exon 1, exon 2, exon 3, or exon 4 of the porcine ApoE gene may be mutated. Exon 1 is positioned at nucleotide 832-857 of the porcine ApoE gene, exon 2 at nucleotide 1663-1728, exon 3 at nucleotides 2473-2662, exon 4 at nucleotides 3037-3879 of the porcine ApoE gene. In a preferred embodiment the one or more exon of ApoE and/or LDL is mutated by disrupting the exon due to the insertion of a nucleotide construct by homologous recombination and knock-out technology.

Furthermore, it is appreciated the genetically modified pig, embryo, blastocyst, donor cell and/or fetus of the present invention comprises the transcriptional product or part thereof and/or the translational product or part thereof of the porcine ApoE and/or LDL genes as described above.

In most cases of atherosclerosis the genetic component is complex, but in some cases the inheritance of the disease is monogenic. These cases are mostly caused by mutations in genes coding for proteins involved in lipoprotein trafficking, and the most severe in humans are caused by mutations affecting LDL receptor-mediated lipoprotein uptake (recessive and autosomal dominant familial hypercholesterolemia). Recently, a gain-of-function mutation in the PCSK9 gene was described as the cause of autosomal dominant familial hypercholesterolemia (17) PCSK9 binds to the LDL receptor leading to its degradation (18). Therefore, gain-of-function mutations in humans and overexpression of PCSK9 transgenes in mice leads to functional LDL receptor deficiency (19). The modified pig, embryo, blastocyst, fetus and/or donor cell comprises at least one human and/or porcine PCSK9 gene or part thereof, transcriptional and/or translational product or part thereof.

In one embodiment the modified pig, embryo, blastocyst, fetus and/or donor cell comprises at least one porcine PCSK9 gene or part thereof, transcriptional and/or translational product thereof. In a preferred embodiment the modified pig, embryo, blastocyst, fetus and/or donor cell comprises at least one human PCSK9 gene or part thereof, transcriptional and/or translational product thereof.

Sequence Identity

Functional equivalents and variants are used interchangeably herein. In one preferred embodiment of the invention there is also provided variants of the LDL receptor and/or the apolipoprotein A gene. When being polypeptides, variants are determined on the basis of their degree of identity or their homology with a predetermined amino acid sequence, said predetermined amino acid sequence being the LDL receptor and/or the apolipoprotein A gene products as described herein, or, when the variant is a fragment, a fragment of any of the aforementioned amino acid sequences, respectively.

Accordingly, variants preferably have at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the predetermined sequence.

The following terms are used to describe the sequence relationships between two or more polynucleotides: "predetermined sequence", "comparison window", "sequence identity", "percentage of sequence identity", and "substantial identity".

A "predetermined sequence" is a defined sequence used as a basis for a sequence comparision; a predetermined sequence may be a subset of a larger sequence, for example, as a segment of a full-length DNA or gene sequence given in a sequence listing, such as a polynucleotide sequence of the LDL receptor and/or the apolipoprotein A genes as described herein or may comprise a complete DNA or gene sequence. Generally, a predetermined sequence is at least 20 nucleotides in length, frequently at least 25 nucleotides in length, and often at least 50 nucleotides in length.

Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a predetermined sequence of at least 20 contiguous nucleotides and wherein the portion of the polynucleotide sequence in the comparison window may comprise additions or deletions (i.e., gaps) of 20 percent or less as compared to the predetermined sequence (which does not comprise additions or deletions) for optimal alignment of the two sequences.

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a predetermined sequence over a comparison window of at least 20 nucleotide positions, frequently over a window of at least 25-50 nucleotides, wherein the percentage of sequence identity is calculated by comparing the predetermined sequence to the polynucleotide sequence which may include deletions or additions which total 20 percent or less of the predetermined sequence over the window of comparison. The predetermined sequence may be a subset of a larger sequence, for example, as a segment of the full-length LDL receptor and/or apolipoprotein A gene polynucleotide sequence illustrated herein.

Sequence identity is determined in one embodiment by utilising fragments of porcine or human ApoE sequence, or porcine or human LDL peptides, porcine or human PCSK9 peptides comprising at least 25 contiguous amino acids and having an amino acid sequence which is at least 80%, such as 85%, for example 90%, such as 95%, for example 96%, such as 97%, for example 98%, such as 99% identical to the amino acids as described herein, wherein the percent identity is determined with the algorithm GAP, BESTFIT, or FASTA in the Wisconsin Genetics Software Package Release 7.0, using default gap weights.

Conservative Amino Acid Substitutions:

Substitutions within the groups of amino acids, shown below, are considered conservative amino acid substitutions. Substitutions between the different groups of amino acids are considered non-conservative amino acid substitutions.

P, A, G, S, T (neutral, weakly hydrophobic)
Q, N, E, D, B, Z (hydrophilic, acid amine)
H, K, R (hydrophilic, basic)
F, Y, W (hydrophobic, aromatic)
L, I, V, M (hydrophobic)
C (cross-link forming)

By the term "transcriptional or translational products" is meant herein products of gene transcription, such as a RNA transcript, for example an unspliced RNA transcript, a mRNA transcript and said mRNA transcript splicing products, and products of gene translation, such as polypeptide(s) translated from any of the gene mRNA transcripts and various products of post-translational processing of said polypeptides, such as the products of post-translational proteolytic processing of the polypeptide(s) or products of various post-translational modifications of said polypeptide(s).

As used herein, the term "transcriptional product of the gene" refers to a pre-messenger RNA molecule, pre-mRNA, that contains the same sequence information (albeit that U nucleotides replace T nucleotides) as the gene, or mature messenger RNA molecule, mRNA, which was produced due to splicing of the pre-mRNA, and is a template for translation of genetic information of the gene into a protein.

Phenotypes

The phenotypes associated with atherosclerosis are many. It is appreciated that the pig model of the present invention expresses at least one phenotype associated with atherosclerosis, such as three, for example four, five, six, seven, eight, nine, ten, eleven, 12, 13, 14, 15, 16, 17, 18, 19 or 20 phenotypes associated with atherosclerosis. Non-limiting examples of said phenotypes are hypercholesterolemia, accumulation of fat, cholesterol and other substances in the walls of arteries, plaque formation, stenosis, blockage of blood flow, plaque rupture, infarction, and/or claudication.

At least one phenotype associated with atherosclerosis is hypercholesterolemia. Hypercholesterolemia is an increase in cholesterol amount as compared to a standard level in the pig observed before the onset of an increase in cholesterol amount or compared to a standard level determined from a population of pigs. The cholesterol amount is preferably measured in the plasma of pigs. An increase in plasma cholesterol is at least 10% compared to a standard level, such at least 15%, for example 20%, such as 25%, for example 30%, such at least 35%, for example at least 40%, such as at least 45%, for example at least 50%, such at least 55%, for example at least 60%, such as at least 65%, for example at least 70%, such at least 75%, for example at least 80%, such as at least 85%, for example at least 90%, such at least 95%, for example at least 100%, such as at least 110%, for example at least 120%, such at least 150%, for example at least 175%, such as at least 200%, for example at least 250%, such as at least 300%, for example at least 350%, such at least 400%, for example at least 450%, such as at least 500 compared to a standard level.

Thus, a 10% increase in hypercholesterolemia in a pig having a standard level of 2 mmol/l corresponds to an amount of cholesterol of 2.2 mmol/l.

The phenotypes associated with atherosclerosis comprise the building up of fat, cholesterol and other substances in the walls of arteries and form plaques. Eventually, the plaque deposits can make the artery less flexible. The hardening of the artery may result in decreased blood flow (stenosis) and even blockage of blood flow. Consequently, insufficient blood supply to the organs. The artery may compensate for narrowing of the artery by enlarging the artery which when excessive leads to the formation of an aneurysm. If blood flow in the arteries leading to the heart is reduced, chest pain can occur. Plaques can also break apart (plaque rupture), causing pieces of material to move through the artery, causing the formation of a thrombus that will rapidly slow or stop blood flow, leading to death of the tissues affected by stop of blood flow, also known as infarction. This is a common cause of heart attack and stroke. Blood clots can also form around the plaque deposits. Clots block blood flow. If the clot moves into the heart, lungs, or brain, it can cause a stroke, heart attack, or pulmonary embolism.

Also claudication due to insufficient blood supply to the legs, typically due to a combination of both stenosis and aneurysmal segments narrowed by clots is an embodiment of the phenotypes associated with atherosclerosis. Another phenotype of the genetically modified pig is hypercholesterolemia in which consistently high levels of low-density lipoprotein (LDL) is observed compared to normal levels, leading to premature atherosclerosis of the coronary arteries. Typically in affected men, heart attacks occur in their 40s to 50s. In humans, hypercholesterolemia is often in the form of familial hypercholesterolemia which is mostly due to mutations in genes coding for proteins involved in lipoprotein trafficking, caused by homozygous null mutations in the LDL receptor.

A number of tests exist which aids in the diagnosis of atherosclerosis are known to the person skilled in the art such as a cardiac stress test which is a medical test performed to evaluate arterial blood flow to the myocardium (heart muscle) during physical exercise, compared to blood flow while at rest. Also low intensity ultrasound is used to detect blood flow velocity in arteries known as a Doppler study, magnetic resonance arteriography, CT scanning, arteriography using x-ray and special dye to see inside the arteries, intravascular ultrasound and/or ultrasonic duplex scanning are used to diagnose atherosclerosis.

Methods for Producing Pig Model for Studying Atherosclerosis

The present invention provides improved procedures for cloning pigs by nuclear transfer which refers to the introduction of a full complement of nuclear DNA from one cell to an enucleated cell. The genetically modified pig of the present invention may be produced using any technique in which modified genetic material, transcriptional product and/or translational product or part thereof is transferred from at donor cell to a host cell, such as an enucleated oocyte. A number of techniques exist such as introducing genetic material from a genetically modified somatic cell into an enucleated oocyte by for example microinjection or by nuclear transfer In cloning, the transfer of the nucleus of a somatic (body) cell or somatic cell into an egg cell (oocyte) which has had its own nucleus removed (denucleated or enucleated) is called somatic cell nuclear transfer. The new individual will develop from this reconstructed embryo and be genetically identical to the donor of the somatic cell. In the present invention the modified pig model, porcine embryo, blastocyst and/or fetus is obtainable by somatic cell nuclear transfer comprising the steps of a) establishing at least one oocyte having at least a part of a modified zona pellucida, b) separating the oocyte into at least two parts obtaining at least one cytoplast, c) establishing a donor cell or cell nucleus having desired genetic properties, d) fusing at least one cytoplast with the donor cell or membrane surrounded cell nucleus, e) obtaining a reconstructed embryo, f) activating the reconstructed embryo to form an embryo; and g) transferring said cultured embryo to a host mammal such that the embryo develops into a genetically modified fetus, wherein said genetically modified embryo obtainable by nuclear transfer comprises steps a) to e) and/or f), wherein said genetically modified blastocyst obtainable by nuclear transfer comprises steps a) to e) and/or f), wherein said genetically modified fetus obtainable by nuclear transfer comprises steps a) to g).

The oocyte of b) may in another embodiment be separated into at least three parts obtaining at least two cytoplasts. It is appreciated that the donor cell or cell nucleus of c) harbours genetic determinants for atherosclerosis, for example in the form of modified human or porcine ApoE gene or part thereof and/or modified human or porcine LDL gene or part thereof. The host mammal of g) is in one embodiment a pig, preferably a Yucatan mini pig.

However, the present invention also relates to a method for producing a transgenic pig, porcine blastocyst, embryo and/or fetus as a model for atherosclerosis comprising the steps of a) establishing at least one oocyte, b) separating the oocyte into at least three parts obtaining at least two cytoplasts, c) establishing a donor cell or cell nucleus having desired genetic properties, d) fusing at least one cytoplast with the donor cell or membrane surrounded cell nucleus, e) obtaining a reconstructed embryo, f) activating the reconstructed embryo to form an embryo; and g) transferring said cultured embryo to a host mammal such that the embryo develops into a genetically modified fetus, wherein said genetically modified embryo obtainable by nuclear transfer comprises steps a) to e) and/or f), wherein said genetically modified blastocyst obtainable by nuclear transfer comprises steps a) to e) and/or f), wherein said genetically modified fetus obtainable by nuclear transfer comprises steps a) to g)

It is appreciated that the donor cell or cell nucleus of c) harbours genetic determinants for atherosclerosis, for example in the form of modified human or porcine ApoE gene or part thereof and/or modified human or porcine LDL gene or part thereof and/or transcriptional and/or translational products thereof, and/or the insertion of a porcine and/or human PCSK9 gene. The host mammal of g) is in one embodiment a pig, preferably a Yucatan mini pig.

The various parameters are described in detail below.

Oocyte

The term 'oocyte' according to the present invention means an immature female reproductive cell, one that has not completed the maturing process to form an ovum (gamete). In the present invention an enucleated oocyte is the recipient cell in the nuclear transfer process.

The oocytes according to the present invention are isolated from oviducts and/or ovaries of a mammal. Normally, oocytes are retrieved from deceased pigs, although they may be isolated also from either oviducts and/or ovaries of live pigs. In one embodiment the oocytes are isolated by oviductal recovery procedures or transvaginal recovery methods. In a preferred embodiment the oocytes are isolated by aspiration. Oocytes are typically matured in a variety of media known to a person skilled in the art prior to enucleation. The oocytes can also be isolated from the ovaries of a recently sacrificed animal or when the ovary has been frozen and/or thawed. Preferably, the oocytes are freshly isolated from the oviducts.

Oocytes or cytoplasts may also be cryopreserved before use. While it will be appreciated by those skilled in the art that freshly isolated and matured oocytes are preferred, it will also be appreciated that it is possible to cryopreserve the oocytes after harvesting or after maturation. If cryopreserved oocytes are utilised then these must be initially thawed before placing the oocytes in maturation medium. Methods of thawing cryopreserved materials such that they are active after the thawing process are well-known to those of ordinary skill in the art. However, in general, cryopreservation of oocytes and cytoplasts is a very demanding procedure, and it is especially difficult in pigs, because of the above mentioned general fragility of pig oocytes and cytoplasts, and because of the high lipid content that makes them very sensitive to chilling injury (i.e. injury that occurs between +15 and +5° C. during the cooling and warming procedure).

In another embodiment, mature (metaphase II) oocytes that have been matured in vivo, may be harvested and used in the nuclear transfer methods disclosed herein. Essentially, mature metaphase II oocytes are collected surgically from either nonsuperovulated or superovulated pigs 35 to 48 hours past the onset of estrus or past the injection of human chorionic gonadotropin (hCG) or similar hormone.

Where oocytes have been cultured in vitro, cumulus cells that are surrounding the oocytes in vivo may have accumulated may be removed to provide oocytes that are at a more suitable stage of maturation for enucleation. Cumulus cells may be removed by pipetting or vortexing, for example, in the presence of in the range of 0.1 to 5% hyaluronidase, such as in the range of 0.2 to 5% hyaluronidase, for example in the range of 0.5 to 5% hyaluronidase, such as in the range of 0.2 to 3% hyaluronidase, for example in the range of 0.5 to 3% hyaluronidase, such as in the range of 0.5 to 2% hyaluronidase, for example in the range of 0.5 to 1% hyaluronidase, such as 0.5% hyaluronidase.

The first step in the preferred methods involves the isolation of a recipient oocyte from a suitable pig. In this regard, the oocyte may be obtained from any pig source and at any stage of maturation.

The stage of maturation of the oocyte at enucleation and nuclear transfer has been reported to be of significance for the success of nuclear transfer methods. Immature (prophase I) oocytes from pig ovaries are often harvested by aspiration. In order to employ techniques such as genetic engineering, nuclear transfer and cloning, such harvested oocytes are preferably matured in vitro before the oocyte cells may be used as recipient cells for nuclear transfer.

Preferably, successful pig embryo cloning uses the metaphase II stage oocyte as the recipient oocyte because it is believed that at this stage of maturation the oocyte can be or is sufficiently activated to treat the introduced nucleus as if it were a fertilising sperm. However, the present invention relates to any maturation stage of the oocyte which is suitable for carrying out somatic cell nuclear transfer, embryos, blastocysts, and/or transgenic pigs obtainable by the method of somatic cell nuclear transfer of the present invention.

The in vitro maturation of oocytes usually takes place in a maturation medium until the oocyte has reached the metaphase II stage or has extruded the first polar body. The time it takes for an immature oocyte to reach maturation is called the maturation period.

In a preferred embodiment of the present invention the oocyte is from sow or gilt, preferably from a sow.

The donor (somatic cell or nucleus of somatic cell) and recipient (cytoplast) involved in the cell nuclear transfer method according to the present invention is a pig. Likewise, reconstructed embryos may be implanted in a pig according to the present invention. The different pigs suitable as donor, recipient or foster mother are described elsewhere herein.

The donor pig according to the present invention may be female, or male. The age of the pig can be any age such as an adult, or for example a fetus.

Embryo

According to the present invention a reconstructed embryo (i.e. single cell embryo) contains the genetic material of the donor cell. Subsequently, the reconstructed embryo divides progressively into a multi-cell embryo after the onset of mitosis. In vitro the onset of mitosis is typically induced by activation as described herein.

In the present invention the term 'embryo' also refers to reconstructed embryos which are embryos formed after the process of nuclear transfer after the onset of mitosis by activation. Reconstructed embryos are cultured in vitro.

When the embryo contains about 12-16 cells, it is called a "morula". Subsequently, the embryo divides further and many cells are formed, and a fluid-filled cystic cavity within its center, blastocoele cavity. At this stage, the embryo is called a "blastocyst". The developmental stage of the "fertilized" oocyte at the time it is ready to implant; formed from the morula and consists of an inner cell mass, an internal cavity, and an outer layer of cells called trophectodermal cells.

The blastocyst according to the present invention may be implanted into the uterus of a host mammal and continues to grow into a fetus and then an animal. In the methods provided herein for producing genetically modified or transgenic non-human mammal, for cloning a non-human mammal, for culturing a reconstructed embryo, and/or for cryopreservation of a pig embryo, the embryo may be cultured in vitro. The embryo may for example be cultured in sequential culture. It will be appreciated that the embryo may be a normal embryo, or a reconstructed embryo as defined elsewhere herein.

The present invention thus relates to a modified porcine embryo, blastocyst and/or fetus derived from the genetically modified pig model as disclosed herein and/or the modified porcine embryo comprises at least one modified human ApoE gene or part thereof and/or, human LDL gene or part thereof and/or, porcine APoE gene or part thereof and/or, porcine LDL gene or part thereof, and/or comprises a human PCSK9 gene or part thereof, transcriptional and/or translational product or part thereof.

It is appreciated that the modified porcine embryo, blastocyst and/or fetus derivable from the modified pig model for studying atherosclerosis, expressing at least one phenotype associated with atherosclerosis may have been the result of the crossing of for example a pig transgenic for at least one ApoE mutation and a pig transgenic for at least one LDL mutation, and/or a pig comprising a human PCSK9 gene.

Cytoplast

An oocyte or a part of an oocyte from which the nucleus has been removed.

Donor Cell

By the term 'donor cell' of the present invention is meant somatic cell and/or cells derived from the germ line.

By the term 'somatic cell' of the present invention is meant any (body) cell from an animal at any stage of development. For example somatic cells may originate from fetal or adult tissue. Especially preferred somatic cells are those of foetal origin. However, cells from a germ line may also be used. According to the present invention a donor cell is a somatic cell. In another embodiment of the present invention the donor cell is a cell derived from a germ cell line.

In a preferred embodiment of the present invention the donor cell harbours desired genetic properties. However, the donor cell may harbour desired genetic properties which have been gained by genetic manipulation as described elsewhere herein.

Somatic cells are selected from the group consisting of epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells.

These may be obtained from different organs, e.g., skin, lung, pancreas, liver, stomach, intestine, heart, reproductive organs, bladder, kidney, urethra and other urinary organs.

The pigs from which the somatic cells may be derived are described elsewhere herein. A preferred embodiment of the invention is the use of somatic cells originating from the same species as the recipient oocyte (cytoplast).

Preferably, the somatic cells are fibroblast cells as the can be obtained from both developing fetuses and adult animals in large quantities. Fibroblasts may furthermore be easily propagated in vitro. Most preferably, the somatic cells are in vitro cultured fibroblasts of foetal origin.

In a preferred embodiment the somatic cells are genetically modified. In yet a further preferred embodiment of the present invention the somatic cells are preferably of foetal origin, or for example from adults.

The present invention thus relates to a modified porcine donor cell derived from the genetically modified pig model as disclosed herein and/or the modified porcine embryo comprises at least one modified human ApoE gene or part thereof and/or, human LDL gene or part thereof and/or, porcine APoE gene or part thereof and/or, porcine LDL gene or part thereof, and/or comprises a human PCSK9 gene or part thereof, transcriptional and/or translational product or part thereof.

It is appreciated that the modified porcine donor cell from the modified pig model for studying atherosclerosis, expressing at least one phenotype associated with atherosclerosis may have been the result of the crossing of for example a pig transgenic for at least one ApoE mutation and a pig transgenic for at least one LDL mutation, and/or a pig comprising a human PCSK9 gene.

Type of Genetic Modification

The donor cells may be genetically modified by any of standard method known in the art. The genetic modification may be a modification of the genomic DNA by deletion, insertion, duplication and/or other forms of mutation, including point mutation. The modification may be made in coding sequences and/or non-coding sequences. DNA constructs for insertion may harbour a gene of interest and/or regulatory sequences such as promoters, insulators, enhancers, repressors or ribosomal entry sites. In some embodiments, only one genetic modification is introduced in the genome. In other embodiments, however, the genome may be modified at more than one site. Suitable techniques for genetic modification of mammalian cells, such as fibroblasts, include techniques such as gene addition by nonhomologous recombination, gene replacement by homologous recombination, and gene editing. This may include the use of retroviral insertion, transposon transfer and/or artificial chromosome techniques. Non-homologous DNA recombination may e.g. be carried out as described in Kragh et al. (2004) Reprod. Fert. Dev. 16:290 or Kragh et al. (2004) Reprod. Fert. Dev. 16:315, Transposon-based gene transfer may be carried out as described in Izsvak et al. (1997) Cell 91:501. Gene replacement by homologous recombination may e.g. involve the techniques described by Urnow et al. (2005) Nature 435:646. Techniques for gene editing have been described in Andersen et al. (2002) J. Mol. Med. 80:770, Liu et al (2002) Gene Ther. 9:118 and Sørensen et al. (2005) J. Mol. Med. 83:39.

In a preferred embodiment the donor cell is genetically modified by random integration, homologous recombination of the genes disclosed herein into the genome of the donor cell, or the transcriptional product or part of the human PCSK9 gene is modified by RNA interference.

In a preferred embodiment of the present invention the donor cell is genetically modified (as described in a copending application). The donor cell or nucleus carries a SB tagged genome containing a Flp recombination target site for site specific gene insertion or integration. The SB tagged genome result from the integration of a recombinant target vector comprising a DNA transposon construct and a bicistronic gene cassette comprising (i) a FRT recombination site and (ii) an IRES-driven selection gene. The DNA transposon construct may be any construct in which any DNA transposon is present. In the present invention the DNA transposon construct is the Sleeping Beauty (SB) DNA transposon vector. The FRT recombination site may be embedded in the coding sequence of a selection gene which allows for detecting whether a transposition has occurred. The selection gene of the present invention is not limited to any particular selection gene. In preferred embodiments the selection gene are genes conferring resistance to antibiotics or drugs, such as puromycin, tetracycline, streptomycin or hygromycin resistance genes, or the enhanced green fluorescent protein (eGFP) gene, red fluorescent protein genes or the like. The FRT recombination site may thus be embedded in a SV40 promoter driven fusion variant of the selection gene. However, any promoter suitable for conferring expression of a selection gene may be used according to the present invention. Non-limiting examples of such promoters are CMV (cytomegalovirus) or PGK promoter.

The IRES-driven selection gene is similarly not limited to any particular selection gene. In preferred embodiments the selection gene are genes conferring resistance to antibiotics or drugs, such as puromycin, tetracycline, streptomycin or hygromycin resistance genes, or the enhanced green fluorescent protein (eGFP) gene, red fluorescent protein genes or the like.

The recombinant vector construct may also comprise at least one site for Cre recombinase. The at least one site for Cre recombinase may be located as disclosed in the examples herein.

The donor cell or nucleus may also originate from a genetically modified pig comprising at least one site for integration of at least one transgene. A preferred embodiment is a donor cell or nucleus in the form of a fibroblast, such as a primary fibroblast.

The present invention also relates to a method for producing a porcine cell comprising a SB tagged genome containing a Flp recombination target site for site-specific gene insertion. The method comprises the steps of
a) providing a mammalian cell, b) transfecting the cell of a) with a plasmid expressing a transposase and a recombinant target vector comprising a DNA transposon construct and a bicistronic gene cassette comprising (i) a FRT recombination site and ii) an IRES-driven selection gene, c) selecting SB tagged cells.

As described elsewhere herein the mammalian cell may be any cell. In one embodiment in which the porcine cell is subsequently to be used for producing a genetically modified pig by nuclear transfer according to the hand-made protocol as described herein, the porcine cell is in a preferred embodiment a fibroblast and most preferred a porcine primary fibroblast.

It is appreciated that a desired transgene may be integrated directly into the at least one site for integration present in the genome of the cell. However, the cell in which the genome carries the at least one site for integration is in another embodiment used as a donor cell for the production of a genetically modified pig by for example microinjection of the donor cell or nucleus thereof into a oocyte or by for example somatic nuclear transfer. In a preferred embodiment the donor cell or the nucleus thereof is used for the production of a genetically modified pig by somatic nuclear transfer using the procedure as described elsewhere herein.

The transgene or gene of interest to be integrated in the targeted cells of the present invention is not limited to any particular gene. In one embodiment the gene to be integrated is a disease-causing gene which results in the formation of a genetically modified pig displaying a phenotype of interest. According to the present invention the gene of interest to be integrated into the porcine cell is Apolipoptrotein-E (ApoE) and/or LDL receptor.

The integration of the transgene into the at least one site for integration present in the genome of the cell is employed by transfection into the cell of plasmid DNA containing the gene of interest and also FRT sites, and a plasmid expressing the Flp-recombinase used to support integration at the FRT sites.

Enucleation

The method of enucleation of an oocyte may be selected from the group of methods consisting of aspiration, physical removal, use of DNA-specific fluorochromes, exposure to ultraviolet light and/or chemically assisted enucleation. In one embodiment the present invention relates to the use of DNA-specific fluorochromes. Enucleation may, however, be performed by exposure with ultraviolet light. In a particular embodiment enucleation is chemically assisted prior to physical removal of the nucleus. Chemically assisted enucleation using for example antineoplastic agents, such as demecolcine (N-deacetyl-N-methyl 1 colchicine), and/or for example etoposide or related agents may be performed prior to enzymatic modification of zona pellucida.

Chemically assisted enucleation comprises culturing matured COCs in maturation medium as described elsewhere herein supplemented with demecolcine for a particular period of time. In the range of 0.1 µg/ml to 10 µg/ml demecolcine, such as 0.2 µg/ml to 10 µg/ml, for example 0.3 µg/ml to 10 µg/ml, such as 0.25 µg/ml to 5 µg/ml, for example 0.3 µg/ml to 1 µg/ml, such as 0.25 µg/ml to 0.5 µg/ml, for example 0.4 µg/ml demecolcin may be supplemented to the maturation medium. Similarly, maturation medium may be supplemented with etoposide for example in the range of 0.1 µg/ml to 10 µg/ml etoposide, such as 0.2 µg/ml to 10 µg/ml, for example 0.3 µg/ml to 10 µg/ml, such as 0.25 µg/ml to 5 µg/ml, for example 0.3 µg/ml to 1 µg/ml, such as 0.25 µg/ml to 0.5 µg/ml, for example 0.4 µg/ml etoposide may be supplemented to the maturation medium. The time for culturing the COCs in the presence of antineoplastic agents ranges from 10 min to 5 hrs, such as 30 minutes to 5 hrs, for example 10 minutes to 2 hrs, such as 30 min to 2 hrs, for example 10 min to 1.5 hrs, such as 20 min to 3 hrs, for example 10 min to 3 hrs, such as 30 min to 1.5 hrs, for example 45 min.

In a particular embodiment chemically assisted enucleation is performed using 0.45 µg/ml demecolcine and/or etoposide added to the maturation medium for 45 min.

In a particular embodiment it is preferred that the enucleation is by physical removal of the nucleus. The physical removal may be by separation for example by bisection of the oocyte into two halves (two parts), one which contains the nucleus and the enucleated oocyte half, known as the cytoplast, removing the nucleated half of the oocyte and selecting the resulting cytoplast for further procedures of the invention. Alternatively the separation is by trisection, resulting in three parts of which two parts are cytoplasts. In another embodiment the oocyte may be separated into four parts, resulting in the production of three cytoplasts. The oocyte may even be separated into five parts by physical removal, resulting in four cytoplasts. Similarly, the oocyte may be separated into six parts, for example seven parts, such as eight parts, for example nine parts, such as ten or more parts.

The physical separation of the oocyte and subsequent removal of the nucleus-bearing part of the oocyte may be achieved by the use of a microsurgical blade. The oocytes may be screened to identify which oocytes have been successfully enucleated. Oocyte parts that harbour nuclear DNA may be identified by staining with Hoechst fluorochrome, the staining procedure of which is known to a person skilled in the art. Oocyte parts harbouring nuclear DNA are discarded and the enucleated oocytes (cytoplasts) are selected for further procedures.

Zona Pellucida

Zona pellucida is a thick, transparent, noncellular layer or envelope of uniform thickness surrounding an oocyte Generally, an intact zona pellucida is considered to be important in cell nuclear transfer due to a number of parameters. One parameter is to keep the polar body close to the metaphase plate of the oocyte in order to indicate the appropriate site for enucleation. Another parameter relates to the keeping of the donor cell close to the oocyte cytoplast before and during fusion. The zona is also believed to confer protection for the donor cell and cytoplast during fusion. Finally, embryo development after reconstitution and activation is believed to be supported by the zona pellucida.

Modification of at least a part of the zona pellucida can be performed by a number of methods. For example physical manipulation can be used to modify the zona. But also chemical treatment with agents such as acidic solutions (acidic Tyrode) can be employed. One example of chemical agents that can be employed in the present invention is acidic solutions, for example Tyrode. In a particular embodiment of the invention the zona pellucida is modified by enzymatic digestion. Such enzymatic digestion may be performed by enzymes comprising for example trypsin. Alternatively a specific protease may be used, such as pronase.

In a preferred embodiment the enzymatic digestion results in at least a partial digestion of a part of zona pellucida which in a preferred embodiment of the present invention means that at least a part of the zona pellucida is being removed, or that the zona pellucida is partly removed. In the present context the zona pellucida is not completely removed.

According to an especially preferred embodiment of the present invention the partially digested part of zona pellucida is characterized by the zona pellucida still being visible and by the fact that the oocyte has not become misshaped.

The partial digestion may be achieved by exposure to a protease. In another embodiment of the present invention the partial digestion may be accomplished by the use of a pronase. In yet another embodiment the partial digestion may be achieved by a combination of a protease and pronase.

In a preferred embodiment the concentration of pronase is in the range of 0.1 mg/ml to 10 mg/ml, such as 0.5 mg/ml to 10 mg/ml, for example 1 mg/ml to 10 mg/ml, such as 1.5 mg/ml to 10 mg/ml, for example 2 mg/ml to 10 mg/ml, such as 2.5 mg/ml to 10 mg/ml, for example 2.75 mg/ml to 10 mg/ml, such as 3 mg/ml to 10 mg/ml, for example 3.25 mg/ml to 10 mg/ml, such as 3.3 mg/ml to 10 mg/ml, for example 3.5 mg/ml to 10 mg/ml.

A preferred embodiment is a pronase concentration in the range of 2 mg/ml to 5 mg/ml, such as 2.25 mg/ml to 5 mg/ml, for example 2.5 mg/ml to 5 mg/ml, such as 2.75 mg/ml to 5 mg/ml, for example 2.8 mg/ml to 5 mg/ml, such as 2.9 mg/ml to 5 mg/ml, for example 3 mg/ml to 5 mg/ml, such as 3.1 mg/ml to 5 mg/ml, for example 3.2 mg/ml to 5 mg/ml, such as 3.3 mg/ml to 5 mg/ml.

A particular embodiment of the present invention is a pronase concentration in the range of 1 mg/ml to 4 mg/ml, for example 1 mg/ml to 3.9 mg/ml, such as 1 mg/ml to 3.8 mg/ml, for example 1 mg/ml to 3.7 mg/ml, such as 1 mg/ml to 3.6 mg/ml, for example 1 mg/ml to 3.5 mg/ml such as 1 mg/ml to 3.4 mg/ml, for example 1 mg/ml to 3.3 mg/ml.

In a preferred embodiment the pronase concentration is in the range of 2.5 mg/ml to 3.5 mg/ml, such as 2.75 mg/ml to 3.5 mg/ml, for example 3 mg/ml to 3.5 mg/ml. In a special embodiment the pronase concentration is 3.3 mg/ml.

It is clear to the skilled person that the pronase should be dissolved in an appropriate medium, one preferred medium according to the present invention is T33 (Hepes buffered TCM 199 medium containing 33% cattle serum (as described earlier—*Vajta*, et al., 2003).

The time of incubation of the oocyte in the pronase solution is in the range of 1 second to 30 seconds, such as 2 seconds to 30 seconds, for example 3 seconds to 30 seconds, such as 4 seconds to 30 seconds, such as 5 seconds to 30 seconds.

In another embodiment of the present invention the incubation time is in the range of 2 seconds to 15 seconds, such as 2 seconds to 14 seconds, for example 2 seconds to 13 seconds, such as 2 seconds to 12 seconds, for example 2 seconds to 11 seconds, such as 2 seconds to 10 seconds, for example 2 seconds to 9 seconds, such as 2 seconds to 8 seconds, for example 2 seconds to 7 seconds, such as 2 seconds to 6 seconds, for example 2 seconds to 5 seconds.

In a particular embodiment of the present invention the incubation time is in the range of 3 seconds to 10 seconds, such as 3 seconds to 9 seconds, for example 4 seconds to 10 seconds, such as 3 seconds to 8 seconds, for example 4 seconds to 9 seconds, such as 3 seconds to 7 seconds, for example 4 seconds to 8 seconds, such as 3 seconds to 6 seconds, for example 4 seconds to 7 seconds, such as 3 seconds to 5 seconds, for example 4 seconds to 6 seconds, such as 4 seconds to 5 seconds. An especially preferred incubation time is 5 seconds.

In a preferred embodiment of the present invention the oocyte is treated for 5 seconds in a 3.3 mg/ml pronase solution at 39° C.

Reconstructed Embryo

By the term 'reconstructed embryo' is meant the cell which is formed by insertion of the donor cell or nucleus of the donor cell into the enucleated oocyte which corresponds to a zygote (during normal fertilisation). However, the term 'reconstructed embryo' is also referred to as the 'reconstituted cell'. In the present invention the donor cell is a somatic cell. However, the donor cell may also be derived from a germ line cell.

Fusion

The transfer of a donor cell or a membrane surrounded nucleus from a donor cell to at least cytoplast is according to the present invention performed by fusion. In the scenarios described below the term 'donor cell' also refers to a membrane surrounded nucleus from a donor cell. Fusion may be achieved by a number of methods.

Fusion may be between a donor cell and at least one cytoplast, such as between a donor cell and at least two cytoplasts, for example between a donor cell and at least two cytoplasts, such as between a donor cell and at least three cytoplasts, such as between a donor cell and at least four cytoplasts, for example between a donor cell and at least five cytoplasts, such as between a donor cell and at least six cytoplasts, for example between a donor cell and at least seven cytoplasts, such as between a donor cell and at least eight cytoplasts.

Fusion may be performed according to the listed combinations above simultaneously or sequentially. In one embodiment of the present invention the fusion is performed simultaneously. In another embodiment fusion of the at least one cytoplast and a donor cell is performed sequentially.

For example fusion may be achieved by chemical fusion, wherein a donor cell and the at least one cytoplast are exposed to fusion promoting agents such as for example proteins, glycoproteins, or carbohydrates, or a combination thereof. A variety of fusion-promoting agents are known for example, polyethylene glycol (PEG), trypsin, dimethylsulfoxide (DMSO), lectins, agglutinin, viruses, and Sendai virus. Preferably phytohemaglutinin (PHA) is used. However mannitol and, or polyvinylalcohol may be used.

Alternatively, fusion may be accomplished by induction with a direct current (DC) across the fusion plane. Often an alternating current (AC) is employed to align the donor and recipient cell. Electrofusion produces a sufficiently high pulse of electricity which is transiently able to break down the membranes of the cytoplast and the donor cell and to reform the membranes subsequently. As a result small channels will open between the donor cell and the recipient cell. In cases where the membranes of the donor cell and the recipient cell connect the small channels will gradually increase and eventually the two cells will fuse to one cell.

Alignment of the at least one cytoplast and the donor cell may be performed using alternating current in the range of 0.06 to 0.5 KV/cm, such as 0.1 to 0.4 KV/cm, for example 0.15 to 0.3 KV/cm. In a preferred embodiment alignment of the at least one cytoplast and the donor cell may be performed using alternating current at 0.2 KV/cm.

Fusion may be induced by the application of direct current across the fusion plane of the at least one cytoplast and the donor cell. Direct current in the range of 0.5 to 5 KV/cm, such as 0.75 to 5 KV/cm, for example 1 to 5 KV/cm, such as 1.5 to 5 KV/cm, for example 2 to 5 KV/cm. Another preferred embodiment of the present invention is the application of direct current in the range of 0.5 to 2 KV/cm. In a further preferred embodiment the direct current may be 2 KV/cm.

The direct current may preferably be applied for in the range of 1-15 micro seconds, such as 5 to 15 micro seconds, for example 5 to 10 micro seconds. A particular embodiment may be 9 micro seconds.

In an especially preferred embodiment fusion with direct current may be using a direct current of 2 KV/cm for 9 micro seconds.

Electrofusion and chemical fusion may however be also be combined.

Typically electrofusion is performed in fusion chambers as known to the skilled person.

Fusion may be performed in at least one step, such as in two steps, for example three steps, such as in four steps, for example in five steps, such as six steps, for example seven steps, such as in eight steps.

Fusion may be performed in for example a first step wherein the at least one cytoplast is fused to the donor cell. A second step of fusion may comprise fusion of the fused pair (cytoplast-donor cell, reconstructed embryo) with at least one cytoplast, such as at least two cytoplasts, for example three cytoplasts, such as four cytoplasts, for example five cytoplasts, such as six cytoplasts, for example seven cytoplasts, such as eight cytoplasts. The second step of fusion with fusion of at least one cytoplast and the fused pair may be performed sequentially or simultaneously. In one embodiment the at least two cytoplasts are fused to the fused pair simultaneously. In another embodiment the at least two cytoplasts are fused to the fused pair sequentially.

In one embodiment of the invention the second step of fusion may also be an activation step wherein the reconstructed embryo is activated to enter mitosis. As described elsewhere herein.

Activation

In a preferred embodiment the reconstructed embryo may be allowed to rest prior to activation for a period of time in order to allow for the nucleus of the donor cell to reset its genome and gain toti potency in the novel surroundings of the enucleated cytoplast. The reconstructed embryo may for example rest for one hour prior to activation.

Preferably, the reconstructed embryo may be activated in order to induce mitosis. Methods for activation may preferably be selected from the group of consisting of electric pulse, chemically induced shock, increasing intracellular levels of divalent cations or reducing phosphorylation. A combination of methods may be preferred for activation.

In one particular embodiment of the invention the activation and the second step of fusion may be performed simultaneously. However, the activation of the reconstituted embryo and the at least one additional step of fusion between the reconstructed embryo and the at least one cytoplast may be performed sequentially.

Reducing the phosphorylation of cellular proteins in the reconstructed embryo by known methods such as for example by the addition of kinase inhibitors may activate the reconstituted embryo. A preferred embodiment may involve the use of agents that inhibit protein synthesis, for example cycloheximide. A further preferred embodiment may be using agents that inhibit spindle body formation, for example cytochalasin B.

In one embodiment of the invention the intracellular levels of divalent cations may be increased. Divalent cations such as for example calcium may be in comprised in the activation medium. Preferably, the cations may enter the reconstructed embryo, particularly upon subjecting the reconstructed embryo to an electric pulse. In a preferred embodiment the electric pulse may cause entering of calcium into the reconstructed embryo.

The application of an electrical pulse using direct current may be an activation step. However, in a preferred embodiment the electrical pulse applied for activation may also serve as an additional fusion step.

Prior to applying an electrical pulse using direct current the at least one cytoplast and the at least one reconstructed embryo may be aligned by the application of alternating current. The alternating current may be in the range of the range of 0.06 to 0.5 KV/cm, such as 0.1 to 0.4 KV/cm, for example 0.15 to 0.3 KV/cm. In a preferred embodiment alignment of the at least one cytoplast and the donor cell may be performed using alternating current at 0.2 KV/cm.

Activation may be induced by the application of direct current across the fusion plane of the at least one cytoplast and the donor cell. Direct current in the range of 0.2 to 5 KV/cm, such as 0.4 to 5 KV/cm, for example 0.5 to 5 KV/cm. Another preferred embodiment of the present invention is the application of direct current in the range of 0.5 to 2 KV/cm. In a further preferred embodiment the direct current may be 0.7 KV/cm.

The direct current may preferably be applied for in the range of 10 to 200 micro seconds, such as 25 to 150 micro seconds, for example 50 to 100 micro seconds. A particular embodiment may be 80 micro seconds.

In an especially preferred embodiment fusion with direct current may be using a direct current of 0.7 KV/cm for 80 micro seconds.

An especially preferred embodiment of activation according to the present invention may be use of an electrical pulse in combination with subjecting the reconstructed embryo to agents that inhibit protein synthesis, spindle body formation, and divalent cations.

Activation may be performed by any combination of the methods described above.

In Vitro Culture of Embryos

One aspect of the invention relates to a method of in vitro culturing embryos, whereby the blastocyst rate increased to 25.3%. Thus, a method of culturing a reconstructed embryo is within the scope of the present invention, comprising the steps of a) establishing at least one oocyte having at least a part of zona pellucida, b) separating the oocyte into at least two parts obtaining an oocyte having a nucleus and at least one cytoplast, c) establishing a donor cell or cell nucleus having desired genetic properties, d) fusing at least one cytoplast with the donor cell or membrane surrounded cell nucleus, e) obtaining the reconstructed embryo, f) activating the reconstructed embryo to form an embryo, and e) culturing said embryo.

Another aspect of the invention relates to a method of cell nuclear transfer in which a step of culturing the embryo is included.

In a preferred embodiment in relation to the methods described herein embryos are cultured in a sequential set of media. Preferably the blastocysts are grown in traditional medium such as for example NCSU37 or equivalent medium as known to a person skilled in the art, wherein glucose is removed and substituted by other agents. One agent may be pyruvate. Another agent may be lactate. The agents may also be combined and replace glucose in the traditional medium.

The embryos may be cultured in the substituted media as described above from Day 0 to Day 3, such as from Day 0 to Day 2.

The pyruvate concentration may range from 0.05 to 1 mM, such as 0.1 to 1 mM, for example 0.125 to 1 mM, such as 0.15 to 1 mM. However the concentration of sodium pyruvate may also range from 0.05 mM to 0.9 mM, such as 0.05 to 0.8 mM, for example 0.05 to 0.7 mM, such as 0.05 to 0.6 mM, for example 0.05 to 0.5 mM, such as 0.05 to 0.4 mM, for example 0.05 to 0.3 mM, such as 0.05 to 0.2 mM. Preferably the concentration ranges between 0.05 to 0.17 mM. A preferred concentration of sodium pyruvate is 0.17 mM.

The lactate concentration may range from 0.5 to 10 mM, such as 0.75 to 10 mM, for example 1 to 10 mM, such as 1.5 to 10 mM, such as 1.75 to 10 mM, for example 2 to 10 mM, such as 2.5 to 10 mM. However the concentration of sodium lactate may also range from 0.5 mM to 9 mM, such as 0.5 to 8 mM, for example 0.5 to 7 mM, such as 0.5 to 6 mM, for example 0.5 to 5 mM, such as 0.5 to 4 mM, for example 0.5 to 03 mM. Preferably the concentration ranges between 1 to 5 mM, such as 2 to 4 mM, for example 2 to 3 mM. A preferred concentration of sodium lactate is 2.73 mM.

After the initial glucose-free incubation medium glucose is again replacing the pyruvate and lactate. The embryos may be cultured in the glucose containing medium from Day 4 to Day 3, preferably from Day 3 to Day 7. The glucose concentration may range from 1 to 10 mM, such as 2 to 10 mM, for example 3 to 10 mM, such as 4 to 10 mM, for example 5 to 10 mM. However, the glucose concentration may also range from 1 to 9 mM, such as 2 to 8 mM, for example 3 to 7 mM, such as 4-6 mM. A preferred concentration of glucose according to the present invention is 5.5 mM of glucose.

Organ or Tissue Donation

In one embodiment, the animals of the invention may be used as a source for organ or tissue donation for humans or other animals, either animals of the same species or animal of other species. Transfer between species is usually termed xenotransplantation. Entire organs that may be transplanted include the heart, kidney, liver, pancreas or lung. Alternatively, parts of organs, such as specific organ tissues may be transplanted or transferred to humans or other animals. In a yet further embodiment, an individual cell or a population of individual cells from an animal of the invention may be transferred to a human being or another animal for therapeutic purposes.

Cryopreservation

The term 'cryopreserving' as used herein can refer to vitrification of an oocyte, cytoplast, a cell, embryo, or pig of the invention. The temperatures employed for cryopreservation is preferably lower than −80 degree C., and more preferably at temperatures lower than −196 degree C. Oocytes, cells and embryos of the invention can be cryopreserved for an indefinite amount of time. It is known that biological materials can be cryopreserved for more than fifty years.

It is within the scope of the present invention that embryos may be cryopreserved prior to transfer to a host pig when employing methods for producing a genetically engineered or transgenic non-human mammal. Such cryopreservation prior to transfer may be at the blastocyst stage the of embryo development. Vitrification is a form of cryopreservation where living cells are rapidly cooled so that the fluid of the cell does not form into ice. Thus, vitrification relates to the process of cooling where cells or whole tissues are preserved by cooling to low sub-zero temperatures, such as (typically) −80 C. or −196 C.

In particular the invention relates to the vitrification of an oocyte, however, the invention also relates to the vitrification of embryos, preferably embryos at the blastocyst stage. In one embodiment, the embryo is cultured to blastocyst stage prior to vitrification. Especially pig embryos are covered by the present invention. Also vitrified cytoplasts are covered by the present invention, as are cells.

Yet another aspect of the invention relates to the cryopreservation of a pig embryo derived by a method for cell nuclear transfer as described herein comprising a step of vitrifying a pig embryo. A further aspect of the invention relates to pig embryos obtained, or obtainable by the methods provided herein.

Mitochondria

Cells of the tissue of the genetically modified non-human mammals and/or non-human embryos obtainable by the present invention may harbour mitochondria of different maternal sources. In a preferred embodiment the non-human mammals and/or non-human embryos may harbour mitochondria from only one maternal source, However, in another preferred embodiment the non-human mammals and/or non-human embryos may harbour mitochondria from at least two maternal sources, such as three maternal sources, for example four maternal sources, such as five maternal sources, for example six maternal sources, such as seven maternal sources, for example eight maternal sources, such as nine maternal sources, for example ten maternal sources. The probability of having a specific number of maternal sources can be calculated based on the observed types of mitochondria.

Evaluation of Treatment and Methods for Diagnosis

The present invention offers a method for screening the efficacy of a pharmaceutical composition, wherein the method comprises the steps of i) providing the pig model of the present invention, ii) expressing in said pig model the genetic determinant and exerting said phenotype for said disease, iii) administering to the pig model a pharmaceutical composition the efficacy of which is to be evaluated, and iv) evaluating the effect, if any, of the pharmaceutical composition on the phenotype exerted by the genetic determinant when expressed in the pig model. In one preferred embodiment the preclinical testing of drugs targeting plaque stability and superimposed thrombosis is within the scope of the present invention.

Furthermore, within the scope of the present invention is a method for evaluating the response of a therapeutical treatment of atherosclerosis, wherein the method comprises the steps of i) providing the pig model of the present invention, ii) treating said pig model with a pharmaceutical composition exerting an effect on said phenotype, and iii) evaluating the effect observed. Based on the evaluation one could further advise on the treatment based on the observed effects.

In addition, the present invention relates to a method for treatment of a human being suffering from atherosclerosis, wherein the method comprises the initial steps of i) providing the pig model of the present invention, ii) expressing in said pig model said genetic determinant and exerting said phenotype for said disease, iii) administering to said pig model a pharmaceutical composition the efficacy of which is to be evaluated, and v) evaluating the effect observed, and v) treating said human being suffering from atherosclerosis based on the effects observed in the pig model. In a preferred embodiment the treatment comprises treating a human being suffering from familial hypercholesterolemia.

It is therefore appreciated that the pig model according to the present invention may also receive medicaments for diseases other than atherosclerosis in order to test the combined effect of a drug for atherosclerosis and other drugs administered to the pig.

Furthermore, the pig model of the present invention also allows for the development of bioimaging technology for diagnosis of atherosclerosis. Thus, the present invention offers a method for evaluating a bioimaging technology for the diagnosis of atheroclerosis, wherein the method comprises the steps of i) providing the pig model of the present invention, ii) expressing in said pig model the genetic determinant and exerting said phenotype for said disease, iii) bioimaging the pig model and iv) evaluating the result, if any, of the bioimaging technology of the phenotype exerted by the genetic determinant when expressed in the pig model.

The genetically modified pig of the present invention may also be used in order to improve catheter-based therapies.

EXAMPLES

Lipoprotein Metabolism in Pigs

Lipoprotein metabolism in pigs is reasonably well described. The distribution and composition of plasma lipoproteins in swine are similar to those in humans, and LDL is the major cholesterol transporting lipoprotein in both species.[12] Like humans, all VLDL particles secreted by the liver contain the long non-edited form of apoB100 rather than the truncated apoB48 form, which is dominant in mice[13].

Apolipoprotein B-containing lipoproteins are cleared by hepatic uptake via 1) the LDL receptor that binds to apolipoprotein E in IDL particles and to apolipoprotein B100 in LDL particles[14], and 2) the LDL receptor-related protein (LRP) that binds to apolipoprotein E in apoB48-containing chylomicron remnants[15]. The relative importance of these pathways varies between species. In mice deficiency of apolipoprotein E has a more severe atherosclerotic phenotype than LDL receptor deficiency, whereas the opposite is true in humans. The impact of apoE and LDL receptor deficiency on lipid metabolism in pigs is not known.

Example 1

Production of ApoE Knockout Pigs

ApoE Knockout Pig by Homologous Recombination

The pig apolipoprotein E gene (GenBank accession no. U70240) has been sequenced.[11,16] A targeting vector construct containing the gene and downstream non-coding sequence is created with a promoter-less neomycin resistance gene cassette inserted into one of the exons to disrupt gene function. The targeting vector is linearized and transfected into Yucatan fetal fibroblasts, isolated from new born Yucatan ear biopsies. Plasmids encoding zinc finger nucleases constructed to recognize and cleave a site in the targeted genomic sequence may be used to increase efficiency of homologous recombination. Fibroblasts are cultured in the presence of G418. Resistant clones are screened for homologous recombination by PCR. Yucatan minipigs with knockout of one or both apoE alleles are created from recombinant cells by "hand-made" cloning.

1. Cloning of Targeting Constructs

A 1.6 kb fragment containing the 5"-end of the ApoE gene, a 3.2 kb fragment containing the entire ApoE gene, and a 6.1 kb fragment containing the 3"-end of the ApoE gene were all amplified by PCR using genomic DNA extracted from fibroblasts isolated from newborn Yucatan minipigs as template (see below). Upon subcloning and sequencing, parts of the resulting PCR products were used for further cloning into the targeting vector pKO Scrambler NTKV-1903 (Stratagene) comprising a neomycin resistance gene.

SEQ ID NO: 15: 1.6 kb ApoE fragment (5'-end of ApoE)—primers used for amplification are underlined:

```
5'-
gcctgggaatgagtgccagctcctccagttccacgtggcctcaccacacacctcaactctgagtctgggagtcgtgtaac agggctgctgggggatggggggtgcagtcagcgctcaccaatctgtcacagaagttaactggaactgttctttgttctatc cccggatgatggggttaaatgcaaccattttccccgtcttagtggaccgagaaacaatgttcagagaggctaggtcatttg ctcaaggtcacacagctgacaacccgcagagcctggattcaggcctggaggctttggttccagagttcacagtccgaac caggcgacgggacaggaacactcccaggcctgtggaaggcgcggtatgcaggccgcgagctcctggaatgcgcaa ggcttatgtgggggcagagagctgcatcctcattgcacaaatcaggaaagcggctcagagaagcactcagatgtgccc aaggtcacggcctcgagagggagtgagggttaaaactctgtggtgcaacggaaacgaatccaactgggaaccatga ggctgtgggttggatccccggcctcgctcaatgggttaaggatccagcacggcgctgccgtgagctgtggtgtaggtcgc agacgaggcttggatcccacttggctgtggctgtggctgtggctgtggtgtaggcccgcagctgtaactgtaattcgacccc tagcctgggaacctccacaagccacgggtgtggccctaaaaagcaaaaaaacgaaagcaaaaagaacactctcaa agcctaaactttcagcaaaaagaacactctcaaagcctaaactttgagcagatgccttacaccgccccacgcctctcat ccccttttctgtctgggcctccagctcccttccccttaacccagaaatcccagacctcagacccaggatttcgagtccccag ccttgcccaattctattcatccaagcacaggacaagagagaggcagggccgggccttctggtcctgctccttctccctgc ccagcccacccccaccagtggcatggagaaaggctcgggagttactgggtgagagacacctctttccatggggctgg gagtaaggggggggtgataggctgccaagcccacccctccctccctccctccccctccctgctgtgtgaaaggg gaggccagcccacctcgtgacccgacgggggctggcccagctggcccagttctggaggagtgggcggggcgggg
```

-continued ggagccctataattggccgaatctgggctccctgaatcctactcagccccggaggaggaaggaggaaggaggagga ggaagcaaccggtgaggagcagacctgggggcacagagatgggctcggggcttcggtgtggagggtgggctgtag ggggaggaggaaatgacctggccccccggggccaccaccgaggcaggagttggggatgaggctagagcccaggg actggacctagaaggagggtgggcagcaggaggaggttatccgccttggctggaaggggaggtcagggaagcagc gggacctgtaggaagaac<u>cagacgagccagagccgacgaattgtactggc</u>-3'

SEQ ID NO: 16: 3.2 kb ApoE fragment (entire ApoE gene)—[10]
primers used for amplification are underlined:

5'-
<u>gcccagctggccccagttctggaggag</u>tgggcggggcgggggagccctataattggccgaatctgggctccctgaat cctactcagccccggaggaggaaggaggaaggaggaggaagcaaccggtgaggagcagacctgggggcac agagatgggctcggggcttcggtgtgggggggtgggctgtaggggaggaggaaatgacctggccccccggggcca ccaccgaggcaggagttggggatgaggctagagcccaggactggacctagaaggagggtgggcagcaggagga ggttatccgccttggctggaaggggaggtcagggaagcagcgggacctgtaggaagaaccagacgagccagagcc gacgaattgtactggcaggtatggcgcatctactcaagttttgagcacactaagagctccatcgaggagacccagggt ggcggcgaccagggtgacctcgaccgggctggcggcagggtagctagagcgttggtggaaggacatgtaaatgag gattaaattagggaatgagtggaaaacagggtttagatgtgaagttggagcttggaatgtgaaggtaccaggaagaacg tgagcttggagcccagaaagcaaggctggggctcacatgggactccaggtggaggggtgggggcgacgtgggt ggaatttgaaccctgggagagagggaaggcttttggccgcagccgacctggggatggggagataggagaagacaat gagggaattacacggacaatggaaaggatctgctcgggaaatatctgcttggattaggctgatgcagataaggggggtgc aaggcttggaaggctgtgactggacagggctgggctctgggtggggaggagcgagccccgccgctgttgagtgacaattt ctccctcctgcaggttggccaatcgcaagccagaagatgagggttctgtgggttgctttggtggtaaccctcctcgcaggta tgggggtggggcttgctcaggttccctgcccctcccccatccccggctgtacccggtgcccctccttcatccctgggtctcttc tgctggtctctcttccccttgaggagaggcctagatgtgaggcctctctggcactccttgcttctgaacagctcgtttttactctct gagcctcagtttccccatctttaaaatgggagttatgttgagagattccagctgtggctcagcaggttaagaacccgactag tatccatgaggaagagggttcaatccctggcttcgctcagcgggttaaggatccggcgttgccatgagctgcggcataag tcgcagatgcagctcgaatcgggtgttgctgtggctgtggtgcaggctggcagctatcgcttccatcggacccctcgcctg ggaacttccacgtatgccactggtgcagcccctaaaagacaaacaaacaaaaacgaaagaaagagaaaagaaagg aaaggggcttctgtttctaatgcgttgttgcctggcagggcgtgagcattagatacgtgtcagctgtgactagcgtgcacg gagcacacaatccatgcttgtccagtaattagacaggctgggtgtccttccaccccctcctgcccaccagtgctctagag aagcccaccccaccagggctgggggagccacctgctctgtaccaggtaccgtgtgctgggagggggcagaggacctgat ggctgtgaactggctcggtgcaggatgccggacagaggacgagccggggccgccgccggaggtgcacgtgtggtgg gaggagcccaagtggcagggcagccagccctgggagcaggccctgggccgcttctgggattacctgcgctgggtgca gtccctgtctgaccaagtgcaggaggagctgctcagcaccaaggtcacccaggaactgacgtaagtgcccacccgact cccgccgcgcgcgcgcgcgcgcgcgcgcctgaccctcctggcggaccgtgtgttctggaccctcaggctccaccg tccgggtttccttctgtccttgtcgccaactcttgggggtctgggtctctgtttcttttttttccttcttccttttttggggggagtttacttttt tctttttttctttcatttgacttcatgtcttgctttcttccatcttgagctcctgccttcgcctgtctctgggtcagtcttgccgtccttgctg tctctgaatctctggcacgtcctggccatcgccagctcaggagccctccttctccccccccgccccgccctctctgcgc ccagggagctgatagaggagagcatgaaggaggtgaaggcctaccgcgaggagctggaggcgcagctgggcccc gtgacccaggagacgcaggcgcgcctgtccaaggagctgcaggcggcgcaggcccgcgtgggcgccgacatgga ggacgtgcgcaaccgcttggtgctctaccgcagcgaggtgcacaacatgttgggccagaccaccgaggagctgcgga -continued

```
gccgcctggcttcccacctgcgcaagctgcgcaagcggctgctccgcgacaccgaggacctgcagaagcgcctggcc gtgtaccaggcggggctgcgcgagggcgccgagcgcagcgtgagcgccctccgcgagcgcctcgggcccctggtgg agcagggccgattgcgcgccgccaccctgagtaccagggccggccagccgctgcgcgagcgcgccgaagcctggg gccagaagctgcgcggacggctggaggagatgggcagccggacccgcgaccgcctggatgagatgcgtgagcagc tggaggaggtgcgcaccaaagtggaggagcagggcagccagttgcgcctgcaggccgaggccttccaggcccgcct caaaggctggttcgagcctctggtggaagacatgcggcgccagtgggccgggctggtggagaggatgcagtcggccg tgagcatcagctcctccacctctgcgcccagtgataatcagtgagtgccctctcatccgggcaccccttcggggccccgt tcctgcccaactcccccgcctcccccagccttagctgccctcttggtgggccctgcttaataaagattcatcaaagcttcaca gcagcttctgggtgtc-3'
```

SEQ ID NO: 17: 6.1 kb ApoE fragment (3'-end of ApoE)—
primers used for amplification are underlined:

```
5'-
attcatcaagcttcacagcagcttctgggtgtccccgtgtgatttctcagctccagcctcagtttccctttccttccctgcactga ccacccagttctctgtcctgccctctgcctgtgtgtgtctatttgtctcttctccccttttcttttttttggccgagcccatggcatgc ggaagttccccggccagggattgaacccatgccacagccgccacaacgaaggatccttaactactaggccaccaggg aactccatcctttctaactctgtctttgctttccctttttttagcgttttagggctgcaccctcagcatgtggaagtccccaggctag gggtcaaattggcgctacagctgccagcctacaccacagccccagcaacgcaggatccaagccacatctttgacctac accacagctcatggtaacaccagatccttaacccactgagcaagggattgaacccacatcctcatggatactagtcggg tttgttaatcactgagccacggcaggaacccacccctgactactgtgggcaaaaaagcaacttcagagttcctgttgtgg ctcagtgggttatgaacccaactagtatccatgagggtgcgggttcgatccctgatcctgctcagtgggttaaggatctgac attgccatgagctccagtataggtaacagaaatgtcttgcatccacaccgctgtggctgtgacgtaggctggcagtttagct ctgattcgaccctagcctgggaacttccttatgcccagggtttaaccctagaaaagagggggaaaaaaatcaacatctg agcctcggttggcccagcttaaaatgcctgcttcatggccttgttactcaaaagacctgaaaccactgccatttggttttttttt taagtgtctttttttttttttaacgatttttatttttccattgtagttggtttacagcgttctgtgagttttctacggacccagtcacacac atatatacattcttttgtcacatcatcctccatcctgctccatccccagtgactagatatagttcccagtgctctacagcaggat ctcattgcttatcctctccagatgcaatggtttacgtctattaaaccagactcccagtccatcccacgccctccccttccccc ccactgccatttttgttgagccattttcatttttttttcctccctctccctctcttacccgattctgcctccttctgctcctggcctctgttc tcagtcctgctctccctgagaggcttcatttctctggcttcctcttttcctccgcctcttttgtcctctcccccctctggttgctcctgc ccctggccctgcttgtttctagttgcccttcctccaggtttgccctcgccaccacgtgggccctctcttttttttttttttttacttcccc cgaccaggaatcgaaccctagccatagaagtcacaatgccagatccttagctactagcccaccagggagttccatctcc cctcatccttctctcctccctggatcactggcctcttggctaccttgacaagcctaccaggtgctgggtgcaggctggaga gaggggccagcctgtgaccttggtattaagggcggggccatcatgttgggagctgacacgcagcatggctggagcct ggagaagcaggagcttcctcccacgccctcagttctcaggaggggagcaggattccatccagagccagcggacttgt gtcttccaggcgggcctctgccccgcttggctctggtaaactctgtgctcactccgcgctttccctgccctgcttgccgctgtg gaatcaggctccctcccccagccagatgttccaccttgggactgtgtgaggcggggctacatctgtgtgaggcagggc caagtttctgctgattcactcactgtgtgtccagggcctgggcatctcattcccagatgtcggggagtggggctctcagcc atatctcccattttaaaagctggatcttggagttcccttcatggctcgatggaagcaaatctggctagcatccatgaggatgc gggttcgatccctggcctcactcagtaggttaaggatctggtgttgccgagagctggggtgtaggtagcagatggggctgt ggctgtggtgcaggccggcagctgcagctccagtttgacccctaacctgggaacctccatgtgcactgggtgcggccta aaataaataaatgcatacgtaactaaatacatacatacatacataataaaaataaaaaaattaaaagctggatctc
```

-continued

```
aaattctgtttgaagccagctaggcggagaggggcgctcaccaccacaccccagcagcccaggttcctctctcagtgaa aggaggctggcaggggggcagtggggtggcggctgacccagcagggatccagagagtcagcctgaaggggggg aagatgatgaaggacagagaaggggcggcacgcagcctctcattgagcctctgaaccttcttagctgcccatcagtttc cccctccctaaacggaggtgacagtgacgatgagactggccaaaccaagctgtcatccggggtggggagggagga gagcagacattcgggtggatgtggggagcgctgggctcacagaggaagcagccctcatcagaggggcctgggggc tggcgggggctggatgcactcggagggctgttgcaatccggccagggtagcatctgtgcttgtctttcacaaccatcccct cctcgcccaaggctgacacgtggttgttgggcacgaggccagccaacctagcgtctggggccagggcctctctcccc agctgccagggatcacgagcagtcaaaggcagctggaggaaggggcagcctaggccggcagccctgccaacca atgtggaggaagggacagggagagtgcgtggtggtaggagtggccaagaggggggcatgagagcagatggagtgttt ccagggacctggaggcttgcagaggcagggaacccagcgtcggggaacagggtttctggtggacccagtggagggc acagattaggagccttgcagctgaggttctgcctctttttttatttttagtgctgtacccgcggcatagggacgttctcagcctag gagtcgaatcagagctgcagctgctggcctacaccacagccacgccagatccaagctgcttctgcgacctaaaccaca gcttacagcaatgacggatccttgacccactgagtggggccagggatggaactggcatcctgagccacaacagaaact catctgcacttctgacaggttcaggacaacctcctccaggagttccccattgtggcgcagcagaaacgaatccaactagg aaccacgatgttgtaggttcgacccctggcctcgctcagtggcttaaggatctgacatgtgagctgtggtgtaggtcgcata catggcttggatctagtgtttctgcggctgtggagtagagcagcagccgtagctcccatgggaccctaacctgggaacct ccatgtgccgcaggtacggcccta aaaagaaaaaaaaaaaaaaaaaaagagaaagagagagagaccctccact gaaggaagattgggggctgtgaaattaaggctccagagagcgtccagggaggcctgggagtctcccagatgcagag agagggagaatggaagggctagtcggacagtgatattggagatggcatggtgggcaggtgtgtggaggcagactat gagaccccagactcctgaagagtcttgagctgaagagacctactaagaaggggaggaggagttgccatcctggctca gtggttaacgaatccgacgaggaaccatgaggttgcgggttcgatccccggccctgctcagtgggttaaggatccggc gttgccatgagctgtggtgtaggttgcagacgtggctcggatcccgtgtggctgtggctctggcgtaggccggcggctaca gctccgattggaccctagcctgggaacctccatatgccatgggagcggcccaagaaatggcaaaaagacaaaaaa aaaaagactccttccaagaacttgggtgctatgcactattaaggccatgaggggtaataccctcagagggcccagagat gtaaagtcacacagccagcatgcggacaactggatcggggccccccagcctcaggcaatcactccactaccctcctcc tgggctgggctgcccaagataaggaacattatcttgggctgattcaccaccaggcacacagaaggcatttattacacttctt cttctttttttttttttttaatttttgtcttttcagagctgcacccacagcttatagaggtacccaggctaggggtcgaatcagagc agcagctgccagcctgcaccacagccacagcaacgtgggatccgagctgcatcttaaactaccccacagctcacagc aacaccggatccttaacccactgagtgaggccagggatcgaacgaacctacgtcctcatggatgctactcaggttcattt ccgctgagccacgatgggaactcctgttgattacacttt caaaggataatgaagggggatgtgagagaggtcaaaggtg gacaagggctagagccctcaaacagaccgaccaaccccccctctccaagtctcagctctgatgtccctcctccaggaa gccctccttgacccaggttgaatcgagcccctcatctcagccctgtctactctgggtcatcactctctggggatggatgg gcctgtcccccgaccccaccccaccccactggaccgtgagccctgggggacagggacagggcttcatcggcacc atgctcaggcataacccagcacatgactaggcctggcacgggcactcattatttggtgaaacgagtatgctacctatgca aagaaaataaataaacatgacattttcataaaaccctctgaggtagatttgtttccactgagccacgatgggagctccattt aaaaatttttttaggagttcccgtcatggcgcagtggttaaccaatccgactaggaaccatgaggttgcgggttcgatccct gcccttgctcagtgggttaacgatctggcgttgccgtgagctgtggtgcaggttgtagacgtggctcagttgctgtggccctg gtgtgtaggccagcggcttcagctccgattagaccctagcctgggaacctccatgtgacgcaggagaggcccaagaa atggctaggaatcatgaggttgcaggttcgatccctggccttgctcaatgggttaaggatccagtgttgtcgtgagctgtggt gtaggttgcagatgaggctcagatcccacattgctgtggctctggcatgggctggcggctacagctccaattcgacccta gcctgggaacctccatatgccgtgggagcggctctagaaatggcaaaaagaccaaaagaaaaagaaaaagaaa
```

```
aaaaaagaaaaagtgggcgggggccatagaggtggcctggggacacagtgtaaattgaattacttgtctggcttttttcttt ctttcttttttagggccgcaccggcggcttatggacatatggaggttcccaggctaggggtcgaatcggagctgcacctgggt tctctcggggttccgctcaggctctctcaggctgccccaggggggtggtgatctgcccaggggagccctggcagccaatg acgtagtcatgcccattcctccgggattggctgtcttgcttttacagctaagaaagggtggggtcctggtctagtgctgagag gaaagcacgtcacagcctcttgagccccacctggtcgctctagtaccctctcctacattttaacaccatgaccccaagac tcacattcaaggatctcctttaccatccctggagtctcaccccaagagctcccaatactgaatgttttgcaccctgcccctttt ctgggtaggctcagcccagcctaggtgacccag-3'
```

2. Transfection and Screening of Targeted Porcine Cells

Porcine fibroblasts from newborn or fetal Yucatan minipigs are cultured from ear biopsies. Cells are grown to 50% confluence in a 75 cm² flask (TPP, Switzerland), trypsinized and resuspended in 40 ml medium (DMEM, Lonza, Switzerland). One fourth (10 ml) were subsequently seeded in a 10 cm² petri dish. The cells are transfected with 6 ug of vector DNA in FuGENE 6 transfection reagent according to the protocol of the manufacturer (Roche Applied Science). The cells are grown under geneticin (Gibco Invitrogen) selection (1 mg/ml) for 8 days, neomycin resistant cell colonies were isolated, and each colony was transferred to a 1.9 cm² well (24-well plate, TPP, Switzerland) and grown to 80% confluence. Each colony is transferred to 9.4 cm² well (6-well plate TPP, Switzerland), grown to 80% confluence, and ⅓ of the cells is used for RNA isolation whereas ⅔ of the cells is transferred to a 25 cm² flask, grown to 80% confluence and stored at −135° C. in DMEM containing 10% DMSO until further use in handmade cloning.

Screening for locus-specific targeting events is performed by PCR and Southern Blotting using genomic DNA extracted from the neomycin-resistant clones as template. For PCR, a forward primer situated 5'-upstream for the ApoE homology region and a reverse primer located within the neomycin resistance gene, or a forward primer situated within the neomycin resistance gene and a reverse primer located 3'-downstream for the ApoE homology arm, is used.

Southern blot is performed to verify the locus-specific targeting events. Genomic DNA was digested and the blots probed with a DNA-probe situated outside the region of ApoE homology.

The resulting transgenic ApoE knockout porcine fibroblasts are subsequently used for somatic cell nuclear transfer (SCNT) by handmade cloning.

Example 2

ApoE Knockout Pig Created by AAV-Mediated Homologous Recombination

1. Cloning of Targeting Constructs

Part of ApoE intron 2 (left homology arm) and intron 3 (right homology arm) was amplified by PCR and used together with a gel extracted fragment of the vector pNeDaKO-Neo (containing a neomycin resistance gene) in a 3-fusion PCR as described by Kohli et al. (Nucleic Acids Research 2004, vol. 32, no. 1).

The resulting PCR product comprising the ApoE gene sequences flanking exon 3 and a neomycin resistance gene was cloned into the adeno-associated virus (AAV) vector pAAV-MCS (Stratagene). Packaging of this targeting construct (see below) and subsequent production of viral lysate for infection of porcine cells were performed as described by Kohli et al. (2004).

SEQ ID NO: 18: AAV-MCS/ApoE KO targeting construct—sequence (4054 bp)

(shaded region=Neo-sequence from pNeDaKO-Neo, unshaded regions=ApoE gene sequences, primer sequences are underlined)

```
atacatacgcggccgcggatctgctcgggaaatatctgcttggattaggctgatgcagataagggggtgcaaggcttg gaaggctgtgactggacagggctgggctctgggtgggaggagcgagccccgccgctgttgagtgacaatttctccctcct gcaggttggccaatcgcaagccagaagatgagggttctgtgggttgctttggtggtaaccctcctcgcaggtatgggggtg gggcttgctcaggttccctgcccctccccatcccggctgtaccggtgccctccttcatccctgggtctcttctgctggtct ctcttccccttgaggagaggcctagatgtgaggcctctctggcactccttgcttctgaacagctcgttttactctctgagcctca gtttccccatctttaaaatgggagttatgttgagagattccagctgtggctcagcaggttaagaacccgactagtatccatga ggaagagggttcaatccctggcttcgctcagcgggttaaggatccggcgttgccatgagctgcggcataagtcgcagat gcagctcgaatcgggtgttgctgtggctgtggtgcaggctggcagctatcgcttccatcggacccctcgcctgggaacttcc acgtatgccactggtgcagccctaaaagacaaacaaacaaaaacgaaagaaagagaaaagaaaggaaagggggg cttctgttttctaatgcgttgttgcctggcagggcgtgagcattagatacgtgtcagctgtgactagcgtgcacggagcacac aatccatgcttgtccagtaattagacaggctgggtgtccttccaccccctccctgcccaccagtgctctagagaagcccac ccaccagggctgggggagcacctgctctgtaccaggtaccgtgtgctgctaaagggaacaaaagctggagctccac cgcggataacttcgtatagcatacattatacgaagttatcgcgccctaccgggtaggggaggcgcttttcccaaggcagtc
```

```
tggagcatgcgctttagcagccccgctgggcacttggcgctacacaagtggcctctggcctcgcacacattccacatcca
ccggtaggcgccaaccggctccgttctttggtggcccttcgcgccaccttctactcctcccctagtcaggaagttccccc
cgccccgcagctcgcgtcgtgcaggacgtgacaaatggaagtagcacgtctcactagtctcgtgcagatggacagcac
cgctgagcaatggaagcgggtaggcctttggggcagcggccaatagcagctttggctccttcgctttctgggctcagagg
ctgggaaggggtgggtccggggcgggctcaggggcgggctcaggggcggggcgggcgcccgaaggtcctccgg
aagcccggcattctgcacgcttcaaaagcgcacgtctgccgcgctgttctcctcttcctcatctccgggcctttcgacctgca
gccaatatgggatcggccattgaacaagatggattgcacgcaggttctccggccgcttgggtggagaggctattcggcta
tgactgggcacaacagacaatcggctgctctgatgccgccgtgttccggctgtcagcgcaggggcgcccggttctttttgtc
aagaccgacctgtccggtgccctgaatgaactgcaggacgaggcagcgcggctatcgtggctggccacgacgggcgt
tccttgcgcagctgtgctcgacgttgtcactgaagcgggaagggactggctgctattgggcgaagtgccggggcaggat
ctcctgtcatctcaccttgctcctgccgagaaagtatccatcatggctgatgcaatgcggcggctgcatacgcttgatccgg
ctacctgcccattcgaccaccaagcgaaacatcgcatcgagcgagcacgtactcggatggaagccggtcttgtcaatca
ggatgatctggacgaagagcatcaggggctcgcgccagccgaactgttcgccaggctcaaggcgcgcatgcccgac
ggcgaggatctcgtcgtgacccatggcgatgcctgcttgccgaatatcatggtggaaaatggccgcttttctggattcatcg
actgtggccggctgggtgtggcggatcgctatcaggacatagcgttggctacccgtgatattgctgaagagcttggcggc
gaatgggctgaccgcttcctcgtgctttacggtatcgccgctcccgattcgcagcgcatcgccttctatcgccttcttgacga
gttcttctgagggatcaattctctagagctcgctgatcagcctcgactgtgccttctagttgccagccatctgttgtttgcccct
cccccgtgccttccttgaccctggaaggtgccactcccactgtcctttcctaataaaatgaggaaattgcatcgcattgtctg
agtaggtgtcattctattctgggggtgggtggggcaggacagcaaggggggaggattgggaagacaatagcaggca
tgctggggatgcggtgggctctatggcttctgaggcggaaagaaccagctggggctgcagcacgtgttgacaattaatc
atcggcatagtatatcggcatagtataatacgactcactataggagggccaccatggccaagttgaccagtgccgttccg
gtgctcaccgcgcgcgacgtcgccggagcggtcgagttctggaccgaccggctcgggttctcccgggacttcgtggagg
acgacttcgccggtgtggtccgggacgacgtgaccctgttcatcagcgcggtccaggaccaggtggtgccggacaaca
ccctggcctgggtgtgggtgcgcggcctggacgagctgtacgccgagtggtcggaggtcgtgtccacgaacttccggga
cgcctccgggccggccatgaccgagatcggcgagcagccgtgggggcgggagttcgccctgcgcgacccggccgg
caactgcgtgcacttcgtggccgaggagcaggactgaataacttcgtatagcatacattatacgaagttatggtacccaat
tcgccctatagtgagtcgtattaccggaccgtgtgttctggaccctcaggctccacccgtccgggtttccttctgtccttgtcgcc
aactcttgggggtctgggtctctgtttcttttttttccttcttccttttttgggggagtttactttttctttttttctttcatttgacttcatg
tcttgctttctttccatcttgagctcctgccttcgcctgtctctgggtcagtcttgccgtccttgctgtctctgaatctctggcacgtcc
tggccatcgccagctcaggagccctccttctcccccccccgccccgccctctctgcgcccagggagctgatagagga
gagcatgaaggaggtgaaggcctaccgcgaggagctggaggcgcagctgggccccgtgacccaggagacgcagg
cgcgcctgtccaaggagctgcaggcggcgcaggcccgcgtgggcgccgacatggaggacgtgcgcaaccgcttggt
gctctaccgcagcgaggtgcacaacatgttgggccagaccaccgaggagctgcggagccgcctggcttcccacctgc
gcaagctgcgcaagcggctgctccgcgacaccgaggacctgcagaagcgcctggccgtgtaccaggcggggctgcg
cgagggcgccgagcgcagcgtgagcgccctccgcgagcgcctcgggcccctggtggagcagggccgattgcgcgc
cgccaccctgagtaccaggccggccagccgctgcgcgagcgcgccgaagcctggggccagaagctgcgcggac
ggctggaggagatgggcagccggacccgcgaccgcctggatgagatgcgtgagcagctggaggaggtgcgcacca
aagtggaggagcagggcagccagttgcgcctgcaggccgagg
```
gcggccgcgtatgtat

2. Transduction and Screening of Targeted Porcine Cells

Transduction of porcine fibroblasts from newborn or fetal Yucatan minipigs was performed in 75 cm² flasks as described by Kohli et al. (2004). Briefly, cells were infected with the virus for 2-3 hours and subsequently allowed to grow for 48 hours. The cells were harvested by trypsinization 48 hours post transduction and seeded into 96-well plates with media containing geneticin to select for targeted cells and allowed to grow for 2-3 weeks.

Initial screening for locus-specific targeting events was performed by PCR using genomic DNA extracted from the neomycin-resistant clones as template. For this PCR, a forward primer situated outside the left ApoE homology arm and a reverse primer located within the neomycin resistance gene, or a forward primer situated within the neomycin resistance gene and a reverse primer located outside the right ApoE homology arm, was used.

Southern blot was performed to verify the locus-specific targeting events. Genomic DNA was digested and the blots probed with a DNA-probe upstream for the left ApoE homology arm or downstream for the right ApoE homology arm.

The resulting transgenic ApoE knockout porcine fibroblasts were subsequently used for somatic cell nuclear transfer (SCNT) by handmade cloning.

Example 3

Proprotein Convertase Subtilisin/Kexin Type 9 (PCSK9)

In most cases of atherosclerosis the genetic component is complex, but in some cases the inheritance of the disease is monogenic. These cases are mostly caused by mutations in genes coding for proteins involved in lipoprotein trafficking, and the most severe in humans are caused by mutations affecting LDL receptor-mediated lipoprotein uptake (recessive and autosomal dominant familial hypercholesterolemia). Recently, a gain-of-function mutation in the PCSK9 gene was described as the cause of autosomal dominant familial hypercholesterolemia (17) PCSK9 binds to the LDL receptor leading to its degradation (18). Therefore, gain-of-function mutations in humans and overexpression of PCSK9 transgenes in mice leads to functional LDL receptor deficiency (19).

1. Cloning of Constructs

Donor cells transgenic for human proprotein convertase subtilisn/kexin type 9 (PCSK9) were produced using the DNA transposon-based vector pSBT-HCR-hAAT-PCSK9-bpA. Briefly, human PCSK9 was amplified by PCR from a PCSK9 cDNA clone (OriGene Technologies, Rockville, USA) using Pfx polymerase (Invitrogen) and the following primers.

The forward primer includes an AscI restriction site, consensus Kozak sequence and the beginning of the coding sequence of the human PCSK9 gene. The reverse primer includes a C-terminal FLAG tag (Asp-Tyr-Lys-Asp-Asp-Asp-Asp-Lys), a stop codon and an FseI restriction site.

The human hepatocyte control region (HCR) of the apolipoprotein E gene followed by the human $\alpha_1$-antitrypsin (hAAT) promoter was amplified by PCR from the plasmid pBS-apoEHCR-hAATp-hFIXmg-bpA (Miao C H et al. Mol. Ther. 2000; 1(6):522-532) (Pfx polymerase, 25 cycles, Invitrogen) using primers Fw2 and Rv2.

```
SEQ ID NO: 21: Fw2: 5'-AAATTAATTAACTAGT CTGCA GGCTC AGAGG-3'

SEQ ID NO: 22: Rv2: 5'-GGCCGGCC GTTTAAAC GGCGCGCC GCAGATTGTGAAAGT
                    GGTCG-3'
```

The bovine growth hormone polyadenylation signal (bpA) was amplified by PCR from pBS-apoEHCR-hAATp-hFIXmg-bpA using primers Fw3 and Rv3 (25 cycles, Pfx polymerase).

```
SEQ ID NO:  Fw3:
23          5'-GGCGCGCCGTTTAAACGGCCGGCCTCAGCCTCGA
            CTGTGCCTTC-3'
SEQ ID NO:  Rv3:
24:         5'-GCGCTTAATTAAAGCCCCAGCTGGTTCCATAG-3'
```

The Rv2 and Fw3 primers contain a complementary region with AscI and FseI restriction enzyme sites, and the HCR-hAAT and bpA segments were joined by fusion PCR using the primers Fw2 and Rv3. The fused PCR product was cloned into the unique PacI site of the Sleeping Beauty transposon-based vector pSBT-PGK-puro. (Yant and Kay. Mol Cell Biol. 2003; 23(23):8505-18). The human PCSK9 cDNA was thereafter cloned into the unique AscI and FseI restriction sites.

Vector Construct for Liver-Specific Overexpression of a Native Human Pcsk9 Transgene A Sleeping Beauty transposon-based vector was created containing the human hepatocyte control region (HCR) of the apolipoprotein E gene,[23] human $\alpha_1$-antitrypsin (hAAT) promoter, human PCSK9 cDNA with a consensus Kozak sequence and an C-terminal FLAG tag,[18] and a bovine growth hormone polyadenylation signal (bpA) (pSBT-PCSK9). The construct includes a puromycin resistance gene under the control of the PGK promoter.

2. Transfection

Porcine fibroblasts from newborn or fetal Yucatan minipigs were cultured in DMEM (Lonza, Switzerland) containing 15% fetal calf serum (Lonza). Cells were seeded in a 10 cm Petri dish at 1%, 0.25% or 0.1% confluency on day 0. On day 1, pSBT-HCRapoE-hAAT-PCSK9-BpA was co-transfected with a plasmid expressing the hyperactive Sleeping Beauty transposase mutant HSB3 (pCMV-HSB3, Yant S R et al. Mol Cell Biol. 2004; 24(20):9239-47) or the inactive transposase mutant mSB (pCMV-mSB, Yant et al. Nat. Genet. 2000; 25(1):35-41). From day 3, the cells were selected in 0.6 microgram/ml puromycin (Sigma) for 14 days. Number of

```
SEQ ID NO: 19: Fw1 5'-AAAGGCGCGCCACCATGGGCACCGTCAGCTCCAGG-3'

SEQ ID NO: 20: Rv1 5'-AAAGGCCGGCCTCACTCACTTGTCATCGTCGTCCTTGTAGTCC
                     TGGAGCTCCTGGGAGGCCTG-3'
``` resistant clones were counted (FIG. 1) and HSB3-tagged colonies were then cultured in 15% FCS in DMEM until hand-made cloning.

Figure 2:
FIG. 2 shows transient expression of pSBT-HCRapoE-hAAT-PCSK9-BpA in HepG2 cells followed by immunocytochemical staining for PCSK9-FLAG using an anti-FLAG antibody and Alexa-594-conjugated streptavidin (red fluorescence). A. Non-transfected control HepG2 cells. B. pSBT-HCRapoE-hAAT-PCSK9-BpA transfected HepG2 cells. C. Transient transfection of the enhanced green fluorescent protein (eGFP)-expressing plasmid pEGFP-N1 (Invitrogen) to indicate transfection efficiency.

To confirm the integrity of the pSBT-HCRapoE-hAAT-PCSK9-BpA construct it was transiently transfected into the hepatocarcinoma cell line, HepG2. After 72 hours, the cells were stained for the PCSK9-FLAG protein using a biotinylated anti-FLAG antibody (1:1000, Sigma) and an Alexa 594-conjugated streptavidin (1:400) (FIG. 2).

3. Transgene Expression and Copy Number

Blood samples are obtained from newborn cloned pigs, and the presence and level of the transgenic PCSK9-FLAG protein in plasma is measured by ELISA using an anti-FLAG antibody (Sigma). Genomic DNAs of blood samples of the transgenic piglets and the surrogate mother are extracted according to the Chemagen DNA-extractor protocol. Southern blotting using a puromycin resistance gene (pac) probe is used to determine the number of integration sites.

Example 4

LDL Receptor Knockout Pig by Homologous Recombination

Part of the pig LDL receptor coding sequence has been sequenced (GenBank accession no. AF065990). A targeting vector containing part of the gene sequence is created with a promoter-less neomycin resistance gene cassette inserted into one of the exons to disrupt gene function. The targeting vector is linearized and transfected into Yucatan fetal fibroblasts. Fibroblasts are cultured in the presence of G418. Resistant clones are screened for homologous recombination by PCR. Yucatan minipigs with knockout of one or both apoE alleles are created from recombinant cells by "hand-made" cloning.

Example 5

LDL Receptor Knockdown Pig by RNA Interference

Part of the pig LDL receptor coding sequence has been sequenced (GenBank accession no. AF065990). Efficient targets for RNA interference will be determined empirically by transient expression of vectors containing 1) a short hairpin RNA sequence expressed under a U6 or H1 promoter targeting a 19 nucleotide sequence in LDL receptor mRNA.

For stable short hairpin RNA expression, a transposon-based or retroviral vector is constructed with 1) a short hairpin RNA sequence expressed under an U6 or H1 promoter targeting a 19 nucleotide sequence in LDL receptor mRNA, 2) a puromycin resistance gene cassette, and 3) two flanking insulator sequences. The transposon-based targeting vector is cotransfected with transposase-expressing plasmid into Yucatan fetal fibroblast cultures. The retroviral vector is transduced into Yucatan fetal fibroblast cultures. Fibroblasts are cultured in the presence of puromycin. Resistant clones are screened for efficient down-regulation of LDL receptor mRNA and protein. LDL receptor knockdown Yucatan minipigs are created from transgenic cells by "hand-made" cloning.

Identification of Effective shRNAs

In this example, a human-sized model of atherosclerosis is created by development of genetically engineered Yucatan minipigs in which RNA effector molecules directed against the endogenous LDL-receptor induce reduce lipoprotein clearance and hypercholesterolemia.

Ten shRNA-expressing plasmids targeting different 19-nucleotide sequences in Yucatan minipig LDL receptor mRNA and one control pSUPER.retro.puro expressing an irrelevant shRNA was created in pSUPER.retro.puro (Oligoengine) using manufacturer's recommendations.

TABLE 2

Targets for shRNA directed LDL receptor knockdown

| | First base in pig cDNA AF065990 sequence | Sequence |
|---|---|---|
| T1 | 763 | tgtcaaagcggcgagtgca (SEQ ID NO: 5) |
| T2 | 889 | tcccatatctgcaatgacc (SEQ ID NO: 6) |
| T3 | 1150 | accctggaccgtagtgagt (SEQ ID NO: 7) |
| T4 | 1308 | tgacaccattattggcgaa (SEQ ID NO: 8) |
| T5 | 1309 | gacaccattattggcgaag (SEQ ID NO: 9) |
| T6 | 1439 | agactctcttccaagagaa (SEQ ID NO: 10) |
| T7 | 1553 | tgaacggagtggacgtcta (SEQ ID NO: 11) |
| T8 | 1814 | tcacaggctcggacataca (SEQ ID NO: 12) |
| T9 | 858 | ccaacgagtgtctggacaa (SEQ ID NO: 13) |
| T10 | 1109 | cctacctcttcttcaccaa (SEQ ID NO: 14) |

To measure the capacity of these shRNAs to target and facilitate degradation of LDL-receptor RNA we set up a *Renilla luciferase* screening-assay based upon targeting of a *Renilla luciferase*-LDL-receptor fusion mRNAs in HEK293 cells. Part of the coding sequence of the porcine LDL receptor was amplified by PCR from DNA obtained from Yucatan minipig fibroblasts using the following primers.

SEQ ID NO: 25: Fw
5' AAAACTAGTGCCAAGACGGGAAATGCATC 3'

SEQ ID NO: 26: Rv
5' AAAACGGGTGCTGTTGATGCTCTTAAGCC 3'

The forward primer contained a SpeI site and the reverse an AgeI site and the LDL receptor segment was cloned into unique SpeI and AgeI sites in the 5'UTR region of the *Renilla luciferase* gene in a modified version of the pSiCheck-2 vector (Promega) to make the pSiCheck2-LDLR vector.

Figure 4:
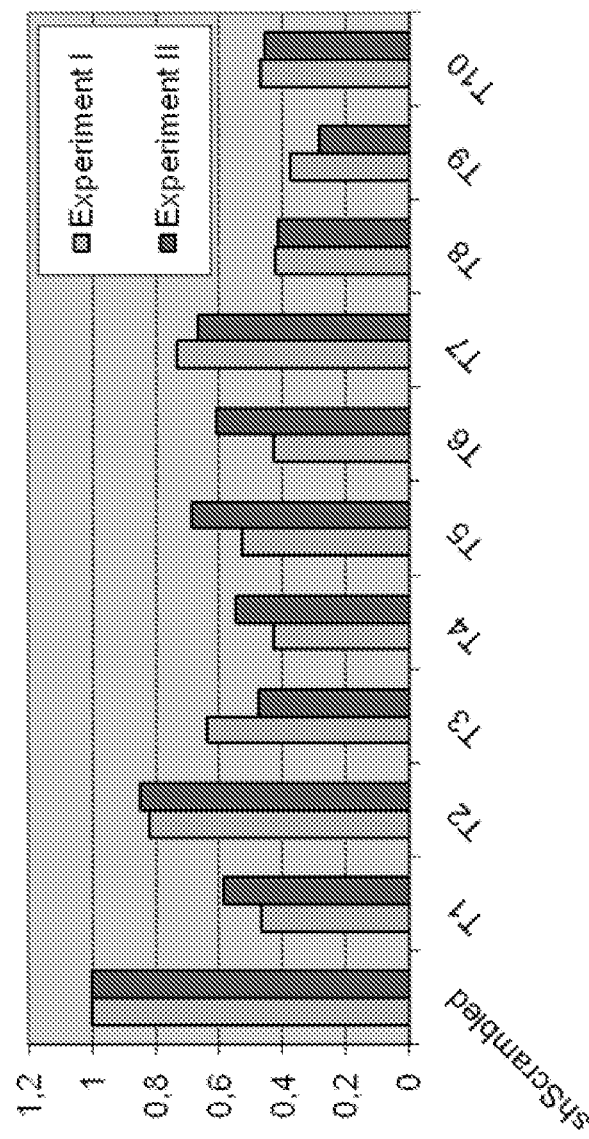
FIG. 4 shows the knockdown efficiency of shRNA directed towards the 19-nucleotide targets T1 to T10 in *Renilla lucifease*-LDL receptor fusion RNAs. T8 and T9 perform best in the screening assay.

HEK293 cells were seeded at 19000 cells per well in 24-well plates (TPP) in DMEM containing 10% fetal calf serum (Lonza) on day 0. On day 1, cells were co-transfected with 0.04 µg pSiCheck2-LDLR and 0.36 µg pSUPER.retro.puro.T1-T10 or pSUPER.retro.puro.shScrambled using FuGene 6 transfection reagent (Roche Applied Science). On day 3, luciferase activity was measured using the Dual-Luciferase® Reporter Assay System from Promega. The assay was performed in triplicates. The experiment was repeated twice. Results are given in FIG. 4.

Figure 3:
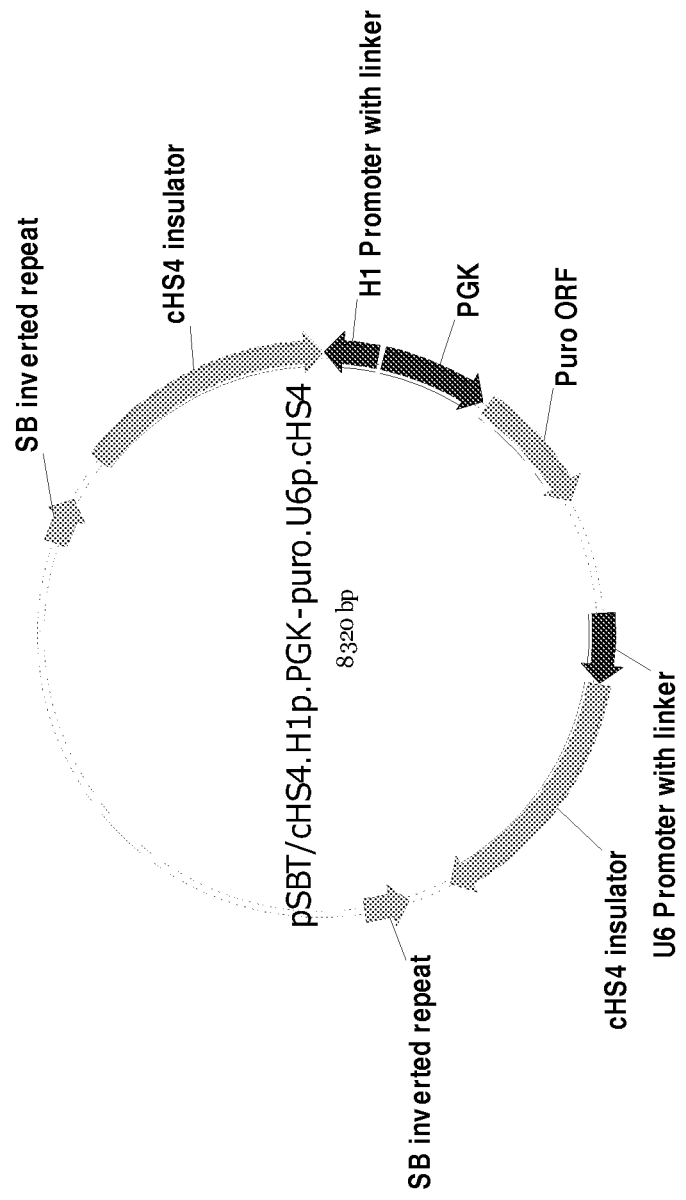
FIG. 3 shows the Sleeping Beauty transposon-based pSBT/cHS4.H1p.PGK-puro.U6p.cHS4 plasmid for stable expression of shRNAs. Short hairpin RNAs can be expressed under the U6 or H1 promoter, or both. The expression cassettes are flanked by cHS4 insulator sequences (Chung J H et al. Proc Natl Acad Sci USA. 1997; 94(2):575-580) to protect the expression cassettes from silencing position effects after genomic integration.

To facilitate stable expression of effective shRNAs in Yucatan minipig fibroblasts, shRNA sequences are cloned into one or both linkers of the plasmid pSBT/cHS4.H1p.PGK-puro.U6p.cHS4, in which shRNAs are expressed under an U6 or H1 polymerase III promoter, see FIG. 3.

Transfection

Porcine fibroblasts from newborn or fetal Yucatan minipigs are cultured in DMEM (Lonza, Switzerland) containing 15% fetal calf serum (Lonza). Cells are seeded in a 10 cm Petri dish at 1%, 0.25% or 0.1% confluency on day 0. On day 1, pSBT-shLDLR plasmid is co-transfected with a plasmid expressing the hyperactive Sleeping Beauty transposase mutant HSB3 (pCMV-HSB3, Yant S R et al. Mol Cell Biol. 2004; 24(20): 9239-47). From day 3, the cells are selected in 0.6 microgram/ml puromycin (Sigma) for 14 days. Number of resistant clones are counted (FIG. 4) and HSB3-tagged colonies are then cultured in 15% FCS in DMEM until hand-made cloning.

Transgene Expression and Copy Number

Fibroblasts are cultured from newborn cloned pigs in DMEM supplemented with 10% fetal calf serum. For analysis of the level of LDL receptor knockdown, fibroblasts are cultured in DMEM supplemented with 10% lipoprotein-deficient serum for 48 hours and the level of LDL receptor mRNA is determined by quantitative PCR. Genomic DNA is isolated from fibroblasts by standard procedures. Southern blotting using a puromycin resistance gene (pac) probe is used to determine the number of integration sites.

Example 6

Handmade cloning (HMC) and establishment of pregnancies for examples 1, 2, 3, 4 and 5.

For the cloning and delivery of transgenic fibroblasts are used in HMC. Recipient sows receive a total of in the range of 60-70 of a mixture of day 5 and/or 6 blastocysts.

Except where otherwise indicated all chemicals were obtained from Sigma Chemical Co. (St Louis, Mo., USA).

Oocyte Collection and In Vitro Maturation (IVM)

Cumulus-oocyte complexes (COCs) are aspirated from 2 to 6 mm follicles from slaughterhouse-derived sow ovaries and matured in groups of 50 in 400 µl IVM medium consisting of bicarbonate-buffered TCM-199 (GIBCO BRL) supplemented with 10% (v/v) cattle serum (CS), 10% (v/v) pig follicular fluid, 10 IU/ml eCG, 5 IU/ml hCG (Suigonan Vet; Skovlunde, Denmark) at 38.5° C. in 5% $CO_2$ in humidified air in the Submarine Incubation System (SIS; Vajta et al., 1997) for 41-44 h. HMC is performed by a procedure based on partial digestion of the zona pellucida, as described earlier (Du et al., 2005 and 2007). Matured COCs are freed from cumulum cells in 1 mg/ml hyaluronidase in Hepes-buffered TCM-199. From this point (except where otherwise indicated) all manipulations are performed on a heated stage adjusted to 39° C., and all drops used for handling oocytes are of 20 µl covered with mineral oil. Zonae pellucidae of are partially digested with 3.3 mg/ml pronase solution dissolved in T33 (T for Hepes-buffered TCM 199 medium; the number means percentage (v:v) of CS supplement, here 33%) for 20 s, then oocytes are washed quickly in T2 and T20 drops. Oocytes with distended and softened zonae pellucidae are lined up in T20 drops supplemented with 2.5 µg/ml cytochalasin B. With a finely drawn glass pipette, oocytes are rotated to locate the polar body on the surface. By oriented bisection with an Ultra Sharp Splitting Blade (AB Technology, Pullman, Wash., USA) less than half of the cytoplasm close to the polar body is removed manually from the remaining putative cytoplast.

Transgenic donor fibroblasts grown to a confluent monolayer in DMEM supplemented with 10% FCS were trypsinized and kept in T20 (Kragh et al., 2004). Fusion is performed in two steps. For the first step, 50% of the available cytoplasts are transferred into 1 mg/ml of phytohemagglutinin (PHA; ICN Pharmaceuticals, Australia) dissolved in TO for 3 s, then each one was quickly dropped over a single transgenic fibroblast. After attachment, cytoplast-fibroblast cell pairs are equilibrated in fusion medium (0.3 M mannitol and 0.01% PVA) for 10 s and transferred to the fusion chamber (BTX microslide 0.5 mm fusion chamber, model 450; BTX, SanDiego, Calif., USA). Using an alternating current (AC) of 0.6 kV/cm and 700 kHz, pairs are aligned to the wire of a fusion chamber with the somatic cells farthest from the wire, then fused with a direct current of 2.0 kV/cm for 9 µs. After the electrical pulse, cell pairs are incubated in T10 drops to observe whether fusion has occurred.

Approximately 1 h after the first fusion, each pair is fused with another cytoplast and activated simultaneously in activation medium (0.3 M mannitol, 0.1 mM $MgSO_4$, 0.1 mM $CaCl_2$ and 0.01% PVA). By using an AC of 0.6 kV/cm and 700 kHz, one fused pair and one cytoplast was aligned to one wire of the fusion chamber, with fused pairs contacting the wire, followed by a single DC pulse of 0.85 kV/cm for 80 µs. When fusion has been observed in T10 drops, reconstructed embryos are transferred into porcine zygote medium 3 (PZM-3; Yoshioka et al., 2002) supplemented with 5 µg/ml cytochalasin B and 10 µg/ml cycloheximide. After a 4 h incubation at 38.5° C. in 5% $CO_2$, 5% $O_2$ and 90% $N_2$ with maximum humidity, embryos are washed three times in PZM-3 medium before culture Embryo Culture and Transfer Embryos are cultured at 38.5° C. in 5% $CO_2$, 5% $O_2$ and 90% $N_2$ with maximum humidity in PZM-3 medium in the well of well system (WOWs; Vajta et al., 2000). Day 5 and 6 blastocysts with clearly visible inner cell mass are surgically transferred to Danish landrace sows on day 4 or 5 after weaning. Pregnancies are diagnosed by ultrasonography on day 21 and confirmed every second week. Piglets are delivered by Caesarean section on day 114, 24 h after treatment with prostaglandin F2.

Example 7

Examination of Phenotype of Transgenic Atherosclerotic Pigs

On conventional diets (~3% fat, w/w), Yucatan minipigs have low plasma cholesterol levels (~2 mmol/l) and do not develop atherosclerosis. Transgenic minipig models of atherosclerosis has an expected total cholesterol level of >5 mM total cholesterol on normal pig diet, which can be further accentuated by feeding a diet containing 20% saturated fat and even more by feeding a diet containing 20% saturated fat and 1% cholesterol.

To characterize the level of hypercholesterolemia that can be obtained in transgenic Yucatan minipigs, transgenic and normal Yucatan minipigs are maintained on normal pig diet, pig diet supplemented with 20% saturated fat or pig diet supplemented with 20% saturated fat and 1% cholesterol. Blood samples are taken at time of weaning and every 3 months thereafter.

Plasma total cholesterol and triglycerides are measured on a Vitros 950 analyzer (Ortho-Clinical Diagnostics). HDL cholesterol (HDL-C) is measured enzymatically on a Kone 30 analyzer (Thermo) using kits from ABX (Triolab, Copenhagen, Denmark). The distribution of cholesterol within lipoprotein fractions is analyzed by fast protein liquid chromatography.

To characterize the level of atherosclerosis induced by the hypercholesterolemia, pigs are examined by intravascular ultrasound (IVUS) at 6 months, 9 months and 12 months of age. After the last examination, the minipigs are killed and the heart and all major arteries are removed and opened longitudinally to identify atherosclerotic lesions. Atherosclerotic lesions are fixed in 4% formaldehyde for 24 hours and embedded in paraffin. Specimens are serially sectioned, stained by elastin-trichrome and analyzed microscopically. Atherosclerotic lesions are characterized according to the classification described by Virmani et al. Transgenic pigs are expected to exhibit pathological intimal thickening and fibrous cap atheromas.

Example 8

The Use of a Porcine Model of Atherosclerosis in Testing Preventive and Therapeutic Strategies Molecular Imaging of Atherosclerosis:

Diagnostic imaging of atherosclerosis, which is becoming theoretically possible with the advent of new high-resolution imaging technology, is a promising new tool for risk stratification of asymptomatic persons. However, to develop tracers/contrast agents and imaging sequences that are able to visualize atherosclerotic plaques and atherosclerotic disease activity, we need a human-sized animal model of the disease that can be examined in patient CT, MR, and PET-scanners.

Example: Substance X is administered intravenously and accumulation in atherosclerotic plaques is analyzed by MR scanning, CT scanning, SPECT scanning, PET scanning or intravascular ultrasound. After the scanning, the minipigs are killed. Arterial specimens containing atherosclerotic lesions are fixed, paraffin-embedded, sectioned, stained and microscopically analyzed. Results obtained by imaging are compared to the histological findings.

Effect of stenting on atherosclerotic plaques: Plaques in the coronary arteries of a one-year old transgenic pig is mapped by intravascular ultrasound (IVUS) and a drug X-eluting stent and control stent is placed at the locations of two fibrous cap atheromas.

After 3 months, pigs are killed and the pathology of the stented atherosclerotic lesions is compared by histological techniques.

Drug Study:

Atorvastatin (3 mg/kg per day) or placebo is given to transgenic minipigs (6 months of age) for 3 months. Blood samples are obtained at the initiation of the study and every month hereafter. IVUS examinations of the coronary arteries are carried out at the initiation of the study and after 3 months. After the last IVUS examination, the minipigs are killed and atherosclerotic lesions are processed for histological analysis. The effect of atorvastatin on atherosclerosis is determined by comparing the serial IVUS data and the histology of atherosclerosis at study end between atorvastatin and placebo-treated minipig groups.

Example 9

Alternatively, the shRNA and promoter cassette will be inserted into fetal fibroblasts using the "Master pig system"

Based on the well-described mechanisms of SB transposition (4-8) and Flp recombination (9, 10), the present invention discloses a new target vector for site-specific integration into the genome. This vector carries within the context of a SB transposon vector a bicistronic gene cassette containing (i) the FRT recombination site embedded in the coding sequence of eGFP and (ii) an IRES-driven puromycin resistance gene. We demonstrate efficient selective plasmid insertion into SB-tagged genomic loci. In an attempt to further improve the performance of these vectors, we have analyzed the effect of insulator elements, believed to protect inserted foreign genes against transcriptional silencing, within the context of SB vectors. Our investigations indicate that insulators flanking the FRT gene expression cassette may serve to maintain and stabilize gene expression of Flp-inserted transgenes.

Figure 5:
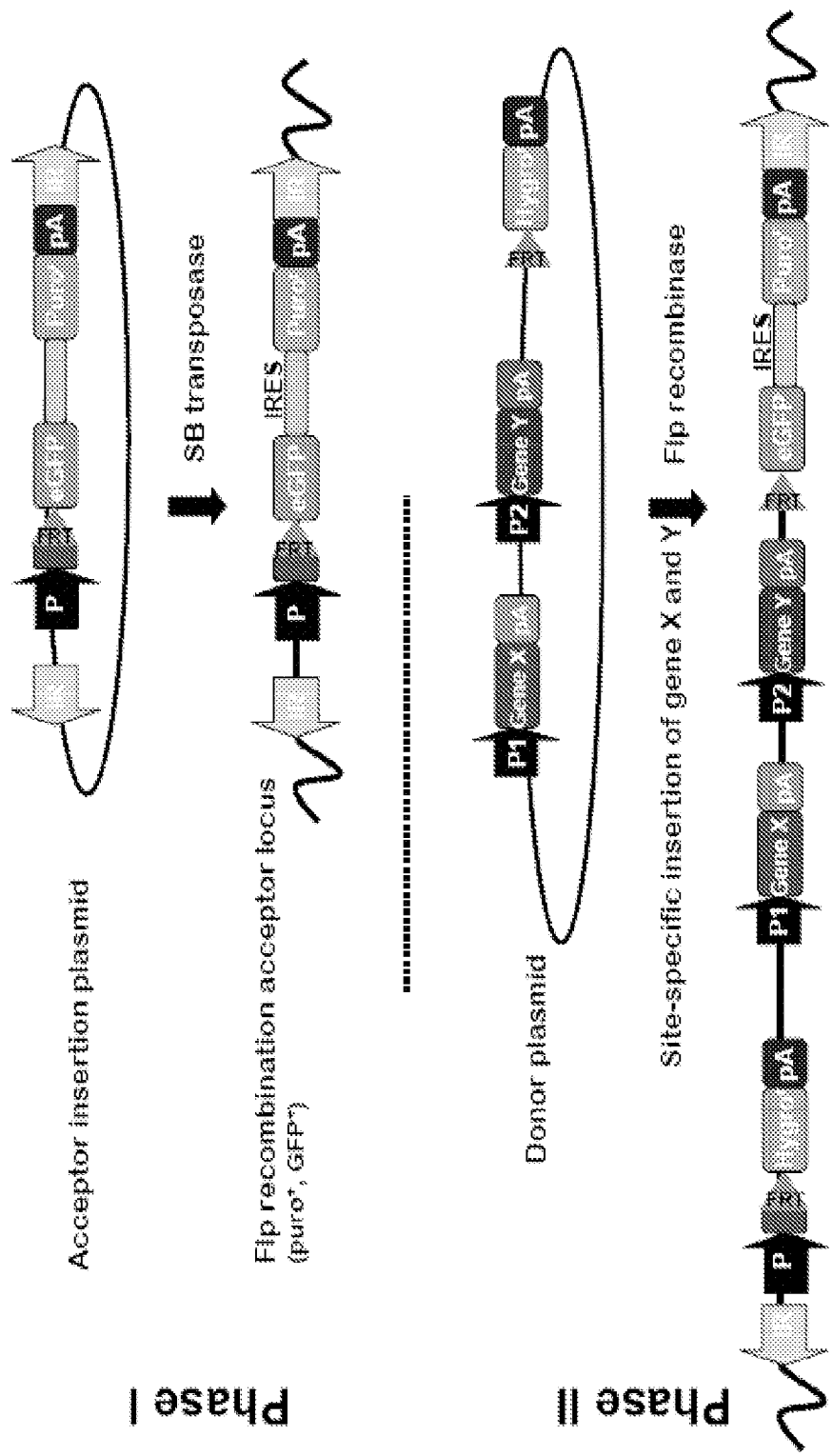
FIG. 5 shows the bi-phased technology of the present invention in which an integrating SB vector, carrying a reporter gene and a selective marker gene, serves as a reporter for continuous gene expression and hence as a target for gene insertion. In a second modification step this vector may serve as a target for insertion of one or more gene expression cassettes in a well-characterized locus.

Two nonviral integration technologies are employed in the present invention, the SB transposon system and the Flp recombinase, in a combined effort to achieve active locus detection, mediated by SB, and site-directed insertion at an attractive site, mediated by Flp. A bi-phased technology is disclosed in which an integrating SB vector, carrying a reporter gene and a selective marker gene, may first serve as a reporter for continuous gene expression and hence as a target for gene insertion (FIG. 5). By using an actively integrated vector as opposed to plasmid DNA that is randomly recombined into the genome we certify (i) that only a single copy, and not concatemers, of the vector are inserted and, moreover, (ii) that the reporter cassette is not flanked by sequences derived from the bacterial plasmid backbone which may have a detrimental effect on the locus activity over time. In a second modification step this vector may serve as a target for insertion of one or more gene expression cassettes in a well-characterized locus.

Vector Construction

The SB transposon-based vector used in this study was derived from the pSBT/SV40-GFIP.loxP vector. This vector contains, within the context of a SB transposon, a bicistronic FRTeGFP-IRES-puro (GFIP) cassette flanked upstream by an ATG start codon and downstream by a poly A sequence. Moreover, the vector contains a recognition site for the Cre recombinase (loxP) located between the upper inverted repeat of the vector and the SV40 promoter driving expression of the FRTeGFP-IRES-puro cassette.

Construction of pSBT/SV40-GFIP.loxP Vector

Figure 6:
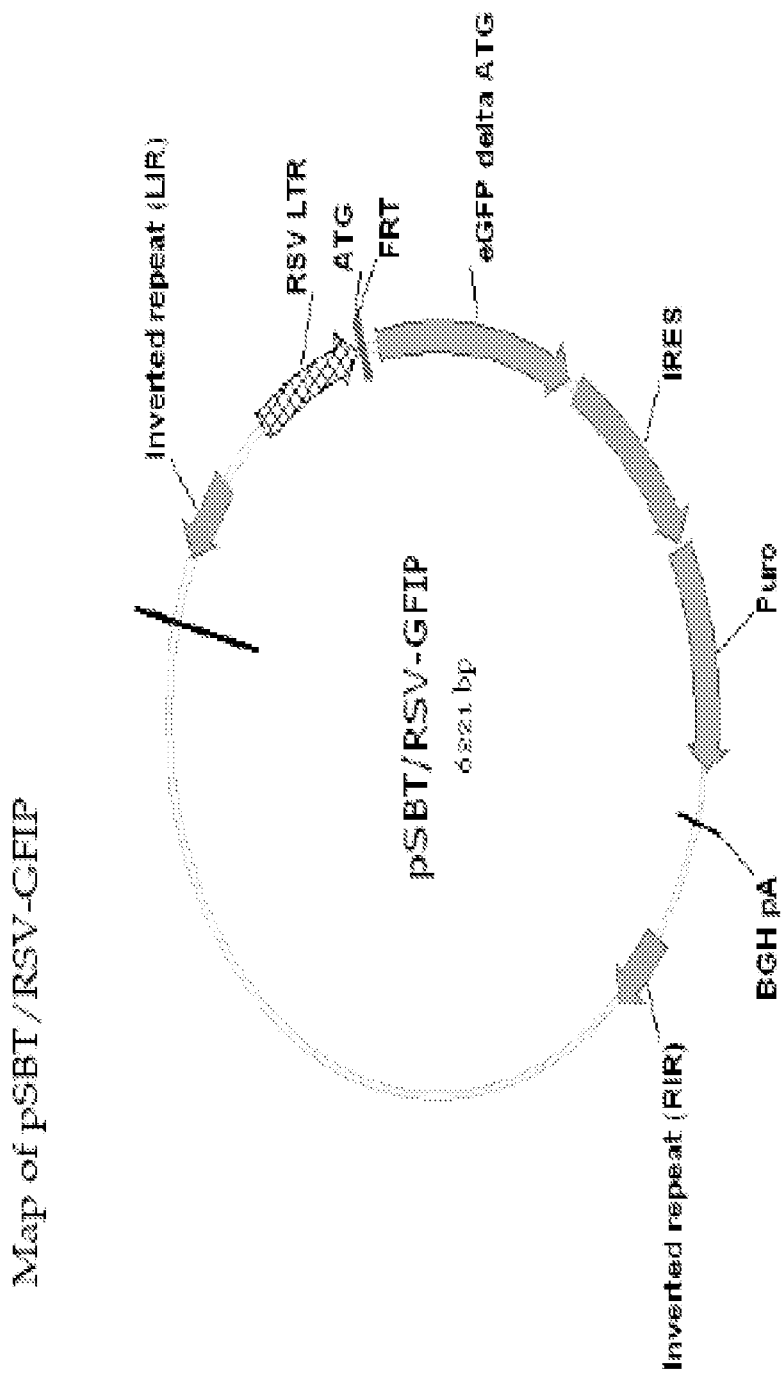
FIG. 6 shows a schematic representation of pSBT/RSV-GFIP.

The pSBT/RSV-GFIP vector contains the terminal inverted of the SB DNA transposon flanking a FRT-GFP.IRES.puro bicistronic gene cassette driven by a promotor derived from Rous sarcoma virus (RSV). The eGFP sequence was amplified from peGFP.N1 (Clontech) using a forward primer containing the 48-bp FRT sequence. To analyze FRT-GFP functionality, the FRT-eGFP fusion was inserted into an expression vector containing the SV40 promoter. The PCR-fragment containing FRT-tagged eGFP fusion gene was digested with MluI and XmaI and inserted into MluI/XmaI-digested pSBT/RSV-hAAT (pT/hAAT in ref. (8), obtained from Mark Kay, Stanford University, USA), generating a transposon vector with RSV-driven eGFP expression (pSBT/RSV-eGFP). An IRES-puro cassette was PCR-amplified from pecoenv-IRES-puro (provided by Finn Skou Pedersen, University of Aarhus, Denmark), digested with XmaI, and inserted into XmaI-digested pSBT/RSV-eGFP, generating pSBT/RSV-GFIP (see FIG. 6). Alternative versions of this vector containing the SV40 promoter (pSBT/SV40-GFIP) and the promoter derived from the human ubiquitin gene (pSBT/Ubi-GFIP), were generated. In addition, by inserting a Cre recombination target site (loxP) into the MluI site located between the left inverted repeat of the transposon and the SV40 promoter of pSBT/SV40-GFIP, the vector pSBT/SV40-GFIP.loxP was created. The donor plasmid pcDNA5/FRT, containing a FRT-hygro fusion gene without a start codon, was obtained from Invitrogen. The Flp-encoding plasmid, pCMV-Flp was obtained from A. Francis Stewart, University of California San Francisco, USA). This plasmid encodes the enhanced Flp variant designated Flpx9 (11). A SB-vector containing two copies of the 1.2-kb chicken DNase hypersensitive site 4 (cHS4)-derived insulator element (12, 13) was generated by inserting PCR-amplified cHS4 sequences and an intervening linker into NotI/SpeI-digested pSBT/PGK-puro (obtained from Mark Kay, Stanford University, USA). The PGK-puro cassette was cloned back into construct by using restriction sites located in the linker, generating pSBT/cHS4.PGK-puro.cHS4

For further use in pigs an alternative Cre recognition site (loxP-257) was inserted into a unique AscI site that was created by mutagenesis at a position located between the poly A sequence and the lower inverted repeat of the vector. This vector was designated pSBT/loxP.SV40-GFIP.loxP257. The presence of two Cre recombination sites allows Cre recombinase-mediated cassette exchange after Flp-based plasmid insertion, thereby facilitating, if needed, removal of plasmid sequences and selection genes.

SB Transposition in Primary Pig Fibroblasts

The SB transposon vectors, either SBT/PGK-puro or the target transposon SBT/loxP.RSV-GFIP.loxP257, were inserted into the genome of pig fibroblast by co-transfecting (using Fugene-6 from Roche) 1.5 µg pSBT/lox.RSV-GFIP.loxP257 (or pSBT/PGK-puro) with 1.5 µg pCMV-SB (or 1.5 µg pCMV-mSB as a negative control). pCMV-SB (rights held by Perry Hackett, University of Minnesota, Minnesota, USA) encodes the Sleeping Beauty transposase reconstructed from fossil DNA transposable elements of salmoid fish. pCMV-SB, pCMV-mSB, and the hyperactive variant pCMV-HSB3 were obtained from Mark Kay, Stanford University, USA. SB-tagged cell clones appeared as a result of selecting transfected cells with puromycin (0.5 µg/ml). Colonies were fixed and stained in methylene blue in methanol and subsequently counted.

Solid SB Transposition in Primary Pig Fibroblasts

Figure 7:
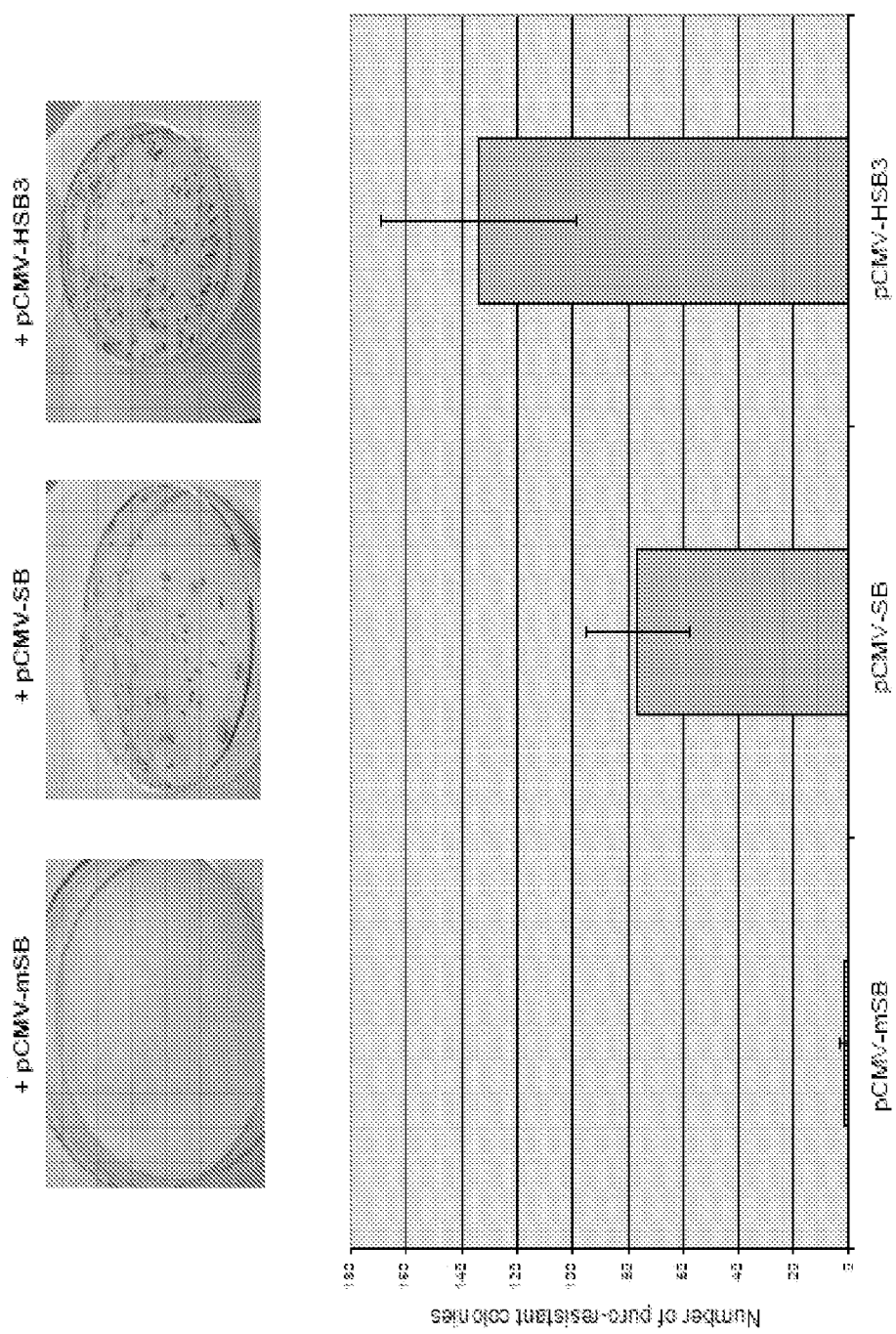
FIG. 7 shows transposition of SB vectors in porcine fibroblasts. A standard transposon encoding a puromycin resistance gene (SBT/PGK-puro) was employed and varying levels of transposition were detected, resulting in about 75 drug-resistant colonies in cultures of fibroblasts co-transfected with pSBT/PGK-puro and pCMV-SB, less than 3 colonies appeared after transfection with pSBT/PGK-puro and pCMV-mSB, the latter which encodes an inactive version of the transposase. Interestingly, a mean of almost 140 colonies was obtained using the hyperactive transposase variant HSB3, indicating that HSB3 also in porcine cells mediates higher levels of transposition compared to the original SB transposase.

SB transposes efficiently in most mammal cells but with higher efficacy in human cells than in murine cells. Transposition of SB vectors has never been analyzed in porcine cells, and we therefore initially tested activity in primary pig fibroblasts. We utilized a standard transposon encoding a puromycin resistance gene (SBT/PGK-puro) and found decent levels of transposition, resulting in about 75 drug-resistant colonies in cultures of fibroblasts co-transfected with pSBT/PGK-puro and pCMV-SB (FIG. 7). Less than 3 colonies appeared after transfection with pSBT/PGK-puro and pCMV-mSB, the latter which encodes an inactive version of the transposase. Interestingly, a mean of almost 140 colonies was obtained using the hyperactive transposase variant HSB3, indicating that HSB3 also in porcine cells mediates higher levels of transposition compared to the original SB transposase.

Efficient Insertion of a FRT-Tagged SB Vector in Pig Fibroblasts

Figure 8:
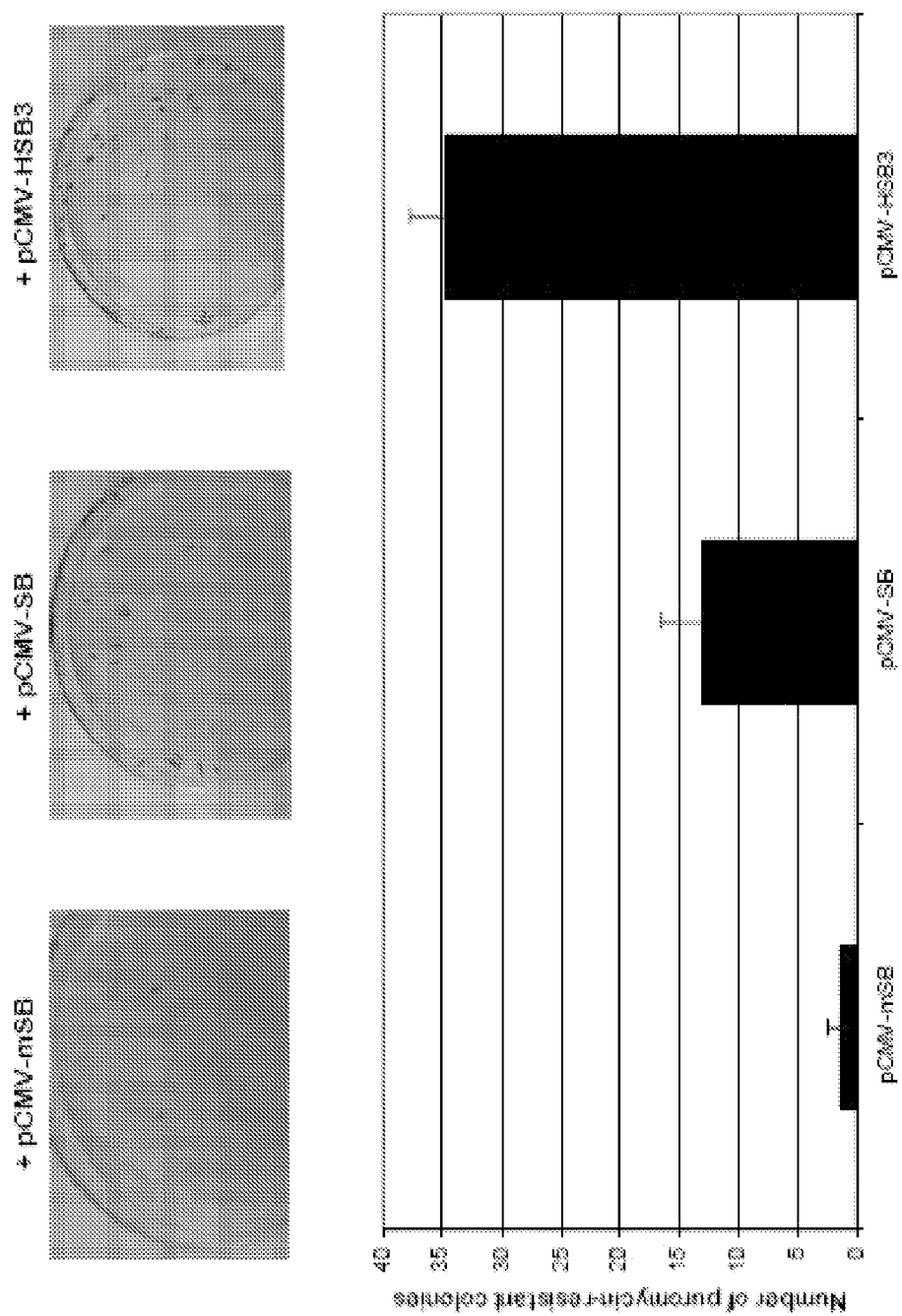
FIG. 8 shows efficient insertion of a FRT-tagged SB vector in pig fibroblasts SB-tagged cell clones containing a Flp recombination target site for site-specific gene insertion were co-transfected the pSBT/loxP.SV40-lopP257 plasmid with pCMV-mSB, pCMV-SB, and pCMV-HSB3, respectively. HSB3 again showed the highest activity, resulting in about 30 drug-resistant colonies after transfection of 3H $10^4$ fibroblasts.

To generate SB-tagged cell clones containing a Flp recombination target site for site-specific gene insertion, we co-transfected the pSBT/loxP.SV40-lopP257 plasmid with pCMV-mSB, pCMV-SB, and pCMV-HSB3, respectively. HSB3 again showed the highest activity, resulting in about 30 drug-resistant colonies after transfection of 3H $10^4$ fibroblasts (FIG. 8).

Figure 9:
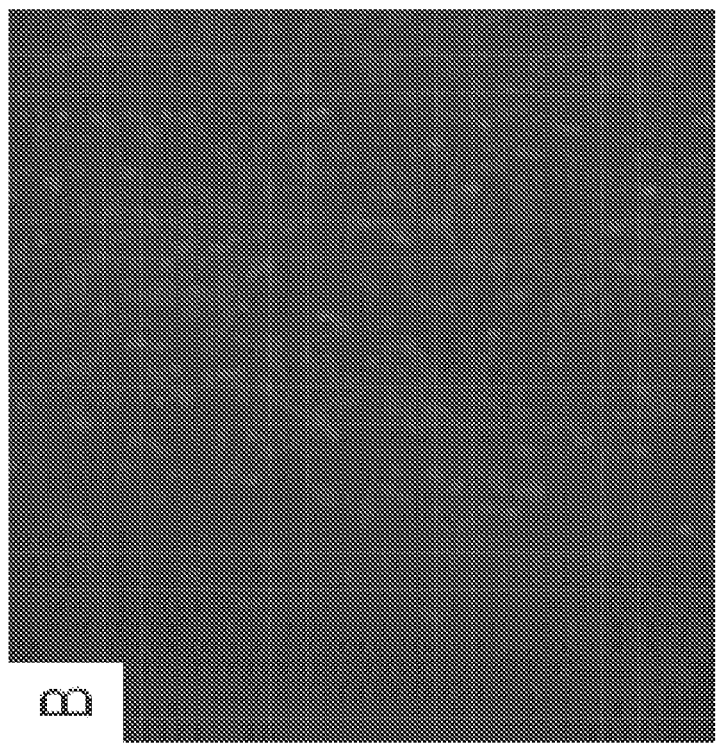
FIG. 9 shows clone analysis by fluorescence microscopy of isolated and expanded puromycin-resistant colonies demonstrates efficient FRTeGFP expression FIG. 10. (a) Oocytes trisection; (b) couplets of fibroblast-oocyte fragment for the first fusion; (c) embryos reconstructed with triplets (note elongation under the AC currency); (d) triplets fusion. Scale bar=50 μm.
Figure 9:
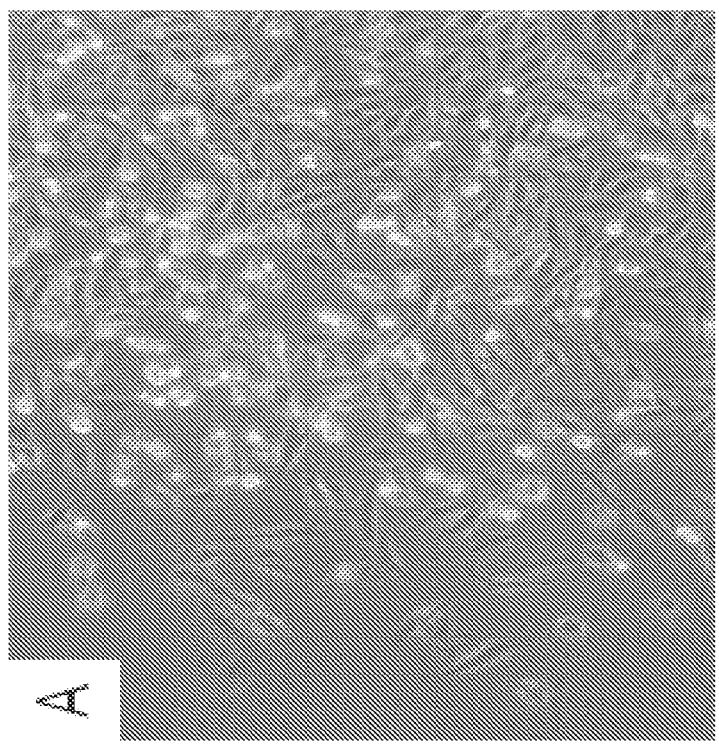

Puromycin-resistant colonies were isolated and expanded. Clone analysis by fluorescence microscopy demonstrated efficient FRTeGFP expression (FIG. 9), demonstrating vector functionality and easy FRTeGFP detection in pig fibroblasts. These fluorescent cell clones carrying the Flp FRT recombination sequence are currently being used for creation of cloned transgenic animals by hand-made cloning.

Verification of SBT/loxP.SV40-GFIP.loxP257 as Target for Flp Recombination

Due to limitations of long-term growth of primary pig fibroblasts in tissue culture we were not able to demonstrate Flp-based gene insertion into FRT-tagged SB vectors in pig fibroblasts. We therefore chose to test functionality of the FRT-containing vector by a standard set of recombination experiments carried out in HEK-293 cells. We generated clones of HEK-293 cells containing the transposed SBT/loxP.SV40-GFIP.loxP257 vector. By co-transfection of such clones with (i) a pcDNA5/FRT-derived substrate plasmid containing a FRT-hygro fusion gene and a red fluorescent protein (RFP) expression cassette and (ii) a plasmid encoding the Flp recombinase (pCMV-Flpx9), we subsequently identified hygromycin B resistant colonies. By fluorescence microscopy we observed that site-specifically engineered clones, as expected, turned-off eGFP expression and turned-on RFP expression (data not shown). This 'green-to-red' phenotypic change indicates that the integrated SB-derived target vector serves as acceptor site for Flp-based recombination.

In conclusion, the Sleeping Beauty DNA transposon-based vector of the present invention serves in its integrated form as a target for recombinase-based gene insertion. The SB vector is efficiently transferred by cut-and-paste transposition into the genome of primary porcine fibroblasts and therefore is not flanked by plasmid-derived bacterial sequences. Use of these genetically engineered primary cells in for example microinjection and hand-made cloning allows subsequent detailed analyses of SB vector-derived eGFP expression in cloned pigs and identification of animals with attractive expression profiles (e.g. ubiquitous, tissue-specific). Primary fibroblasts from such 'master pigs' is further modified by Flp-based recombination, allowing site-directed gene insertion in a SB vector-tagged locus which is not silenced in the tissue of interest. Cloned pigs harboring a site-specifically inserted disease gene of interest or a shRNA expression cassette for downregulation of endogenous genes can be generated by a second round of animal cloning.

Example 10

Production of Disease Model by Handmade Cloning

Except where otherwise indicated all chemicals were obtained from Sigma Chemical Co. (St Louis, Mo., USA).

Oocyte Collection and In Vitro Maturation (IVM)

Cumulus-oocyte complexes (COCs) were aspirated from 2-6 mm follicles from slaughterhouse-derived sow or gilt ovaries. COCs were matured in groups of 50 in 400 µl bicarbonate-buffered TCM-199 (GIBCO BRL) supplemented with 10% (v/v) cattle serum (CS), 10% (v/v) pig follicular fluid, 10 IU/ml eCG, 5 IU/ml hCG (Suigonan Vet; Skovlunde, Denmark) at 38.5° C. in the "Submarine Incubation System" (SIS; Vajta, et al. 1997) in 5% $CO_2$ in humidified air for 41-44 hours.

In Vitro Fertilization (IVF)

IVF experiments were performed with in vitro matured oocytes in 3 identical replicates. After maturation, COCs were washed twice with mTBM containing 2 mM caffeine (mTBM$_{fert}$) and transferred in groups of 50 to 400 µl mTBM$_{fert}$. Freshly ejaculated semen was treated as described previously (Booth, et al., in press). After 2 h capacitation at 38.5° C. and in 5% $CO_2$ in humidified air, sperm was added to the oocytes with the adjusted final concentration of $1 \times 10^5$ sperm/ml. Fertilization was performed at 38.5° C. and in 5% $CO_2$ in humidified air in the SIS for 3 h. After the insemination, the presumptive zygotes were vortexed in mTBM$_{fert}$ to remove cumulus cells before washing in IVC medium and placing in culture dishes (see Embryo culture and evaluation).

Handmade Cloning (HMC)

Figure 10:
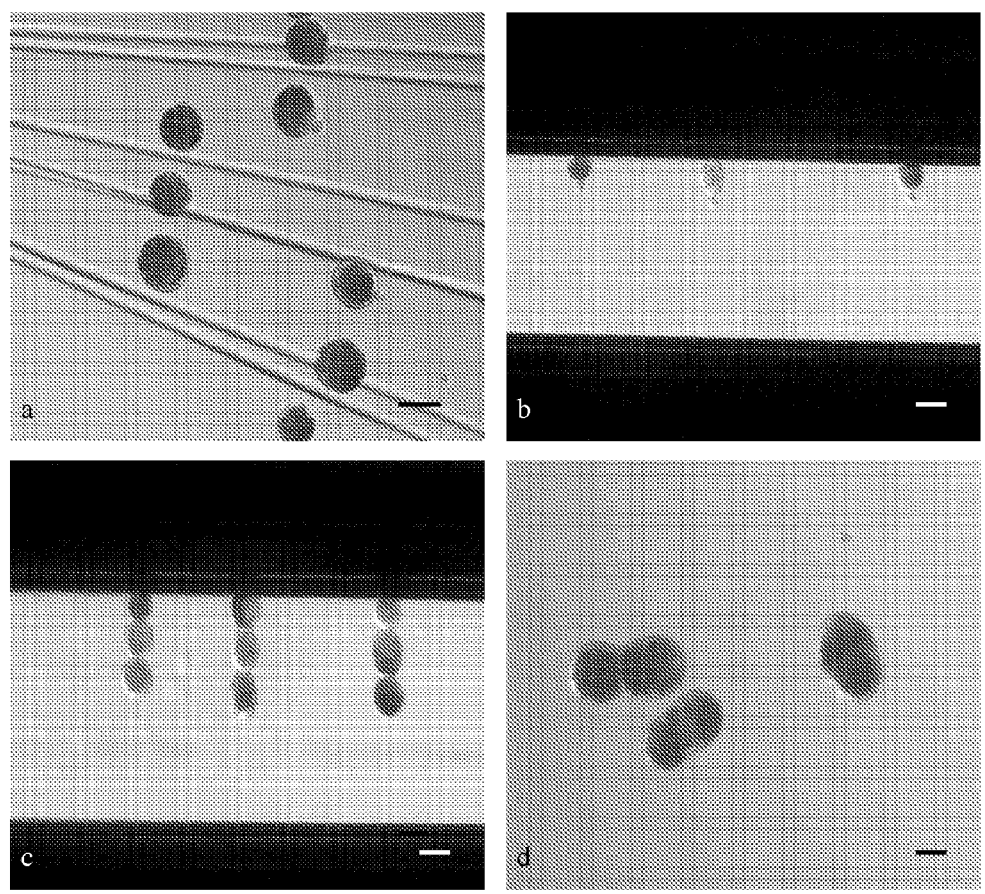

The applied HMC method was based on our previous work in cattle and pig (Kragh, et al., 2004; Peura and Vajta, 2003; Vajta, et al., 2003), but with significant modifications. Briefly, at 41 h after the start of maturation, the cumulus investment of the COCs was removed by repeated pipetting in 1 mg/ml hyaluronidase in Hepes-buffered TCM199. From this point (except where otherwise indicated), all manipulations were performed on a heated stage adjusted to 39° C., and all drops used for handling oocytes were of 20 μl volume covered with mineral oil. Oocytes were briefly incubated in 3.3 mg/ml pronase dissolved in T33 (T for Hepes-buffered TCM 199 medium; the number means percentage (v/v) of CS supplement, here 33%) for 5 s. Before the oocytes started to become misshaped in pronase solution, they were picked out and washed quickly in T2 and T20 drops. Oocytes with partially digested but still visible zona were lined up in drops of T2 supplemented with 3 mg/ml polyvinyl alcohol (TPVA) and 2.5 μg/ml cytochalasin B. Trisection instead of bisection was performed manually under stereomicroscopic control with Ultra Sharp Splitting Blades (AB Technology, Pullman, Wash., USA; FIG. 10a). Fragments of trisected oocytes were collected and stained with 5 μg/ml Hoechst 33342 fluorochrome in TPVA drops for 5 min, then placed into 1 μl drops of the TPVA medium on the bottom of a 60 mm Falcon Petri dish covered with oil (3-4 fragments per drop). Using an inverted microscope and UV light, positions of fragments without chromatin staining (cytoplasts) were registered and later collected under a stereomicroscope in T10 drops until the start of the fusion.

Fetal fibroblast cells were prepared as described previously (Kragh, et al., in press). Fusion was performed in two steps where the second one included the initiation of activation, as well. For the first step, one third of the selected cytoplasts (preferably the smaller parts) were used. With a finely drawn and fire-polished glass pipette, 10 cytoplasts were transferred as a group to 1 mg/ml of phytohaemagglutinin (PHA; ICN Pharmaceuticals, Australia) for 3 s, then quickly dropped onto one of the few fibroblast cells individually that were sedimented in a T2 drop. After attachment, 10 cytoplast-fibroblast cell pairs were equilibrated in fusion medium (0.3 M mannitol and 0.01% PVA) for 10 s. Using an alternative current (AC) of 0.6 KV/cm and 700 KHz, cell pairs were aligned to the wire of a fusion chamber (BTX microslide 0.5 mm fusion chamber, model 450; BTX, SanDiego, Calif., USA) with the donor cells farthest from the wire (FIG. 10b), then fused with a direct current (DC) of 2.0 KV/cm for 9 μs. After the electrical pulse, cell pairs were removed carefully from the wire, transferred to T10 drops and incubated to observe whether fusion had occurred.

Approximately 1 hour after the first fusion, fused pairs together with the remaining two thirds of cytoplasts were equilibrated in activation medium drops separately (0.3 M mannitol, 0.1 mM $MgSO_4$, 0.1 mM $CaCl_2$ and 0.01% polyvinylalcohol (PVA)). Under a 0.6 KV/cm AC, cytoplast-fused pair-cytoplast triplets were aligned sequentially to the wire in groups of 10, with fused pairs located in the middle (FIG. 10c). A single DC pulse of 0.7 KV/cm for 80 μs was used for the second fusion and initiation of activation. The triplets were then removed from the wire and transferred carefully to T10 drops to check the fusion (FIG. 10d). Reconstructed embryos were incubated in culture medium (see Embryo culture and evaluation) supplemented with 5 μg/ml cytochalasin B and 10 μg/ml cycloheximide for 4 h at 38.5° C. in 5% $CO_2$, 5% $O_2$ and 90% $N_2$ with maximum humidity, then washed thoroughly for 3 times in IVC medium before culture.

Parthenogenetic Activation (PA)

Parthenogenetically activated oocytes were produced either separately or in parallel with HMC. Oocytes were denuded in the same way as above except that a longer incubation in pronase was used to get the zona pellucida completely removed. Zona free (ZF) oocytes were then equilibrated for 10 s in activation medium (0.3 M mannitol, 0.1 mM $MgSO_4$, 0.1 mM $CaCl_2$ and 0.01% PVA) and transferred to the fusion chamber (BTX microslide 0.5 mm fusion chamber, model 450; BTX, SanDiego, Calif., USA). A single DC pulse of 0.85 KV/cm for 80 μs was generated with a BLS CF-150/B cell fusion machine (BLS, Budapest, Hungary) and applied to ZF oocytes. For zona intact (ZI) oocytes, a single DC pulse of 1.25 KV/cm for 80 μs was used (according to our unpublished preliminary experiments, these parameters resulted in the highest activation and subsequent in vitro development for ZI and ZF oocytes, respectively). The procedure after the electrical pulse was the same as for HMC reconstructed embryos.

Embryo Culture and Evaluation

All porcine embryos produced by the above treatments were cultured in a modified NCSU37 medium (Kikuchi, et al., 2002) containing 4 mg/ml BSA at 38.5° C. in 5% $O_2$, 5% $CO_2$ and 90% $N_2$ with maximum humidity. The culture medium was supplied with 0.17 mm sodium pyruvate and 2.73 mm sodium lactate from Day 0 (the day for fertilization and activation) to Day 2, then sodium lactate and sodium pyruvate was replaced with 5.5 mm glucose from Day 2 to Day 7. All ZF embryos were cultured in the WOW system (Vajta, et al., 2000) in the same culture medium and gas mixture as used above, with careful medium change on Day 2 without removing the embryos from the WOWs. The blastocyst rate was registered on Day 7. To determine total cell numbers, blastocysts were fixed and mounted to a glass microscopic slide in glycerol containing 20 μg/μl Hoechst 33342 fluorochrome. After staining for 24 h, embryos were observed under a Diaphot 200 inverted microscope with epifluorescent attachment and UV-2A filter (Nikon, Tokyo, Japan).

10. 1

Differences in developmental competence between sow (2.5 years, 170 Kg in weight) derived oocytes and gilt (5.5~6 months, 75 Kg in weight) derived oocytes were investigated through ZF and ZI PA after 44 h in vitro maturation. Four combined groups were investigated in 3 identical replicates: (1) ZF oocytes from sows (2) ZI oocytes from sows (3) ZF oocytes from gilts (4) ZI oocytes from gilts. For ZF activation, a single DC pulse of 0.85 KV/cm for 80 μs was applied, while a single 1.25 KV/cm pulse was used to activate ZI oocytes. Following 7 days culture as described above, the percentage of blastocysts per activated embryo was determined.

The in vitro developmental competence of parthenogenetically activated oocytes derived from either sows or gilts was investigated. As shown in Table 3, the blastocyst rates of parthenogenetically activated oocytes from sows were significantly higher than those from gilts, either after ZF or ZI PA.

TABLE 3

Blastocyst development of Day 7 parthenogenetically activated sow and gilt oocytes

| | Zona Free | | Zona Intact | |
| --- | --- | --- | --- | --- |
| | No. of activated oocytes | No. of blastocysts (%)* | No. of activated oocytes | No. of blastocysts (%)* |
| sow | 103 | 43(42 ± 4)[a] | 110 | 61(55 ± 6)[c] |
| gilt | 85 | 17(20 ± 2)[b] | 137 | 36(26 ± 5)[d] |

[a,b]Different superscripts mean significant differences ($p < 0.05$).
[c,d]Different superscripts mean significant differences ($p < 0.05$).
*Percentage (Mean ± S.E.M) of embryos developed to blastocysts.

The difference in oocytes developmental competence between sows and gilts has been examined in in vitro production (IVP) and somatic cell nuclear transfer (SCNT) embryos separately, resulting in a similar conclusion as in the earlier publication of other research groups (Sherrer, et al., 2004; Hyun, et al., 2003), i.e. that embryos from sow-derived oocytes are superior to those from gilt-derived oocytes in supporting blastocyst development. Although gilts used in our study were at the borderline of maturity, the difference between Day 7 blastocyst rates after PA was significant, proving the superior developmental competence of sow oocytes.

10.2

The feasibility of modified porcine HMC was investigated in 6 identical replicates, with IVF and in parallel ZF PA as controls. The more competent sow oocytes (according to Example 1) were used in Example 2. Seven days after reconstruction and/or activation, the number of blastocysts per reconstructed embryo and total cell numbers of randomly selected blastocysts were determined.

More than 90% of oocyte fragments derived from morphologically intact oocytes could be recovered for HMC after the trisection. In average, 37 embryos could be reconstructed out of 100 matured oocytes. The developmental competence of all sources of porcine embryos is shown in Table 4. On Day 7, the development of reconstructed embryos to the blastocyst stage was 17±4% with mean cell number of 46±5, while the blastocyst rates for IVF, and ZF PA were 30±6% and 47±4% (n=243, 170, 97) respectively.

TABLE 4

In vitro development of embryos produced by HMC, IVF and ZF PA

| Embryo origins | No. of embryos/oocytes in culture | No. of blastocysts | blastocyst rates (Mean ± S.E.M). | Mean cell number of blastocysts |
| --- | --- | --- | --- | --- |
| HMC | 243 | 41 | 17 ± 4$^a$ | 46 ± 5$^d$ |
| IVF | 170 | 52 | 30 ± 6$^b$ | 74 ± 6$^e$ |
| ZF PA | 97 | 46 | 47 ± 4$^c$ | 53 ± 7$^d$ |

$^{a,b,c}$Different superscripts mean significant differences (p < 0.05).
$^{d,e}$Different superscripts mean significant differences (p < 0.05).

Although the theoretical maximum efficiency was still not approached, the integration of zona partial digestion and oocyte trisection almost doubled the number of reconstructed embryos compared to our earlier system (Kragh, et al., 2004 Reprod. Fertil. Dev 16, 315-318). This increase in reconstruction efficiency may have special benefits in porcine cloning since oocyte recovery after aspiration is more demanding and time-consuming than in cattle. An even more important point is the high embryo number required for establishment of pregnancies following porcine nuclear transfer. IVC in pigs is also regarded as a demanding and inefficient procedure (Reed, et al., 1992 Theriogeneology 37, 95-109). A disadvantage of ZF systems is that the embryos have to reach at least the compacted morula or early blastocyst stage in vitro to avoid disintegration in the oviduct without the protective layer of the zona pellucida. On the other hand, once in the blastocyst stage, zona free embryos can be transferred successfully as proved by calves born after either embryonic or somatic cell nuclear transfer (Peura et al., 1998; Tecirlioglu et al., 2004; Oback et al., 2003; Vajta, et al., 2004) and also by the piglets born after zona-free IVP of oocytes (Wu, et al., 2004). NCSU37 medium has been the most widely and successfully used medium for the culture of pig embryos. However, despite the improved embryo development compared with other media, the viability of IVP porcine embryos is still compromised after IVC. Some reports suggested that glucose is not metabolized readily by early porcine embryos before the eight-cell stage but used in higher amounts in embryos between the compacted morula and blastocysts stages (Flood, et al., 1988). The replacement of glucose with pyruvate and lactate in NCSU37 for the first 2 days culture resulted in a blastocyst rate of 25.3% for IVP porcine embryos in Kikuchi's study (Kukuchi, et al., 2002), which was further corroborated by our present studies with an IVP blastocysts rate of 30% in average. Moreover, the first evaluation of this sequential culture system on porcine HMC and ZF PA embryos has resulted in blastocyst rates of 17% and 47% respectively. Sometimes, the blastocyst rate of ZI PA could even reach levels as high as 90% (Du, unpublished)

Statistical Analysis

ANOVA analysis was performed using SPSS 11.0. A probability of P<0.05 was considered to be statistically significant.

10.3

Vitrification of hand-made cloned porcine blastocysts produced from delipated in vitro matured oocytes.

Recently a noninvasive procedure was published for delipation of porcine embryos with centrifugation but without subsequent micromanipulation (Esaki et al. 2004 Biol Reprod. 71, 432-6).

Cryopreservation of embryos/blastocysts was carried out by vitrification using Cryotop (Kitazato Supply Co, Fujinomiya Japan) as described previously (Kuwayama et al. 2005a; 2005b). At the time of vitrification, embryos/blastocysts were transferred into equilibration solution (ES) consisting of 7.5% (V/V) ethylene glycol (EG) and 7.5% dimethylsulfoxide (DMSO) in TCM199 supplemented with 20% synthetic serum substitute (SSS) at 39° C. for 5 to 15 min. After an initial shrinkage, embryos regained their original volume. 4~6 embryos/blastocysts were transferred into 20 ul drop of vitrification solution (VS) consisting of 15% (V/V) EG and 15% (DMSO) and 0.5M sucrose dissolved in TCM199 supplemented with 20% SSS. After incubation for 20 s, embryos were loaded on Cryotop and plunged into liquid nitrogen. The process from exposure in VS to plunging was completed with 1 min.

Embryos/blastocysts were thawed by immersing Cryotop directly into thawing solution (TS) consisting of 1.0M sucrose in TCM199 plus 20% SSS for 1 min, then transferred to dilution solution (DS) consisting of 0.5 M sucrose in TCM199 plus 20% SSS for 3 min. To remove cryoprotectant, embryos/blastocysts were kept twice in a washing solution (WS; TCM199 plus 20% SSS), 5 min for each time. Survival of vitrified blastocysts was determined according to reexpansion rates after 24 h recovery in culture medium supplemented with 10% calf serum (CS).

The non-invasive delipation method was applied to in vitro matured porcine oocytes and further development of delipated oocytes after parthenogenetic activation was investigated in 4 identical replicates. Oocytes were randomly separated into delipation and control groups.

Figure 11:
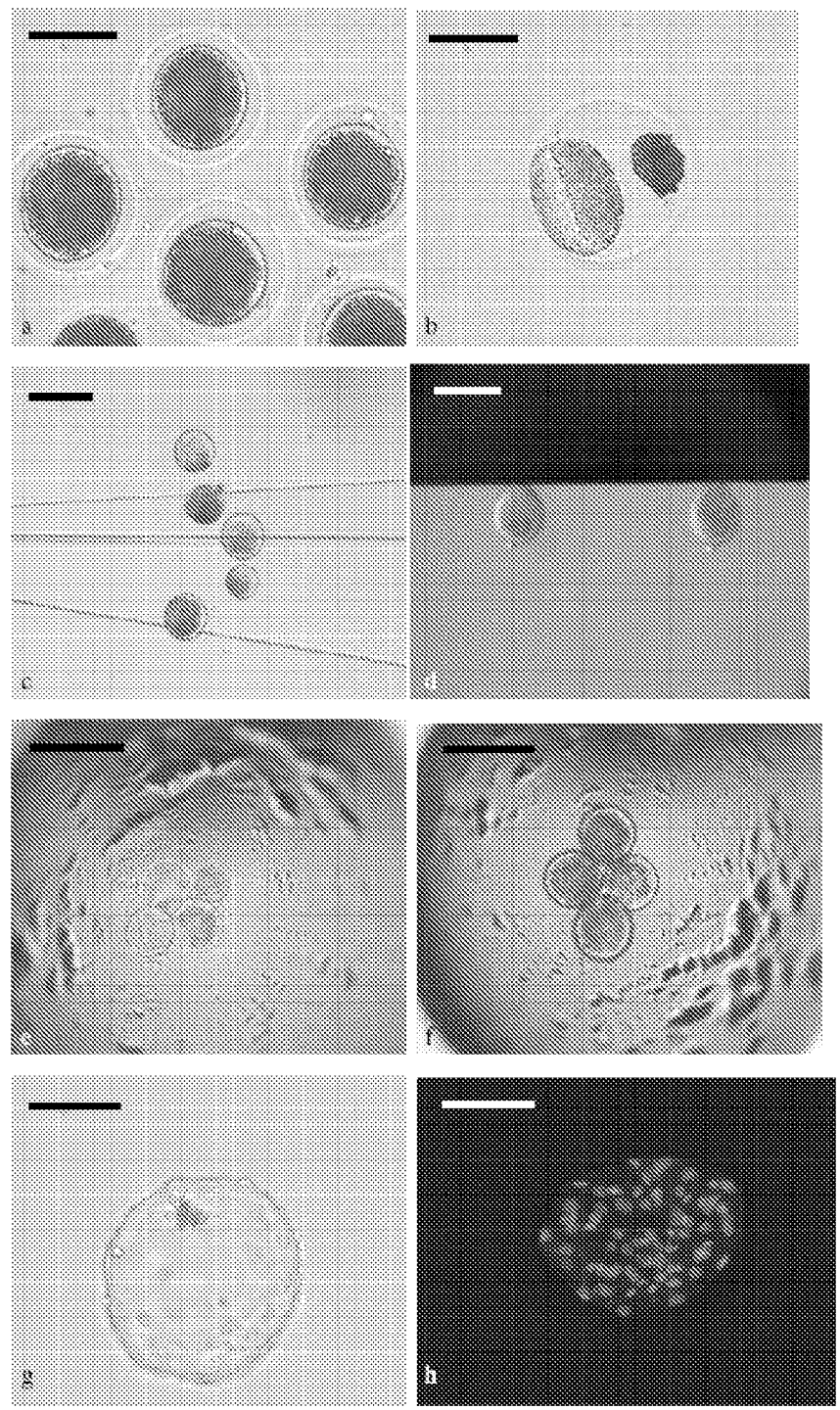
FIG. 11. (a) In vitro matured oocytes after partial zona digestion. (b) Delipated oocytes after centrifugation. (c) Bisection of delipated oocytes. (d) Couplets of fibroblast-oocyte fragment for the first fusion. (e) Four-cell stage reconstructed embryos developed from delipated oocytes. (f) Four-cell stage reconstructed embryos developed from intact oocytes. (g) Re-expanded blastocysts from delipated embryos after warming. (h) Hoechst staining and UV illumination of re-expanded blastocysts from delipated embryos after warming. Bar represents 100 μm.

For delipation, oocytes were digested with 1 mg/ml pronase in the presence of 50% cattle serum (CS) for 3 min, and washed in Hepes-buffered TCM-199 medium supplemented with 20% CS which results in partial zona pellucida digestion (FIG. 11a). Subsequently 40-50 oocytes were centrifuged (12000×g, 20 min) at room temperature in Hepes-buffered TCM-199 medium supplemented with 2% CS, 3 mg/ml PVA and 7.5 µg/ml cytochalasin B (CB) (FIG. 11b). Zonae pellucidea of both centrifuged and intact oocytes were removed completely with further digestion in 2 mg/ml pronase solution. For activation, a single direct current of 85 Kv/cm for 80 us was applied to both groups, followed by 4 h treatment with 5 μg/ml CB and 10 μg/ml cycloheximide (CHX). All embryos were then cultured in the modified NCSU37 medium. Day 7 blastocysts were vitrified and warmed by using the Cryotop technique (Kuwayama et al., RBM Online, in press) at 38.5° C. Survival of vitrified blastocysts was determined according to reexpansion rates after 24 h recovery in culture medium supplemented with 10% CS. Cell numbers of reexpanded blastocysts from both groups were determined after Hoechst staining. Results were compared by ANOVA analysis. Partial zona digestion and centrifugation resulted in successful delipation in 173/192 (90%) of oocytes. The development to blastocysts was not different between delipated and intact oocytes (28±7% vs.28±5% respectively; P>0.05). However, survival rates of blastocysts derived from delipated oocytes were significantly higher than those developed from intact oocytes (85±6% vs.32±7% respectively; P<0.01). There is no difference in average cell number of reexpanded blastocysts derived from either delipated or intact oocytes (36±7 vs. 38±9, respectively; P>0.05). The results demonstrate that the simple delipation technique does not hamper the in vitro development competence of activated porcine oocytes, and improves the cryosurvival of the derived blastocysts without significant loss in cell number.

After delipation, zona pellucida of oocytes from both groups was removed completely. The same parameters as described above for electrical activation were applied to both groups. Seven days after activation, blastocyst rates and blastocyst cell numbers were determined.

The feasibility of applying a non-invasive delipation technique to in vitro matured porcine oocytes was investigated. 90% (173/192) oocytes can be delipated successfully. As shown in table 5, the development to blastocysts was not different between delipated and intact oocytes (28±7% vs.28±5% respectively; P>0.05). However, survival rates of blastocysts derived from delipated oocytes were significantly higher than those developed from intact oocytes (85±6% vs.32±7% respectively; P<0.01). There is no difference in average cell number of reexpanded blastocysts derived from either delipated or intact oocytes (36±7 vs. 38±9, respectively; P>0.05).

TABLE 5

Developmental competence and cryosurvival of vitrified-thawed embryos from delipated and intact activated oocytes.

| Oocyte treatment | Activated oocyte | Blastocyst rate (%) | Reexpanded blastocyst after warming (%) | Mean cell number of reexpanded blastocysts |
|---|---|---|---|---|
| Delipated | 173 | 28 ± 7 | 85 ± 6 | 36 ± 7 |
| Intact | 156 | 28 ± 5 | 32 ± 7 | 39 ± 9 |

Handmade Cloning of Delipated Oocytes

Delipated oocytes were used for HMC in 5 replicates. Four identical replicates of non-delipated oocytes for HMC were used as a control system. Seven days after reconstruction, blastocysts produced from both groups were vitrified with Cryotop. Survival rates and cell numbers of re-expanded blastocysts were determined as described for the blastocysts produced by PA.

Except where otherwise indicated, all manipulations were performed on a heated stage adjusted to 39° C., and all drops used for handling oocytes were of 20 μl volume covered with mineral oil. For somatic cell nuclear transfer, the handmade cloning (HMC) described in our previous work (Du, et al., 2005) was applied with a single modification: for enucleation of both delipated and control oocytes, bisection instead of trisection was applied.

Briefly, after the removal of cumulus investment, control oocytes were incubated in 3.3 mg/ml pronase dissolved in T33 for 10 s. Before the oocytes started to become misshaped in pronase solution, they were picked out and washed quickly in T2 and T20 drops. Delipated oocytes after centrifugation were digested in the 3.3 mg/ml pronase solution for an additional 5 s.

Both control and delipated oocytes with partially digested, distended and softened zonae pellucidae were lined up in T2 drops supplemented with 2.5 μg/ml cytochalasin B. Bisection was performed manually under stereomicroscopic control (FIG. 11c) with Ultra Sharp Splitting Blades (AB Technology, Pullman, Wash., USA). Halves were collected and stained with 5 μg/ml Hoechst 33342 fluorochrome in T2 drops for 5 min, and then placed into 1 μl drops of T2 medium on the bottom of a 60 mm Falcon Petri dish covered with oil (3-4 halves per drop). Using an inverted microscope and UV light, positions of halves without chromatin staining (cytoplasts) were registered. Cytoplasts were later collected under a stereomicroscope and stored in T10 drops.

Porcine foetal fibroblast cells were prepared with trypsin digestion from monolayers as described previously (Kragh, et al., 2005). Fusion was performed in two steps where the second one included the initiation of activation, as well. For the first step, 50% of the available cytoplasts were transferred into 1 mg/ml of phytohaemagglutinin (PHA; ICN Pharmaceuticals, Australia) dissolved in TO for 3 s, then quickly dropped over single fibroblast cells. After attachment, cytoplast-fibroblast cell pairs were equilibrated in fusion medium (0.3 M mannitol and 0.01% PVA) for 10 s and transferred to the fusion chamber. Using an alternating current (AC) of 0.6 KV/cm and 700 KHz, pairs were aligned to the wire of a fusion chamber with the somatic cells farthest from the wire (FIG. 11d), then fused with a direct current of 2.0 KV/cm for 9 μs. After the electrical pulse, cell pairs were removed carefully from the wire, transferred to T10 drops and incubated to observe whether fusion had occurred.

Approximately 1 hour after the first fusion, each pair was fused with another cytoplast in activation medium. AC current and a single DC pulse of 0.7 KV/cm for 80 μs were applied as described above. Fusion was detected in T10 drops, then reconstructed embryos were transferred into IVC0-2 medium (see Embryo culture and evaluation) supplemented with 5 μg/ml cytochalasin B and 10 μg/ml cycloheximide. After a 4 h incubation at 38.5° C. in 5% $O_2$, 5% $O_2$ and 90% $N_2$ with maximum humidity, embryos were washed 3 times in IVC0-2 medium before culture.

TABLE 6

Developmental competence and cryosurvival of vitrified-thawed embryos of SCNT porcine embryos derived from delipated and intact oocytes.

| HMC group | No. of reconstructed embryos | Blastocyst rate (%)* | Reexpanded blastocyst after warming (%)* | Mean cell number of reexpanded blastocysts* |
|---|---|---|---|---|
| Delipated | 240 | 21 ± 6$^a$ | 79 ± 6$^b$ | 41 ± 7$^d$ |
| Intact | 150 | 23 ± 6$^a$ | 32 ± 8$^c$ | 39 ± 5$^d$ |

Different superscripts mean significant differences (p < 0.05).
*mean ± S.E.M.

In vitro developmental competence was observed in HMC with delipated oocytes when Day 7 blastocyst rates were compared with control HMC group (21±6% vs. 23±6% respectively; P>0.05; Table 6). Cryosurvival rate after vitrification of cloned blastocysts derived from delipated oocytes was significantly higher than those developed from intact oocytes (79±6% vs. 32±8, respectively; P<0.01).

10. 4

Chemically Assisted Handmade Enucleation (CAHE) and Comparison to Existing Methods After 41-42 h maturation in vitro, COCs were further cultured for 45 min in the same solution supplemented by 0.4 µg/ml demecolcine. Cumulus cells were then removed by pipetting in 1 mg/ml hyaluronidase dissolved in Hepes-buffered TCM-199. From this point (except where otherwise indicated), all manipulations were performed on a heated stage adjusted to 39° C. All drops used for handling oocytes were of 20 µl in volume, and were covered with mineral oil.

Figure 12:
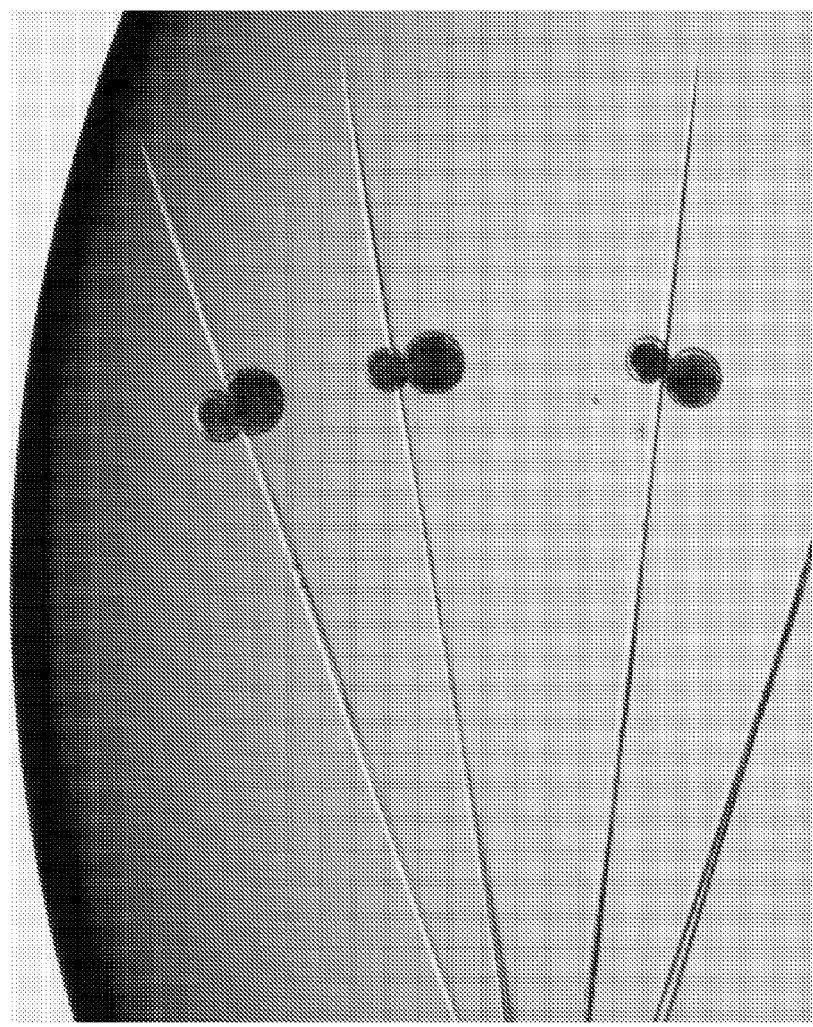
FIG. 12. Bisection at chemically assisted enucleation. Note the extrusion cone or polar body connected to the smaller part (putative karyoplast). Stereomicroscopic picture. Bar represents 50 μm.

Basic steps of the HMC procedure have been described elsewhere herein. Briefly, oocytes without cumulus cells were incubated in 3.3 mg/ml pronase dissolved in T33 (T for Hepes-buffered TCM 199 medium; the number means percentage [v/v] of CS supplement, here 33%) for 20 s. When partial lyses of zonae pellucidae and slight deformation of oocytes occurred, they were picked up and washed quickly in T2 and T20 drops. Nine oocytes were lined up in one T2 drop supplemented with 2.5 µg/ml cytochalasin B (CB). By using a finely drawn and fire-polished glass pipette, oocytes were rotated to find a light extrusion cone and/or strongly attached polar body on the surface, and oriented bisection was performed manually under stereomicroscopic control with a microblade (AB Technology, Pullman, Wash., USA). Less than half of the cytoplasm (close to the extrusion or PB) was separated from the remaining part (FIG. 12). After bisection of all 9 oocytes in the drop, larger parts and smaller parts (with the extrusion or attached PB) were collected and placed into separate drops of T2, respectively.

Oriented Handmade Enucleation without Demecolcine Treatment (OHE)

All steps were similar to the previously described procedure, but demecolcine preincubation was not applied.

Random Handmade Bisection for Enucleation (RHE)

Demecolcine preincubation was omitted from the pretreatment of this group, as well. After removal of cumulus cells, zonae pellucidae were partially digested by pronase as described above. Random handmade equal bisection was applied in drops of T2 supplemented with 2.5 µg/ml CB. All demi-oocytes were selected and stained with 10 µg/ml Hoechst 33342 in T2 drops for 10 min, then placed into 1 µl drops of T2 medium covered with mineral oil (three demi-oocytes into each drop). Using an inverted microscope and UV light, the positions of chromatin free demi-oocytes, i.e. cytoplasts were registered. These cytoplasts were later collected under a stereomicroscope and stored in T2 drops before further manipulations.

Fusion and Initiation of Activation

Porcine fetal fibroblast cells were prepared as described previously (Kragh, et al., 2005, Du, et al., 2005). Fusion was performed in two steps, where the second one included the initiation of activation as well. For the first step, with a finely drawn and fire-polished glass pipette, approximately 100 somatic cells were placed into a T2 drop, and 20-30 cytoplasts were placed into a T10 drop. After a short equilibration, groups of 3 cytoplasts were transferred to 1 mg/ml of phytohaemagglutinin (PHA) for 2-3 sec, then each was quickly dropped over a single somatic cell. Following attachment, cytoplast-somatic cell pairs were picked up again and transferred to a fusion medium (0.3 M mannitol supplemented with 0.01% [w/v] PVA). By using an alternative current (AC) of 0.6 KV/cm and 700 KHz, equilibrated pairs were aligned to one wire of a fusion chamber (BTX microslide 0.5 mm fusion chamber, model 450; BTX, San Diego, Calif.) with the somatic cells farthest from the wire, then fused with a single direct current (DC) impulse of 2.0 KV/cm for 9 µsec. Pairs were then removed carefully from the wire to a T10 drop, and incubated further to observe whether fusion had occurred.

Approximately 1 h after the fusion, fused pairs and the remaining cytoplasts were separately equilibrated in activation medium (0.3 M mannitol, 0.1 mM $MgSO_4$, 0.1 mM $CaCl_2$, supplemented with 0.01% [w/v] PVA). By using a 0.6 KV/cm AC, one pair and one cytoplast was aligned to one wire of the fusion chamber, with fused pairs contacting the wire. A single DC pulse of 0.86 KV/cm for 80 µsec was used for the second fusion and initiation of activation. Fusion was checked in after incubation in T10 drops.

Traditional Cloning (TC)

Micromanipulation was conducted with a Diaphot 200 inverted microscope (Nikon, Tokyo, Japan), as described before (Chen et al., 1999; Zhang et al., 2005). Briefly, after 42-44 h in vitro maturation, the cumulus cells were removed as described above. All manipulations were performed on a heated stage adjusted to 39° C. A single 50 µL micromanipulation solution drop was made in the central area on a lid of 60 mm culture dish and covered with mineral oil. Groups of 20-30 oocytes and fetal fibroblast cells were placed in the same drop. After incubation for 15-30 min, the oocyte was secured with a holding pipette (inner diameter=25-35 µm and outer diameter=80-100 µm). After being placed at the position of 5-6 o'clock, the first polar body and the adjacent cytoplasm (approx. 10% of the total volume of the oocyte) presumptively containing metaphase plate were aspirated and removed with a beveled injection pipette (inner diameter=20 µm). A fetal fibroblast cell was then injected into the space through the same slit. After nuclear transfer (NT), reconstructed couplets were transferred into drops of media covered with mineral oil for recovery for 1-1.5 h until fusion and activation was conducted. The recovery medium was NCSU-23 supplemented with 4 mg/mL BSA and 7.5 µg/mL CB. Reconstructed couplets were incubated in fusion medium for 4 min. Couplets were aligned manually using a finely pulled and polished glass capillary to make the contact plane parallel to electrodes. A single, 30 µsec, direct current pulse of 2.0 kV/cm was then applied. After culture in drops of IVC0-2 (specified in "Embryo culture and evaluation") supplemented with 7.5 µg/mL CB for 30-60 min, fusion results were examined under a stereomicroscope. Fused couplets were subjected to a second pulse in activation solution. After 30 min incubation in T10 they were transferred to IVC0-2 to evaluate in vitro development.

Further Steps of Activation

After the activation impulse, all reconstructed embryos were incubated in IVC0-2 supplemented with 5 µg/ml CB and 10 µg/ml cycloheximide at 38.5° C. in 5% $CO_2$, 5% $O_2$, and 90% $N_2$, with maximum humidity.

Embryo Culture and Evaluation 4 h later, all reconstructed and activated embryos were washed and cultured in Nunc four-well dishes in 400 µl IVC0-2 covered by mineral oil at 38.5° C. in 5% $CO_2$, 5% $O_2$, and 90% $N_2$, with maximum humidity. IVC0-2 was a modified NCSU37 medium (Kikuchi, et al., 1999), containing 4 mg/ml BSA, 0.17 mM sodium pyruvate, and 2.73 mM sodium lactate from Day 0 (the day for activation) to Day 2. Sodium pyruvate and sodium lactate were replaced with 5.5 mM glucose from Day 2 to Day 7 (IVC2-7). All zonae free embryos were cultured in the Well of the Well (WOW) system (Vajta et al., 2000) in the same culture medium and gas mixture as used above, with careful medium change on Day 2 without removing the embryos from the WOWs. TC embryos were cultured in groups of 15 to 30 in wells of four-well dishes by using the same medium amount and composition. Cleavage and blastocyst rates were registered on Day 2 and Day 7, respectively. To determine total cell numbers, blastocysts were fixed and mounted to a glass microscope slide in a small amount (<2 µl) of glycerol containing 10 µg/ml Hoechst 33342. After staining for several hours at room temperature, embryos were observed under a Diaphot 200 inverted microscope with epifluorescent attachment and UV-2A filter (Nikon, Tokyo, Japan).

Comparison of Efficiency of CAHE vs. OHE

Figure 13:
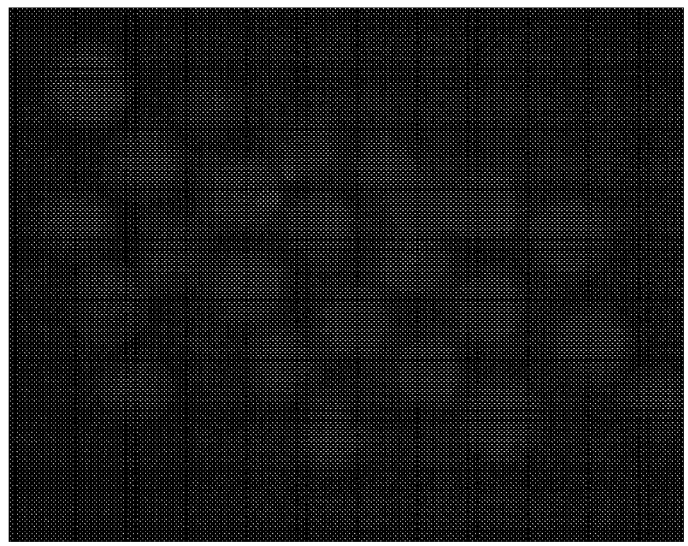
FIG. 13. Hoechst staining and UV illumination of the absence and presence of chromatin. UV light, inverted fluorescent microscopic picture. Bar represents 50 μm. (a) The absence of chromatin in putative cytoplasts (b) The presence of chromatin in putative karyoplasts.
Figure 13:
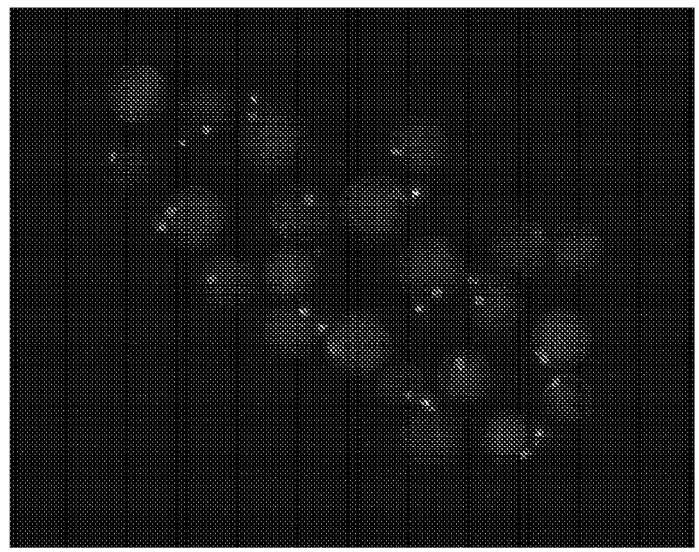

The efficiency and reliability of CAHE was tested in 12 identical replicates by using a total of 620 oocytes. After 41-42 h maturation, oocytes were subjected to demecolcine incubation. Oriented bisection was performed in oocytes where an extrusion cone and/or a strongly attached PB was detected after partial pronase digestion. Percentages of bisected vs. total oocytes and surviving vs. bisected oocytes were registered. Subsequently both putative cytoplasts and karyoplasts were collected separately and stained with Hoechst 33342 (10 µg/ml in T2 for 10 min). The presence or absence of chromatin was detected under an inverted fluorescent microscope (FIG. 13).

The efficiency and reliability of OHE was investigated in 9 identical replicates using a total of 414 oocytes. After 42-43 h in vitro maturation, oriented bisection was performed in matured oocytes where an extrusion cone and/or a PB was detected after partial pronase digestion. Results were evaluated as described in the previous paragraph.

The results are shown in Table 7.

TABLE 7

The efficiency of chemically assisted handmade enucleation (CAHE) and oriented handmade enucleation (OHE)

| Groups | No. of treated oocytes | Bisected/ total oocytes (%)* | Cytoplast/ bisection (%)* | Cytoplast/ total oocyte (%)* |
|---|---|---|---|---|
| CAHE | 620 | 96 ± 1$^a$ | 94 ± 2$^b$ | 90 ± 3$^c$ |
| OHE | 414 | 92 ± 2$^a$ | 88 ± 3$^b$ | 81 ± 4$^d$ |

*mean ± A.D. (absolute deviations)
Different superscripts mean difference (P < 0.05)

No differences between groups regarding extrusion cones and/or attached polar bodies allowing oriented bisection or in the lysis rates were detected, and the successful enucleation per bisected oocyte ratio was also similar. However the overall efficiency of the procedure measured by the cytoplast per total oocyte number was higher in the CAHE than in the OHE group.

Comparison of In Vitro Development of Embryos Produced with CAHE, RHE and TC

In 8 replicates, a total of 468 in vitro matured oocytes were randomly distributed and subjected to three of the enucleation procedures described above. Fusion rates between cytoplast and donor fibroblasts were registered. Reconstructed embryos were activated and cultured as described earlier. Cleavage and blastocyst rates were determined on Day 2 and Day 7, respectively. Stereomicroscopic characteristics of the developed blastocysts were compared between groups.

TABLE 8

Developmental competence of embryos derived from chemically assisted handmade enucleation (CAHE), random handmade enucleation (RHE) and traditional, micromanipulator based cloning (TC).

| Groups | No. of reconstructed embryos | Fusion rate (%)* | Cleavage rate (%)* | Blastocyst rate (%)* | Cell no. of blastocysts (Day 7) |
|---|---|---|---|---|---|
| CAHE | 150 | 87 ± 7$^a$ | 97 ± 6$^b$ | 28 ± 9$^d$ | 57 ± 6$^e$ |
| RHE | 86 | 81 ± 4$^a$ | 87 ± 8$^b$ | 21 ± 9$^d$ | 49 ± 7$^e$ |
| TC | 178 | 81 ± 10$^a$ | 69 ± 9$^c$ | 21 ± 6$^d$ | 53 ± 6$^e$ |

*mean ± A.D. (absolute deviations)
Different superscripts mean difference (P < 0.05).

Fusion rates after enucleation were similar between CAHE, RHE and TC, respectively. The second fusion and activation resulted in negligible (<1%) losses in the first two groups. Although TC resulted in lower cleavage per reconstructed embryo rates than the other two groups, this difference was not present in the blastocyst per reconstructed embryo rates.

Figure 14:
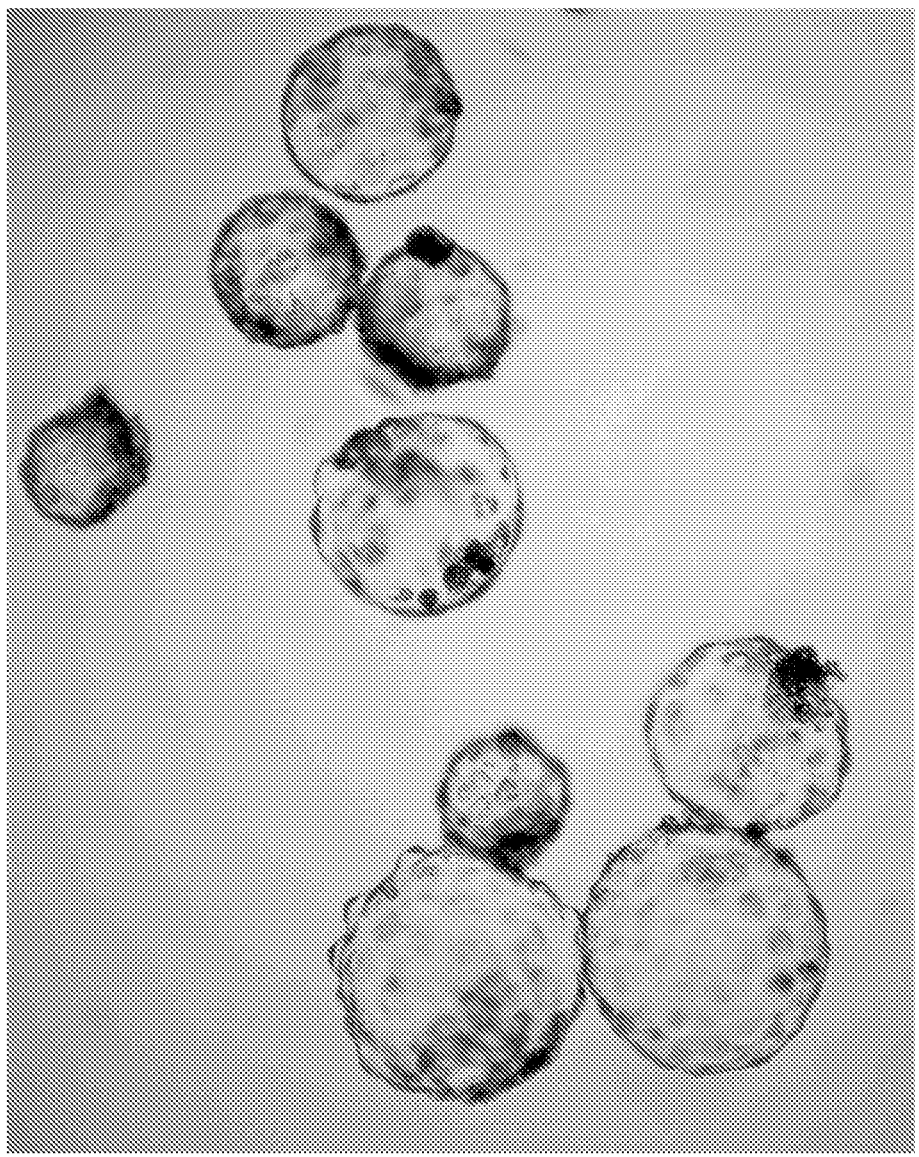
FIG. 14. Stereomicroscopic picture of Day 7 blastocysts produced with chemically assisted handmade enucleation (CAHE). Bar represents 50 μm.
Figure 15:
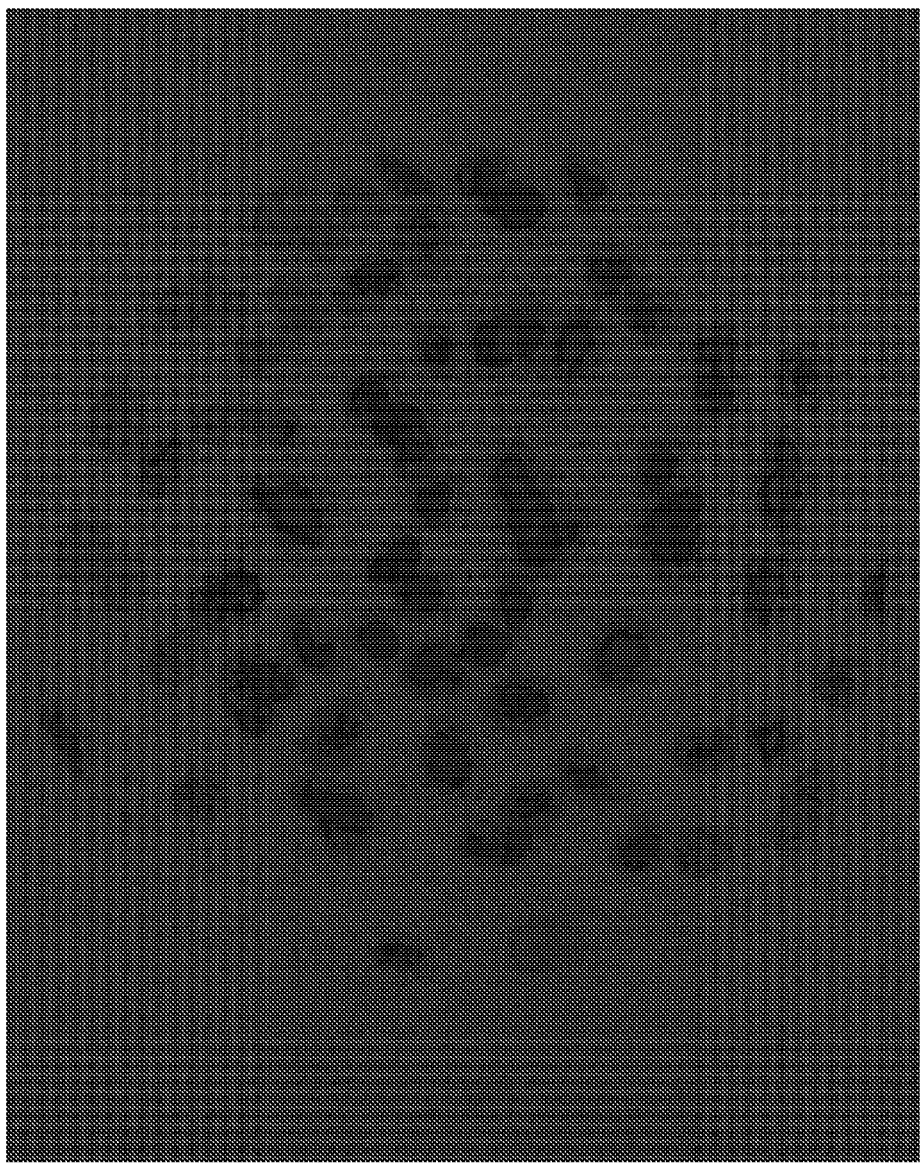
FIG. 15. Hoechst staining and UV illumination of blastocyst developed after chemically assisted handmade enucleation (CAHE). Bar represents 50 μm.

Stereomicroscopic characteristics (size; estimated proportion and outlines of the inner cell mass) did not differ between groups. Cell numbers (57±6 vs. 49±7 vs. 53±6) of the produced blastocysts from CAHE, RHE and TC are shown in Table 8, FIG. 14 and FIG. 15.

Statistical Analysis

AVEDEV was performed by Microsoft XP Excel software and ANOVA was performed by SAS system. A probability of P<0.05 was considered to be statistically significant.

10.5

Production of Piglets

Handmade Cloning (HMC)

Forty one hrs after the start of in vitro maturation, the cumulus investment of the COCs was removed by repeated pipetting in 1 mg/ml hyaluronidase in Hepes-buffered TCM199. From this point (except where otherwise indicated) all manipulations were performed on a heated stage adjusted to 39° C., and all drops used for handling oocytes were of 20 µl volume covered with mineral oil. Oocytes were briefly incubated in 3.3 mg/ml pronase dissolved in T33 (T for Hepes-buffered TCM 199 medium; the number means percentage (v/v) of calf serum (CS) supplement, here 33%) for 20 sec and then quickly washed in T2 and T20 drops. Oocytes with partially digested but still visible zona were lined up in drops of T2 supplemented with 2.5 µg/ml cytochalasin B (CB). With a finely drawn and fire-polished glass pipette, oocytes were rotated to find the polar body (PB) on the surface, and oriented bisection was performed manually under stereomicroscopic control with a microblade (AB Technology, Pullman, Wash., USA). Thus, less than half of the oocyte cytoplasm (close to the extrusion or PB) was removed from the remaining putative cytoplast. Cytoplasts were washed twice in T2 drops and collected in a T10 drop.

Fetal fibroblast cells were prepared as described previously (Kragh, P. M. et al. *Theriogenology* 64, 1536-1545 (2005).

Fusion was performed in two steps where the second one included the initiation of activation, as well. For the first step, halves of putative cytoplasts were used. With a finely drawn and fire-polished glass pipette, 10 cytoplasts were transferred as a group to 1 mg/ml of phytohaemagglutinin (PHA; ICN Pharmaceuticals, Australia) for 3 sec, then quickly dropped individually onto one of the few fibroblast cells that were sedimented in a T2 drop. After attachment, 10 cytoplast-fibroblast cell pairs were equilibrated in fusion medium (0.3 M mannitol and 0.01% PVA) for 10 sec. Using an alternative current (AC) of 0.6 KV/cm and 700 KHz, cell pairs were aligned to the wire of a fusion chamber (BTX microslide 0.5 mm fusion chamber, model 450; BTX, SanDiego, Calif., USA) with the somatic cells farthest from the wire, then fused with a direct current (DC) of 2.0 KV/cm for 9 μsec. After the electrical pulse, cell pairs were removed carefully from the wire, transferred to T10 drops and incubated to observe whether fusion had occurred.

Approximately 1 hr after the first fusion, fused pairs together with the remaining cytoplasts were equilibrated in activation medium drops separately (0.3 M mannitol, 0.1 mM MgSO$_4$, 0.1 mM CaCl$_2$ and 0.01% PVA). Under a 0.6 KV/cm AC, cytoplast-fused pair were aligned sequentially to the wire in groups of 10, with fused pairs far from the wire. A single DC pulse of 0.7 KV/cm for 80 μsec was used for the second fusion and initiation of activation. The pairs were then removed from the wire and transferred carefully to T10 drops to check the fusion. Reconstructed embryos were incubated in PZM-3 medium supplemented with 5 μg/ml CB and 10 μg/ml cycloheximide for 4 hr at 38.5° C. in 5% O$_2$, 5% O$_2$ and 90% N$_2$ with maximum humidity, then washed thoroughly before culture.

Traditional Cloning (TC)

Micromanipulation was conducted with a Diaphot 200 inverted microscope (Nikon, Tokyo, Japan). Cumulus cells were removed as described above after 42 to 44 hr maturation. All manipulations were performed on a heated stage adjusted to 39□. A single 50 μL drop of micromanipulation solution (NCSU-23 supplemented with 4 mg/mL BSA and 7.5 μg/mL CB) was made in the central area on a lid of 60 mm culture dish and covered with mineral oil. Groups of 20 to 30 oocytes and fetal fibroblast cells were placed in the same drop. After incubation for 15 to 30 min, one oocyte was secured with a holding pipette (inner diameter=25-35 μm and outer diameter=80-100 μm). After being placed at the position of 5-6 o'clock, the first polar body and the adjacent cytoplasm (approx. 10% of the total volume of the oocyte) presumptively containing metaphase plate were aspirated and removed with a beveled injection pipette (inner diameter=20 μm). A fetal fibroblast cell was then injected into the space through the same slot. After nuclear transfer (NT), reconstructed couplets were transferred into drops of media covered with mineral oil for recovery for 1 to 1.5 hrs until fusion and activation was conducted. Reconstructed couplets were incubated in fusion medium for 4 min. Couplets were aligned manually using a finely pulled and polished glass capillary to make the contact plane parallel to electrodes. A single, 30 μsec, direct current pulse of 2.0 kV/cm was then applied. After culture in drops of PZM-3 medium supplemented with 7.5 μg/mL CB for 30-60 min, fusion results were examined under a stereomicroscope. Fused couplets were subjected to a second pulse in activation solution. After 30 min incubation in T10 they were transferred to PZM-3 medium to evaluate in vitro development.

Embryo Culture and Transfer

Reconstructed embryos were cultured in PZM-3 medium (Dobrinsky, J. T. et al. *Biol Reprod* 55, 1069-1074 (1996) supplemented with 4 mg/ml BSA. Zona-free embryos produced from HMC were cultured in the modified WOWs system (Feltrin, C. Et al. *Reprod Fertil Dev* 18, 126 (2006). Two different cell lines (LW1-2 for HMC, LW2 for TC) were used as nuclear donor cells for HMC and TC to allow the identification of the offspring from the two procedures. LW1-2 and LW2 originate from fetuses from a cross (with Duroc) and pure Danish landrace, respectively.

The average blastocyst per reconstructed embryo rate after in vitro culture for 7 days was 50.1±2.8% (mean±S.E.M), which is significantly higher (p<0.01) for HMC than that of TC performed in parallel in our laboratory (Table 9) and also the highest one that has ever been reported in pig cloning.

TABLE 9

In vitro development of embryos produced from handmade cloning and traditional cloning

| Group | Somatic cell donor | No. of reconstructed embryos | Cleavage rate (%) | Blastocyst rate (%) |
|---|---|---|---|---|
| HMC | LW1-2 | 643 | 83.7 ± 4.90[a] | 50.06 ± 2.80[a] |
| TC | LW2 | 831 | 74.86 ± 13.16[b] | 28.98 ± 2.84[b] |

[a,b]Values of different superscripts within columns are significantly different (p < 0.05).
*mean ± S.E.M.

Mixed blastocysts produced from both HMC and TC were surgically transferred to 11 naturally synchronized sows on Day 4 or 5 of estrous cycle. Six (55%) recipients were diagnosed pregnant by ultrasonography, 2 aborted and by the time of writing 2 have delivered 3 and 10 piglets, respectively. A litter size of 10 cloned piglets is, according to our knowledge, the largest litter size so far achieved in pig cloning. All of them are healthy and behave normally except one showed rigid flexure of distal joint of one foreleg. %).

Preliminary results suggest that when embryos of similar stages were transferred, recipients on Day 4 of the estrous cycle supported pregnancy establishment better than those of Day 5 (Table 10).

TABLE 10

In vivo development of cloned porcine embryos

| Recipient number | Embryos transferred HMC embryo | Embryos transferred TC embryo | Embryo stage (Day) | Recipient cycle (Day) | Pregnancy status | No. of piglets born piglets from HMC | No. piglets from TC | Gestation length (Day) |
|---|---|---|---|---|---|---|---|---|
| 1327 | 22 | 10 | D 5, 6, 7 | 4 | Y | 2 | 1 | 116 |
| 1539 | 36 | 10 | D 7 | 4 | Y | 8 | 2 | 115 |
| 1309 | 30 | 28 | D 5, 6 | 4 | Y | | | |
| 1553 | 45 | 44 | D 5, 6 | 4 | Y | | | |
| 1668 | 48 | 18 | D 5, 6 | 5 | Y, aborted | | | |
| 1428 | 78 | 22 | D 5, 6 | 5 | Y, aborted | | | |
| 1725 | 44 | 4 | D 5, 6, 7 | 5 | N | — | — | — |
| 1643 | 22 | 11 | D 5, 6, 7 | 4 | N | — | — | — |
| 1520 | 30 | 26 | D 5, 6 | 4 | N | — | — | — |

TABLE 10-continued

In vivo development of cloned porcine embryos

| Recipient number | Embryos transferred | | Embryo stage (Day) | Recipient cycle (Day) | Pregnancy status | No. of piglets born | | Gestation length (Day) |
| --- | --- | --- | --- | --- | --- | --- | --- | --- |
| | HMC embryo | TC embryo | | | | piglets from HMC | No. piglets from TC | |
| 1363 | 37 | 7 | D 6, 7 | 5 | N | — | — | — |
| 1560 | 99 | 42 | D 5, 6, 7 | 5 | N | — | — | — |

Microsatellite Analysis

Parental analysis using 10 different porcine microsatellite markers confirmed the identical genotype of cloned piglets and donor cells used for nuclear transfer. Identification was done by microsatellite analysis of genomic DNA from each of the newborn piglets, the surrogate sow, and the donor skin fibroblasts LW1-2 and LW2 originating from two fetuses that represent Danish landrace and Duroc, respectively. Ten polymorphic microsatellite loci (SW886, SW58, SW2116, SW1989, SW152, SW378, KS139, S0167, SW1987, SW957) located on different porcine chromosomes were amplified by 3-color multiplex PCR and the products analyzed on the Genetic Analyzer 3130 X1 (Applied Biosystems) using the program Gene Mapper 3.7.

For the second recipient, the offspring per embryo rate (22%) was the highest one ever reported so far in pig cloning (Walker, S. C. et al. *Cloning Stem Cells* 7, 105-112 (2005); Hoshino, Y. et al. *Cloning Stem Cells* 7, 17-26 (2005)). Comparable live birth/transferred embryo efficiencies were obtained in HMC (17%) and TC (15%).

Statistical Analysis

Differences between the experimental groups were evaluated using independent-samples t-test by SPSS 11.5. $P<0.05$ was considered significant.

Sequence Listing

```
SEQ ID NO: 1: Sus scrofa ApoE gene sequence
   1 ctcgagaggg agtgagggtt aaaactctgt ggtgcaacgg aaacgaatcc aactgggaaa 61 ccatgaggct gtgggttgga tccccggcct cgctcaatgg gttaaggatc cagcacggcg 121 ctgccgtgag ctgtggtgta ggtcgcagac gaagcttgga tcccacttgg ctgtggctgt 181 ggctgtggct gtggtgtagg cccgcagctg taactgtaat tcgaccccta gcctgggaac 241 ctccacaagc cacgggtgtg gccctaaaaa gcaaaaaaac gaaagcaaaa agaacactct 301 caaagcctaa actttgagca aaaagaacac tctcaaagcc taaactttga gcagatgcct 361 tacaccgccc ccacgcctct catcccttt ctgtctgggc ctccagctcc cttcccctt 421 aacccagaaa tcccagacct cagacccaag gatttcgaat ccccaggcct tggcccaatt 481 ctatcatccc agcacaggac aagaaaaaag cagggccggg ccttctggtc ctgctcctct 541 ccctgccagc ccaccccacc agtggcatgg aaaaagctcc ggaattactg ggtgaaaaaa 601 acctcttcca tggggctgg aattaggggg ggggtgatgg ttgccaaccc caccccctccc 661 ctccctccct tcccccaccc tgctgtgtga aagggaggc cagcccactt cgtgacccga 721 cgggggctgg cccagctggc cccagttctg gaggagtggg cggggcgggg ggagccctat 781 aattggccga atctgggctc cctgaatcat actcagcccc ggaggaggaa ggaggaagga 841 ggaggaggaa gcaaccggtg aggagcagac ctgggggcac agagatgggc tcggggcttc 901 ggtgtggggg ggtgggctgt cgggggagga ggaaatgacc tggcccccccg gggccaccac 961 cgaggcagga gttggggatg aggctagagc ccagggactg gacctagaag gagggtgggc 1021 agcaggagga ggttatccgc cttggctgga aggggaggtc agggaagcag cgggacctgt 1081 aggaagaacc agacgagcca gagccgacga attgtactgg caggtatggc gcatctactc 1141 aagttttgag cacactaaga gctccatcga ggagacccag gggtggcggc gaccaggggt 1201 gacctcgacc gggctggcgg cagggtagct agagcgttgg tggaaggaca tgtaaatgag 1261 gattaaatta gggaatgagt ggaaaacagg gtttagatgt gaagttggag cttggaatgt 1321 gaaggtacca ggaagaacgt gagcttggag cccagaaagc aaggctgggg ctcacatggg
```

-continued

```
1381 actccagggt ggaaggggtg gggggcgacg tgggtggaat ttgaaccctg ggaaaaaagg
1441 aaggcttttg gccgcacccg acctgggat ggggagatag gagaagacaa tgagggaatt
1501 acacggacaa tggaaaggat ctgctcggga aatatctgct tggattaggc tgatgcagat
1561 aagggggtgc aaggcttgga aggctgtgac tggacagggc tgggctctgg gtgagaggag
1621 cgagccccgc cgctgttgag tgacaatttc tccctcctgc aggttggcca atcgcaagcc
1681 agaagatgag ggttctgtgg gttgctttgg tggtaaccct cctcgcaggt atggggtgg
1741 ggcttgctca ggttccctgc ccctccccca tccccggtgc ccctccttca tccctgggtc
1801 tcttctgctg gtctctcttc cccttgagga gaggcctaga tgtgaggcct ctctggcact
1861 ccttgcttct gaacagctcg ttttactctc tgagcctcag tttccccatc tttaaaatgg
1921 gagttatgtt gagagattcc agctgtggct cagcaggtta agaacccgac tagtatccat
1981 gaggaagagg gttcaatccc ctggcttcgc tcagcgggtt aaggatccgg cgttgccatg
2041 agctgcggca taagtcgcag atgcagctcg aatcgggtgt tgctgtggct gtggtgcagg
2101 ctggcagcta tcgcttccat cggacccctc gcctgggaac ttccacgtat gccactggtg
2161 cagccctaaa agacaaacaa acaaaaacga aagaaagaga aagaaaggaa aagggggctt
2221 ctgtttctaa tgcgttgttg cctggcaggg cgtgagcatt agatacgtgt cagctgtgac
2281 tagcgtgcac ggagcacaca atccatgctt gtccagtaat tagacaggct gggtgtcctt
2341 ccaccccctc cctgcccacc agtgctctag agaagcccac ccaccagggc tgggggagca
2401 cctgctctgt accaggtacc gtgtgctggg aggggcaga ggacctgatg ctgtgaact
2461 ggctcggtgc aggatgccgg acagaggacg agccggggcc gccgccggag gtgcacgtgt
2521 ggtgggagga gcccaagtgg cagggcagcc agccctggga gcaggccctg gccgcttct
2581 gggattacct cgcgctgggtg cagtcccgt ctgaccaagt gcaggaggag ctgctcagca
2641 ccaaggtcac ccaggaactg acgtaagtgc ccacccgact cccgccgcgc gcgcgcgcgc
2701 gcgcgcgcgc gcctgaccct cctggcgaac cgtgtgttct ggaccctcag gctccacccg
2761 tccgggttc cttctgtcct tgtcgccaac tcttgggggt ctgggtctct gtttcttttt
2821 tttccttcct cctttttggg gggaaaaaa cttttcttt tttcttcat ttgacttcat
2881 gtcttgcttt cttttccatct tgagctcctg ccttcgcctg tctctgggtc agtcttgccg
2941 tcccttgctg tctctgaatc tctggcacgt cctggccatc gccagctcag gagccctcct
3001 tctccccctc accgccccg ccctctctgc gcccagggag ctgatagagg agagcatgaa
3061 ggaggtgaag gcctaccgcg aggagctgga ggcgcagctg ggccccgtga cccaggagac
3121 gcaggcgcgc ctgtccaagg agctgcaggc ggcgcaggcc cgcgtgggcg ccgacatgga
3181 ggacgtcgcg aaccgcttgg tgctctaccg cagcgaggtg cacaacatgt tgggccagac
3241 caccgaggag ctgcggagcc gcctggcttc ccacctgcgc aagctgcgca agcggctgct
3301 ccgcgacacc gaggacctgc agaagcgcct ggccgtgtac caggcggggc tgcgcgaggg
3361 cgccgagcgc agcgtgagcg ccctccgcga gcgcctcggg ccctggtgg agcagggccg
3421 attgcgcgcc gccaccctga gtaccagggc cggccagccg ctgcgcgagc gcgcggaagc
3481 ctggggccag aagctgcgcg gacggctgga ggagatgggc agccggaccc gcgaccgcct
3541 ggatgagatg cgtgagcagc tgaggaggt gcgcaccaaa gtggaggagc agggcagcca
3601 gttgcgcctg caggccgagg gattccacgc cctcctcaaa ggctggttcg agcctctggt
3661 ggaagacata cggcgccagt gggccgggct ggtggagagg atgcagtcgg gcgtgagcat
3721 aagctcctcc acctctgcgc ccagtgataa tcagtgagtg ccctctcatc cgggcacccc
3781 cttcggggcc ccgttcctgc ccaactcccc cgcctccccc agccttagat gccctcttgg
```

-continued

```
3841 tgggccctg cttaataaag attcatcaag cttcacagca gcttctgggt gtccccggtg 3901 tgatttctca gctccagcct cagtttccct ttccttccct gcactgacca cccagttctc 3961 tgtcctgccc tctgcctgtg tgtgtctatt tgtctcttct ccccttttc tttttttttg 4021 gccgagccca tggcatgcgg aagttccccc ggccagggat tgaacccatg ccacagccgc 4081 cacaacgaag gatccttaac tactaggcca ccagggaact ccatcctttc taactctgtc 4141 tttgctttcc cttttttagc gttttagggc tgcaccctca gcatgtggaa gtccccaggc 4201 taggggtcaa attggcgcta cagctgccag cctacaccac agcccagca acgcaggatt 4261 cctcgag
```

15

ApoE *Sus scrofa*

```
LOCUS       SSU70240 4267 bp DNA linear MAM 10-AUG-
            1998
DEFINITION  Sus scrofa apolipoprotein-E (Apo-E) gene, complete cds.
ACCESSION   U70240
VERSION     U70240.1 GI: 2388608
KEYWORDS    .
SOURCE      Sus scrofa (pig)
ORGANISM    Sus scrofa
            Eukaryota; Metazoa; Chordata; Craniata; Vertebrata;
            Euteleostomi; Mammalia; Eutheria; Laurasiatheria;
            Cetartiodactyla; Suina; Suidae;
            Sus.
REFERENCE   1 (bases 1 to 4267)
AUTHORS     Ramsoondar, J. J., Rucker, E. B., Vasquez, J. C.,
            Gallagher, D. S., Grimm, D. R., Lunney, J. K., Schook,
            L. B. and Piedrahita, J. A.
TITLE       Isolation and genetic characterization of the porcine
            apolipoprotein E gene
JOURNAL     Anim. Genet. 29 (1), 43-47 (1998)
PUBMED      9682450
REFERENCE   2 (bases 1 to 4267)
AUTHORS     Ramsoondar, J. J. and Piedrahita, J. A.
TITLE       Direct Submission
JOURNAL     Submitted (10-SEP-1996) VAPH, Texas A&M University, College
            Station, TX 77843, USA
FEATURES             Location/Qualifiers
source          1 . . . 4267
                /organism="Sus scrofa"
                /mol_type="genomic DNA"
                /db_xref="taxon:9823"
gene            832 . . . 3879
                /gene="Apo-E"
mRNA            join(832 . . . 857, 1686 . . . 17282473 . . .
                2662, 3037 . . . 3879)
                /gene="Apo-E"
exon            832 . . . 857
                /gene="Apo-E"
                /number=1
intron          858 . . . 1662
                /gene="Apo-E"
                /number=1
exon            1663 . . . 1728
                /gene="Apo-E"
                /number=2
CDS             join(1686 . . . 1728, 2473 . . . 2662, 3037 . . . 3757)
                /gene="Apo-E"
                /note="plasma lipoprotein"
                /codon_start=1
                /product="apolipoprotein-E"
                /protein_id="AAC29512.1"
                /db_xref="GI:2388609"
```

SEQ ID NO: 2: *Sus scrofa* ApoE protein
/translation="MRVLWVALVVTLLAGCRTEDEPGPPPEVHVWWEEPKWQGSQPWE

QALGRFWDYLRWVQSLSDQVQEELLSTKVTQELTELIEESMKEVKAYREELEAQLGPV

TQETQARLSKELQAAQARVGADMEDVRNRLVLYRSEVHNMLGQTTEELRSRLASHLRK

-continued

LRKRLLRDTEDLQKRLAVYQAGLREGAERSVSALRERLGPLVEQGRLRAATLSTRAGQ

PLRERAEAWGQKLRGRLEEMGSRTRDRLDEMREQLEEVRTKVEEQGSQLRLQAEGFHA

LLKGWFEPLVEDIRRQWAGLVERMQSGVSISSSTSAPSDNQ"

```
SEQ ID NO: 27: Homo sapiens ApoE protein sequence
LOCUS           AF261279 5491 bp DNA linear PRI
                27-OCT-2000
DEFINITION      Homo sapiens apolipoprotein-E gene, complete cds.
ACCESSION       AF261279
VERSION         AF261279.1 GI: 11034800
KEYWORDS        .
SOURCE          Homo sapiens (human)
ORGANISM        Homo sapiens
                Eukaryota; Metazoa; Chordata; Craniata; Vertebrata;
                Euteleostomi;
                Mammalia; Eutheria; Euarchontoglires; Primates;
                Haplorrhini;
                Catarrhini; Hominidae; Homo.
REFERENCE       1 (bases 1 to 5491)
AUTHORS         Nickerson, D. A., Taylor, S. L., Fullerton, S. M., Weiss, K. M.,
                Clark, A. G., Stengard, J. H., Salomaa, V., Boerwinkle, E. and
                Sing, C. F.
TITLE           Sequence diversity and large-scale typing of SNPs in the
                human
                apolipoprotein E gene
JOURNAL         Genome Res. 10 (10), 1532-1545 (2000)
PUBMED          11042151
REFERENCE       2 (bases 1 to 5491)
AUTHORS         Nickerson, D. A.
TITLE           Direct Submission
JOURNAL         Submitted (27-APR-2000) Department of Molecular
                Biotechnology,
                University of Washington, Box 357730, Seattle, WA 98195,
                USA
FEATURES        Location/Qualifiers
source          1 . . . 5491
                /organism="Homo sapiens"
                /mol_type="genomic DNA"
                /db_xref="taxon:9606"
                /chromosome="19"
                /map="19q13.2"
repeat_region   <3 . . . >108
                /note="putative"
                /rpt_family="MIR"
                /rpt_type=dispersed
variation       73
                /frequency="0.01"
                /replace="t"
repeat_region   <207 . . . >295
                /note="putative"
                /rpt_family="MIR"
                /rpt_type=dispersed
variation       308
                /frequency="0.01"
                /replace="t"
satellite       <320 . . . >339
                /note="putative"
                /rpt_type=tandem
repeat_region   <340 . . . >637
                /note="putative"
                /rpt_family="Alu"
                /rpt_type=dispersed
variation       471
                /frequency="0.01"
                /replace="g"
variation       545
                /frequency="0.01"
                /replace="t"
variation       560
                /frequency="0.22"
                /replace="t"
variation       624
                /frequency="0.07"
                /replace="c"
```

-continued

```
satellite        <638 . . . >718
                 /note="putative"
                 /rpt_type=tandem
variation        832
                 /frequency="0.45"
                 /replace="t"
mRNA             join(1060 . . . 1094, 1855 . . . 1920, 3013 . . . 3205,
                 3786 . . . 4645)
                 /product="apolipoprotein-E"
variation        1163
                 /frequency="0.35"
                 /replace="c"
variation        1522
                 /frequency="0.01"
                 /replace="a"
variation        1575
                 /frequency="0.01"
                 /replace="t"
CDS              join(1878 . . . 1920, 3013 . . . 3205, 3786 . . . 4503)
                 /note="APOE"
                 /codon_start=1
                 /product="apolipoprotein-E"
                 /protein_id="AAG27089.1"
                 /db_xref="GI:11034801"
/translation="MKVLWAALLVTFLAGCQAKVEQAVETEPEPELRQQTEWQSGQRW

ELALGRFWDYLRWVQTLSEQVQEELLSSQVTQELRALMDETMKELKAYKSELEEQLTP

VAEETRARLSKELQAAQARLGADMEDVCGRLVQYRGEVQAMLGQSTEELRVRLASHLR

KLRKRLLRDADDLQKRLAVYQAGAREGAERGLSAIRERLGPLVEQGRVRAATVGSLAG

QPLQERAQAWGERLRARMEEMGSRTRDRLDEVKEQVAEVRAKLEEQAQQIRLQAEAFQ

ARLKSWFEPLVEDMQRQWAGLVEKVQAAVGTSAAPVPSDNH"

variation        1998
                 /frequency="0.10"
                 /replace="a"
repeat_region    <2124 . . . >2435
                 /note="putative"
                 /rpt_family="Alu"
                 /rpt_type=dispersed
variation        2440
                 /frequency="0.21"
                 /replace="a"
repeat_region    <2569 . . . >2848
                 /note="putative"
                 /rpt_family="Alu"
                 /rpt_type=dispersed
variation        2907
                 /frequency="0.01"
                 /replace="g"
variation        3106
                 /frequency="0.01"
                 /replace="c"
repeat_region    <3472 . . . >3588
                 /note="putative"
                 /rpt_family="Alu"
                 /rpt_type=dispersed
variation        3673
                 /frequency="0.01"
                 /replace="g"
variation        3701^3702
                 /frequency="0.01"
                 /replace="ct"
variation        3937
                 /frequency="0.14"
                 /replace="c"
variation        4036
                 /frequency="0.01"
                 /replace="t"
variation        4075
                 /frequency="0.07"
                 /replace="t"
repeat_region    <4755 . . . >5056
                 /note="putative"
                 /rpt_family="Alu"
                 /rpt_type=dispersed
```

```
repeat_region   <5065 . . . >5476
                /note="putative"
                /rpt_family="Alu"
                /rpt_type=dispersed
variation       5229^5230
                /frequency="0.03"
                /replace="gg"
variation       5229
                /frequency="0.07"
                /replace="t"
variation       5229^5230
                /frequency="0.40"
                /replace="g"
variation       5230
                /frequency="0.13"
                /replace=""
variation       5361
                /frequency="0.06"
                /replace="c"
```

SEQ ID NO: 28: *Homo sapiens* ApoE gene sequence

```
   1 cttgatgctc agagaggaca agtcatttgc ccaaggtcac acagctggca actggcagag
  61 ccaggattca cgccctggca atttgactcc agaatcctaa ccttaaccca gaagcacggc
 121 ttcaagcccc tggaaaccac aatacctgtg gcagccaggg ggaggtgctg aatctcatt
 181 tcacatgtgg ggagggggct cccctgtgct caaggtcaca accaaagagg aagctgtgat
 241 taaaacccag gtcccatttg caaagcctcg acttttagca ggtgcatcat actgttccca
 301 cccctcccat cccacttctg tccagccgcc tagccccact ttcttttttt tctttttttg
 361 agacagtctc cctcttgctg aggctggagt gcagtggcga gatctcggct cactgtaacc
 421 tccgcctccc gggttcaagc gattctcctg cctcagcctc ccaagtagct aggattacag
 481 gcgcccgcca ccacgcctgg ctaactttg tattttagt agagatgggg tttcaccatg
 541 ttggccaggc tggtctcaaa ctcctgacct taagtgattc gcccactgtg gcctcccaaa
 601 gtgctgggat tacaggcgtg agctaccgcc cccagcccct cccatcccac ttctgtccag
 661 cccctagcc ctactttctt tctgggatcc aggagtccag atccccagcc ccctctccag
 721 attacattca tccaggcaca ggaaaggaca gggtcaggaa aggaggactc tgggcggcag
 781 cctccacatt cccttccac gcttggcccc cagaatggag gagggtgtct ggattactgg
 841 gcgaggtgtc ctcccttcct ggggactgtg gggggtggtc aaaagacctc tatgccccac
 901 ctccttcctc cctctgccct gctgtgcctg gggcagggg agaacagccc acctcgtgac
 961 tgggggctgg cccagcccgc cctatccctg ggggagggg cgggacaggg ggagccctat
1021 aattggacaa gtctgggatc cttgagtcct actcagcccc agcggagtg aaggacgtcc
1081 ttccccagga gccggtgaga agcgcagtcg ggggcacggg gatgagctca ggggcctcta
1141 gaaagagctg ggaccctggg aagccctggc ctccaggtag tctcaggaga gctactcggg
1201 gtcgggcttg gggagaggag gagcgggggt gaggcaagca gcagggact ggacctggga
1261 agggctgggc agcagagacg acccgacccg ctagaaggtg gggtggggag agcagctgga
1321 ctgggatgta agccatagca ggactccacg agttgtcact atcatttatc gagcacctac
1381 tgggtgtccc cagtgtcctc agatctccat aactgggag ccaggggcag cgacacggta
1441 gctagccgtc gattggagaa ctttaaaatg aggactgaat tagctcataa atggaacacg
1501 gcgcttaact gtgaggttgg agcttagaat gtgaagggag aatgaggaat gcgagactgg
1561 gactgagatg gaaccggcgc tgggagggg gtgggggat ggaatttgaa ccccgggaga
1621 ggaagatgga attttctatg gaggccgacc tgggatggg gagataagag aagaccagga
1681 gggagttaaa tagggaatgg gttgggggcg gcttggtaaa tgtgctggga ttaggctgtt
1741 gcagataatg caacaaggct tggaaggcta acctggggtg aggccgggtt ggggccgggc
1801 tgggggtggg aggagtcctc actggcggtt gattgacagt ttctccttcc ccagactggc
```

-continued

```
1861   caatcacagg caggaagatg aaggttctgt gggctgcgtt gctggtcaca ttcctggcag
1921   gtatggggc ggggcttgct cggttccccc cgctcctccc cctctcatcc tcacctcaac
1981   ctcctggccc cattcaggca gaccctgggc cccctcttct gaggcttctg tgctgcttcc
2041   tggctctgaa cagcgatttg acgctctctg ggcctcggtt tccccatcc ttgagatagg
2101   agttagaagt tgttttgttg ttgttgtttg ttgttgttgt tttgtttttt tgagatgaag
2161   tctcgctctg tcgcccaggc tggagtgcag tggcgggatc tcggctcact gcaagctccg
2221   cctcccaggt ccacgccatt ctcctgcctc agcctcccaa gtagctggga ctacaggcac
2281   atgccaccac acccgactaa cttttttgta ttttcagtag agacggggtt tcaccatgtt
2341   ggccaggctg gtctggaact cctgacctca ggtgatctgc ccgtttcgat ctcccaaagt
2401   gctgggatta caggcgtgag ccaccgcacc tggctgggag ttagaggttt ctaatgcatt
2461   gcaggcagat agtgaatacc agacacgggg cagctgtgat ctttattctc catcaccccc
2521   acacagccct gcctggggca cacaaggaca ctcaatacat gcttttccgc tgggcgcggt
2581   ggctcacccc tgtaatccca gcactttggg aggccaaggt gggaggatca cttgagccca
2641   ggagttcaac accagcctgg gcaacatagt gagaccctgt ctctactaaa aatacaaaaa
2701   ttagccaggc atggtgccac acacctgtgc tctcagctac tcaggaggct gaggcaggag
2761   gatcgcttga gcccagaagg tcaaggttgc agtgaaccat gttcaggccc ctgcactcca
2821   gcctgggtga cagagcaaga ccctgtttat aaatacataa tgctttccaa gtgattaaac
2881   cgactccccc ctcaccctgc ccaccatggc tccaaagaag catttgtgga gcaccttctg
2941   tgtgccccta ggtactagat gcctggacgg ggtcagaagg accctgaccc accttgaact
3001   tgttccacac aggatgccag gccaaggtgg agcaagcggt ggagacagag ccggagcccg
3061   agctgcgcca gcagaccgag tggcagagcg gccagcgctg ggaactggca ctgggtcgct
3121   tttgggatta cctgcgctgg gtgcagacac tgtctgagca ggtgcaggag gagctgctca
3181   gctcccaggt cacccaggaa ctgaggtgag tgtccccatc ctggcccttg accctcctgg
3241   tgggcggcta tacctcccca ggtccaggtt tcattctgcc cctgtcgcta agtcttgggg
3301   ggcctgggtc tctgctggtt ctagcttcct cttcccattt ctgactcctg gctttagctc
3361   tctggaattc tctctctcag ctttgtctct ctctcttccc ttctgactca gtctctcaca
3421   ctcgtcctgg ctctgtctct gtccttccct agctcttta tatagagaca gagagatggg
3481   gtctcactgt gttgcccagg ctggtcttga acttctgggc tcaagcgatc ctcccgcctc
3541   ggcctcccaa agtgctggga ttagaggcat gagccacctt gcccggcctc ctagctcctt
3601   cttcgtctct gcctctgccc tctgcatctg ctctctgcat ctgtctctgt ctccttctct
3661   cggcctctgc cccgttcctt ctctccctct tgggtctctc tggctcatcc ccatctcgcc
3721   cgccccatcc cagcccttct ccccgcctcc cactgtgcga caccctcccg ccctctcggc
3781   cgcagggcgc tgatggacga gaccatgaag gagttgaagg cctacaaatc ggaactggag
3841   gaacaactga ccccggtggc ggaggagacg cgggcacggc tgtccaagga gctgcaggcg
3901   gcgcaggccc ggctgggcgc ggacatggag gacgtgtgcg gccgcctggt gcagtaccgc
3961   ggcgaggtgc aggccatgct cggccagagc accgaggagc tgcgggtgcg cctcgcctcc
4021   cacctgcgca agctgcgtaa gcggctcctc cgcgatgccg atgacctgca gaagcgcctg
4081   gcagtgtacc aggccggggc ccgcgagggc gccgagcgcg gcctcagcgc catccgcgag
4141   cgcctggggc ccctggtgga acagggccgc gtgcgggccg ccactgtggg ctccctggcc
4201   ggccagccgc tacaggagcg ggcccaggcc tggggcgagc ggctgcgcgc gcggatggag
```

```
4261  gagatgggca gccggacccg cgaccgcctg gacgaggtga aggagcaggt ggcggaggtg 4321  cgcgccaagc tggaggagca ggcccagcag atacgcctgc aggccgaggc cttccaggcc 4381  cgcctcaaga gctggttcga gcccctggtg aagacatgca gcgccagtg ggccgggctg 4441  gtggagaagg tgcaggctgc cgtgggcacc agcgccgccc ctgtgccag cgacaatcac 4501  tgaacgccga agcctgcagc catgcgaccc cacgccaccc cgtgcctcct gcctccgcgc 4561  agcctgcagc gggagaccct gtccccgccc cagccgtcct cctggggtgg accctagttt 4621  aataaagatt caccaagttt cacgcatctg ctggcctccc cctgtgattt cctctaagcc 4681  ccagcctcag tttctctttc tgcccacata ctggccacac aattctcagc cccctcctct 4741  ccatctgtgt ctgtgtgtat ctttctctct gccctttttt tttttttag acggagtctg 4801  gctctgtcac ccaggctaga gtgcagtggc acgatcttgg ctcactgcaa cctctgcctc 4861  ttgggttcaa gcgattctgc tgcctcagta gctgggatta caggctcaca ccaccacacc 4921  cggctaattt ttgtattttt agtagagacg agctttcacc atgttggcca ggcaggtctc 4981  aaactcctga ccaagtgatc caccgccgg cctcccaaag tgctgagatt acaggcctga 5041  gccaccatgc ccggcctctg cccctctttc tttttagg ggcagggaaa ggtctcaccc 5101  tgtcacccgc catcacagct cactgcagcc tccacctcct ggactcaagt gataagtgat 5161  cctcccgcct cagccttcc agtagctgag actacaggcg cataccacta ggattaattt 5221  gggggggggg tggtgtgtgt ggagatgggg tctggctttg ttggccaggc tgatgtggaa 5281  ttcctgggct caagcgatac tcccaccttg gcctcctgag tagctgagac tactggctag 5341  caccaccaca cccagctttt tattattatt tgtagagaca aggtctcaat atgttgccca 5401  ggctagtctc aaaccctgg gctcaagaga tcctccgcca tcggcctccc aaagtgctgg 5461  gattccaggc atgggctccg agcggcctgc c
```

SEQ ID NO: 29: *Homo sapiens* ApoE gene

```
   1  gggatccttg agtcctactc agccccagcg gaggtgaagg acgtccttcc ccaggagccg 61  actggccaat cacaggcagg aagatgaagg ttctgtgggc tgcgttgctg gtcacattcc 121  tggcaggatg ccaggccaag gtggagcaag cggtggagac agagccgag cccgagctgc 181  gccagcagac cgagtggcag agcggccagc gctgggaact ggcactgggt cgcttttggg 241  attacctgcg ctgggtgcag acactgtctg agcaggtgca ggaggagctg ctcagctccc 301  aggtcaccca ggaactgagg gcgctgatgg acgagaccat gaaggagttg aaggcctaca 361  aatcggaact ggaggaacaa ctgacccgg tggcggagga cgcgggca cggctgtcca 421  aggagctgca ggcggcgcag gcccggctgg gcgcggacat ggaggacgtg tgcggccgcc 481  tggtgcagta ccgcggcgag gtgcaggcca tgctcggcca gagcaccgag gagctgcggg 541  tgcgcctcgc ctcccacctg cgcaagctgc gtaagcggct cctccgcgat gccgatgacc 601  tgcagaagcg cctggcagtg taccaggccg ggcccgcga gggcgccgag cgcggcctca 661  gcgccatccg cgagcgcctg gggcccctgg tggaacaggg ccgcgtgcgg gccgccactg 721  tgggctccct ggccggccag ccgctacagg agcgggccca ggcctggggc gagcggctgc 781  gcgcgcggat ggaggagatg ggcagccgga cccgcgaccg cctggacgag gtgaaggagc 841  aggtggcgga ggtgcgcgcc aagctggagg agcaggccca gcagatacgc ctgcaggccg 901  aggccttcca ggcccgcctc aagagctggt tcgagcccct ggtggaagac atgcagcgcc 961  agtgggccgg gctggtggag aaggtgcagg ctgccgtggg caccagcgcc gcccctgtgc
```

-continued

```
1021    ccagcgacaa tcactgaacg ccgaagcctg cagccatgcg accccacgcc acccgtgcc 1081    tcctgcctcc gcgcagcctg cagcgggaga ccctgtcccc gcccagccg tcctcctggg 1141    gtggacccta gtttaataaa gattcaccaa gtttcacgca aaaaaaaaaa aaaaaaaaa 1201    aaaaaaaaaa aaaaaaaaaa aaa
```

SEQ ID NO: 3
LDL Receptor cDNA Sequence

```
Sus scrofa low density lipoprotein receptor (LDLR) mRNA, LDLR-N
allele, partial cds.
ACCESSION   AF065990
VERSION     AF065990.1 GI: 3153894
KEYWORDS    .
SOURCE      Sus scrofa (pig)
ORGANISM    Sus scrofa
            Eukaryota; Metazoa; Chordata; Craniata; Vertebrata;
            Euteleostomi;
            Mammalia; Eutheria; Laurasiatheria; Cetartiodactyla;
            Suina; Suidae;
            Sus.
REFERENCE   1 (bases 1 to 2403)
AUTHORS     Hasler-Rapacz, J., Ellegren, H., Fridolfsson, A. K.,
            Kirkpatrick, B.,
            Kirk, S., Andersson, L. and Rapacz, J.
TITLE       Identification of a mutation in the low density
            lipoprotein
            receptor gene associated with recessive familial
            hypercholesterolemia in swine
JOURNAL     Am. J. Med. Genet. 76 (5), 379-386 (1998)
PUBMED      9556295
REFERENCE   2 (bases 1 to 2403)
AUTHORS     Hasler-Rapacz, J., Ellegren, H., Fridolfsson, A. K.,
            Kirkpatrick, B.,
            Kirk, S., Andersson, L. and Rapacz, J.
TITLE       Direct Submission
JOURNAL     Submitted (16-MAY-1998) Genetics & Animal Science,
            University of
            Wisconsin, 1675 Observatory Drive, Madison, WI 53706, USA
FEATURES    Location/Qualifiers
source      1 . . . 2403
            /organism="Sus scrofa"
            /mol_type="mRNA"
            /db_xref="taxon:9823"
            /chromosome="2"
            /map="2q; near the centromere"
            /tissue_type="liver"
gene        <1 . . . >2403
            /gene="LDLR"
            /allele="N (normal)"
CDS         <1 . . . >2403
            /gene="LDLR"
            /allele="N (normal)"
            /note="LDL-receptor; normolipidemic"
            /codon_start=1
            /product="low density lipoprotein receptor"
            /protein_id="AAC17444.1"
            /db_xref="GI:3153895"

1 ttccagtgcc aagacgggaa atgcatctcc tacaagtgga tttgtgatgg gaacaccgag 61 tgcaaggacg ggtccgatga gtccctggag acgtgcatgt ctgtcacctg caagataggg 121 gactttagct gtggggccg tgtcaaccgc tgcattcctg agtcttggag gtgtgacggt 181 cagcaggact gcgagaatgg ctcagatgag gaaggctgtt ccccaagac gtgctcccaa 241 gatgagttcc gctgccagga cggcaagtgc atcgccccaa agtttgtctg tgactcggac 301 cgggactgcc tggacggctc ggatgaagca tcctgcccca cccacctg tggccccgcc 361 agcttccagt gcaacagctc cacctgcatc cctgagctgt gggctgtga tggtgatcct 421 gactgcgagg acggctcaga cgagtggcca cagcactgca ggagccacag ctcatcactc 481 cccgagagga gcaacaaccc ctgctcagcc ctcgagttcc actgccacag tggcgagtgc
```

-continued

```
 541 atccactcca gctggcgctg cgacggagac actgactgca aggacaagtc tgacgaggag 601 aactgcgatg tggccacgtg ccggcctgac gagttccagt gctcagacgg gacctgcatc 661 catggtagcc ggcagtgcga cagggaatat gactgcaagg acatgagcga cgagcagggc 721 tgtgtcaatg cgactctgtg cgaggggccc aacaagttca gtgtcaaag cggcgagtgc 781 atctccttgg acaaagtgtg caactcagtc agggactgcc gggactggtc agacgagccc 841 ctcaaggagt gtgggaccaa cgagtgtctg acaacaagg gtggctgctc ccatatctgc 901 aatgacctca agatcggcta tgagtgcctc tgtcccgagg gcttccagct ggtggataag 961 cacagatgcg aagatatcga cgagtgtcag gacccagacg cctgcagcca gatctgcgtg 1021 aacctcgagg gcagctacaa gtgccagtgt gaggagggct tccagctgga gcctctcacc 1081 aaggcctgca aggccatagg caccatcgcc tacctcttct tcaccaaccg ccacgaggtg 1141 aggaagatga ccctggaccg tagtgagtac accagcctca tccccaacct gaagaacgtg 1201 gtcgctctgg acactgaggt ggccagcaat agaatctact ggtctgacct gtctcagagg 1261 aagatctaca gtacccagat cgacagggcc cccagctttt cctcctatga caccattatt 1321 ggcgaagatc tccaggcccc cgatgggctg gcggtggact ggatccacag caacatatac 1381 tggactgact ccatcctggg cactgtctcc gtggctgaca ccaagggcgt gaagaggaag 1441 actctcttcc aagagaaagg ctccaagcca cgggccattg tggtggaccc tgtccatggc 1501 ttcatgtact ggactgattg ggaaccccc gccaagatca agaagggcgg cctgaacgga 1561 gtggacgtct actcgctggt gacggaggac atccagtggc ccaatggcat caccctggat 1621 ctttctggcg gccgccttta ctgggtcgac tccaagctcc actccatctc cagcatcgat 1681 gtcaacgggg gaaccggaa gaccgtcctg gaggacaaga cgaagctggc gccccttc 1741 tccttggcca ttttgagga taaagtatt tggacagata taatcaacga gccatttc 1801 agtgccaacc gcctcacagg ctcggacata catttgatgg cagaaaacct gttgtctcca 1861 gaggacattg tccttttcca caacctcaca cagccgagg gggtgaactg gtgtgaaagg 1921 accgccctcc aaaacggtgg ctgccagtac ctgtgtctgc agctccaca gatcaaccca 1981 cgctcgccga agttcacctg tgcctgcccg gatggcatgc tgttggccaa ggacatgagg 2041 agctgtctca cagagactga acctgcagga accacccagg gaccttccat ggtcaactcg 2101 acagctgtgg ggcaaaagca caccgccagc tctgagctca ccacagccga gtcagtgacg 2161 atgtcccaac atgccctggg cgacgttgct ggccgaggag tcactgagaa gccccagagc 2221 gtgggtgctc tgtacattgt cctccccatt gcactgctca cctcctcttt cttcggaacc 2281 ttcctcctct ggaagaactg gaggcttaag agcatcaaca gcattaactt cgacaaccct 2341 gtgtaccaga gaccacggaa agacgaggtc cacatctgcc gcagccagga cggctacacc 2401 tac
```

SEQ ID NO: 4
Porcine LDL Amino Acid Sequence

FQCQDGKCISYKWICDGNTECKDGSDESLETCMSVTCKIGDFSC
GGRVNRCIPESWRCDGQQDCENGSDEEGCSPKTCSQDEFRCQDGKCIAPK
FVCDSDRDCLDGSDEASCPTPTCGPASFQCNSSTCIPELWACDGDPDCED
GSDEWPQHCRSHSSSLPERSNNPCSALEFHCHSGECIHSSWRCDGDTDCK
DKSDEENCDVATCRPDEFQCSDGTCIHGSRQCDREYDCKDMSDEQGCVNA
TLCEGPNKFKCQSGECISLDKVCNSVRDCRDWSDEPLKECGTNECLDNKG
GCSHICNDLKIGYECLCPEGFQLVDKHRCEDIDECQDPDACSQICVNLEG
SYKCQCEEGFQLEPLTKACKAIGTIAYLFFTNRHEVRKMTLDRSEYTSLI
PNLKNVVALDTEVASNRIYWSDLSQRKIYSTQIDRAPSFSSYDTIIGEDL
QAPDGLAVDWIHSNIYWTDSILGTVSVADTKGVKRKTLFQEKGSKPRAIV
VDPVHGFMYWTDWGTPAKIKKGGLNGVDVYSLVTEDIQWPNGITLDLSGG
RLYWVDSKLHSISSIDVNGGNRKTVLEDKTKLAHPFSLAIFEDKVFWTDI

-continued

INEAIFSANRLTGSDIHLMAENLLSPEDIVLFHNLTQPRGVNWCERTALQ
NGGCQYLCLPAPQINPRSPKFTCACPDGMLLAKDMRSCLTETEPAGTTQG
PSMVNSTAVGPKHTASSELTTAESVTMSQHALGDVAGRGVTEKPQSVGAL
YIVLPIALLILLFFGTFLLWKNWRLKSINSINFDNPVYQKTTEDEVHICR
SQDGYTY

SEQ ID NO: 30: Human LDL receptor genomic sequence Chromosome 19. Coding sequence underlined

```
   1 gccccgagtg caatcgcggg aagccagggt ttccagctag gacacagcag gtcgtgatcc
  61 gggtcgggac actgcctggc agaggctgcg agcatggggc cctggggctg gaaattgcgc
 121 tggaccgtcg ccttgctcct cgccgcggcg gggactgcag gtaaggcttg ctccaggcgc
 181 cagaataggt tgagagggag ccccgggg gcccttggga atttattttt ttgggtacaa
 241 ataatcactc catccctggg agacttgtgg ggtaatggca cggggtcctt cccaaacggc
 301 tggaggggc gctggagggg ggcgctgagg ggagcgcgag ggtcgggagg agtctgaggg
 361 atttaaggga aacggggcac cgctgtcccc caagtctcca cagggtgagg gaccgcatct
 421 tctttgagac ggagtctagc tctgtcgccc aggatggagt gcagtggcac gatctcagct
 481 cactgcaacc tccgcctccc gggtttaagc gagtctcctc tctcagcctc ccgaatagct
 541 gggattacag gcgcccaacc accacgcccg cctaattttt gtattttag tagagacggg
 601 ttttcaccat tttggccagg ctggtctcga accccgacct caggtgatct gcccaaaagt
 661 gctgggatta caggcgtcag ccaccgcgcc cggccgggac cctctcttct aactcggagc
 721 tgggtgtggg gacctccagt cctaaaacaa gggatcactc ccaccccgc cttaagtcct
 781 tctggggcg agggcgactg gagacccgga tgtccagcct ggaggtcacc gcgggctcag
 841 gggtcccgat ccgctttgcg cgaccccagg gcgccactgc catcctgagt tgggtgcagt
 901 cccgggattc cgccgcgtgc tccgggacgg gggccacccc ctcccgcccc tgccccgcc
 961 cctttggccc gccccccgaa ttccattggg tgtagtccaa caggccaccc tcgagccact
1021 ccccttgtcc aatgtgaggc ggtggaggcg gaggcgggcg tcgggaggac ggggcttgtg
1081 tacgagcggg gcggggctgg cgcggaagtc tgagcctcac cttgtccggg gcgaggcgga
1141 tgcaggggag gcctggcgtt cctccgcggt tcctgtcaca aaggcgacga caagtcccgg
1201 gtccccggag ccgcctccgc gacatacacg agtcgccctc cgttatcctg ggccctcctg
1261 gcgaagtccc cggtttccgc tgtgctctgt ggcgacacct ccgtccccac cttgtcctgg
1321 ggggcgccct cgccccacca gccccgatca agttcacaga ggggccccg gccaccctca
1381 aggcctcggt tccttacgag gttgaaacgt tgcctcagaa tctccccgcc cctccttggt
1441 ctgcagccga gatcttcagc cacggtgggg cagctatccc ccgggaccga ccccctgggg
1501 tggcctcgct tcttcagagg ctgtgaatgc cttcggttca gctgtccaag cggcgatttt
1561 tcctctgggt gaaatggatt agatttaga tttccacaag aggctggtta gtgcatgatc
1621 ctgagttaga gcttttagg tggctttaaa ttagttgcag agagacagcc tcgccctaga
1681 caacagctac atggcccttt ccctcctgag aaccagccta gcctagaaaa ggattgggat
1741 tgcctgatga acacaaggat tgcaggaaac ttttttttta attggcaagg gggttggctt
1801 tgactggatg gagagctttg aactgccttg aaattcacgc tgtaactaac acaccagttt
1861 cctctgggag gccagagagg gagggagggt gtaatgaaat acggatgatt gttcttttat
1921 ttttatttac ttatttattt tttaactttt gtagagatg aggtctcgct tggttgctca
1981 ggctggtctt gaactcctgg cctcaagcga tcctcctacc tcagcctccc aaagtgttgg
2041 gattacagga gtgagccacc gcgcccacc ggggatgatg atgattgcaa acattctgcc
```

-continued

```
2101  actcagtttt acaaaagaaa gagaggcact ggattaatgt gtatctcact caccaatcaa
2161  cctcttcctt aagagaaaat gttaaggaag tcttaggcaa ggccttgttt gttcatcact
2221  ttagtttctc tctcccggga tggctgagaa tgtgatgttt cctctgttgt caaggagact
2281  acacccctga tgttttcctc cagacttctg agagctggtg tgtgtttcta gcactttcta
2341  gctgcaccac ctcacgctgt agctggcttc aaggcatatc caggggggag tttcttgtcc
2401  atttccttta caaagggaag ttgttggaat ctgaaccgca agccttcact tagaccaaaa
2461  tcaggcaaca gcggtgagcg cagctccaaa cgtgtcaatg actcacccaa atttgagtaa
2521  gggagttggc tgctttaacg agccgcaggg tgattccctt gtcatttccg gaaataccta
2581  tcttccaggg aacactggga aaaacaggg agacctttgt tgagacagaa aacctgtagg
2641  ggaattctgt tcctcattcc tgctcttatc tgtagacttc ctccctgata agatccaatt
2701  ctagatgggt cggttgctcc ttgctttgat gggtgctttg atgggcttta ttattattat
2761  tattattatt attattattt tgatgggctt tttgatgtcc cttttccttc cacactctgt
2821  cccaactgtc aagcaaatag cctttgttg ctaagagact gcagatgtaa ccgaccagca
2881  gcaaacagtg agtcaggctc tctcttccgg aagcaaaatc aattgctgag atcactctgg
2941  ggaaaatacc caccttattt ggaaagaagc actgatcaat tgatgtctat ttttttttt
3001  tttgagttgg agtctcgccc tgtcacccag gctggagtgc aatggcataa tctcgcctca
3061  ctgcaatccc cgcctccgg gttccagcaa ttctcctgcc tcagcctcct gagtagctgg
3121  aattataggc gcctgccaca cacccggct aatttttgta tttgtagtag atgggggtt
3181  tcaccacgtt ggccaggctg gtctcgaact cctgacctcg tgatccaccc gcctcagcct
3241  cccaaagtcc aaggattgca ggcgtgaccc actgtgccag ccaatcaatt gatttctcat
3301  tcattttcag ctggctctgt tcccttaagc cagggggattt tcgtttgttt gtttccccttt
3361  caaggaaatg attctagcta cagttttgat ttccttgtac aactgttttc agtagcacag
3421  ggaaagaaaa catcgaaagc attcaccacc tcatttgtgt gctgggggaa aaagcagaaa
3481  tgtgtattct ctttttttgt ttcgatgacc ttgttcctga cttgttactc gtgacttgag
3541  agatcagagg gctagaggac tagaatttat agaggtgttt ttttgtttg tttattttg
3601  ttcgagttgc ccaggctgga gtgcagtggc gcaatctcgg ctcactgcaa cctctgcctc
3661  ccaggttcaa gcgattcttc ggcctcagcc tcctgagtag ctggaactac aggcgcccgc
3721  caccacaccc agctaatttt tgtattttc agtagagatg ggatttcacc atattggtca
3781  agctggcctc gaactcctga cctcgtgatc cacccgcctc agtttcccaa agtgctggga
3841  gtacaggcgt gagccgccgt gcccggcctt tttgtgtttt tgtgttttg agaggagctc
3901  attgcttttt aggcttccct agcgtgagaa aatctgggga tccatgctct agtttacttc
3961  ctttttttt tttttttga gatggagtct cgcttagatt gcctaatctc agctcattgc
4021  aacttctgcc tccggggttc aagggattct cgtgtctcag cctcctgggt agctaggata
4081  cgggcacccg ctaccatgcc tggctaattt tgtactttta gtagagacag ggtttcgcca
4141  cgttggccag gctggtctcg aactcctgac ctcaggtgag ccgcctgcct tggcctccca
4201  aagtgctgag attacaggcg tgagccaccg cgcttggcct aatttgcttt tctgaaatt
4261  caaatggtct aatatgaaaa acgccaacct tgcttgaaag aataagaaag aggtgcggtt
4321  tcgttgggcc gttgatgttt ggaacaggac tggttttgtc cccttgctcg gaaagggcag
4381  caactgtgag gacagctccc tgacgtgctc tcactcagca ctgttccgtt cctgagcact
4441  gtccccacta gctaggccaa gggagctcat ttggcaggca actgctgtct ggctgcgcct
4501  gtggcagtaa aatctgcctt tattttttgg aggcagggtc ttgccctgtc gctcaggctg
```

-continued

```
4561 aagtgtgcag ttatagctca ctgcagcctc cagcttctgt actcaactga tcctcctctc 4621 tcagcctcct gagtagctgg gactatacgc acgtgttacc actcccacct cagtttgttt 4681 gtttatttat ttatttattt atttattgag atggagtttt gctcttgctg cccaggctgg 4741 agtgcaatgg cgcgatctcg gctcaccgca acctccacct cctggttcaa gcgattctcc 4801 tgcctcagcc tcctgagtag ctgggattac aggcatgcac caccacgccc ggctaatttt 4861 gtattttttcg tagagatggg gtttctccac attggttcag gctgttctcg aactcccaac 4921 ctcaggtgat ccacccgcct cagcctccca aagtgctggg attataggcg tgagcccccg 4981 aacccggcca ctcccagcta agtttaaatt tttgtttgt ttgttcgttt gttttttattt 5041 tttgagacag agtctcccgc ccaggctgga gcgcagatca ctgcatcctt gacctcccag 5101 gcttaagcca tcctccccac tcagcctccc aagtagctgg gattacaggt gtgtgccact 5161 atgcttggct aagttgtgta ttttttgtag atgggggtt caagggattc tcgctttgtt 5221 gcctcggttg gtctcaaact cctgggctca gcagtcctc cctcctcagc ctcccaaggt 5281 gctggggaaa tccacttttg aaacattgtc tggagagttg cccaggtggt agatcacaga 5341 aataggtcat cgtggggtcc ttcccatggg tgcagtcttg agccacctgt ggccagcaaa 5401 tatttggaga ataatagtca ggggagagct tgaggtccag ggaaaggttt tgttttttctt 5461 cagggaaagg ttttttattgt tctttatccc tccttaaagg accttcaggt gttactgaca 5521 ttcccggtct acccagtggc acatttagtt tgtaagctgg gccctcgtac agaggtaggg 5581 aggtgagagc attggattag tggtcaccaa agctgcggtc acctagtggg gtgatcagag 5641 gctcctccct taagatcttg attgccaacg cctctggccc aactttcctt tttatttatc 5701 gcaagcctcc tggaatctca attgcttttt gcccacccgg tgtgtcagca caagaaatga 5761 gtcatttcct cctttaagca cagttgaaat tgagctgtga gtcagtgagg tgtgtacgat 5821 attgtcaaag cggggtgtgt acagtattga cagatctgta gttgggcaag agaattatca 5881 gagtttgtga ccacagcaga ttccaaagct cgactcattt tcttctctct tccttccctt 5941 ttttctttttc ttttttttttt tttttttgac agagtctcgc tctgttgccc aggctggagt 6001 gcagtggcac aatctgggct cactgcagcc cctgcctcct gggttcaaat gattctcatg 6061 tttcagcctc ccgagtagct gcaattacag gcattcgggt tcaagtgatt ctcctgcctc 6121 agccacctga gcagctggga ttacaggcgc ccgccaccac gcccggctaa ttttttgtatt 6181 tttagtagag acggggtttc accatgttgg ccaggctggt ctcgaactcc tgaactcagg 6241 tgatccgccc acttcggcct cccaaagtgc tgagattaca gacgtgagtc accgcgccca 6301 gcctgttctg ttctttaatt ctcaaaacac cctctaggaa gtagagactg ccattctccc 6361 ccattttaca gatcaggaaa ctgagtccca gaaggattta gtcagttacc caagttgttc 6421 tagttaaatg gcctggaaag ccagtgaagc ccaggattgt ctatctaacc cccttactac 6481 tctaactttc agggaatcca catgaatgtg ctgggtcaac catcaaagtt gaaatggata 6541 aaggggggctg gatgcggtgg ctgatgcctg taatcctagc actttgggag gccgagatgg 6601 gtgggtggat tgcttgagcc caagagtttg agaccagcct gggcaacata gtgagacacc 6661 tgtctctgca aaaataaat aaaaagttag ctgagtgtga tggtgcaccc ctctagtcac 6721 agctgttgag ttaggcttag gcaggaggat cgcatgaacc tgggaggtgg aggcggccgt 6781 gagcctcagt catgccactg cactccaacc tgggcaacag agtgaaagcc ggtgtccgaa 6841 agagaaagaa aaaaagacat agatacatct tttaaagtta ggttgtatgt taattaccta 6901 caactcagtt tcaactgtgc ttaaaggagg aaatgactca tttcttgcta catatcaaat
```

```
6961 tagcccaaaa tgtagtggct taaaacaaca catttatgat ttctcagttt ttgcgtgtca
7021 ggaatttgga agcagcacag ctagacggtt ccagctcagg gtctctcatg aagttgcaat
7081 caaaatattg gcaggagaga aaaacatatt ttcagaagct gcaggcatag gaagacttgg
7141 ctggggttga aggatccact tccaagatgg cgcactcagt ggctcttggc tggaggcctc
7201 agttccctgc tgcgtggagc tctccctcca gctgcttgag tggactcatg acatgcagct
7261 ggcctcccct ggagcagtcg atccaacaat gagcatggcc atgaactagg ctcagaagcc
7321 actccctgtc gtctctacat tttcctatca gaagcaagtc attaaaagtc cagtgccact
7381 ccagggggaga cgaattaggc tctgccttct gaaaggatta tcacagaaga tgcggtccta
7441 tattcttttt ttaaaattat tctttttttt attttgtaga gatggggtct tggtatgttg
7501 cctaggccag tctggaattc ctgggctcaa acaatcctgt ctctgcctcc caaagtgttg
7561 ggattacagg catgagccac tgcacctggt catgtggtca tattttcttt ttctttttt
7621 ttttttttg agacagagtc tctgtcgccc aggctggagt atggtggcgt gatctcagtt
7681 cactgcagcc tccgcctccc gggttcaagc gattctcctg cctcagcctc ctgagtagct
7741 gggattacag gcgcccgcca acatgcccag ctaattttt tagtagagat ggggtttcac
7801 catgttagcc aggatggtct cgatctcctg atttggtgat ccgcccacct tggcctccca
7861 aagtttcaac catcgatcag aacttattga tgtacttatg tagctaggca cggtggcgcg
7921 tgcctgtaat cccagctact tggaagggtt aaggcaggag aatcgcttga acctgggagg
7981 cagaggttac agtgagtcaa gatcatacca ttgcactcca gtctgggcaa cagaatgaga
8041 ctctgtctca aaaacaaaaa acaaaccctt gtatgtgatt ttcctggata gcatctgtta
8101 catcttcaca aagataaaaa gtcagacttg gctgggcatg gtggctcaca cctgtaatcc
8161 cagcactgag aggctgaggc aggcagatca cttgaggtca ggaatttgag accaggctgg
8221 gcagcatggt gaaaccccgt ctctacaaaa aatacaaaaa ttagccgggt gtggtgtcac
8281 gcacctgtat tcccaagcta ctcaggaagc taaggcagga gaatacttg aacccagagg
8341 tggaggtttg cagtgagttg agattgtgcc attgcactcc agcctgggcg acagagtgag
8401 actctgtgtc aaaaataaaa taaaataaaa ttttaaaaaa ggcagatttt tttttcttct
8461 tggtattgtt accttattat agtaataata agtgcatagt gcatgctgag ataagcaatc
8521 ataatttgtt attgcggccg ggcatggtgg ctccagccta taatcccagc actttggtca
8581 ggagttcaag gccagcctgg ccaatatagt gaaactccat ctctactaaa atacaagaaa
8641 ttacctgggc atggtggcag ttgctggtga tccccagcta cttgggaggc tgaggcagga
8701 gaatcgcttg aacctgggaa gcagaggttg cagtgagcca agattgcacc actgcactcc
8761 agcctgggtg acagagtgag actctgtctg aaaataataa taataataat ttgttattgc
8821 ttttattgcc ttagtttaca tagggaatca aagtttatac tttgatttat aaaagttgct
8881 ttgattctag ttcacagaac cagaatcttt catataaagg tattagaggg cccagtgtgg
8941 tggctcatgc ctgtaatccc agcatattgg gaggctgagg agggaggatc actttaggag
9001 tttgaggcca gcctaggcaa catagtgaga ccttgtctct acaaaaaatt ccaacattag
9061 ctgggcatgg tggcatgtgc ctgtagtccc atttatttgg ggggctgagg caggaggatc
9121 acttgagccc acgaggttca atccaggttg cagtaagcca tgatcctgcc actgcactcc
9181 agtttgggta acagagcgaa gctatgtctc aaaaaagaa aaaaaagta ttctaaatcc
9241 aaatttaata tataaaacta aatgcaggcc aagtgtggtg gcatatacct ataatcacaa
9301 cactttggga ggctgaggtg ggaggattgc ttgagcccaa gagttcaaga ccagcctagg
9361 taacacagta agaccccatc tctacaaaaa gtagaaaaat tagcctggca tggtggtgag
```

-continued

```
 9421 tgcttttaat cccaactact taggggggctg agatgggaag attgcttgag cctcagagtt
 9481 tgaggctgca gtgggccgtg atcgctccac tgatcgctct aaagtgagac cctgtctcaa
 9541 aaaaaaagaa aatagaagaa aactaaatac attcaataag actttgatct cttttccaag
 9601 gtgtaaatat attttgggaa attttccagt tactttgttc tcattttaat gtaataatct
 9661 aagtcttggt tttctaagga aaagttttct cttattatat cttttgttaa tgtttctctc
 9721 ccatttcttt tgatctgatc ttcagataca tgattatctt cactgctaaa tttgtgttct
 9781 ctggcctcta catttataat ttctcataat tctttatcta agtatttctt ccctacctac
 9841 tgaagaaaac tcaagttttc ttccaccttta atgattatgc tgtgtctgtg agttttcttc
 9901 atgactcttt acagtacaag ttttttgttt ttgtttttttt aatggtcaga tggatagaac
 9961 aacacaggtt ttgtttgttt tgttttaact tttaaaaaaa ttataataga taaagggtct
10021 cactacgttg tccaggctga tctcatactc ctgggctcaa gcaatccacc cacctctgcc
10081 tcccaaagtg ctgggattac agtcatgagc caacatgcct gggcagtaca ggtttttttt
10141 gagacggagt tttgttcttg ttgccgaggc tggagtgcaa tggcacaatc ttggctcacc
10201 acaaagtctg cctcccaggt tcaagtgatt ctcctgcctc agcctcctga gtagctggga
10261 ttacaggcat gtgccaccac gcccagctaa ttttgtattt tagtagaga cggggtttca
10321 ccatgttggc caggctggtt tcgaactgct gacctcaggt gatctgccca cctcggcctc
10381 ccaaagtgct gggattacag gcatgagcca ccatgcccag ctgtagtaca ggttttaata
10441 tgctaaatac tcttcctttc tttattaatg tgcatggaag ttctaatatt ttttcccat
10501 accccagaga gtccatattt tggaatcaac aacactagcc tttgttgaca agtgtctctc
10561 ttgggttcct tctttgtgtc ctccactgaa ttttggggtt cataaaattt catttgttgt
10621 gcttgcttaa ttccctggga atcagactgt tcctgatcgg atgacatttc tggttaattc
10681 tttagttggc aggaaataga cacaggaaac gtggtcagtt tctgattctg gcgttgagag
10741 accctttctc cttttcctct ctctcagtgg gcgacagatg cgaaagaaac gagttccagt
10801 gccaagacgg gaaatgcatc tcctacaagt gggtctgcga tggcagcgct gagtgccagg
10861 atggctctga tgagtcccag gagacgtgct gtgagtcccc tttgggcatg atatgcattt
10921 attttgtaa tagagacagg gtctcgccat gttggccagg ctggtcttga atttctggtc
10981 tcaagtgatc cgctggcctc ggcctcccaa agtgctggga ttacaggcac cacgcctggc
11041 ctgtgacacg attcttaacc cctttttgat gatggcggct ggaaaagtgg ccagtggatt
11101 ttgatgtatt caatcatgaa ttaggaggtg gggagagaat gaattattgg agctttcctt
11161 aaagccatta aatggctcta ttgttttttc aattgatgtg aatttcacat aacatgaaat
11221 taaccagctc agtggcatta atacatctgc aatgctgtgt ggccaccacc tctatcttgt
11281 tccaaaactt tgcataacct aatgtctttt tttttttttt ttttgagac ggagtctcgt
11341 tccatcaccc aggctggagt gcagtggtgt gatctcagct cactgcaacc tccgcctccc
11401 aggttcacgc catcctcctg cctcagcctc ccgagtagct gggactacag gcaccctcca
11461 ccacatccgg ctaattttt gtatctttag tagagatggg gtttcaccat gttagccggg
11521 atggtctcga tctcctgacc tcgtgatcca cctgcctccg cctcccaaag tgctggcatt
11581 acaggcgtga gccaccatgc ccggcctatt ttttttttta agagatggag tctaattctg
11641 ttgcccaggc tggagtccag tggtaccatc atacttcact gcagccttga cctcttgggc
11701 tcaagtgatt ctcttgcctc gaactcccaa agtattggga ttacaggtgt gagccaccgc
11761 actcagccta atgtccagtt tttaacaagc tccatttaaa tgccctccgt tttgacccat
```

```
11821 aaagggggtag gcttggccgg gcacaatggc ttgtgtctgt agtcccagct acttgggagg
11881 ctgaggcaga aaggcagaaa gattgcttta taaagcccag gagtttgagg gccacctggg
11941 tggcatagct agacctcatc tctaaaaaat aagtaataaa taaatatttg ttttttgtttt
12001 tttcttttc ttttcttttt tttttttttt tgagacgag tcttgctctg ttgcccaggc
12061 tggagtgcag tggcgcgatc tcagctcact gcaagctgtg cctcctgggt tcatgccatt
12121 ctcctgcctc agcctcccga gtagctggga ctacaggcgc ccactaccac gcccagctaa
12181 ttttttgtat ttttagtaga gatggggttt caccacgtta gccaggatgg tctcaatctc
12241 ctgacctcgt gatccgccag ctttggcctc ccaaagtgtt gggattacag gcgtgagcca
12301 ctgagcccgc cccatatgta tgtatatata tatttttta aaatgggaga ccaggcatgg
12361 tggctcatgc ctagaatccc agcactttgg gaagctgagg taggcggatc acttgaggcc
12421 atgagtttga ccagcctg ctcaacatga tgaaacttct atctctacta aaaaaaaag
12481 tgggattagg tcaggcacgg tggctcacac ctgtaatccc agcactttca gaggccgagg
12541 caggaggatc atgaggtcag gagatcgaga ccatcctggc taacacggtg aaaccccgtc
12601 tctactaaaa aaatacaaaa aattagccag gcgtggtggc gggtgcctgt agtcccagct
12661 actcaggagg ctgaggcagg agaatggcgt gaacccggga ggcggagctt gcagtgagcc
12721 aagatcgtgc cactgtactc cagcctgggc gacagagcaa gactctgtct caaaaaaaaa
12781 aaaaaagtg ggattgacat tctcttcaaa gttctggggt tttcctttgc aaagacagga
12841 ttggcaaggc cagtgggtct tttttgtgtg tgtgtgtgtg acggagtctc actctgccac
12901 ccaggctgga gtgcaatggc aggatctcgg ctcaccgcaa cctcctcctc caggttaaa
12961 gtgattctcc tgcctcagcc tcccgagtag ctgggactac aggtgcccgc caccacaccc
13021 aactaatttt tgtattttta gtagagacag gtttcacta tattggccag gctggtcttg
13081 aaccctgac ctcacgtgat ccaccgcct tggcctccca aagtgctggg attacaggcg
13141 tgagccactg tgctcggcct cagtgggtct ttcctttgag tgacagttca atcctgtctc
13201 ttctgtagtg tctgtcacct gcaaatccgg ggacttcagc tgtgggggcc gtgtcaaccg
13261 ctgcattcct cagttctgga ggtgcgatgg ccaagtggac tgcgacaacg gctcagacga
13321 gcaaggctgt cgtaagtgtg gccctgcctt tgctattgag cctatctgag tcctggggag
13381 tggtctgact ttgtctctac ggggtcctgc tcagctgcaa aggcagctgc cccgaactgg
13441 gctccatctc ttgggggctc ataccaagcc tcttccgccc ttcaaatccc cccttgacca
13501 ggaggcatta caaagtgggg atggtgctac ctcttcgggt ttgtcacgca cagtcaggga
13561 ggctgtccct gccgagggct agccacctgg cacacacact ggcaagccgc tgtgattccc
13621 gctggtcgtg atccccgtga tcctgtgatc cccgccccgt gaggctgaac acatagtgac
13681 gcttgctagc caagcctcaa tgacccacgt aacatgaagg gggaaaagcc agaaagttct
13741 gccaaggagc aaggccaaga atcccgaagg gaaatggact ttgaagctgg gcgtcttctt
13801 ggctgtctta atacaagtgg cacatccaaa tccaaaaccc cgaaattcaa agtcttgagc
13861 acccgaaatt ctgaaacgtc ttgagcactg acctttagaa ggaaatgctt attggagcat
13921 tttggatttc ggattttttac cactgagtgt ggagtcctaa ttaggaaaaa aaccaggctg
13981 accgaaccaa aggaaagcaa taaaagaagg cagatagggt caggcacggt ggctcacccc
14041 tgtaatccca gcctttttgag aggctgaggc gggtggatca cttgaggtca ggagttcgag
14101 agcagcctgg ccaacacggt gaaaccccat ctctactgaa aatacaaaaa ctagccaggt
14161 atggtggcgt ctgcctgtaa tcccagctac tcgggaggct gagacaggag aatcacttga
14221 acctgggagg cagaggttgc agtgagccaa tatcacgcca ttgcactcca gcctggggga
```

-continued

```
14281 caagagcgaa attctgtctc aaaaaaaaag aagaagaagg ccgacaaact atgtaactct 14341 gcctttctcc atggtccaga acacacagcc ctcctgcgta ataactcct tatcttcctg 14401 ctcccagcta tcatcagaca cctcggctga tagaaaattg caagttagct cactgcaacc 14461 tcggcattat aagtactgca caaagccctc ttcagcgcac agcacaagca ccattctata 14521 aaatctccag caagcggcca ggtgcagtgg ctcatacctg taatcccagc attttgggag 14581 actgaggcgg gcggatcacc tgaggtcagg agtttgagac cagcctggcc aacatggtga 14641 aaccccgtct ctattaaaaa tacaaaaaaa ttagccaggc gtggtggcag gtgcctgtaa 14701 tcccagctac ttggaaggct gaggcaggag aatcgcttga acccgggagg tggaagttgc 14761 agtgagccga gatcttgcca tcgcactcca gcctggggga caagagtgag acttcgtctc 14821 aaaaaaaaaa aaaaaaattc ccagcaagcc tttgtcttct ggcagtcagc tcctctcttg 14881 ctgacctgct cattgctttc ttgcaaggta ttttcctacc tactttctgg aataaatctg 14941 tctttctgta cttacaacta cctttttaa aatttctttc ttttttgaga tggagtctca 15001 ctctgtttgc ccaggctgga gttcagtggt gcaatctcag ctcactgcaa cctctaccta 15061 ctgggttcaa gcgattctcc tgcctcagct tcccgagtag ctgggattac aggcgtgcac 15121 cagcacgcag gctaattttt gtattttag tagagacggg gtttcaccat gttggccaag 15181 gtggtcttga actcctgacc tcaagtgatc ctcccacctc agcctcccaa agcgctagga 15241 ttacggccat gagccactga ggccggctgc acctacaact gtcttgataa attcttaccc 15301 ccacaccact ggtccagata gtcagtgctc acccacaaca ttaaggatat tccaaatttg 15361 aaacattcca aaatcagaaa aatattccaa ctctgaaaat attccaaaat ccaaaaaaat 15421 tcaaaatcca aaacacttct ggtcccaagc attttagaga agggatactc aacccaaaat 15481 aaggacagca attctataaa ttgtgctacc atcttgcagg tctcagttta acagctttac 15541 acctattagc gcaccagtgc tcatagcagt gctgggaaat gtgtacagat gaggaaactg 15601 aggcaccgag agggcagtgg ttcagagtcc atggcccctg actgctcccc agcccgcctt 15661 tccaggggcc tggcctcact gcggcagcgt ccccggctat agaatgggct ggtgttggga 15721 gacttcacac ggtgatggtg gtctcggccc atccatccct gcagccccca agacgtgctc 15781 ccaggacgag tttcgctgcc acgatgggaa gtgcatctct cggcagttcg tctgtgactc 15841 agaccgggac tgcttggacg gctcagacga ggcctcctgc ccggtgctca cctgtggtcc 15901 cgccagcttc cagtgcaaca gctccacctg catcccccag ctgtgggcct gcgacaacga 15961 ccccgactgc gaagatggct cggatgagtg gccgcagcgc tgtagggggtc tttacgtgtt 16021 ccaagggac agtagcccct gctcggcctt cgagttccac tgcctaagtg gcgagtgcat 16081 ccactccagc tggcgctgtg atggtggccc cgactgcaag gacaaatctg acgaggaaaa 16141 ctgcggtatg ggcggggcca gggtgggggc ggggcgtcct atcacctgtc cctgggctcc 16201 cccaggtgtg ggacatgcag tgatttaggt gccgaagtgg atttccaaca acatgccaag 16261 aaagtattcc catttcatgt ttgtttcttt tttttctttt ctttctttat tttgttttg 16321 agatggagtc tcactctgtg atttttttca tctctaaatt tcctacatcc atatggccac 16381 catgaggccc caggctggcc gatggttgct gttagcttat tgggaaatca ctgtttggaa 16441 ggtgctggtt gttttttgtt gtttgttgtt tttgttttg ttttgttttt gagacggagt 16501 ctcgctctgt cgccagggtg gagtgcagtg gcgcgatcag ctcactgcaa cctccgcttc 16561 ctgggttcaa gccattctcc tgcctcagcc tcccaagtag cgcggattac aggcatgtgc 16621 caccacctcc ggctattttt ttttctattt agtagagatg gggtttcacc atgttagtca
```

-continued

```
16681 ggctggtcat gaactcttga cctcaggtga tccacccgcc tcggcctccc aaagtgctgg 16741 gattacaggc gtgcactgct gcacccagcc ttttttttgtt tttttgagac agggtcttgc 16801 tgtcacccag gttgaagtaa ggtggcacga ttatggctca ctgcggcctt gatctccttg 16861 gctcaagcga tcctctcact tcagcctctc aagcagttgg aaccacaggc tgtaccacca 16921 agcctggcca atttttttgt acagacacag gctggtcttg aactcctggg ctcaagcaat 16981 cctcctgcct tggcctccca aagtgctggg attccaggca tgagccgctg cacccggcaa 17041 aaggccctgc ttcttttttct ctggttgtct cttcttgaga aaatcaacac actctgtcct 17101 gttttccagc tgtggccacc tgtcgccctg acgaattcca gtgctctgat ggaaactgca 17161 tccatggcag ccggcagtgt gaccgggaat atgactgcaa ggacatgagc gatgaagttg 17221 gctgcgttaa tggtgagcgc tggccatctg gttttccatc ccccattctc tgtgccttgc 17281 tgcttgcaaa tgatttgtga agccagaggg cgcttccctg gtcagtctg caccagctgt 17341 gcgtctgtgg gcaagtgact tgacttctca gagcctcact tccttttgtt ttgagacgga 17401 gtctcgctct gacacccagg ctggagtgct gtggcacaat cacagctcac ggcagcctct 17461 gcctctgatg tccagtgatt ctcctgcctc agcctcccga gtagctgaga ttaaaggcgt 17521 ataccaccac gcccggctaa ttttttgtat ttttattaga cagggtttt ctccatgttg 17581 gccaggctgg tcttgaactc ctggtctcag gtgatccacc cgcctcggcc tcccaaagtg 17641 ctaggattac aggtgtgagc cactgcgcca ggcctaattt ttttgtattt ttagtagaga 17701 tgcggttttg ccatattgcc caggctggtc tcgaactcct gggctcaagc gatctgcctg 17761 ccttggcctc ccaaagtgct gggattacag gcacaaacca ccgtgcccga cgcgttttct 17821 taatgaatcc atttgcatgc gttcttatgt gaataaacta ttatatgaat gagtgccaag 17881 caaactgagg ctcagacaca cctgaccttc ctccttcctc tctctggctc tcacagtgac 17941 actctgcgag ggacccaaca agttcaagtg tcacagcggc gaatgcatca ccctggacaa 18001 agtctgcaac atggctagag actgccggga ctggtcagat gaacccatca aagagtgcgg 18061 tgagtctcgg tgcaggcggc ttgcagagtt tgtggggagc caggaaaggg actgagacat 18121 gagtgctgta gggttttggg aactccactc tgcccaccct gtgcaaaggg ctccttttt 18181 cattttgaga cagtctcgca cggtcgccca ggctggagcg caatggcgcg atctcggctc 18241 actgcaacct ctgcctccca ggttcaagtg attctcctgc ctcagcctcc tgagtagctg 18301 ggattacagg cgcccaccac caagcccggg taattttttg tatgtttagt agagatgggg 18361 tttcactatg ttggccaggc tggtgttgaa ctcctgacct catgatccgc ccacctcggc 18421 ctcccaaagt gctgggatta caggcgtgac ccaccccatg aaaaaaaatt aaaaaatgaa 18481 gcgatgctgg gcgcggtgga tcacgcctgt aatcccagca ctttgggaag ctgaggcagg 18541 cagatcacga gggcaggaga ttgagaccat cctggctaat acggtgaaac cccatctcta 18601 ctaaaactac aaaaaattag ccgggtgtgg tggcaggcac ctgtgatccc agctactcag 18661 gaggctgagg caggagaatc gcttgaaccc aggaggtgga ggttgcagtg agccgggatc 18721 acaccattgc actccagcct gggtgacaga gtgagactct gtctcaaaaa aaaaaaaaaa 18781 aaaaaagcg aattctgaaa tacatgaatt ctttccctta gatgcctgct tctgtcttga 18841 ggtttgttgt tgttatttcg aaacagagtc ttgctctgtc gctcaggctg gagtgcagtg 18901 gcatgatctt ggctcaccac aacctccggc tcccaggttc aagcgattct tctgcctcag 18961 cctcctgagt agctgggatt acagctgaat gccaccttgc tgggctaatt tttgtatttt 19021 tagtagagat gggggtttcac catgttggcc aggctggcct cgaactcctg acctcgagtg 19081 atctgcccgc ctcctgaagt gctgggatta caggcgtgag ccacctcgtc ctggtgaggg
```

-continued

```
19141 tttttttttt tccccaaccc tctgtggtgg atactgaaag accatattag gataactgta
19201 cagtatagag aaggcagtgg caagttttct ctgtcatata ccagagtggg cttggcatg
19261 gtggcatact cctgtagtct cagctaatca ggaggctgag gaaggaggat cgcttgggcc
19321 caggagttgg agactgtagt gagctgtgat cacaccacca cacttcaatc tgggcaacag
19381 agcaagagac cctatctcta aaaaaaagta agtatttcgg acactgtggg ccatacggtc
19441 tctggtgcag tttctcaaca tggctgttgg gtgaacacaa ccacgcacag aacgcaaacc
19501 aatacacgtg gctgtgggcc cagaaaatgt tatttatgga cacaaaaatt ggaatttcat
19561 ataactgttt tgtgtcatga aaatgatttc ccttttatt tttattttc ttctcaagta
19621 tttaaatatg taaaagccat ttttaggcct ggcaggatgg ttcacagctg taatcccagc
19681 actttgggag gtcgaggcgg gaggatcacg aggtcaggag atcgagacca tcctggccaa
19741 cacagtgaaa ccccgtctct actaaaaata caaaaaatta accaggcttg gtggcgcgcg
19801 tctgtagtcc cagctgctca ggaggctgag gcaggagaat cgcttgaatg caggaggcgg
19861 aggttgtagt gagccgaggt tgcaccactg cactccagcc tgagcgacag agtgagagtc
19921 cgcctcaaac aaaaaaatgt ttgcccatgc tggtcttgaa ctcctgggct caagctatct
19981 gcctgccttg gtctcccaaa gttctgggat tacaggcatg agctacagcg cccggacttt
20041 tgttgtttta tatctatata tctatatata acttgtttta tgtatatata aacttgttt
20101 tatatatata cataaactgc agtaaaaaac atgtaacata aaatttacct tctcaaacct
20161 tattaagtgc acagttctgt gccattagca aattcacact gttgtacaac atcacaacca
20221 ccatctccag aactttttt tttttttta ttcttttga gacagagtct cactcgtcgc
20281 acgggctgga gtgcagtggt gcgatctcgg ttcactgcaa cctccaccta ccaggttcaa
20341 gcaattctcc tgcctcagcc cctcagtag ctgggattac aggtgcccgt cctaccacgc
20401 ccagctaatt tttgtatttt cagtagagac tgactgggtt tcaccatgtt ggccaggctg
20461 gtctcgaact cctgacctca agtgatcctc ccacctcagc ctcccaaagt gctgggaata
20521 caggcatgag ccactgcgcc cggccccaga actcttttat cttcccaaac tgaagctctg
20581 tccccatgaa acactcactc tccatccct ccccaactcc tggcacccac cattctactt
20641 tctgtcccta tgaatgtgat ggctctaggg acctcctctg agtggaatca gacagcattt
20701 tccttttttg actggcttat ttcactgagc caagtgcggt ggcacacgcc tgtaatccca
20761 aaactttggg agaccgaggc gggcgcatca cctgaggtca ggagttcgag accagcccgg
20821 ccaacatggt gaaaccccat ctctagtaaa aatacaaaaa attagcctgt catggtcgtg
20881 ggtgcctgta atcccagcta gtgggaggc tgaggcagga gaatcgcttg tacccaggag
20941 gcggaggtcg cagtgagccg agatcgtgcc attacactcc agcctgggca acaagagtga
21001 aactccgtct ctcctaaaaa tacaaaaaaa ttagctgggc atggtggcac atgcctgtag
21061 tcccagctac tgggaggct gaggcaggag aatcacttga acccgggagg tggaggttgt
21121 aatgagccaa ggttggcggc gaagggatgg gtagggccc gagagtgacc agtctgcatc
21181 ccctggccct gcgcagggac caacgaatgc ttggacaaca acggcggctg ttcccacgtc
21241 tgcaatgacc ttaagatcgg ctacgagtgc ctgtgccccg acggcttcca gctggtggcc
21301 cagcgaagat gcgaaggtga tttccgggtg ggactgagcc ctgggccccc tctgcgcttc
21361 ctgacatggc aaccaaaccc ctcatgcctc agtttcccca tctgttaagt gtgcttgaaa
21421 gcagttagga gggtttcatg agattccacc tgcatggaaa actatcattg gctggccaga
21481 gtttcttgcc tctggggatt agtaattaag aaatttcagg ccgggtgcgt aatccctgta
```

-continued

```
21541 atcccaacac cttgggacgc cgaggcgggc agatcacctg aggtcgggag ttccagacca
21601 gcctgaccaa catggagaaa ccccgtctct actaaaaata caaaattagc cgggcttggt
21661 ggtgcatgcc tataatccca gctactcagg aggctgaggc aggagaatca cttgaacctg
21721 ggaggtggag gttgtggtga ccaagatcg tgccattgca ctccagcctg gcaacaaga
21781 gtgaaactcc atccaaaaaa aaagaaaag aaaagaaaaa aagaaaaga aatttcagct
21841 gacacagctt cacactcttg gttgggttcc cgtggtgaat gatgaggtca ggtgatgact
21901 ggggatgaca cctggctgtt tccttgatta catctcccga gaggctgggc tgtctcctgg
21961 ctgccttcga aggtgtgggt tttggcctgg ccccatcgc tccgtctcta gccattgggg
22021 aagagcctcc ccaccaagcc tctttctctc tcttccagat atcgatgagt gtcaggatcc
22081 cgacacctgc agccagctct gcgtgaacct ggagggtggc tacaagtgcc agtgtgagga
22141 aggcttccag ctggaccccc acacgaaggc ctgcaaggct gtgggtgagc acgggaaggc
22201 ggcgggtggg ggcggcctca ccccttgcag gcagcagtgg tgggggagtt tcatcctctg
22261 aactttgcac agactctat ccccctgaccg ggaggctgtt tgctcctgag ggctctggca
22321 ggggagtctg ccgccctgtt aggacttggg cttgccaggg ggatgcctgc atatgtccta
22381 gttttttggga atatccagtt aacggaaccc tcagccctac tggtggaaca ggaaccggct
22441 ttcctttcag ggacaacctg gggagtgact tcaaggggtt aaagaaaaaa aattagctgg
22501 gcatggtgcc acacacctgt ggtcccagct actcagaagg ctgaggcggg aggattgctt
22561 gagggcagga ggattggttg atcctcccac ctcagcctcc ggagtagctg ggacctcagg
22621 tgcatgccac tatgcctggc taatttttctt tttttctttt tttttttttt cgagacggag
22681 tctcgctctg ttgcccaggc tggagtgcag tggcaggatc tcggctcact gcaagctccg
22741 cctcccgggt tcacgccatt ctcctgcctc agcctcccca gtagctggga ctacaggagc
22801 ccgccactgc accaggccaa ttttttttgta ttttagtag agacggggtt tcactgtgtt
22861 agccaggatg gtctcgatct cctgacttcg tgatccgccc acctcggcct tccaaagtgc
22921 tcggattaca ggcgtgagcc actgcgccca gccgctaatt ttcatatttt tagtaaaaac
22981 agggtttcac catgttggcc aggctagtct tgaactcctg aacccaagtg atcctcctgc
23041 cttggcctcc caaagtgctg ggattacaga caccacacct ggctattatt attttttaga
23101 gacagggtgc tgctctatct tccagcctgt agtgcagtgc agcctccatc atagctcgct
23161 gcagccttga cctcctgggt tcacgtgatc gtcccgccta agcctctgga ggagctggga
23221 gtactggcat gtgccaccat gcctggttaa ttttttttttt tttttttttg agacagagtc
23281 tcattctgtc acccaggctg gagtgcggtg gtgcgatctt ggcttactga aacctccacc
23341 tcccaggttc cagcaattct cctgcctcac ccttctgagt agctgggatt acaggttccg
23401 gctaccaaac ctggctagtt tttgtatgtt tagtagagac agggtttcac catgttggtg
23461 aggctggtct cgattctccc gcctcagcct cccaaagtgc tgggattaca ggcttgagcc
23521 accgtgcctg gcttttttttt tttttttttt ttttgtggca ataaggtctc attgtcttgc
23581 ccaggctagc cttatgctcc tagcctcaag tgatcctcct ccctcagcct cccaaagtgc
23641 tgggattaca ggtgggcgcc actgtgcctg ttcccgttgg gaggtctttt ccaccctctt
23701 tttctgggtg cctcctctgg ctcagccgca ccctgcagga tgacacaagg ggatggggag
23761 gcactcttgg ttccatcgac gggtccctc tgaccccctg acctcgctcc ccggaccccc
23821 aggctccatc gcctacctct tcttcaccaa ccggcacgag gtcaggaaga tgacgctgga
23881 ccggagcgag tacaccagcc tcatccccaa cctgaggaac gtggtcgctc tggacacgga
23941 ggtggccagc aatagaatct actggtctga cctgtcccag agaatgatct gcaggtgagc
```

```
24001  gtcgccsctg cctgcagcct tggcccgcag gtgagatgag ggctcctggc gctgatgccc 24061  ttctctcctc ctgcctcagc acccagcttg acagagccca cggcgtctct tcctatgaca 24121  ccgtcatcag cagagacatc caggcccccg acgggctggc tgtggactgg atccacagca 24181  acatctactg gaccgactct gtcctgggca ctgtctctgt tgcggatacc aagggcgtga 24241  agaggaaaac gttattcagg gagaacggct ccaagccaag ggccatcgtg gtggatcctg 24301  ttcatgggtg cgtatccacg acgctgaggg ctgcagaggg aatggaggga gcaggaagga 24361  gcttcaggaa ctggttagtg ggctgggcat ggtggctcaa agcacctgta atcccagcac 24421  tttgggaggc caaggtgggt ggatcatcaa gaccagcctg accaacatgg tgaaacctcg 24481  tctctactaa aaatacaaaa attagccggg tgtggtggtg ggcacctgta atcccagctg 24541  ctcgggaggc tgaggcagga gaatcacttg aacctgggag atggaggttg cagtgagcca 24601  agacagcccc actgcactcc agcctgggtg acagagtgag actccgtctc aaaaaaaaaa 24661  aaaaaaacta acaaaaaaac tggttagtgg ctagacaaca ggatggtatc ttccaagccc 24721  atggctgact cagcagctcc tgggtcaaga cactgtgacc tgtgtcccct ggcaggaagc 24781  atcgcccctg ccacctgccc ggtgtactct gtacctgtca ggtgacatct gctacctaag 24841  cacgtgagag gtggcatttc acagtttcag tgtggtgctg acaacccggg acgcacactg 24901  tccttgcagc tacaatcagg aggtgaatgt tgggtttcca gcagagaaca ctggagaagg 24961  cacacttggt gtctggaagg gaaaagcagg gaagagagca tcatcagatg cctgcgggtg 25021  aaggtgggcc cgctatggcc agcgtccctt tttatttta tttatttatt tatttgagat 25081  ggaatctcgc tctgtcgccc agactgtagt gcagtggtgc gatcacggct cactgcaagc 25141  tccgcctcac aggttcacgc cattctcctg cctcagcctc ccgagtagct gggactacag 25201  gcacccgcca ccacgcccgg ttaattttt gcatttttat tagagacggg gtttcaccgc 25261  gttagccagg atggtctaaa tctcctgacc ctgtgatcca cccgcctcgg cctccctaag 25321  tgcttggatt acaagcgtga gccaccacgc ccggccccct ttttatttt tatttttga 25381  gacggagtct cgctctgtcg cccaggctag attgcagtgg cgtgatctcg gctcactgca 25441  gcctccgcct cccaggttca agtgattctc ctgcctcaac ctcccaacta attaggatta 25501  caagcatgta ccaccatgcc tgactaattt tttgtatttt tagtagagac tgggtttcac 25561  catgttggct aggctggtct cgaacccta gcctcaagta atctgcctgc ctcagcctcc 25621  caaacagcgg ggattacagg catgagccac tgtgcccaac ccaaccctgg atctctttta 25681  aacaagacaa tgctcgctgt tgccacagaa caatgggtgg ggtacatgtg gcccagtgtg 25741  tttggccaca taactgccag gccagaggga aagagactct cagactgtct ccactcagat 25801  acaaatgtgt gtgttgtgtg cgtgtgttct ggtctcatat ttgtttgttt tgagacaggg 25861  tgtcgctctg tcactgagtc tggagtgcag tggcgcaatc agagttcact gcagcctcaa 25921  actcttgggc tcagttgatt ctcccacttc agcctcccaa gtagctggaa ctacaggtga 25981  acaccactgt gcccagctaa tttatttat ttttagtaga gatgaggtct cactatgttg 26041  cccaggctgg tcttgacctc ctagcctcaa gcaatcctcc tgccttggtc tcccaaagtg 26101  ctgggattac acgtgcgagc cattgcgcat ggcttgtgtt cttgtgtttc ttcctttttc 26161  tttcgagatg gcgtctcagt ctgccaccca ggctggagtg cagtggtgtg atcatagctc 26221  actgtagcct caacttcctg ggctcaagca atcctcttga tttcagcctc ccgggcctgg 26281  ccagcatggt gaaacccgt ctctactaaa aatacaaaaa tgtagccagg cgtggtggtg 26341  ggcgcctgta atcccagcta caccagaggc tgaggcagga gaatcgcttg agcctggaag
```

-continued

```
26401 gtggaggttg cagcaagcca agatcgtgcc actgcactcc agcctgggca acagagacag 26461 actctgtctc aaaaaaaaaa aaaaaaaacc caaacaagcc acatttggag tttggggttc 26521 ccagcaggac tatttcccaa gcctgagcct ggctgtttct tccagaattc gttgcacgca 26581 ttggctggga tcctccccg cctccagcc tcacagctat tctctgtcct cccaccagct 26641 tcatgtactg gactgactgg ggaactcccg ccaagatcaa gaaaggggc ctgaatggtg 26701 tggacatcta ctcgctggtg actgaaaaca ttcagtggcc caatggcatc accctaggta 26761 tgttcgcagg acagccgtcc cagccagggc cgggcacagg ctggaggaca gacggggtt 26821 gccaggtggc tctgggacaa gcccaagctg ctccctgaag gtttccctct ttctttttctt 26881 tgttttttct tttttgaga tgaggtcttg gtctgtcacc caggctggag tgcactggcg 26941 caatcgtagc tcactgcagc ctccacctcc caggctcaag tgatcctcct gcctcaccct 27001 cctgagtagc tgagattaca gacacgtgcc accacggcag actaattta ttttatttt 27061 gggaagagac aaagtcttgt tatgttggcc tggctggtct caaactcagg gtgcaagcga 27121 tcctcccgcc tcagccttcc aaactgctgg gattacaggc gtgggccacc gtacccagcc 27181 tccttgaagt ttttctgacc tgcaactccc ctacctgccc attggagagg gcgtcacagg 27241 ggaggggttc aggctcacat gtggttggag ctgcctctcc aggtgctttt ctgctaggtc 27301 cctggcaggg ggtcttcctg cccggagcag cgtggccagg ccctcaggac cctctgggac 27361 tggcatcagc acgtgacctc tccttatcca cttgtgtgtc tagatctcct cagtggccgc 27421 ctctactggg ttgactccaa acttcactcc atctcaagca tcgatgtcaa cggggcaac 27481 cggaagacca tcttggagga tgaaaagagg ctggcccacc ccttctcctt ggccgtcttt 27541 gaggtgtggc ttacgtacga gatgcaagca cttaggtggc ggatagacac agactataga 27601 tcactcaagc caagatgaac gcagaaaact ggttgtgact aggaggaggt cttagacctg 27661 agttatttct attttcttct ttcttttttt tttttttttt gagacagagt tttgctctcg 27721 tttcccaggc tggagggcaa tggcatgatc tcggctcacc gcaacctcca cctcccaggt 27781 tcaagtgatt ctcctgtctc aggctcccca gtagctggga ttacaggcat gcaccaccac 27841 catgcccggc taattttgta tttttagtag agacggagtt tctccatgtt ggtcaggctg 27901 gtctcgaact cccgacctca ggtgatctgc ctgcctcggc ctcccaaagt gctgggatta 27961 cagacttgag ccaccgcgcc cagctatttc tgttttcttt cttcttctt cttcttttt 28021 tttttctaag agacaggatc tcactctgtc cccaggcagg agtgcagtgc tgtgatcata 28081 gctcactgca gccttaacct cctgggctca agtgatcttc cacctcagc ctcccaagta 28141 gctggaacta caggtgcaca ccaccatgcc cagctcattt ttgtatttt ttttttttg 28201 agacagtctc gttctgtcac cccggctgga gtgcagtggt acaatcttgg ctcactgcaa 28261 cctctgcctc ccaggttcaa gcgattctcc tgcctcagcc tcctgagtag ttgagattac 28321 aggcatgtgt gccatcatac ctggctgatt tttgtatttt ttttagaga tggggtctca 28381 gtatgttgac caggcttgtc ttaaactccc ggcctcagt gatcctccca cttcagtctc 28441 ccaaagtgct gggattacag gcatgagcca ctgcggccgg tttgttttct tttttttc 28501 gtttttgga gacggaattt cacctttgtt gcccaggatg gagtgcaatg gcacgatatc 28561 gcctcaccac aacctctgcc tctgggttc aaaccatttt cctgcctcag ccttcttagt 28621 agctgggatt acaagcatgt gccaccacgc ccggctgatt ttgtatttt agtagagatg 28681 gggtttctcc atgttggcca ggctggtctc gaactcctga cctcaggtca ttcgcccacc 28741 tctgcctccc aaagtgctgg gattacaggc gtgagccacc gtgcccggtg gtttgtattc 28801 tttttactga gagtcgtgaa aggcagtgat cctctgtcac atgtgatctt ggctctcagg
```

```
28861 ggacatttgg caatttctag agattttttg gttgtcacaa gtcaatgggg aagactgttg
28921 gcatttagtg ggtagaggct ggtgacgctg ctgaacaccc agaacaggga agtagcaggc
28981 cctagataga gccatcgtgg ggaaaccctg ctctaaggaa atggcgctat tttataaccc
29041 cacgttcctg gcatgattac caacagccaa aagtggagtc cccccaagtg tgttcgtcca
29101 tttgcattgc agtaaaggaa tagctgaggc cgggtaattt ataaagaaaa gagatttaaa
29161 ctgggtatgg cagtttatgc ctataatccc agaactttgg gaggctgagg caggaggatc
29221 gcttgagtcc aggagtgtga gaccgagacc agcctggcca acatgacgaa actctgtctc
29281 tacaaaaaat acaaaaagta ggccaggcac ggtggttcac gcctgtaatc ccagcacttt
29341 gggaggccga ggcgggcgga tcacgaggtc aggagatcga gaccatcctg gctaacacgg
29401 tgaaaccccg tctctactaa aaatacaaaa acaaaattag ccgggtgtgg tggcaggcgc
29461 ctgtagtccc agctactcgg gaggctgagg cgggagaatg gcgtgaaccc gggaggcgga
29521 gcttgcagtg agccaagatc gcgccactgc actccagcct gggtgaccga gttgagactc
29581 cgtctcaaaa aaaaaaaaaa aaaaaaaaat acaaaaagta gccaggtgtg gtggcaggca
29641 cctgtaatcc tgggttctcg agaccgaggc atgagaattg cctgacccca ggaggtggag
29701 gctgcagtga gccaagatca tgccactgca ctccagcctg gcgacagag tgggactctg
29761 tctcaaaaaa caacaaaaaa aaagttctgg aaatggatgg tggtgatggt gatacttcca
29821 caacagcgtg aatctgctta aggccaccga actgtgcact cacaaatagt cgagatggta
29881 cattttatgt tatgtgtatt tcaccacaat taaaaactag ttgtgggcca ggtgtggtgg
29941 ttcatgcctg taatcccagc actttgggag gtcagaggga ggtggatcat gaggtcagca
30001 gttcgagacc agccaggcca acatggtgaa accccatctc tactaaaaat acaaaaatta
30061 gccaggcgtg gtggcacatg cctgtagtcc cagctacttg agaggctgaa gcaggagaat
30121 cgcttgaacc tgggaggcta agattgcagt gagccgagat cgtgccactg cactccagcc
30181 tggacgacag agtgagactt cgtctcaaaa aaaaaaccaa aaaaaaatt agctgtgggt
30241 caggcactgt ggctcacgcc tgtaatccca gcactttggg agaccgaggt aggtggatgg
30301 cctgaggtca ggagttcgaa tccagcctgg ccaacatggt gaaagcccgt ctctactaaa
30361 aatacaaaaa attagtcagg tatgttggca cacctgtaat cccagctact cgggaggctg
30421 aagcaagaga atcgtttgaa cccaggaggt ggacgttgca gtgagccgag attgggccac
30481 tgtactccag cctgggcaac aaaagtgaaa ctctgtctga acaaacaaa caaacaaaca
30541 aacagacaaa caaaaaaact agttgtggag agagggtggc ctgtgtctca tcccagtgtt
30601 taacgggatt tgtcatcttc cttgctgcct gtttag<u>gaca aagtattttg gacagatatc</u>
30661 <u>atcaacgaag ccatttcag tgccaaccgc ctcacaggtt ccgatgtcaa cttgttgct</u>
30721 <u>gaaaacctac tgtccccaga ggatatggtt ctcttccaca acctcaccca gccaagaggt</u>
30781 aagggtgggt cagccccacc cccccaacct tgaaacctcc ttgtggaaac tctggaatgt
30841 tctggaaatt tctggaatct tctggtatag ctgatgatct cgttcctgcc ctgactccgc
30901 ttcttctgcc ccag<u>gagtga actggtgtga gaggaccacc ctgagcaatg gcggctgcca</u>
30961 <u>gtatctgtgc ctccctgccc cgcagatcaa cccccactcg cccaagttta cctgcgcctg</u>
31021 <u>cccggacggc atgctgctgg ccaggacat gaggagctgc ctcacaggtg</u> tggcacacgc
31081 cttgtttctg cgtcctgtgt cctccaactg cccctcctg agcctctctc tgctcatctg
31141 tcaaatgggt acctcaaggt cgttgtaagg actcatgagt cgggataacc atactttct
31201 tggatggaca catcagcacc gggcttgaca tttacccagt tcccctttga tgcctggttt
```

```
                        -continued
31261 cctctttccc ggcccctga agaggtgatc tgattctga caggagccct gagggaggaa 31321 atggtcccct tgttgactt ttcttttct ttatttttt cttttgagat ttgctgtcac 31381 ccagcctgga atgcagtggt gccatcttgg ctcactgcta cctctcccac tgggttcaag 31441 caattctcct gcctcagcct cccaagtagc tgggattaca agcatgcgcc accatgcctg 31501 gctaagtttt gtattttag tacagacagg gtttctccat ggtggccagg ctggtcttga 31561 actcctgacc tcaggtgatc ctcccacctc tgcctcccga agtgctacga ttacaggcat 31621 gagccaccgc gcccatcccc ctttgttgac ttttctcatc ctctgagaaa gtctcagttg 31681 aggccagcac ctccctcaag tgaattgaat ctcccttttg aacaacaaca aataacaata 31741 tgacccagac gtggtggctc acacctgtgg tcccagctac tcgggaggct gaggtgtgag 31801 gattgcttga gcccaggagg tcaaggctac agagagctat aatcacacca cttcactcca 31861 gcctggggga caaagtgaaa ccctgtctga aaaaacaaa aaagaaaaa ggaaaaagaa 31921 acaatacgat cacaaagtag atattcatag tgtttatttt cagtactctt tttttttt 31981 tttttttttt ttgagacgga gtcttgctct gttgcccagg ctggagtgca gtggcacgat 32041 cttggctcac tgcagcctct gcctcccagg ttcaagcgct tggctcactg caacctccgc 32101 ctcctgggtt caagcgcttc ttctgcctca gcctcccag tagctgggac tataggcacg 32161 tcccactacg cccagctaat tttttgtatt ttttagtaga gatggggttt cactatgtta 32221 gccaggatgg tctcgatctc ctgacctcgt gatctgcctg ccttgggctc ccaaagtgtt 32281 gggattatgg gcatgagcca ctgcacctgg ccttttttt tttttttt gagatggagt 32341 ttcgctcttg ttgcccaggc tggagtgcaa tggtgtgatc tcggctcact gcaacctctg 32401 cctcctgggt tcaagcaatt ctcctgcctc agcctcccga gtagctggga ttacaggcac 32461 ctgccaccac gcctggctaa ttttgtact tttagtagag acggggtttc tccatgttgg 32521 tcaggctggt ctcaaactcc tgacctcagg tgatccaccc acctcggcct cccaaagttc 32581 tgggattaca gacatgagcc accgcgcctg gccgtgtctg gctttttta gttatttctt 32641 tttttttt ttttttttt gagacagagt cttactccgt cgcccaggct ggagtgcagc 32701 ggtgcgatgt ctgcgcactg caagctccgc ccctgggtt catgccattc tcctgcctca 32761 gccttctgag tagctgggac tgcaggcgcc tgccactacg cccggctact tttttgtata 32821 tttagtagag atggagtttc actgtgttag ccaggatggt ctcgatctcc tgactttgtg 32881 atccgcccgc ctcggcctcc caaagtgctg ggattacagg cgtgagccac catgccaggc 32941 tttttttt tttttttt ttgagacgga gtcttgctct gtcgcccagg ctggagtgca 33001 gtgccatgat ctcagctcac tgcaagctcc acttcccagg ctcacgccat tctccagcct 33061 cagcctccca agtagctgag actacagggg cccgccacca cactcggcta attttttgt 33121 attttagta gagacggggt ttcaccatgt tagccaggct ggtcttgaac tcctaacctc 33181 aggcgattca cctgcctcgg cctcccaaag tgctgggatt aaaggtatga gccacctcgc 33241 ctggtgtgag ccacctcgcc cagcctgagc cacctcaccc agcctaagcc actgtgcctg 33301 gcctgatttt ggacttttta aaatttat taataattat ttttgggttt cttttttttg 33361 agacagggtc ttactctgtc atccaggcca tcctgtctgt ctgtcatccc agtgatggga 33421 tcatacccttg ctgcagcctc tacctcctgg gctcaagcga tcctccccc tcagcctcct 33481 gagtagctgg gagtacaggt gtgcaccacc acacctggct aatttttt tttttttg 33541 tatatagaga tggtattttg ccatgttgac caggctagtc ttaaactcct ggactcactc 33601 aagagatcct cctgccttgg cctcccaagg tcatttgaga ctttcgtcat taggcgcaca 33661 cctatgagaa gggcctgcag gcacgtggca ctcagaagac gtttatttat tctttcag<u>ag</u>
```

-continued

```
33721 gctgaggctg cagtggccac ccaggagaca tccaccgtca ggctaaaggt cagctccaca 33781 gccgtaagga cacagcacac aaccacccga cctgttcccg cacctcccg gctgcctggg 33841 gccaccctg ggctcaccac ggtggagata gtgacaatgt ctcaccaagg taaagactgg 33901 gccctcccta ggccctctt cacccagaga cgggtccctt cagtggccac gaacattttg 33961 gtcacgagat ggagtccagg tgtcgtcctc actcccttgc tgaccttctc tcacttgggc 34021 cgtgtgtctc tgggccctca gtttccctat ctgtaaagtg gtctaataa cagttcttgc 34081 cctctttgca aggattaaat gggccaaatc atatgagggg ccaggtcctt caggctcctg 34141 gttcccaaag tcagccacgc accgtgtggg tcccaaaatt ttatcaaggc acattcgttg 34201 cctcagcttc aggcatctgc ccaaaaaggc caggactaag gcaaggagag ggagggattc 34261 ctcagtactc agcttttcac agaggctcca aaaggctaag gaatccagta acgttttaac 34321 acaattttac aattttttt tttgagacgg agttttgctc ttgttgccca ggctggagtg 34381 cagtggcacg atctcggctc actgcaacct ctggctcccg ggttcaagcg attctcctgc 34441 ctcagtctcc cgagtagctg ggattacagg catgcgccac cacgctcggc taattttgta 34501 tttttagtac agaaggggct tctctgttgg tcaggctggt cgtgaactct caacctcagg 34561 tgagccaccc gcctgagcct cccaaagtgc tgggattaca ggtgtgagcc accacgcctg 34621 gccttttttt tgagacagag tctcgctctc gcccatgctg tactgcagtg acgcagtctg 34681 ggctcactgt aacctccgct tcccaggttc aagtgattct tctgccgcag cctcccatgt 34741 agagtagctg ggattacagg caccgccac catgcctggc taattcttgc attttagta 34801 gagatggggt ttcacagtgt tggccaggct ggtctcaaac ttctgacctc aagtcatctg 34861 cctgccttgg ccctgccaaa gtgctgggat tatagatgtg agccaccgcg cctggcctac 34921 agtttattct ttggtggctc acacctgtaa tctcagcact ttgggaggcc aaggtgggag 34981 aatggcttga gcccaggagt tcaagtccag cctgggcaac atagcaagac cctatctcta 35041 ctacaaaata aataataaat aaactaattt ttttctttt aaaacccaac tattcaacat 35101 ggcaatgcaa tatattaaaa aaattttttt tttctttgaa acggagtctc tcactgtcac 35161 ccgggctgga gtgcagtgtc gccatcttgg ctcactgcaa cctccgcctc ccaggtccaa 35221 gtgattctcc tgcttcagcc tcccgagtag ctgggattac aggcacccac caccatacccc 35281 agctaatatt tttgtatttt tagtagagat ggggtttcac tatgttgggc aggctggtct 35341 ggaactcctg acctcgtgat ctgcccgagg atcggcggcc tcccaaagtg ctggggattg 35401 caggcatgag ccaccgtgcc cagccaaaac tttttattt ttattttttt gggacacggt 35461 ctcactgtgt accccagact ggagtgatag agtgctgtca tggctcactg cagcctcaac 35521 ctccctgggc tcaggtgatc ttcctgcttc agtctcccag gtagctggga ctacaggcat 35581 gagccaccac acccagctaa ttttgaatt ttttgtaga cagggttt caccttgtgg 35641 cccagacttg tctctaactc cagggctcaa gcgatctgcc caccttggcc tcccaaagtg 35701 ctgagattaa tgcaatttaa aaattttttt ggccaggcct ggtggctcat gcctgtattc 35761 acaacaccctt ggaggcaaa ggtgggcaga tcacttgagg tcaggagttc gagactagcc 35821 tggccaacat ggtgaaaccc cctgtctact aaaaaaatac aaaaattacc tgggcacagt 35881 ggtgggtgcc tgtaatccca gctacttggg atgctgaggg tggagaattg cttgaacctg 35941 ggaggcagaa gttgcagtaa gccaagatca tgccactgga ctccagcctc agtgacagag 36001 caaaactctg tctccaaaaa aattgttttt tttttttttt tttcaaatca tcacactaca 36061 gccaaggcct ggccacttac ttttgtaaat aaagttttat tggagccagt ggaccagtga
```

```
36121 ggccgaatct tgcaggtgta agatcacagt ctatccttga aaattttgat attttgttca
36181 ttgggtggtt tttcattaat ttaaatttta aaaaataaca tattaaaggc tggtgtggag
36241 gtgcacgcct gcagtcctag ctactcccag aggctgaggc gggagacttg cttgagccca
36301 agagttgaag tccagcctgg gcaacatagc gagaccccca tctctaaaaa taaaaataat
36361 gcattagaat attattggat tcctgggcag ggcacagtgg ctcacacctg taatcccagc
36421 actttgggag gctgaggtgg gtggatcacc tgaggtcagg agtttgagac cagcctggcc
36481 aacatggtga aacccgtct ctactaaaaa tacaaaaatt agccaggcgt ggtggcaggt
36541 gcctgtaatc ccagctactc gggaggctga agcacgagaa tcgcttgaat ccaggaggcg
36601 gaggttgcag tgagctgaga ttgcgccatt gcactccagc ctggaggaca agagtgaaac
36661 tccattcccc tctgcaaaga aaggaatat tatcagattc ctaagctttt tggctccccc
36721 tttagtttgg gggctggggt ggtgagtgtc tgacctggcc tcactgtcct ccctggatgt
36781 gatgagaccc aggtgtgggt caggatgtca ttcgtttgtc caccagaggg cgcccaaact
36841 gctttgagct gctgggaaat ggtgctccta gactttagc aaacaaacaa aaaaaaatgg
36901 cacatcggca aatttcagac cattcttttt tttttttttt ttggttccag agtagctgaa
36961 atctttgttc agttacaagc aggataaaat ggaaactgcc tgggagaggc tgagaaacct
37021 tcttgcttgg gggaggtggg gcactgctag aattaatcgc ttcacagacc agcccatcca
37081 ggactcctca aatttggcaa aaaagccatt cattcattca ttcatttatg tagagacgag
37141 ggggatctgg ctatattgcc tagattggtc tcaaattcct ggcctcaagt gatcctcctg
37201 ccttggtcta ctaatgtgct gcgattacag gcatgagcca ccgtgcctag ctctagtgga
37261 cttgaaatgt tgccttgccc agggccctta tgttgaatgg cccaggtcca cttgtatggt
37321 tctgtaccaa ggttaacccc atcccataat gcctgggaca gttgatgcag acaatcagc
37381 ttctgtgcca ttcaacctca ggactgagca tgctgggcat tgtggggtcc gaaggtggct
37441 cccctgtccc cttcaaaata ccctcttttt cttttcttct tttttttttt ttttttttt
37501 tgagacgaag tcttgctctg ttgccccagc tagagtgcag tggtgcgatc tcagctcccc
37561 gcaacctctg cttcccgggt tcaggcgatt ctcctgcctc agcctcctga gtagctggga
37621 ttacaggtgc ccaccgccac agctggctaa ttttgtatt tttagtagag acagggtttc
37681 accgtgttgg ccaggctggt cttgaactcc tgacctcagg caacctgccc acctcagcct
37741 cccaaagtgc tgggattaca ggtttgagcc actgggcctg gcctttttt ttttttttg
37801 agagggagtc tcactctgtt gcccaggctg gagtgcaatg gcgcgatctt gactcactgc
37861 aactccattt cccgggttca agtgattctc ctcctcagc ctcccaagta gctgggatta
37921 caggtgcatg ccaccacggc cagctaattt tgtattttta gtagagacag ggtttcacta
37981 tgttgatcat gctggtctca aactcctgac cttaggtgat ctgcccgcct tagcctccca
38041 aagtgttggg attacaggtg tgagccaccg cgcccagacc aaaatatgct cattttaata
38101 aaatgcacaa gtaggttgac aagaatttca cctgcaacct tgtcaaccac ctagaataaa
38161 agcctctgca gccctcccct aaagactcat caatgtgagg ctcaagaacc ttcttaggct
38221 gggctcggtg gctcatttct gtaatccctg cactttggaa ggctgaggca ggaggatctc
38281 ttgaggccag gagttcaaga caagcctggg caacatagcc agacctctgt ttctatcccc
38341 cacaaaaaga accttcttaa accggaattg agtcctacaa cctcgataac tcacaaataa
38401 gcccgtgtgg cctctcacag acttgggaag ttctccaagt gtccaggag atgtgccagg
38461 cgctttcctg ccgtgaccac cgtcctctgc ctgctccatt tcttggtggc cttccttag
38521 acctgggcct cactcttgct tctctcctgc agctctgggc gacgttgctg gcagaggaaa
```

-continued

```
38581 tgagaagaag cccagtagcg tgagggctct gtccattgtc ctccccatcg gtaagcgcgg
38641 gccggtcccc cagcgtcccc caggtcacag cctcccgcta tgtgacctcg tgcctggctg
38701 gttgggcctg ttcactttt ctcctggaca gggaacagcc ccactggtgt cctttatcac
38761 ccccacggcc tctcctggct tggggctgac agtgacaaga tcagacagct aagggtcag
38821 atggaggatg tggagctggg tcccgtgctg tggaatagcc tcaccgagat ttgagtgcct
38881 tctggggaac tggttccctt gcaggggct gtgtggagag gcgcgctctc cctgcctcac
38941 ccatgctcat cctaactcgg ttaccatcac atctctttt tctttttc ttaaatttta
39001 agaaaaaaga aatttaattt ttttgagaga cagagtcttg ctctgtcacc caggctggag
39061 tgcagtggca ccatcatgcc tcgctgcagc tcaatgtct gggctcaagc gatcctccca
39121 cctcagcctc ctgagtagct ggtgcaagcc actatacccc acttcctatt tcttaaaag
39181 tcacagccct gtgtgtggct aatcctggac agaaatctag aagaagtcag ctacttctgg
39241 ggcgtggctc acccagtggg cttcaggtta gatatttctt atacttatga ggctgggtgt
39301 ggtggcttat gcctgtaatc ccagcacttt gggaggctga agtgggtgga ttgcttgggc
39361 tcaggagttc gagaccaacc tgggcaacat ggcgaaaccc tgtttctaga aaggtacaa
39421 aaattagctg gcaggtggc acgtgcctgt ggtaccagct acttgagggc ctgaggcagg
39481 aggatcgctt gaacctggga ggtcgaggtt gcagtgaact gagatcatgt cactgcactc
39541 cagcctggtg acagagcaag accccgtctc aaaaaaaaaa aagaaagaa aaaattctt
39601 atgcatagat ttgcctcttt tctgtttgtt tgttttgaga tggagtctcg ctctgtcgcc
39661 caggctggag tacagtggct caacctcggc tcactgcaac ctctgcctcc cgggttcaag
39721 caattctcct gcctcagcct cctgagtagc tgggactaca ggcgcccgcc accatgccca
39781 gctaattttt gtattttag tagagactga ctgggtttca tcatgttggc caggctggtc
39841 tcgaactctt gacctcatga tccgcccgcc tcagcctccc aaaatgctgg gattacaggc
39901 gtgagccacc aggcccaggc cgcaaggcga tctctaaaca aacataaaag accaggagtc
39961 aaggttatgg tacgatgccc gtgttttcac tccagccacg gagctgggtc tctggtctcg
40021 ggggcagctg tgtgacagag cgtgcctctc cctacagtgc tcctcgtctt cctttgcctg
40081 ggggtcttcc ttctatggaa gaactggcgg cttaagaaca tcaacagcat caactttgac
40141 aaccccgtct atcagaagac cacagaggat gaggtccaca tttgccacaa ccaggacggc
40201 tacagctacc cctcggtgag tgaccctctc tagaaagcca gagcccatgg cggcccctc
40261 ccagctggag gcatatgatc tcaagggac caggccgagg cttccccagc cctccagatc
40321 gaggacagca ttaggtgaat gcttctgtgc gctcattcag aatgtcagcg acaatggcc
40381 ttggtggtgt agaggaatgt tggataagca aatagagagc tccatcagat ggtgacaggg
40441 caaagaaagt caaaggagt tcagaggccg ggcgcggtgg ctcatgcctg taatcccagg
40501 actttgggag gccgaggctg gcggatcacc tgaagtcagg agtttgagac cagcttggcc
40561 atcatgacaa aaccccgtct ctattaaaaa tacaaaaaat tagccaggcg tgggagtggg
40621 cgcctgtaat cccagctact cgggaggccg aggtagaaaa atcgcttgaa cctaggaggc
40681 agaggttgca gtgagccgag atcgcgccac tgcattccag cccgggaggc aagagcaaaa
40741 ctccatctca aaaaaaaaa aaaaggagt tcagaggccc ggcatggtgg ttcacacatg
40801 tgatcccaga acttggggag gttgaggcag gagaatcacc tgagctcaga gttcaagacc
40861 agcctgggca gcacagcaag accccatctc tgcaaaaaat aaaaatttag cccagtgtgg
40921 tgatgagcgc ctagttccag ctactaggga ggctaaggca ggaggattgc ttgaggctaa
```

-continued

```
40981 ggtaggagat tgagactgca gtgacttgtg attgcgtcac tgcgctccag cctgggtgac
41041 agagcaagcc cttgtctctt aaaaaaaaaa aaaaattcaa agaagggttt ccagagggcc
41101 aggagggagg aagggagagg aggtgtttta ttttttttgct tttattttt attttgagac
41161 agagtctctc tctgtcaccc aggttggagt gcagtgctgt gatcttggct cactgcaact
41221 tctgcctcct gggttcaagc aattcttatg cctcagcctc agcctcctga gtagctggga
41281 ttacaacact atgcccgggt aattttttgta ttttttagtag acgaggtt tcgccatgtt
41341 gcccagactg gtctcgaact cctgacctca gtgatccac ccgccttggc ctccccacgt
41401 gctgggattg caggcgtgag ccactgcgcc cgccttgatc tttacacaag gggtttaggg
41461 taggtagcct tctctgaacc aggagaacag cctgtgcgaa ggccctgagg ctggaccgtg
41521 cctgttgggt ttgaggccgt tgtagctgga gcaaacagag agagggtaa aaaggcagga
41581 ggctaccagg caggttgtgc agagccttgt gggccactgg ggaggacttt ggcttttgcc
41641 ctgagagcgg tgggaagtga ctgaatccgg tactcaccgt ctccctctgg cggctcctgg
41701 gggaacatgc ttggggatca ggctggggga ggctgccagg cccaggaggt gagaagtagg
41761 tggcctccag ccgtgtttcc tgaatgctgg actgatagtt tccgctgttt accatttgtt
41821 ggcagagaca gatggtcagt ctggaggatg acgtggcgtg aacatctgcc tggagtcccg
41881 tccctgccca gaacccttcc tgagacctcg ccggccttgt tttattcaaa gacagagaag
41941 accaaagcat tgcctgccag agctttgttt tatatattta ttcatctggg aggcagaaca
42001 ggcttcggac agtgcccatg caatggcttg ggttgggatt ttggtttctt cctttcctcg
42061 tgaaggataa gagaaacagg cccgggggga ccaggatgac acctccattt ctctccagga
42121 agttttgagt ttctctccac cgtgacacaa tcctcaaaca tggaagatga aaggggaggg
42181 gatgtcaggc ccagagaagc aagtggcttt caacacacaa cagcagatgg caccaacggg
42241 accccctggc cctgcctcat ccaccaatct ctaagccaaa cccctaaact caggagtcaa
42301 cgtgtttacc tcttctatgc aagccttgct agacagccag gttagccttt gccctgtcac
42361 ccccgaatca tgacccaccc agtgtctttc gaggtgggtt tgtaccttcc ttaagccagg
42421 aaagggattc atggcgtcgg aaatgatctg gctgaatccg tggtggcacc gagaccaaac
42481 tcattcacca aatgatgcca cttcccagag gcagagcctg agtcactggt cacccttaat
42541 atttattaag tgcctgagac acccggttac cttggccgtg aggacacgtg gcctgcaccc
42601 aggtgtggct gtcaggacac cagcctggtg cccatcctcc cgacccctac ccacttccat
42661 tcccgtggtc tccttgcact ttctcagttc agagttgtac actgtgtaca tttggcattt
42721 gtgttattat tttgcactgt tttctgtcgt gtgtgttggg atgggatccc aggccaggga
42781 aagcccgtgt caatgaatgc cggggacaga gaggggcagg ttgaccggga cttcaaagcc
42841 gtgatcgtga atatcgagaa ctgccattgt cgtctttatg tccgcccacc tagtgcttcc
42901 acttctatgc aaatgcctcc aagccattca cttccccaat cttgtcgttg atgggtatgt
42961 gtttaaaaca tgcacggtga ggccgggcgc agtggctcac gcctgtaatc ccagcacttt
43021 gggaggccga ggcgggtgga tcatgaggtc aggagatcga ccatcctg gctaacacgt
43081 gaaacccgt ctctactaaa aatacaaaaa attagccggg cgtggtggcg gcacctgta
43141 gtcccagcta ctcgggaggc tgaggcagga gaatggtgtg aacccgggaa gcggagcttg
43201 cagtgagccg agattgcgcg actgcagtcc gcagtctggc ctgggcgaca gagcgagact
43261 ccgtctcaaa aaaaaaaaac aaaaaaaaac catgcatggt gcatcagcag cccatggcct
43321 ctggccaggc atggcgaggc tgaggtggga ggatggtttg agctcaggca tttgaggctg
43381 tcgtgagcta tgattatgcc actgctttcc agcctgggca acatagtaag accccatctc
```

-continued

```
43441 ttaaaaaatg aatttggcca gacacaggtg cctcacgcct gtaatcccag cactttggga 43501 ggctgagctg gatcacttga gttcaggagt tggagaccag gcctgagcaa caaagcgaga 43561 tcccatctct acaaaaacca aaaagttaaa aatcagctgg gtacggtggc acgtgcctgt 43621 gatcccagct acttgggagg ctgaggcagg aggatcgcct gagcccagga ggtggaggtt 43681 gcagtgagcc atgatcgagc cactgcactc cagcctgggc aacagatgaa gaccctattt 43741 cagaaataca actataaaaa aataaataaa tcctccagtc tggatcgttt gacgggactt 43801 caggttcttt ctgaaatcgc cgtgttactg ttgcactgat gtccggagag acagtgacag 43861 cctccgtcag actcccgcgt gaagatgtca caagggattg gcaattgtcc ccaggggacaa 43921 aacactgtgt ccccccagt gcagggaacc gtgataagcc tttctggttt cggagcacgt 43981 aaatgcgtcc ctgtacagat agtggggatt ttttgttatg tttgcacttt gtatattggt 44041 tgaaactgtt atcacttata tatatatata tacacacata tataaaaat ctatttattt 44101 ttgcaaaccc tggttgctgt atttgttcag tgactattct cggggccctg tgtagggggt 44161 tattgcctct gaaatgcctc ttctttatgt acaaagatta tttgcacgaa ctggactgtg 44221 tgcaacgctt tttgggagaa tgatgtcccc gttgtatgta tgagtggctt ctgggagatg 44281 ggtgtcactt tttaaaccac tgtatagaag gttttgtag cctgaatgtc ttactgtgat 44341 caattaaatt tcttaaatg
```

SEQ ID NO: 31: Human LDL receptor cDNA sequence (NM_000527)   30
Coding Region Underlined.

```
   1 gccccgagtg caatcgcggg aagccagggt ttccagctag gacacagcag gtcgtgatcc 61 gggtcgggac actgcctggc agaggctgcg agcatggggc cctggggctg gaaattgcgc 121 tggaccgtcg ccttgctcct cgccgcggcg gggactgcag tgggcgacag atgtgaaaga 181 aacgagttcc agtgccaaga cgggaaatgc atctcctaca gtgggtctg cgatggcagc 241 gctgagtgcc aggatggctc tgatgagtcc caggagacgt gcttgtctgt cacctgcaaa 301 tccgggact tcagctgtgg gggccgtgtc aaccgctgca ttcctcagtt ctggaggtgc 361 gatggccaag tggactgcga caacggctca gacgagcaag ctgtccccc caagacgtgc 421 tcccaggacg agtttcgctg ccacgatggg aagtgcatct ctcggcagtt cgtctgtgac 481 tcagaccggg actgcttgga cggctcagac gaggcctcct gccgggtgct cacctgtggt 541 cccgccagct tccagtgcaa cagctccacc tgcatccccc agctgtgggc ctgcgacaac 601 gaccccgact gcgaagatgg ctcggatgag tggccgcagc gctgtagggg tctttacgtg 661 ttccaagggg acagtagccc ctgctcggcc ttcgagttcc actgcctaag tggcgagtgc 721 atccactcca gctggcgctg tgatggtggc cccgactgca aggacaaatc tgacgaggaa 781 aactgcgctg tggccacctg tcgccctgac gaattccagt gctctgatgg aaactgcatc 841 catggcagcc ggcagtgtga ccgggaatat gactgcaagg acatgagcga tgaagttggc 901 tgcgttaatg tgacactctg cgagggaccc aacaagttca gtgtcacag cggcgaatgc 961 atcaccctgg acaaagtctg caacatggct agagactgcc gggactggtc agatgaaccc 1021 atcaaagagt gcgggaccaa cgaatgcttg gacaacaacg gcggctgttc ccacgtctgc 1081 aatgaccta agatcggcta cgagtgcctg tgccccgacg gcttccagct ggtgcccag 1141 cgaagatgcg aagatatcga tgagtgtcag gatcccgaca cctgcagcca gctctgcgtg
```

```
1201 aacctggagg gtggctacaa gtgccagtgt gaggaaggct tccagctgga cccccacacg 1261 aaggcctgca aggctgtggg ctccatcgcc tacctcttct tcaccaaccg gcacgaggtc 1321 aggaagatga cgctggaccg gagcgagtac accagcctca tccccaacct gaggaacgtg 1381 gtcgctctgg acacggaggt ggccagcaat agaatctact ggtctgacct gtcccagaga 1441 atgatctgca gcacccagct tgacagagcc cacggcgtct cttcctatga caccgtcatc 1501 agcagggaca tccaggcccc cgacgggctg gctgtggact ggatccacag caacatctac 1561 tggaccgact ctgtcctggg cactgtctct gttgcggata ccaagggcgt gaagaggaaa 1621 acgttattca gggagaacgg ctccaagcca agggccatcg tggtggatcc tgttcatggc 1681 ttcatgtact ggactgactg gggaactccc gccaagatca gaaagggggg cctgaatggt 1741 gtggacatct actcgctggt gactgaaaac attcagtggc ccaatggcat caccctagat 1801 ctcctcagtg gccgcctcta ctgggttgac tccaaacttc actccatctc aagcatcgat 1861 gtcaatgggg gcaaccggaa gaccatcttg gaggatgaaa agaggctggc ccaccccttc 1921 tccttggccg tctttgagga caaagtattt tggacagata tcatcaacga agccattttc 1981 agtgccaacc gcctcacagg ttccgatgtc aacttgttgg ctgaaaacct actgtcccca 2041 gaggatatgg tcctcttcca caacctcacc cagccaagag gagtgaactg gtgtgagagg 2101 accaccctga gcaatggcgg ctgccagtat ctgtgcctcc ctgccccgca gatcaacccc 2161 cactcgccca gtttacctg cgcctgcccg gacggcatgc tgctggccag ggacatgagg 2221 agctgcctca cagaggctga ggctgcagtg gccacccagg agacatccac cgtcaggcta 2281 aaggtcagct ccacagccgt aaggacacag cacacaacca cccggcctgt tcccgacacc 2341 tcccggctgc ctggggccac ccctgggctc accacggtgg agatagtgac aatgtctcac 2401 caagctctgg gcgacgttgc tggcagagga atgagaaga agcccagtag cgtgagggct 2461 ctgtccattg tcctccccat cgtgctcctc gtcttccttt gcctgggggt cttccttcta 2521 tggaagaact ggcggcttaa gaacatcaac agcatcaact ttgacaaccc cgtctatcag 2581 aagaccacag aggatgaggt ccacatttgc cacaaccagg acggctacag ctacccctcg 2641 agacagatgg tcagtctgga ggatgacgtg gcgtgaacat ctgcctggag tcccgcccct 2701 gcccagaacc cttcctgaga cctcgccggc cttgttttat tcaaagacag agaagaccaa 2761 agcattgcct gccagagctt tgttttatat atttattcat ctgggaggca gaacaggctt 2821 cggacagtgc ccatgcaatg gcttgggttg ggattttggt ttcttccttt cctgtgaagg 2881 ataagagaaa caggcccggg gggaccagga tgacacctcc atttctctcc aggaagtttt 2941 gagtttctct ccaccgtgac acaatcctca acatggaag atgaaggc aggggatgtc 3001 aggcccagag aagcaagtgg ctttcaacac acaacagcag atggcaccaa cgggaccccc 3061 tggccctgcc tcatccacca atctctaagc caaaccccta aactcaggag tcaacgtgtt 3121 tacctcttct atgcaagcct tgctagacag ccaggttagc ctttgccctg tcaccccga 3181 atcatgaccc acccagtgtc tttcgaggtg ggtttgtacc ttccttaagc caggaaaggg 3241 attcatggcg tcggaaatga tctggctgaa tccgtggtgg caccgagacc aaactcattc 3301 accaaatgat gccacttccc agaggcagag cctgagtcac cggtcaccct taatatttat 3361 taagtgcctg agacacccgg ttacctggc cgtgaggaca cgtggcctgc acccaggtgt 3421 ggctgtcagg acaccagcct ggtgcccatc ctcccgaccc ctaccacctt ccattcccgt 3481 ggtctccttg cactttctca gttcagagtt gtacactgtg tacatttggc atttgtgtta 3541 ttattttgca ctgttttctg tcgtgtgtgt tgggatggga tcccaggcca gggaaagccc 3601 gtgtcaatga atgccgggga cagagagggg caggttgacc gggacttcaa agccgtgatc
```

-continued

```
3661 gtgaatatcg agaactgcca ttgtcgtctt tatgtccgcc cacctagtgc ttccacttct 3721 atgcaaatgc ctccaagcca ttcacttccc caatcttgtc gttgatgggt atgtgtttaa 3781 aacatgcacg gtgaggccgg gcgcagtggc ctcacgcctg taatcccagc actttgggag 3841 gccgaggcgg gtggatcatg aggtcaggag atcgagacca tcctggctaa caaggtgaaa 3901 ccccgtctct actaaaaata caaaaaatta gccgggcgcg gtggtgggca cctgtagtcc 3961 cagctactcg ggaggctgag gcaggagaat ggtgtgaacc cgggaagcgg agcttgcagt 4021 gagccgagat tgcgccactg cagtccgcag tctggcctgg gcgacagagc gagactccgt 4081 ctcaaaaaaa acaaaacaaa aaaaaaccat gcatggtgca tcagcagccc atggcctctg 4141 gccaggcatg gcgaggctga ggtgggagga tggtttgagc tcaggcattt gaggctgtcg 4201 tgagctatga ttatgccact gctttccagc ctgggcaaca tagtaagacc ccatctctta 4261 aaaaatgaat ttggccagac acaggtgcct cacgcctgta atcccagcac tttgggaggc 4321 tgagctggat cacttgagtt caggagttgg agaccaggcc tgagcaacaa agcgagatcc 4381 catctctaca aaaccaaaa agttaaaaat cagctgggta tggtggcacg tgcctgtgat 4441 cccagctact gggaggctg aggcaggagg atcgcctgag cccaggaggt ggaggttgca 4501 gtgagccatg atcgagccac tgcactccag cctgggcaac agatgaagac cctatttcag 4561 aaatacaact ataaaaaaaa taaataaatc ctccagtctg gatcgtttga cgggacttca 4621 ggttctttct gaaatcgccg tgttactgtt gcactgatgt ccggagagac agtgacagcc 4681 tccgtcagac tccgcgtgta agatgtcaca agggattggc aattgtcccc agggacaaaa 4741 cactgtgtcc cccccagtgc agggaaccgt gataagcctt tctggtttcg gagcacgtaa 4801 atgcgtccct gtacagatag tggggatttt ttgttatgtt tgcactttgt atattggttg 4861 aaactgttat cacttatata tatatataca cacatatata taaaatctat ttattttgc 4921 aaaccctggt tgctgtatt gttcagtgac tattctcggg gccctgtgta gggggttatt 4981 gcctctgaaa tgcctcttct ttatgtacaa agattatttg cacgaactgg actgtgtgca 5041 acgcttttg ggagaatgat gtccccgttg tatgtatgag tggcttctgg gagatgggtg 5101 tcactttta aaccactgta tagaaggttt ttgtagcctg aatgtcttac tgtgatcaat 5161 taaatttctt aaatg
```

SEQ ID NO: 32: Human LDL receptor protein sequence
NP_000518
Protein Sequence of Precursor Protein (1-860).

```
  1 mgpwgwklrw tvalllaaag tavgdrcern efqcqdgkci sykwvcdgsa ecqdgsdesq 61 etclsvtcks gdfscggrvn rcipqfwrcd gqvdcdngsd eqgcppktcs qdefrchdgk 121 cisrqfvcds drdcldgsde ascpvltcgp asfqcnsstc ipqlwacdnd pdcedgsdew 181 pqrcrglyvf qgdsspcsaf efhclsgeci hsswrcdggp dckdksdeen cavatcrpde 241 fqcsdgncih gsrqcdreyd ckdmsdevgc vnvtlcegpn kfkchsgeci tldkvcnmar 301 dcrdwsdepi kecgtnecld nnggcshvcn dlkigyeclc pdgfqlvaqr cedidecqd 361 pdtcsqlcvn leggykcqce egfqldphtk ackavgsiay lfftnrhevr kmtldrseyt 421 slipnlrnvv aldtevasnr iywsdlsqrm icstqldrah gvssydtvis rdiqapdgla 481 vdwihsniyw tdsvlgtvsv adtkgvkrkt lfrengskpr aivvdpvhgf mywtdwgtpa 541 kikkgglngv diyslvteni qwpngitldl lsgrlywvds klhsissidv nggnrktile 601 dekrlahpfs lavfedkvfw tdiineaifs anrltgsdvn llaenllspe dmvlfhnltq
```

```
661 prgvnwcert tlsnggcqyl clpapqinph spkftcacpd gmllardmrs clteaeaava 721 tqetstvrlk vsstavrtqh tttrpvpdts rlpgatpglt tveivtmshq algdvagrgn 781 ekkpssvral sivlpivllv flclgvfllw knwrlknins infdnpvyqk ttedevhich 841 nqdgysypsr qmvsleddva
``` shRNA sequence
siRNAs with target sites in porcine LDL receptor mRNA sequence

| | Startbase in porcine cDNA AF065990 sequence | Sequence |
|---|---|---|
| Target 1 | 763 | tgtcaaagcggcgagtgca (SEQ ID NO: 5) |
| Target 2 | 889 | tcccatatctgcaatgacc (SEQ ID NO: 6) |
| Target 3 | 1150 | accctggaccgtagtgagt (SEQ ID NO: 7) |
| Target 4 | 1308 | tgacaccattattggcgaa (SEQ ID NO: 8) |
| Target 5 | 1309 | gacaccattattggcgaag (SEQ ID NO: 9) |
| Target 6 | 1439 | agactctcttccaagagaa (SEQ ID NO: 10) |
| Target 7 | 1553 | tgaacggagtggacgtcta (SEQ ID NO: 11) |
| Target 8 | 1814 | tcacaggctcggacataca (SEQ ID NO: 12) |

SEQ ID NO: 33: pSUPER.retro.puro sequence
Used Restriction Sites
  BglII: 1447
  XhoI: 1420
Numbers Refer to the Original pSuper.retro.puro Sequence
pSUPER retro.puro SEQUENCE:

```
   1 TGAAAGACCC CACCTGTAGG TTTGGCAAGC TAGCTTAAGT AACGCCATTT TGCAAGGCAT
  61 GGAAAATACA TAACTGAGAA TAGAGAAGTT CAGATCAAGG TTAGGAACAG AGAGACAGCA
 121 GAATATGGGC CAAACAGGAT ATCTGTGGTA AGCAGTTCCT GCCCCGGCTC AGGGCCAAGA
 181 ACAGATGGTC CCCAGATGCG GTCCCGCCCT CAGCAGTTTC TAGAGAACCA TCAGATGTTT
 241 CCAGGGTGCC CCAAGGACCT GAAATGACCC TGTGCCTTAT TTGAACTAAC CAATCAGTTC
 301 GCTTCTCGCT TCTGTTCGCG CGCTTCTGCT CCCCGAGCTC AATAAAAGAG CCCACAACCC
 361 CTCACTCGGC GCGCCAGTCC TCCGATAGAC TGCGTCGCCC GGGTACCCGT ATTCCCAATA
 421 AAGCCTCTTG CTGTTTGCAT CCGAATCGTG GACTCGCTGA TCCTTGGGAG GGTCTCCTCA
 481 GATTGATTGA CTGCCCACCT CGGGGGTCTT TCATTTGGAG GTTCCACCGA GATTTGGAGA
 541 CCCCTGCCCA GGGACCACCG ACCCCCCCGC CGGGAGGTAA GCTGGCCAGC GGTCGTTTCG
 601 TGTCTGTCTC TGTCTTTGTG CGTGTTTGTG CCGGCATCTA ATGTTTGCGC CTGCGTCTGT
 661 ACTAGTTAGC TAACTAGCTC TGTATCTGGC GGACCCGTGG TGGAACTGAC GAGTTCTGAA
 721 CACCCGGCCG CAACCCTGGG AGACGTCCCA GGGACTTTGG GGGCCGTTTT TGTGGCCCGA
 781 CCTGAGGAAG GGAGTCGATG TGGAATCCGA CCCCGTCAGG ATATGTGGTT CTGGTAGGAG
 841 ACGAGAACCT AAAACAGTTC CCGCCTCCGT CTGAATTTTT GCTTTCGGTT TGGAACCGAA
 901 GCCGCGCGTC TTGTCTGCTG CAGCGCTGCA GCATCGTTCT GTGTTGTCTC TGTCTGACTG
 961 TGTTTCTGTA TTTGTCTGAA AATTAGGGCC AGACTGTTAC CACTCCCTTA AGTTTGACCT
1021 TAGGTCACTG GAAAGATGTC GAGCGGATCG CTCACAACCA GTCGGTAGAT GTCAAGAAGA
1081 GACGTTGGGT TACCTTCTGC TCTGCAGAAT GGCCAACCTT TAACGTCGGA TGGCCGCGAG
1141 ACGGCACCTT TAACCGAGAC CTCATCACCC AGGTTAAGAT CAAGGTCTTT TCACCTGGCC
1201 CGCATGGACA CCCAGACCAG GTCCCCTACA TCGTGACCTG GGAAGCCTTG GCTTTTGACC
1261 CCCCTCCCTG GGTCAAGCCC TTTGTACACC CTAAGCCTCC GCCTCCTCTT CCTCCATCCG
```

-continued

```
1321 CCCCGTCTCT CCCCCTTGAA CCTCCTCGTT CGACCCCGCC TCGATCCTCC CTTTATCCAG

1381 CCCTCACTCC TTCTCTAGGC GCCGGAATTA GATCGATCTC
```

SEQ ID NO: 34: a) original pSUPER.retro.puro sequence
TCGAGGTCGA CGGTATCGAT AAGCTTA
SEQ ID NO: 35: b) After cleavage (BglII og XhoI) and insertion of
T1 DNA oligo
TCGAGAAAAA TGTCAAAGCG GCGAGTGCAT TCAAGAGATG CACTCGCCGC
TTTGACAGGG
SEQ ID NO: 36: c) Similar for for T2-T8
         GAT CTGTGGTCTC ATACAGAACT TATAAGATTC CCAAATCCAA AGACATTTCA

```
1501 CGTTTATGGT GATTTCCCAG AACACATAGC GACATGCAAA TATTGCAGGG CGCCACTCCC

1561 CTGTCCCTCA CAGCCATCTT CCTGCCAGGG CGCACGCGCG CTGGGTGTTC CCGCCTAGTG

1621 ACACTGGGCC CGCGATTCCT TGGAGCGGGT TGATGACGTC AGCGTTCGAA TTCTACCGGG

1681 TAGGGGAGGC GCTTTTCCCA AGGCAGTCTG GAGCATGCGC TTTAGCAGCC CCGCTGGGCA

1741 CTTGGCGCTA CACAAGTGGC CTCTGGCCTC GCACACATTC CACATCCACC GGTAGGCGCC

1801 AACCGGCTCC GTTCTTTGGT GGCCCCTTCG CGCCACCTTC TACTCCTCCC CTAGTCAGGA

1861 AGTTCCCCCC CGCCCCGCAG CTCGCGTCGT GCAGGACGTG ACAAATGGAA GTAGCACGTC

1921 TCACTAGTCT CGTGCAGATG GACAGCACCG CTGAGCAATG GAAGCGGGTA GGCCTTTGGG

1981 GCAGCGGCCA ATAGCAGCTT TGCTCCTTCG CTTTCTGGGC TCAGAGGCTG GGAAGGGGTG

2041 GGTCCGGGGG CGGGCTCAGG GGCGGGCTCA GGGGCGGGGC GGGCGCCCGA AGGTCCTCCG

2101 GAGGCCCGGC ATTCTGCACG CTTCAAAAGC GCACGTCTGC CGCGCTGTTC TCCTCTTCCT

2161 CATCTCCGGG CCTTTCGACC TGCAGCCCAA GCTAGCTTAC CATGACCGAG TACAAGCCCA

2221 CGGTGCGCCT CGCCACCCGC GACGACGTCC CCAGGGCCGT ACGCACCCTC GCCGCCGCGT

2281 TCGCCGACTA CCCCGCCACG CGCCACACCG TCGATCCGGA CCGCCACATC GAGCGGGTCA

2341 CCGAGCTGCA AGAACTCTTC CTCACGCGCG TCGGGCTCGA CATCGGCAAG GTGTGGGTCG

2401 CGGACGACGG CGCCGCGGTG GCGGTCTGGA CCACGCCGGA GAGCGTCGAA GCGGGGGCGG

2461 TGTTCGCCGA GATCGGCCCG CGCATGGCCG AGTTGAGCGG TTCCCGGCTG GCCGCGCAGC

2521 AACAGATGGA AGGCCTCCTG GCGCCGCACC GGCCCAAGGA GCCCGCGTGG TTCCTGGCCA

2581 CCGTCGGCGT CTCGCCCGAC CACCAGGGCA AGGGTCTGGG CAGCGCCGTC GTGCTCCCCG

2641 GAGTGGAGGC GGCCGAGCGC GCCGGGGTGC CCGCCTTCCT GGAGACCTCC GCGCCCCGCA

2701 ACCTCCCCTT CTACGAGCGG CTCGGCTTCA CCGTCACCGC CGACGTCGAG GTGCCCGAAG

2761 GACCGCGCAC CTGGTGCATG ACCCGCAAGC CCGGTGCCTG ACGCCCGCCC CACGACCCGC

2821 AGCGCCCGAC CGAAAGGAGC GCACGACCCC ATGCATCGAT AAAATAAAAG ATTTATTTA

2881 GTCTCCAGAA AAGGGGGGA ATGAAAGACC CCACCTGTAG GTTTGGCAAG CTAGAGAACC

2941 ATCAGATGTT TCCAGGGTGC CCCAAGGACC TGAAATGACC CTGTGCCTTA TTTGAACTAA

3001 CCAATCAGTT CGCTTCTCGC TTCTGTTCGC GCGCTTCTGC TCCCCGAGCT CAATAAAAGA

3061 GCCCACAACC CCTCACTCGG CGCGCCAGTC CTCCGATAGA CTGCGTCGCC CGGGTACCCG

3121 TGTATCCAAT AAACCCTCTT GCAGTTGCAT CCGACTTGTG GTCTCGCTGT TCCTTGGGAG

3181 GGTCTCCTCT GAGTGATTGA CTACCCGTCA GCGGGGGTCT TTCATGGGTA ACAGTTTCTT

3241 GAAGTTGGAG AACAACATTC TGAGGGTAGG AGTCGAATAT TAAGTAATCC TGACTCAATT

3301 AGCCACTGTT TTGAATCCAC ATACTCCAAT ACTCCTGAAA TAGTTCATTA TGGACAGCGC

3361 AGAAGAGCTG GGGAGAATTA ATTCGTAATC ATGGTCATAG CTGTTTCCTG TGTGAAATTG

3421 TTATCCGCTC ACAATTCCAC ACAACATACG AGCCGGAAGC ATAAAGTGTA AAGCCTGGGG

3481 TGCCTAATGA GTGAGCTAAC TCACATTAAT TGCGTTGCGC TCACTGCCCG CTTTCCAGTC
```

```
3541 GGGAAACCTG TCGTGCCAGC TGCATTAATG AATCGGCCAA CGCGCGGGGA GAGGCGGTTT

3601 GCGTATTGGG CGCTCTTCCG CTTCCTCGCT CACTGACTCG CTGCGCTCGG TCGTTCGGCT

3661 GCGGCGAGCG GTATCAGCTC ACTCAAAGGC GGTAATACGG TTATCCACAG AATCAGGGGA

3721 TAACGCAGGA AAGAACATGT GAGCAAAAGG CCAGCAAAAG GCCAGGAACC GTAAAAAGGC

3781 CGCGTTGCTG GCGTTTTTCC ATAGGCTCCG CCCCCCTGAC GAGCATCACA AAAATCGACG

3841 CTCAAGTCAG AGGTGGCGAA ACCCGACAGG ACTATAAAGA TACCAGGCGT TTCCCCCTGG

3901 AAGCTCCCTC GTGCGCTCTC CTGTTCCGAC CCTGCCGCTT ACCGGATACC TGTCCGCCTT

3961 TCTCCCTTCG GGAAGCGTGG CGCTTTCTCA TAGCTCACGC TGTAGGTATC TCAGTTCGGT

4021 GTAGGTCGTT CGCTCCAAGC TGGGCTGTGT GCACGAACCC CCCGTTCAGC CCGACCGCTG

4081 CGCCTTATCC GGTAACTATC GTCTTGAGTC AACCCGGTA AGACACGACT TATCGCCACT

4141 GGCAGCAGCC ACTGGTAACA GGATTAGCAG AGCGAGGTAT GTAGGCGGTG CTACAGAGTT

4201 CTTGAAGTGG TGGCCTAACT ACGGCTACAC TAGAAGGACA GTATTTGGTA TCTGCGCTCT

4261 GCTGAAGCCA GTTACCTTCG GAAAAAGAGT TGGTAGCTCT TGATCCGGCA ACAAACCAC

4321 CGCTGGTAGC GGTGGTTTTT TTGTTTGCAA GCAGCAGATT ACGCGCAGAA AAAAGGATC

4381 TCAAGAAGAT CCTTTGATCT TTTCTACGGG GTCTGACGCT CAGTGGAACG AAAACTCACG

4441 TTAAGGGATT TTGGTCATGA GATTATCAAA AAGGATCTTC ACCTAGATCC TTTTAAATTA

4501 AAAATGAAGT TTTAAATCAA TCTAAAGTAT ATATGAGTAA ACTTGGTCTG ACAGTTACCA

4561 ATGCTTAATC AGTGAGGCAC CTATCTCAGC GATCTGTCTA TTTCGTTCAT CCATAGTTGC

4621 CTGACTCCCC GTCGTGTAGA TAACTACGAT ACGGGAGGGC TTACCATCTG GCCCCAGTGC

4681 TGCAATGATA CCGCGAGACC CACGCTCACC GGCTCCAGAT TTATCAGCAA TAAACCAGCC

4741 AGCCGGAAGG GCCGAGCGCA GAAGTGGTCC TGCAACTTTA TCCGCCTCCA TCCAGTCTAT

4801 TAATTGTTGC CGGGAAGCTA GAGTAAGTAG TTCGCCAGTT AATAGTTTGC GCAACGTTGT

4861 TGCCATTGCT ACAGGCATCG TGGTGTCACG CTCGTCGTTT GGTATGGCTT CATTCAGCTC

4921 CGGTTCCCAA CGATCAAGGC GAGTTACATG ATCCCCCATG TTGTGCAAAA AAGCGGTTAG

4981 CTCCTTCGGT CCTCCGATCG TTGTCAGAAG TAAGTTGGCC GCAGTGTTAT CACTCATGGT

5041 TATGGCAGCA CTGCATAATT CTCTTACTGT CATGCCATCC GTAAGATGCT TTTCTGTGAC

5101 TGGTGAGTAC TCAACCAAGT CATTCTGAGA ATAGTGTATG CGGCGACCGA GTTGCTCTTG

5161 CCCGGCGTCA ATACGGGATA ATACCGCGCC ACATAGCAGA ACTTTAAAAG TGCTCATCAT

5221 TGGAAAACGT TCTTCGGGGC GAAAACTCTC AAGGATCTTA CCGCTGTTGA GATCCAGTTC

5281 GATGTAACCC ACTCGTGCAC CCAACTGATC TTCAGCATCT TTTACTTTCA CCAGCGTTTC

5341 TGGGTGAGCA AAAACAGGAA GGCAAAATGC CGCAAAAAAG GGAATAAGGG CGACACGGAA

5401 ATGTTGAATA CTCATACTCT TCCTTTTTCA ATATTATTGA AGCATTTATC AGGGTTATTG

5461 TCTCATGAGC GGATACATAT TTGAATGTAT TTAGAAAAAT AAACAAATAG GGGTTCCGCG

5521 CACATTTCCC CGAAAAGTGC CACCTGACGT CTAAGAAACC ATTATTATCA TGACATTAAC

5581 CTATAAAAAT AGGCGTATCA CGAGGCCCTT TCGTCTCGCG CGTTTCGGTG ATGACGGTGA

5641 AAACCTCTGA CACATGCAGC TCCCGGAGAC GGTCACAGCT TGTCTGTAAG CGGATGCCGG
```

```
5701 GAGCAGACAA GCCCGTCAGG GCGCGTCAGC GGGTGTTGGC GGGTGTCGGG GCTGGCTTAA

5761 CTATGCGGCA TCAGAGCAGA TTGTACTGAG AGTGCACCAT ATGCGGTGTG AAATACCGCA

5821 CAGATGCGTA AGGAGAAAAT ACCGCATCAG GCGCCATTCG CCATTCAGGC TGCGCAACTG

5881 TTGGGAAGGG CGATCGGTGC GGGCCTCTTC GCTATTACGC CAGCTGGCGA AAGGGGGATG

5941 TGCTGCAAGG CGATTAAGTT GGGTAACGCC AGGGTTTTCC CAGTCACGAC GTTGTAAAAC

6001 GACGGCGCAA GGAATGGTGC ATGCAAGGAG ATGGCGCCCA ACAGTCCCCC GGCCACGGGG

6061 CCTGCCACCA TACCCACGCC GAAACAAGCG CTCATGAGCC CGAAGTGGCG AGCCCGATCT

6121 TCCCCATCGG TGATGTCGGC GATATAGGCG CCAGCAACCG CACCTGTGGC GCCGGTGATG

6181 CCGGCCACGA TGCGTCCGGC GTAGAGGCGA TTAGTCCAAT TTGTTAAAGA CAGGATATCA

6241 GTGGTCCAGG CTCTAGTTTT GACTCAACAA TATCACCAGC TGAAGCCTAT AGAGTACGAG

6301 CCATAGATAA AATAAAAGAT TTTATTTAGT CTCCAGAAAA AGGGGGGAA
```

SEQ ID NO: 37: pSBT/SV40-GFIP.loxP, sequence

SB inverted repeats
SV40 promoter
Start codon
FRT site
eGFP
Puro

```
tcgcgcgtttcggtgatgacggtgaaaacctctgacacatgcagctcccggagacggtcacagcttgtctgtaagcggat
gccgggagcagacaagcccgtcagggcgcgtcagcgggtgttggcgggtgtcggggctggcttaactatgcggcatca
gagcagattgtactgagagtgcaccatatgcggtgtgaaataccgcacagatgcgtaaggagaaaataccgcatcagg
cgccattcgccattcaggctgcgcaactgttgggaagggcgatcggtgcgggcctcttcgctattacgccagctggcgaa
agggggatgtgctgcaaggcgattaagttgggtaacgccagggttttcccagtcacgacgttgtaaaacgacggccagt
gaattcgagctcggtacctacagttgaagtcggaagtttacatacacttaagttggagtcattaaaactcgtttttcaactac
tccacaaatttcttgttaacaaacaatagtttttggcaagtcagttaggacatctactttgtgcatgacaaagtcatttttccaa
caattgtttacagacagattatttcacttataattcactgtatcacaattccagtgggtcagaagtttacatacactaagttgact
gtgcctttaaacagcttggaaaattccagaaaatgatgtcatggctttagaagcttctgatagactaattgacatcatttgagt
caattggaggtgtacctgtggatgtatttcaagggaattctgtggaatgtgtgtcagttagggtgtggaaagtccccaggctc
cccaggcaggcagaagtatgcaaagcatcgaggatgtacgggccagatatacgcgataacttcgtataatgtatgctat
acgaagttatcgcgtgaggttttcaccgtcatcaccgaaacgcgcgaggagctgtgtggaatgtgtgtcagttagggtgtgg
aaagtccccaggctcccagcaggcagaagtatgcaaagcatgcatctcaattagtcagcaaccaggtgtggaaagtc
cccaggctcccagcaggcagaagtatgcaaagcatgcatctcaattagtcagcaaccatagtcccgcccctaactcc
gcccatccgcccctaactccgcccagttccgcccattctccgccccatggctgactaattttttttatttatgcagaggccga
ggccgcctcggcctctgagctattccagaagtagtgaggaggcttttttggaggctaccatggagaagttactattccgaa gttcctattctctagaaagtataggaacttcaagcttggcactggtgagcaaggcgaggagctgttcaccggggtggtgc
ccatcctggtcgagctggacggcgacgtaaacggccacaagttcagcgtgtccggcgagggcgagggcgatgccac
ctacggcaagctgaccctgaagttcatctgcaccaccggcaagctgcccgtgccctggcccaccctcgtgaccaccctg
acctacggcgtgcagtgcttcagccgctaccccgaccacatgaagcagcacgacttcttcaagtccgccatgcccgaag
gctacgtccaggagcgcaccatcttcttcaaggacgacggcaactacaagacccgcgccgaggtgaagttcgagggc
gacaccctggtgaaccgcatcgagctgaagggcatcgacttcaaggaggacggcaacatcctggggcacaagctgg
agtacaactacaacagccacaacgtctatatcatggccgacaagcagaagaacggcatcaaggtgaacttcaagatc
cgccacaacatcgaggacggcagcgtgcagctcgccgaccactaccagcagaacacccccatcggcgacggcccc
gtgctgctgcccgacaaccactacctgagcacccagtccgccctgagcaaagaccccaacgagaagcgcgatcacat
ggtcctgctggagttcgtgaccgccgccgggatcactctcggcatggacgagctgtacaagtaaagcggccgcggcca
attgggccaccggtgctagcccccctaacgttactggccgaagccgcttggaataaggccggtgtgcgtttgtctatatgttat
tttccaccatattgccgtcttttggcaatgtgagggcccggaaacctggccctgtcttcttgacgagcattcctaggggtctttc
ccctctcgccaaaggaatgcaaggtctgttgaatgtcgtgaaggaagcagttcctctggaagcttcttgaagacaaacaa
cgtctgtagcgaccctttgcaggcagcggaacccccaccctggcgacaggtgcctctgcggccaaaagccacgtgtat
aagatacacctgcaaaggcggcacaacccccagtgccacgttgtgagttggatagttgtggaaagagtcaaatggctctc
ctcaagcgtattcaacaagggctgaaggatgcccagaaggtacccccattgtatgggatctgatctgggcctcggtgc
acatgctttacatgtgtttagtcgaggttaaaaaacgtctaggcccccccgaaccacggggacgtggttttcctttgaaaaac
acgataataccatgaccgagtacaagcccacggtgcgcctcgcccaccgacgagtcccccgggccgtacgcac
cctcgccgccgcgttcgccgactacccgccacgcgccacaccgtcgatccggaccgccacatcgagcgggtcaccg
agctgcaagaactcttcctcacgcgcgtcggctcgacatcggcaaggtgtggtcgcggacgacgcgcccgcggtg
gcggtctggaccacgccggagagcgtcgaagcggggcggtgttcgccgagatcggcccgcgatggccgagttga
gcggttccccggccggcgcgcagcaacagatggaaggcctcctggcgccgcaccggcccaaggagccgcgtggtt
cctggccaccgtcggcgtctcgcccgaccaccagggcaagggtctgggcagcgccgtcgtgctccccggagtggagg
cggccgagcgcgccggggtgcccgccttcctggagacctccgcgccccgcaacctcccctctacgagcggctcggctt
caccgtcaccgccgacgtcgaggtgcccgaaggaccgcgcacctggtgcatgacccgcaagcccggtgcctgacgc
```

-continued

```
ccgcccacaagacccgcagcgcccgaccgaaaggagcgcacgaccccatgcatcgaatcgatatcgcggccgcga
ctctagatcataatcagcccgggggtgatcagcctcgactgtgccttctagttgccagccatctgttgtttgccctcccccgt
gccttccttgaccctggaaggtgccactcccactgtcctttcctaataaaatgaggaaattgcatcgcattgtctgagtaggt
gtcattctattctgggggtggggtggggcaggacagcaaggggggaggattgggaagacaatagcaggcatgctggg
gatgcggtgggctctatggaaccagctggggctcgacattctagttgtggtttgtccaaactcatcaatgtatcttatcatgtct
ggatcccatcacaaagctctgacctcaatcctatagaaaggaggaatgagccaaaattcacccaacttattgtgggaag
cttgtggaaggctactcgaaatgtttgacccaagttaaacaatttaaaggcaatgctaccaaatactaattgagtgtatgtta
acttctgacccactgggaatgtgatgaaagaaataaaagctgaaatgaatcattctctctactattattctgatatttcacattc
ttaaaataaagtggtgatcctaactgaccttaagacagggaatctttactcggattaaatgtcaggaattgtgaaaagtga
gtttaaatgtatttggctaaggtgtatgtaaacttccgacttaactgtagggatcctctagagtcgacctgcaggcatgcaa
gcttggcgtaatcatggtcatagctgtttcctgtgtgaaattgttatccgctcacaattccacaacatacgagccggaagc
ataaagtgtaaagcctggggtgcctaatgagtgagctaactcacattaattgcgttgcgctcactgcccgctttccagtcgg
gaaacctgtcgtgccagctgcattaatgaatcggccaacgcgcgggagaggcggtttgcgtattgggcgctcttccgctt
cctcgctcactgactcgctgcgctcggtcgttcggctgcggcgagcggtatcagctcactcaaaggcggtaatacggttat
ccacagaatcaggggataacgcaggaaagaacatgtgagcaaaaggccagcaaaaggccaggaaccgtaaaaa
ggccgcgttgctggcgtttttccataggctccgcccccctgacgagcatcacaaaaatcgacgctcaagtcagaggtggc
gaaacccgacaggactataaagataccaggcgtttccccctggaagctccctcgtgcgctctcctgttccgaccctgccg
cttaccggatacctgtccgcctttctcccttcgggaagcgtggcgctttctcaatgctcacgctgtaggtatctcagttcggtgt
aggtcgttcgctccaagctgggctgtgtgcacgaaccccccgttcagcccgaccgctgcgccttatccggtaactatcgtct
tgagtccaacccggtaagacacgacttatcgccactggcagcagccactggtaacaggattagcagagcgaggtatgt
aggcggtgctacagagttcttgaagtggtggcctaactacggctacactagaaggacagtatttggtatctgcgctctgctg
aagccagttaccttcggaaaaagagttggtagctcttgatccggcaaacaaaccaccgctggtagcggtggtttttttgtttg
caagcagcagattacgcgcagaaaaaaaggatctcaagaagatcctttgatcttttctacggggtctgacgctcagtgga
acgaaaactcacgttaagggattttggtcatgagattatcaaaaaggatcttcacctagatccttttaaattaaaaatgaagt
tttaaatcaatctaaagtatatatgagtaaacttggtctgacagttaccaatgcttaatcagtgaggcacctatctcagcgatc
tgtctatttcgttcatccatagttgcctgactccccgtcgtgtagataactacgatacgggagggcttaccatctggccccagt
gctgcaatgataccgcgagacccacgctcaccggctccagatttatcagcaataaaccagccagccggaagggccga
gcgcagaagtggtcctgcaactttatccgcctccatccagtctattaattgttgccgggaagctagagtaagtagttcgcca
gttaatagtttgcgcaacgttgttgccattgctacaggcatcgtggtgtcacgctcgtcgtttggtatggcttcattcagctccgg
ttcccaacgatcaaggcgagttacatgatccccccatgttgtgcaaaaaagcggttagctccttcggtcctccgatcgttgtc
agaagtaagttggccgcagtgttatcactcatggttatggcagcactgcataattctcttactgtcatgccatccgtaagatg
cttttctgtgactggtgagtactcaaccaagtcattctgagaatagtgtatgcggcgaccgagttgctcttgcccggcgtcaat
acgggataataccgcgccacatagcagaactttaaaagtgctcatcattggaaaacgttcttcggggcgaaaactctca
affatcttaccgctgttgagatccagttcgatgtaacccactcgtgcacccaactgatcttcagcatcttttactttcaccagc
gtttctgggtgagcaaaaacaggaaggcaaaatgccgcaaaaaagggaataagggcgacacggaaatgttgaatac
tcatactcttcctttttcaatattattgaagcatttatcagggttattgtctcatgagcggatacatatttgaatgtatttagaaaaat
aaacaaataggggttccgcgcacatttccccgaaaagtgccacctgacgtctaagaaaccattattatcatgacattaac
ctataaaaataggcgtatcacgaggccctttcgtc
```

SEQ ID NO: 38: pSBT/RSV-GFIP, sequence

SB inverted repeats
RSV promoter
Start codon
PRT site
eGFP
Puro

```
tcgcgcgtttcggtgatgacggtgaaaacctctgacacatgcagctcccggagacggtcacagcttgtctgtaagcggat
gccgggagcagacaagcccgtcagggcgcgtcagcgggtgttggcgggtgtcggggctggcttaactatgcggcatca
gagcagattgtactgagagtgcaccatatgcggtgtgaaataccgcacagatgcgtaaggagaaaataccgcatcagg
cgccattcgccattcaggctgcgcaactgttgggaagggcgatcggtgcgggcctcttcgctattacgccagctggcgaa
agggggatgtgctgcaaggcgattaagttgggtaacgccagggttttcccagtcacgacgttgtaaaacgacggccagt
gaattcgagctcggtaccctacagttgaagtcggaagtttacatacacttaagttggagtcattaaaactcgtttttcaactac
tccacaaatttcttgttaacaaacaatagtttttggcaagtcagttaggacatctactttgtgcatgacacaagtcattttttccaa
caattgtttacagacagattatttcacttataattcactgtatcacaattccagtggtcagaagtttacatacactaagttgact
gtgcctttaaacagcttggaaaattccagaaaatgatgtcatggctttagaagcttctgatagactaattgacatcatttgagt
caattggaggtgtacctgtggatgtatttcaagggaattctgtgaatgtgtcagttagggtgtggaaagtccccaggctc
cccaggcaggcagaagtatgcaaagcatcgagatgtacgggccagatatacgcgtatctgagggactaggtgtat
ttaggcgaaagcgggcttcgttgtacgcgcttaggagtcccctcaggatatagtagttccgcttttgcatagggaggc
ggaaatgtagtttttatgcaatacactgtagtttgcaacatggtacgatgattagcaacatgcttacaaggagagaa
aaagcaacgtgcatgcgattggtggaagtaaggtggtacgatcgtgacttattaggaaggcaacagcaaggctgaca
tggattggacgaaccactgaattccgcattgcagagataattgtatttaagtgcctagctcgatacaataaacgccatttga
ccattcaccacattggtgtgcacctccaaagcttgatatctaccatggagaagttactattccgaagttcctattctctagaaa
```

-continued

```
gtataggaacttcaagcttggcactggtgagcaagggcgaggagctgttcaccggggtggtgcccatcctggtcgagct
ggacggcgacgtaaacggccacaagttcagcgtgtccggcgagggcgagggcgatgccacctacggcaagctgac
cctgaagttcatctgcaccaccggcaagctgcccgtgccctggcccacccctcgtgaccaccctgacctacggcgtgcag
tgcttcagccgctaccccgaccacatgaagcagcacgacttcttcaagtccgccatgcccgaaggctacgtccaggagc
gcaccatcttcttcaaggacgacggcaactacaagacccgcgccgaggtgaagttcgagggcgacaccctggtgaac
cgcatcgagctgaagggcatcgacttcaaggaggacggcaacatcctggggcacaagctggagtacaactacaaca
gccacaacgtctatatcatggccgacaagcagaagaacggcatcaaggtgaacttcaagatccgccacaacatcgag
gacggcagcgtgcagctcgccgaccactaccagcagaacacccccatcggcgacggccccgtgctgctgcccgaca
accactacctgagcacccagtccgccctgagcaaagaccccaacgagaagcgcgatcacatggtcctgctggagttc
gtgaccgccgccgggatcactctcggcatggacgagctgtacaagtaaagcatagcggccgtaaattccgcccctctct
ccctccccccccctaacgttactggccgaagccgcttggaataaggccggtgtgcgtttgtctatatgttatttttccaccata
ttgccgtcttttggcaatgtgagggcccggaaacctggccctgtcttcttgacgagcattcctagggggtctttccctctcgcc
aaaggaatgcaaggtctgttgaatgtcgtgaaggaagcagttcctctggaagcttcttgaagacaaacaacgtctgtagc
gaccctttgcaggcagcggaaccccccacctggcgacaggtgcctctgcggccaaaagccacgtgtataagatacac
ctgcaaaggcggcacaaccccagtgccacgttgtgagttggatagttgtggaaagagtcaaatggctctcctcaagcgt
attcaacaagggctgaaggatgcccagaaggtaccccattgtatgggatctgatctggggcctcggtgcacatgcttta
catgtgtttagtcgaggttaaaaaacgtctaggcccccccgaaccacggggacgtggttttcctttgaaaaacacgatgata
agcttgccacaaccatgaccgagtacaagcccacggtgcgcctcgccaccgcgacgacgtccccgggccgtacg
cacctcgccgccgcgttcgccgactacccgccacgcgccacaccgtcgatccggaccgccacatcgagcgggtca
ccgagctgcaagaactcttcctcacgcgcgtcgggctcgacatcgcgaaggtgtgggtcgcggacgacggcgccgcg
gtggcggtctggaccacgccgagagcgtcgaagcggggcggtgttcgccgagatcggccgcgcatggccgagtt
gagcggttcccggctggccgcgcagcaacagatggaaggcctcctggcgccgcaccggcccaaggagccgcgtg
gttcctggccacgtcggcgtctcgcccgaccaccagggcaagggtctgggcagcgccgtcgtgctccccggagtgga
ggcggccgagcgcgccggggtgcccgccttcctggagacctccgcgccccgcaacctcccccttctacgagcggctcgg
cttcaccgtcaccgccgacgtcgaggtgcccgaaggaccgcgcacctggtgcatgaccgcaagcccggtgcctgaa
```

```
gatcccccgggggatcagcctcgactgtgccttctagttgccagccatctgttgtttgccctccccgtgccttccttgaccc
tggaaggtgccactcccactgtcctttcctaataaaatgaggaaattgcatcgcattgtctgagtaggtgtcattctattctgg
ggggtgggttggggcaggacagcaaggggggaggattgggaagacaatagcaggcatgctggggatgcggtgggct
ctatgtaaccagctggggctcgacattctagttgtggtttgtccaaactcatcaatgtatcttatcatgtctggatcccatcaca
aagctctgacctcaatcctatagaaaggaggaatgagccaaaattcacccaacttattgtgggaagcttgtggaaggcta
ctcgaaatgtttgacccaagttaaacaatttaaaggcaatgctaccaaatactaattgagtgtatgttaacttctgaccccact
gggaatgtgatgaaagaaataaaagctgaaatgaatcattctctctactattattctgatatttcacattcttaaaataaagtg
gtgatcctaactgaccttaagacagggaatctttactcggattaaatgtcaggaattgtgaaaaagtgagtttaaatgtatttg
gctaaggtgtatgtaaacttccgacttcaactgtagggatcctctagagtcgacctgcaggcatgcaagcttggcgtaatc
atggtcatagctgtttcctgtgtgaaattgttatccgctcacaattccacaacatacgagccggaagcataaagtgtaaa
gcctgggggtgcctaatgagtgagctaactcacattaattgcgttgcgctcactgcccgctttccagtcgggaaacctgtcgt
gccagctgcattaatgaatcggccaacgcgcggggagaggcggtttgcgtattgggcgctcttccgcttcctcgctcactg
actcgctgcgctcggtcgttcggctgcggcgagcggtatcagctcactcaaaggcggtaatacggttatccacagaatca
ggggataacgcaggaaagaacatgtgagcaaaaggccagcaaaaggccaggaaccgtaaaaaggccgcgttgct
ggcgtttttccataggctccgcccccctgacgagcatcacaaaaatcgacgctcaagtcagaggtggcgaaacccgac
aggactataaagataccaggcgtttccccctggaagctccctcgtgcgctctcctgttccgaccctgccgcttaccggatac
ctgtccgcctttctcccttcgggaagcgtggcgctttctcaatgctcacgctgtaggtatctcagttcggtgtaggtcgttcgctc
caagctgggctgtgtgcacgaacccccgttcagcccgaccgctgcgccttatccggtaactatcgtcttgagtccaaccc
ggtaagacacgacttatcgccactggcagcagccactggtaacaggattagcagagcgaggtatgtaggcggtgctac
agagttcttgaagtggtggcctaactacggctacactagaaggacagtatttggtatctgcgctctgctgaagccagttacc
ttcggaaaaagagttggtagctcttgatccggcaaacaaaccaccgctggtagcggtggtttttttgtttgcaagcagcaga
ttacgcgcagaaaaaaaggatctcaagaagatcctttgatcttttctacggggtctgacgctcagtggaacgaaaactca
cgttaagggattttggtcatgagattatcaaaaaggatcttcacctagatccttttaaattaaaaatgaagttttaaatcaatct
aaagtatatatgagtaaacttggtctgacagttaccaatgcttaatcagtgaggcacctatctcagcgatctgtctatttcgttc
atccatagttgcctgactccccgtcgtgtagataactacgatacgggagggcttaccatctggccccagtgctgcaatgat
accgcgagacccacgctcaccggctccagatttatcagcaataaaccagccagccggaagggccgagcgcagaagt
ggtcctgcaactttatccgcctccatccagtctattaattgttgccgggaagctagagtaagtagttcgccagttaatagtttgc
```

```
gcaacgttgttgccattgctacaggcatcgtggtgtcacgctcgtcgtttggtatggcttcattcagctccggttcccaacgat
caaggcgagttacatgatcccccatgttgtgcaaaaaagcggttagctccttcggtcctccgatcgttgtcagaagtaagtt
ggccgcagtgttatcactcatggttatggcagcactgcataattctcttactgtcatgccatccgtaagatgcttttctgtgactg
gtgagtactcaaccaagtcattctgagaatagtgtatgcggcgaccgagttgctcttgcccggcgtcaatacgggataata
ccgcgccacatagcagaactttaaaagtgctcatcattggaaaacgttcttcggggcgaaaactctcaaffatcttaccg
ctgttgagatccagttcgatgtaacccactcgtgcacccaactgatcttcagcatcttttactttcaccagcgtttctgggtgag
caaaaacaggaaggcaaatgccgcaaaaaagggaataagggcgacacggaaatgttgaatactcatactcttcctttt
ttcaatattattgaagcatttatcagggttattgtctcatgagcggatacatatttgaatgtatttagaaaaataaacaaatagg
ggttccgcgcacatttccccgaaaagtgccacctgacgtctaagaaaccattattatcatgacattaacctataaaaatag
gcgtatcacgaggccctttcgtc
```

SEQ ID NO: 39: pSBT/SV40-GFIP, sequence

SB inverted repeats
SV40 promoter
Start codon
FRT site
eGFP
Puro tcgcgcgtttcggtgatgacggtgaaaacctctgacacatgcagctcccggagacggtcacagcttgtctgtaagcggat
gccgggagcagacaagcccgtcagggcgcgtcagcgggtgttggcgggtgtcggggctggcttaactatgcggcatca
gagcagattgtactgagagtgcaccatatgcggtgtgaaataccgcacagatgcgtaaggagaaaataccgcatcagg
cgccattcgccattcaggctgcgcaactgttgggaagggcgatcggtgcgggcctcttcgctattacgccagctggcgaa
agggggatgtgctgcaaggcgattaagttgggtaacgccagggttttcccagtcacgacgttgtaaaacgacggccagt
gaattcgagctcggtaccctacagttgaagtcggaagtttacatacacttaagttggagtcattaaaactcgtttttcaactac
tccacaaatttcttgttaacaaacaatagttttggcaagtcagttaggacatctacttttgtgcatgacacaagtcattttttccaa
caattgtttacagacagattatttcacttataattcactgtatcacaattccagtgggtcagaagtttacatacactaagttgact
gtgcctttaaacagcttggaaaattccagaaaatgatgtcatggctttagaagcttctgatagactaattgacatcatttgagt
caattggaggtgtacctgtggatgtatttcaagggaattctgtggaatgtgtgtcagttagggtgtggaaagtccccaggctc
cccaggcaggcagaagtatgcaaagcatcgaggatgtacgggccagatatacgcgtgaggttttcaccgtcatcaccg
aaacgcgcgaggcagctgtggaatgtgtgtcagttagggtgtggaaagtccccaggctccccagcaggcagaagtatg
caaagcatgcatctcaattagtcagcaaccaggtgtggaaagtccccaggctccccagcaggcagaagtatgcaaag
catgcatctcaattagtcagcaaccatagtcccgcccctaactccgcccatcccgcccctaactccgcccagttccgccc
attctccgcccatggctgactaatttttttatttatgcagaggccgaggccgcctcggcctctgagctattccagaagtagt
gaggaggcttttttggaggctaccatggagaagttactattccgaagttcctattctctagaaagtataggaacttcaagctt ggcactggtgagcaagggcgaggagctgttcaccggggtggtgcccatcctggtcgagctggacggcgacgtaaacg
gccacaagttcagcgtgtccggcgagggcgagggcgatgccacctacggcaagctgaccctgaagttcatctgcacca
ccggcaagctgcccgtgccctggcccaccctcgtgaccaccctgacctacggcgtgcagtgcttcagccgctaccccga
ccacatgaagcagcacgacttcttcaagtccgccatgcccgaaggctacgtccaggagcgcaccatcttcttcaaggac
gacggcaactacaagacccgcgccgaggtgaagttcgagggcgacaccctggtgaaccgcatcgagctgaagggc
atcgacttcaaggaggacggcaacatcctggggcacaagctggagtacaactacaacagccacaacgtctatatcatg
gccgacaagcagaagaacggcatcaaggtgaacttcaagatccgccacaacatcgaggacggcagcgtgcagctc
gccgaccactaccagcagaacacccccatcggcgacggccccgtgctgctgcccgacaaccactacctgagcaccc
agtccgccctgagcaaagaccccaacgagaagcgcgatcacatggtcctgctggagttcgtgaccgccgccgggatc
actctcggcatggacgagctgtacaagtaaagcggccgcgactcccaattgggccaccggtgctagcccccctaacgttactg
gccgaagccgcttggaataaggccggtgtgcgtttgtctatatgttattttccaccatattgccgtcttttggcaatgtgagggc
ccggaaacctggccctgtcttcttgacgagcattcctaggggtctttcccctctcgccaaaggaatgcaaggtctgttgaat
gtcgtgaaggaagcagttcctctggaagcttcttgaagacaaacaacgtctgtagcgaccctttgcaggcagcggaacc
ccccacctggcgacaggtgcctctgcggccaaaagccacgtgtataagatacacctgcaaaggcggcacaacccca
gtgccacgttgtgagttggatagttgtggaaagagtcaaatggctctcctcaagcgtattcaacaagggctgaaggatg
cccagaaggtacccccattgtatgggatctgatctggggcctcggtgcacatgctttacatgtgtttagtcgaggttaaaaaa
cgtctaggccccccgaaccacggggacgtggttttcctttgaaaaacacgataatacc atgaccggatacaagcccacg
gtgcgcctcgccaccggcgacgacgtcccagggccgtacgcacctcgcgccggttcgccgactaccccgccac
gcgccacaccgtcgatccggaccgccacatcgagcgggtcaccgagctgcaagaactcttcctcacgcgcgtcgggct
cgacatcggcaaggtgtgggtcgcggacgacggcgccgcggtggcggtctggaccacgccggagagcgtcgaagc
gggggcggtgttcgccgagatcggcccgcgcatggcccgagttgagcggttcgccgctggcgtgacccagcggttcg
ccccccttcgccggcaacctcccttcaacccggttcctccccacggcgcggcccagcaccag
gacctccgcgccccgcaacctcccttctacgagcggctcggcttccacgtcaccgcgacgacggccgaagg
accgcgcaccggtgcatgacccgcaagcccggtgcctgacgcccgccgcacaagaccgcaggcccgaccggaa ggagcgcacgacccccatgcatcgaatcgatatcgcggccgcgactctagatcataatcagcccgggggtgatcagcct
cgactgtgccttctagttgccagccatctgttgtttgccctcccccgtgccttccttgaccctggaaggtgccactcccactgt
cctttcctaataaaatgaggaaattgcatcgcattgtctgagtaggtgtcattctattctggggggtggggtggggcaggac
agcaagggggaggattgggaagacaatagcaggcatgctggggatgcggtgggctctatggaaccagctggggctc
gacattctagttgtggtttgtccaaactcatcaatgtatcttatcatgtctggatcccatcacaaagctctgacctcaatcctata
gaaaggaggaatgagccaaaattcacccaacttattgtgggaagcttgtggaaggctactcgaaatgtttgacccaagtt
aaacaatttaaaggcaatgctaccaaatactaattgagtgtatgttaacttctgacccactgggaatgtgatgaaagaaat
aaaagctgaaatgaatcattctctctactattattctgatattttcacattcttaaaataaagtggtgatcctaactgacct taaga
cagggaatctttactcggattaaatgtcaggaattgtgaaaaagtgagttaaatgtattttggctaaggtgtatgtaaacttcc
gacttaactgtagggatcctctagagtcgacctgcaggcatgcaagcttggcgtaatcatggtcatagctgtttcctgtgtg
aaattgttatccgctcacaattccacacaacatacgagccggaagcataaagtgtaaagcctggggtgcctaatgagtg
agctaactcacattaattgcgttgcgctcactgcccgctttccagtcgggaaacctgtcgtgccagctgcattaatgaatcg
gccaacgcgcggggagaggcggtttgcgtattgggcgctcttccgcttcctcgctcactgactcgctgcgctcggtcgttcg
gctgcggcgagcggtatcagctcactcaaaggcggtaatacggttatccacagaatcaggggataacgcaggaaaga
acatgtgagcaaaaggccagcaaaaggccaggaaccgtaaaaaggccgcgttgctggcgtttttccataggctccgcc
ccctgacgagcatcacaaaaatcgacgctcaagtcagaggtggcgaaacccgacaggactataaagataccaggc
gtttccccctggaagctccctcgtgcgctctcctgttccgaccctgccgcttaccggatacctgtccgcctttctcccttcggga
agcgtggcgctttctcaatgctcacgctgtaggtatctcagttcggtgtaggtcgttcgctccaagctgggctgtgtgcacga
accccccgttcagcccgaccgctgcgccttatccggtaactatcgtcttgagtccaacccggtaagacacgacttatcgcc
actggcagcagccactggtaacaggattagcagagcgaggtatgtaggcggtgctacagagttcttgaagtggtggcct
aactacggctacactagaaggacagtatttggtatctgcgctctgctgaagccagttaccttcggaaaaagagttggtagc
tcttgatccggcaaacaaaccaccgctggtagcggtggtttttttgtttgcaagcagcagattacgcgcagaaaaaaagg
atctcaagaagatcctttgatcttttctacggggtctgacgctcagtggaacgaaaactcacgttaagggattttggtcatga
gattatcaaaaaggatcttcacctagatccttttaaattaaaaatgaagttttaaatcaatctaaagtatatatgagtaaacttg
gtctgacagttaccaatgcttaatcagtgaggcacctatctcagcgatctgtctatttcgttcatccatagttgcctgactcccc
gtcgtgtagataactacgatacgggagggcttaccatctggccccagtgctgcaatgataccgcgagacccacgctcac
cggctccagatttatcagcaataaaccagccagccggaagggccgagcgcagaagtggtcctgcaactttatccgcctc
catccagtctattaattgttgccgggaagctagagtaagtagttcgccagttaatagtttgcgcaacgttgttgccattgctac -continued

```
aggcatcgtggtgtcacgctcgtcgtttggtatggcttcattcagctccggttcccaacgatcaaggcgagttacatgatccc
ccatgttgtgcaaaaaagcggttagctccttcggtcctccgatcgttgtcagaagtaagttggccgcagtgttatcactcatg
gttatggcagcactgcataattctcttactgtcatgccatccgtaagatgcttttctgtgactggtgagtactcaaccaagtcatt
ctgagaatagtgtatgcggcgaccgagttgctcttgcccggcgtcaatacgggataataccgcgccacatagcagaactt
taaaagtgctcatcattggaaaacgttcttcggggcgaaaactctcaaggatcttaccgctgttgagatccagttcgatgta
acccactcgtgcacccaactgatcttcagcatcttttactttcaccagcgtttctgggtgagcaaaaacaggaaggcaaaa
tgccgcaaaaaagggaataagggcgacacggaaatgttgaatactcatactcttccttttcaatattattgaagcatttatc
agggttattgtctcatgagcggatacatatttgaatgtatttagaaaaataaacaaatagggttccgcgcacatttccccg
aaaagtgccacctgacgtctaagaaaccattattatcatgacattaacctataaaaataggcgtatcacgaggccctttcg
tc
```

SEQ ID NO: 40: pSBT/SV40-GFIP.loxP, sequence

SB inverted repeats
SV40 promoter
Start codon
FRT site
eGFP
Puro

```
tcgcgcgtttcggtgatgacggtgaaaacctctgacacatgcagctcccggagacggtcacagcttgtctgtaagcggat
gccgggagcagacaagcccgtcagggcgcgtcagcgggtgttggcgggtgtcggggctggcttaactatgcggcatca
gagcagattgtactgagagtgcaccatatgcggtgtgaaataccgcacagatgcgtaaggagaaaataccgcatcagg
cgccattcgccattcaggctgcgcaactgttgggaagggcgatcggtgcgggcctcttcgctattacgccagctggcgaa
agggggatgtgctgcaaggcgattaagttgggtaacgccagggttttcccagtcacgacgttgtaaaacgacggccagt
gaattcgagctcggtaccctacgagttgaagtcggaagtttacatacacttaagttggagtcattaaaactcgttttcaactac
tccacaaatttcttgttaacaaacaatagtttttggcaagtcagttaggacatctactttgtgcatgacacaagtcattttccaa
caattgtttacagacagattatttcacttataattcactgtatcacaattccagtgggtcagaagtttacatacactaagttgact
gtgcctttaaacagcttggaaaattccagaaaatgatgtcatggctttagaagcttctgatagactaattgacatcatttgagt
caattggaggtgtacctgtggatgtatttcaagggaattctgtggaatgtgtgtcagttagggtgtggaaagtcccccaggctc
cccaggcaggcagaagtatgcaaagcatcgaggatgtacgggccagatatacgcgataacttcgtataatgtatgctat
acgaagttatcgcgtgaggttttcaccgtcatcaccgaaacgcgcgaggcagctgtggaatgtgtgtcagttagggtgtgg
aaagtcccccaggctcccagcaggcagaagtatgcaaagcatgcatctcaattagtcagcaaccaggtgtggaaagtc
cccaggctcccagcaggcagaagtatgcaaagcatgcatctcaattagtcagcaaccatagtccgcccctaactcc
gcccatccgcccctaactccgcccagttccgcccattctccgccccatggctgactaattttttttatttatgcagaggccga
ggccgcctcggcctctgagctattccagaagtagtgaggaggcttttttggaggctaccatggagaagttactattccgaa
gttcctattctctagaaagtataggaacttcaagcttggcactggtgagcaagggcgaggagctgttcaccggggtggtgc ccatcctggtcgagctggacggcgacgtaaacggccacaagttcagcgtgtccggcgagggcgagggcgatgccac
ctacggcaagctgaccctgaagttcatctgcaccaccggcaagctgcccgtgccctggcccaccctcgtgaccaccctg
acctacggcgtgcagtgcttcagccgctaccccgaccacatgaagcagcacgacttcttcaagtccgccatgcccgaag
gctacgtccaggagcgcaccatcttcttcaaggacgacggcaactacaagacccgcgccgaggtgaagttcgagggc
gacaccctggtgaaccgcatcgagctgaagggcatcgacttcaaggaggacggcaacatcctggggcacaagctgg
agtacaactacaacagccacaacgtctatatcatggccgacaagcagaagaacggcatcaaggtgaacttcaagatc
cgccacaacatcgaggacggcagcgtgcagctcgccgaccactaccagcagaacacccccatcggcgacggccc
gtgctgctgcccgacaaccactacctgagcacccagtccgccctgagcaaagaccccaacgagaagcgcgatcacat
ggtcctgctggagttcgtgaccgccgccgggatcactctcggcatgacgagctgtacaagtaaagcggccgcggcca
attgggccaccggtctagcccccctaacgttactggccgaagccgcttggaataaggccggtgtgcgtttgtctatatgttat
tttccaccatattgccgtcttttggcaatgtgagggcccggaaacctggccctgtcttcttgacgagcattcctaggggtctttc
ccctctcgccaaaggaatgcaaggtctgttgaatgtcgtgaaggaagcagttcctctggaagcttcttgaagacaaacaa
cgtctgtagcgaccctttgcaggcagcggaacccccacctggcgacaggtgcctctgcggccaaaagccacgtgtat
aagatacacctgcaaaggcggcacaacccagtgccacgttgtgagttggatagttgtggaaagagtcaaatggctctc
ctcaagcgtattcaacaaggggctgaaggatgcccagaaggtacccccattgtatgggatctgatctggggcctcggtgc
acatgctttacatgtgtttagtcgaggttaaaaaacgtctaggccccccgaaccacggggacgtggttttcctttgaaaaac
acgataataccatgaccgagtacaagcccacggtgcgcctcgccaccgcgacgacgtccccccgggcgtacgcac
cctcgccgccgcgttcgccgactaccccgcacgcgccacacgtcgatccggaccgccacatcgagcgggtcaccg
agtgcaagaactcttcctcacgcgcgtcgggctcgacatcggcaaggtgtgggtcgcggacgacggcgccgcggtg
gcggtctggaccacgccggagagcgtcgaagcggggcggtgttcgccgagatcggcccgcgcgatggccgagttga
gcggttcccggctggccgcgcagcaacagatggaaggcctcctggcgccgcaccggcccaaggagcccgcgtggtt
cctggccaccgtcggcgtctcgcccgaccaccagggcaagggtctgggcagcgccgtcgtgctccccggagtggagg
cggccgagcgcgccggggtgcccgccttcctggagacctccgcgccccgcaacctccccttctacgagcggctcggctt
caccgtcaccgcgacgtcgaggtgcccgaaggaccgcgcacctggtgcatgacccgcaagcccggtgcctgacgc
ccgcccacaagacccgcagcgcccgaccgaaaggagcgcacgaccccatgcatcgaatcgatatcgcggccgcga
```

```
ctctagatcataatcagcccgggggtgatcagcctcgactgtgccttctagttgccagccatctgttgtttgcccctccccgt
gccttccttgaccctggaaggtgccactcccactgtcctttcctaataaaatgaggaaattgcatcgcattgtctgagtaggt
gtcattctattctgggggtggggtggggcaggacagcaaggggggaggattgggaagacaatagcaggcatgctggg
gatgcggtgggctctatggaaccagctggggcgcgattaacttcgtataaagtctcctatacgaagttatcgcgccattcta
gttgtggtttgtccaaactcatcaatgtatcttatcatgtctggatcccatcacaaagctctgacctcaatcctatagaagga
ggaatgagccaaaattcacccaacttattgtgggaagcttgtggaaggctactcgaaatgtttgacccaagttaaacaattt
aaaggcaatgctaccaaatactaattgagtgtatgttaacttctgacccactgggaatgtgatgaaagaaataaaagctg
aaatgaatcattctctctactattattctgatatttcacattcttaaaataaagtggtgatcctaactgaccttaagacagggaat
ctttactcggattaaatgtcaggaattgtgaaaaagtgagtttaaatgtatttggctaaggtgtatgtaaacttccgacttaac
tgtagggatcctctagagtcgacctgcaggcatgcaagcttggcgtaatcatggtcatagctgtttcctgtgtgaaattgttat
ccgctcacaattccacacaacatacgagccggaagcataaagtgtaaagcctggggtgcctaatgagtgagctaactc
acattaattgcgttgcgctcactgcccgctttccagtcgggaaacctgtcgtgccagctgcattaatgaatcggccaacgcg
cggggagaggcggtttgcgtattgggcgctcttccgcttcctcgctcactgactcgctgcgctcggtcgttcggctgcggcg
agcggtatcagctcactcaaaggcggtaatacggttatccacagaatcaggggataacgcaggaaagaacatgtgag
caaaaggccagcaaaaggccaggaaccgtaaaaaggccgcgttgctggcgtttttccataggctccgcccccctgacg
agcatcacaaaaatcgacgctcaagtcagaggtggcgaaacccgacaggactataaagataccaggcgtttccccct
ggaagctccctcgtgcgctctcctgttccgaccctgccgcttaccggatacctgtccgcctttctcccttcgggaagcgtggc
gctttctcaatgctcacgctgtaggtatctcagttcggtgtaggtcgttcgctccaagctgggctgtgtgcacgaaccccccgt
tcagcccgaccgctgcgccttatccggtaactatcgtcttgagtccaacccggtaagacacgacttatcgccactggcag
cagccactggtaacaggattagcagagcgaggtatgtaggcggtgctacagagttcttgaagtggtggcctaactacgg
ctacactagaaggacagtatttggtatctgcgctctgctgaagccagttaccttcggaaaaagagttggtagctcttgatcc
ggcaaacaaaccaccgctggtagcggtggtttttttgtttgcaagcagcagattacgcgcagaaaaaaaggatctcaag
aagatcctttgatcttttctacggggtctgacgctcagtggaacgaaaactcacgttaagggattttggtcatgagattatcaa
aaaggatcttcacctagatcctttttaaattaaaaatgaagttttaaatcaatctaaagtatatatgagtaaacttggtctgaca
gttaccaatgcttaatcagtgaggcacctatctcagcgatctgtctatttcgttcatccatagttgcctgactccccgtcgtgta
gataactacgatacgggagggcttaccatctggccccagtgctgcaatgataccgcgagacccacgctcaccggctcc
agatttatcagcaataaaccagccagccggaagggccgagcgcagaagtggtcctgcaactttatccgcctccatcca
gtctattaattgttgccgggaagctagagtaagtagttcgccagttaatagtttgcgcaacgttgttgccattgctacaggcat cgtggtgtcacgctcgtcgtttggtatggcttcattcagctccggttcccaacgatcaaggcgagttacatgatcccccatgtt
gtgcaaaaaagcggttagctccttcggtcctccgatcgttgtcagaagtaagttggccgcagtgttatcactcatggttatgg
cagcactgcataattctcttactgtcatgccatccgtaagatgcttttctgtgactggtgagtactcaaccaagtcattctgaga
atagtgtatgcggcgaccgagttgctcttgcccggcgtcaatacgggataataccgcgccacatagcagaactttaaaag
tgctcatcattggaaaacgttcttcggggcgaaaactctcaaggatcttaccgctgttgagatccagttcgatgtaacccact
cgtgcacccaactgatcttcagcatcttttactttcaccagcgtttctgggtgagcaaaaacaggaaggcaaaatgccgca
aaaaagggaataagggcgacacggaaatgttgaatactcatactcttcctttttcaatattattgaagcatttatcagggttat
tgtctcatgagcggatacatatttgaatgtatttagaaaaataaacaaataggggttccgcgcacatttccccgaaaagtgc
cacctgacgtctaagaaaccattattatcatgacattaacctataaaaataggcgtatcacgaggccctttcgtc
```

Sequence:
pSBT-PCSK9
PCSK9 human coding sequence preceded by a Kozak sequence and constructed with a C-terminal FLAG tag.

tcgcgcgtttcggtgatgacggtgaaaacctctgacacatgcagctcccggagacggtcacagcttgtctgtaagcggatgccggga gcagacaagcccgtcagggcgcgtcagcgggtgttggcgggtgtcggggctggcttaactatgcggcatcagagcagattgtactga gagtgcaccatatgcggtgtgaaataccgcacagatgcgtaaggagaaaataccgcatcaggcgccattcgccattcaggctgcgc aactgttgggaagggcgatcggtgcgggcctcttcgctattacgccagctggcgaaaggggatgtgctgcaaggcgattaagttgg gtaacgccagggttttcccagtcacgacgttgrtaaaacgacggccagtgaattcgagctcggtaccctacagttgaagtcggaagttta catacacttaagttggagtcattaaaactcgtttttcaactactccacaaatttcttgttaacaaacaatagtttggcaagtcagttaggac atctactttgtgcatgacacaagtcatttttccaacaattgtttacagacagattatttcacttataattcactgtatcacaattccagtgggtca gaagtttacatacactaagttgactgtgcctttaaacagcttggaaaattccagaaaatgatgtcatggctttagaagcttctgatagacta attgacatcatttgagtcaattggaggtgtacctgtggatgtatttcaagggaattctgtggaatgtgtgtcagttagggtgtggaaagtccc caggctccccaggcaggcagaagtatgcaaagcatgcatatcgatactagtttaattaactagtctgcaggctcagaggcacacagg agtttctgggctcaccctgcccccttccaacccctcagttcccatcctccagcagctgtttgtgtgctgcctctgaagtccacactgaacaa acttcagcctactcatgtccctaaaatgggcaaacattgcaagcagcaaacagcaaacacacagccctccctgcctgctgaccttgg agctggggcagaggtcagagacctctctgggccatgccacctccaacatccactcgacccccttggaatttcggtggagaggagca gaggttgtcctggcgtggtttaggtagtgtgagagggtccgggttcaaaaccacttgctgggtcgggagtcgtcagtaagtggctatccc ccgaccccgaagcctgtttccccatctgtacaatggaaatgataaagacgcccatctgatagggttttgtggcaaataaacatttggtttt tttgttttgttttgttttgttttttgagatggagtttgctctgtcgcccaggctggagtgcagtgacacaatctcatctcaccacaaccttcccc gcctcagcctcccaagtagctgggattacaagcatgtgccaccacacctggctaattttctatttttagtagagacgggtttctccatgttg gtcagcctcagcctcccaagtaactgggattacaggcctgtgccaccacacccggctaatttttctattttttgacagggacggggtttca
ccatgttggtcaggctggtctagaggtaccggatcttgctaccagtggaacagccactaaggattctgcagtgagagcagagggcca
gctaagtggtactctcccagagactgtctgactcacgccacccctccaccttggacacaggacgctgtgtttctgagccaggtacaa
tgactcctttcggtaagtgcagtggaagctgtacactgcccaggcaaagcgtccgggcagcgtaggcgggcgactcagatcccagc
cagtggacttagcccctgtttgctcctccgataactggggtgaccttggttaatattcaccagcagcctccccgttgccctctggatcca
ctgcttaaatacggacgaggacagggccctgtctcctcagcttcaggcaccactgacctgggacagtcccagatccgcggcctc
gacggtatcgataagcttgatatcgaattctagtcgtcgaccactttcacaatctgcggcgcgccaccatgggcaccgtcagctgagg
cggtcctggtggcagctgccactgctgctgctgctgctgctgctcctgggtccggggagcccgtgcgcaggaggacgaggacggc
gactacgaggagctggtgctagcccttgcgttccgaggaggacggcctggccgaagcacccgagcacggaaccacagccacctc
caccgctgcgcaaggatcgtggaggtgcctggcacctacgtggtggtgctgaaggaggagacccactctctggcagtcagagcg
caactgcccgccgctgcaggcccaggctgccgcgggatacctcaccaagatcctgcatgtcttccatggccttcttctggcttcct
ggtgaagatgagtggcgacctgctggagctggccttgaagttgccccatgtcgactacatcgaggaggactcctctgtctttgcccaga
gcatcccgtggaacctggagcggattacccctccacggtacgggcggatgaataccagccccgacggaggcagcctggtgg
aggtgtatctcctagacaccagcatacagagtgacaccggaaatcgagggcagggtcatggtcaccgacttcgagaatgtgccc
gaggaggacgggaccgcttccacagacaggccagcaagtgtgacagtcatggcatcccacctggcagggtggtcagcggcc
ggatgcacggcgtggccaagggtgccagcatgcgcagcctgcgcgtgctcaactgcaaggggaagggcacggttagcggcacct
catagcctggagtttattccggaaaagccagctggtccagcctgtgggcactggtggtgctgctgccctggcgggtggtacagc
cgcgtcctcaacgccgcctgccagcgcctggcgagggctgggtcgtgctggtcacgctAccggcaacttccggacgatgcctc
cctctactccccagcctcagctcccgaggtcatcacagttggggccaccaatgccaGgaccagccggtgaccctggggacttgg
ggaccaactttggccgctgtgtggacctctttgcccagggagggacatcattggtgcctccagcgactgcagcactgctttgtgtcac
agagtgggacatcacaggctgctgccacgtggctggcattgcagcatgatgctgtctgccgagcggagctcaccctggccgagt
tgaggcagagactgatccacttctctgccaaagatgtcatcaatgaggcctggttccctgaggacagcgggtactgacccccaacct
ggtggccgcctgccccccagcacccatgggcaggttggcagctgtttgcaggactgtGggtcagcacactcggggctacacg
gatggcacagcaAtcgccgctggcCcccagatgaggagctgctgagctgctccagtttctccaggagtggaagcggggc
gagcgcatggaggccaaggggggcaagctggtctgcgggccacaacgctttggggggtgagggtgtctacgccattgccaggtg
ctgcctgctaccccaggccaactgcagcgtccacacagctccaccagctgaaggcagcatggggacccgtgtccactgccaccaa
cagggcacgtcctcacaggctgcagctccaccagctgcagctccactgggagtggaggaccttgcaccaccaagccgctgtgctgaggcacgag
gtcagccaaccagtgcgtgggccacaggaggccagcatccacgcttcctgctgccatgcccaggtctggaatgcaaagtcaa
ggagcatggaatccagccccctcaggagcaggtgaccgtggctgcgaggagggctggacctgactggctgcagtgccctcct
gggacttcccacgtcctggggcctacgccgtagacaacacgtgtgtagtcaggagccgggacgtcagcactacaggcagcacc
agcgaagAggtcgtgacagccgttgccatctgctgcgggagcggcacctggcgcaggcctccaggagctccagctggcgcag
gcctccaggagctccaggactacaaggacgacgatgacaagtgactgaggccggcctcagcctcgactgtgccttctagttgcca
gccatctgttgtttgccctcccccgtgccttccttgaccctggaaggtgccactcccactgtcctttcctaataaaatgaggaaattgcatc
gcattgtctgagtaggtgtcattctattctgggggtggggtggggcaggacagcaaggggggaggattgggaagacaatagcaggc
atgctgggatacgtggctctatggaaccagctgggctttaattaagatctcgacctcgaaattctaccgggtaggggaggcgctt
ttcccaaggagtctggagcatgcgctttagcggccccgctgggcacttggcgctacacaagtggcctctggcctctggcctcgcacacattcca
catccaccggtaggcgccaaccggctccgttcttttggtggccccttcgcgccaccttctactcctcccctagtcaggaagttccccccg

```
ccccgcagctcgcgtcgtgcaggacgtgacaaatggaagtagcacgtctcactagtctcgtgcagatggacagcaccgctgagcaa tggaagcgggtaggcctttggggcagcggccaatagcagctttggctccttcgctttctgggctcagaggctgggaaggggtgggtcc gggggcgggctcaggggcgggctcaggggcggggcgggcgcccgaaggtcctccggaggcccggcattctgcacggettcaaaa gcgcacgtctgccgcgctgttctcctcttcctcatctccgggccttttcgacctgcatccatctagatctcgagcagctgaagcttaccatgac agaagtacaagccaaggtgagcctcgcacacgcgaagacgtcccgggcgtacgaacatcgccgaccgtccgcgacta gcaccacaggcaatcgtgatccggacgccatcgaggggtaccgagctgcaagaactcttcctcatcgacgtcggg ctcgacatcggcaaggtatggtcgcgaaccgcccaccgtaccgctccgaccacccgagaccgtccaaccggaa ggtattccggagatcggccgcgtcatcggccagtcgagcagctccgctgccctgcagcaaacagatggaagctctgacc gagcaacgaccggcccgaatgttctccaacatcgactgtctccgcagcatccgggacatcaaccgtctggaccagcc gttgctcctccggaaccggagaccggaggacgctttcctgagaccctcgcacccgaaccccccttcta agagcgctcggcttaaccgtcacagagacgtcgagtgccgaagacaccacctgatgcatgaccgcaagccgttgc ctgaagccgatccacaagaccgcagggccgaccgaaaggagcgcacgaccccatgcatcgaatcgatatcccggaccgt ctgtaagtctgcagaaatctgatgattatctaaacaataaagatgtcactaaaatggaagttttcctgtcataccttgttaagaagggtga gaacagagtacctacatttgaatggaaggattagagctacgggatggaggtggagagattagataaatgcctgctcttactgaa ggttttaactattgcttatgataacttcatagttgatatatatatatataattaaaaaagcaaaccaattaaagggcagctaatcctcccaa ccatgatctattagatctaagatctcggggatcaattgttctcttgattccaacttgtggtccaagtactgtggtccaaatgtgtcagttt catagcctgaagaaacgagatcagcagcctctgttccacatcacctcattctcagtactgttttgcaaagttctaattccatcagagctgg tggagcgcggccgctgcattctagttgtggtttgtccaaactcatcaatgtatcttatcatgtctggatcccatcacaaagctctgacctc aatcctatagaaaggaggaatgagccaaaattcacccaacttattgtgggaagcttgtggaaggctactcgaaatgtttgacccaagtt aaacaatttaaaggcaatgctaccaaatactaattgagtgtatgttaacttctgacccactgggaatgtgatgaaagaaataaaagctg aaatgaatcattctctctactattattctgatatttcacattcttaaaataaagtggtgatcctaactgaccttaagacagggaatctttactcg gattaaatgtcaggaattgtgaaaaagtgagtttaaatgtatttggctaaggtgtatgtaaacttccgacttcaactgtagggatcctctag agtcgacctgcaggcatgcaagcttggcgtaatcatggtcatagctgtttcctgtgtgaaattgttatccgctcacaattccacacaacat acgagccggaagcataaagtgtaaagcctggggtgcctaatgagtgagctaactcacattaattgcgttgcgctcactgcccgctttcc agtcgggaaacctgtcgtgccagctgcattaatgaatcggccaacgcgcggggagaggcggtttgcgtattgggcgctcttccgcttc ctcgctcactgactcgctgcgctcggtcgttcggctgcggcgagcggtatcagctcactcaaaggcggtaatacggttatccacagaat caggggataacgcaggaaagaacatgtgagcaaaaggccagcaaaaggccaggaaccgtaaaaaggccgcgttgctggcgttt ttccataggctccgcccccctgacgagcatcacaaaaatcgacgctcaagtcagaggtggcgaaacccgacaggactataaagat accaggcgtttccccctggaagctccctcgtgcgctctcctgttccgaccctgccgcttaccggatacctgtccgcctttctcccttcggga agcgtggcgctttctcaatgctcacgctgtaggtatctcagttcggtgtaggtcgttcgctccaagctgggctgtgtgcacgaaccccccg ttcagcccgaccgctgcgccttatccggtaactatcgtcttgagtccaacccggtaagacacgacttatcgccactggcagcagccact ggtaacaggattagcagagcgaggtatgtaggcggtgctacagagttcttgaagtggtggcctaactacggctacactagaaggaca gtatttggtatctgcgctctgctgaagccagttaccttcggaaaaagagttggtagctcttgatccggcaaacaaaccaccgctggtagc ggtggtttttttgtttgcaagcagcagattacgcgcagaaaaaaaggatctcaagaagatcctttgatcttttctacggggtctgacgctca gtggaacgaaaactcacgttaagggattttggtcatgagattatcaaaaaggatcttcacctagatccttttaaattaaaaatgaagtttta aatcaatctaaagtatatatgagtaaacttggtctgacagttaccaatgcttaatcagtgaggcacctatctcagcgatctgtctatttcgtt catccatagttgcctgactccccgtcgtgtagataactacgatacgggagggcttaccatctggccccagtgctgcaatgataccgcga gacccacgctcaccggctccagatttatcagcaataaaccagccagccagccggaagggccgagcgcagaagtggtcctgcaactttatc
```

```
cgcctccatccagtctattaattgttgccgggaagctagagtaagtagttcgccagttaatagtttgcgcaacgttgttgccattgctacag gcatcgtggtgtcacgctcgtcgtttggtatggcttcattcagctccggttcccaacgatcaaggcgagrttacatgatcccccatgttgtgc aaaaaagcggttaggctccttcggtcctccgatcgttgtcagaagtaagttggccgcagtgttatcactcatggttatggcagcactgcata attctcttactgtcatgccatccgtaagatgcttttctgtgactggtgagtactcaaccaagtcattctgagaatagtgtatgcggcgaccga gttgctcttgcccggcgtcaatacgggataataccgcgccacatagcagaactttaaaagtgctcatcattggaaaacgttcttcggggg cgaaaactctcaaggatcttaccgctgttgagatccagttcgatgtaacccactcgtgcacccaactgatcttcagcatcttttactttcac cagcgtttctgggtgagcaaaaacaggaaggcaaaatgccgcaaaaaagggaataagggcgacacggaaatgttgaatactcat actcttccttttcaatattattgaagcatttatcagggttattgtctcatgagcggatacatatttgaatgtatttagaaaaataaacaaatag gggttccgcgcacatttccccgaaaagtgccacctgacgtctaagaaaccattattatcatgacattaacctataaaaataggcgtatc acgaggccctttcgtc
```

Left inverted repeat
HCR/apoE - Hepatocyte control region
hAAT - human alpha-antitrypsin promoter
PCSKg - Coding sequence for proprotein convertase subtilisin/kexin type 9 (PCSK9) with C-terminal FLAG-tag
BGH pA - Bovine growth hormone polyA region
PGK - phosphoglycerate kinase promotr
Puro - Coding sequence for puromycin N-acetyl transferase (PAC)
Right inverted repeat
pSBT/cHS4.H1p.PGK-puro.U6p.cHS4, sequence
SB inverted repeat
cHS4 insulator
H1 promoter with linker (reverse orientation)
PGK promoter
Puro ORF
U6 promoter with linker

```
tcgcgcgtttcggtgatgacggtgaaaacctctgacacatgcagctcccggagacggtcacagcttgtctgtaagcggatgccggga gcagacaagcccgtcagggcgcgtcagcgggtgttggcgggtgtcggggctggcttaactatgcggcatcagagcagattgtactga gagtgcaccatatgcggtgtgaaataccgcacagatgcgtaaggagaaaataccgcatcaggcgccattcgccattcaggctgcgc aactgttgggaagggcgatcggtgcgggcctcttcgctattacgccagctggcgaaaggggggatgtgctgcaaggcgattaagttgg gtaacgccagggttttcccagtcacgacgttgtaaaacgacggccagtgaattcgagctcggtaccctaagttgagtagtggaattcta catcaattagtcgagttattaaaagttcttcaatactaaatttctttaacaagttgtacagaacattttggaagttcaaggtcagaat actagttctgtgatgacaagtcatttttaaaaatgttctacagaagatcattaactataattcctgtatcacaactcgtagtca gaaggtcatagaagtcaagttgactgtcctttaaacagcttggaaaattccagaaaatgatgtcatggctttagaagcttctgatagacta attgacatcatttgagtcaattggaggtgtacctgtggatgtatttcaagggaattctgtggaatgtgtgtcagttagggtgtggaaagtccc caggctccccaggcaggcagaagtatgcaaagcatgcatatcgatactagtgagctcacggggacagccccccccaaagccc cagggatgtaattacgtccctcccccgctaggggcagcagcgagccgcccggggctcccctccggtccggcgctcccccccatc cccgagccggcagcgtgcggggacagcccgggcacgggaaggtggcacgggatcgctttcctctgaacgcttctcgctgctctttg agcctgcagacacctgggggataccggggaaaaagctttaggctgaaagagagatttagaatgacagaatcatagaacggcctg ggttgcaaaggagcacagtgctcatccagatccaacccctgctatgtgcagggtcatcaaccagcagcccaggctgcccagagcc acatccagcctggccttgaatgcctgcagggatggggcatccacagcctccttgggcaacctgttcagtgcgtcaccaccctctgggg gaaaaactgcctcctcatatccaacccaaacctcccctgtctcagtgtaaagccattccccccttgtcctatcaaggggggagtttgctgtga
```

```
cattgttggtctggggtgacacatgtttgccaattcagtgcatcacggagaggcagatcttggggataaggaagtgcaggacagcatg
gacgtgggacatgcaggtgttgagggctctgggacactctccaagtcacagcgttcagaacagccttaaggataagaagataggat
agaaggacaaagagcaagttaaaacccagcatggagaggagcacaaaaaggccacagacactgctggtccctgtgtctgagcct
gcatgtttgatggtgtctggatgcaagcagaagggtggaagagcttgcctggagagatacagctgggtcagtaggactgggacag
gcagctggagaattgccatgtagatgttcatacaatcgtcaaatcatgaaggctggaaaagccctccaagatccccaagaccaacc
ccaacccacccaccgtgcccactggccatgtccctcagtgccacatccccacagttcttcatcacctccaggacggtgacccccc
acctccgtgggcagctgtgccactgcagcaccgctctttggagaaggtaaatcttgctaaatcagcccgacccctccctggcacaac
gtaaggccattatctctcatccaactccaggacggagtcagtgagaatatttaattaacctaggtgtacaggcgcgccaagcttagatc
tgtggtctcatacagaacttataagattcccaaatccaaagacatttcacgtttatggtgatttcccagaacacatagcgacatgcaaata
ttgcagggcgccactccctgtccctcacagccatcttcctgccagggcgcaccgcgctgggtgttcccgcctagtgacactgggcc
cgcgattccttggagcgggttgatgagtcagcgttcgaattcttaattaagatctcgacctcgaaattc
``` cctgcatccatctagatctcgagcagctgaagcttaccatga cgcccgcccacaagacccgcagcgcccgaccgaaaggagcgcacgacccccatgcatcgaatcgatatccccgggccgtc
ctgtaagtctgcagaaattgatgatctattaaacaataaagatgtccactaaaatggaagttttttcctgtcatactttgttaagaagggtga
gaacagagtacctacattttgaatggaaggattggagctacgggggtggggtggggtgggattagataaatgcctgctctttactgaa
ggctcttttactattgctttatgataatgtttcatagttggatatcataatttaaacaagcaaaaccaaattaagggccagctcattcctcccac
tcatgatctatagatctatagatctctcgtgggatcattgttttctcttgattcccactttgtggttctaagtactgtggtttccaaatgtgtcagttt
catagcctgaagaacgagatcagcagcctctgttccacatacacttcattctcagtattgttttgccaagttctaattccatcagaagctgg
tcgagctagc gagctcacggggacagcccccccaaagcccccagggatgtaattacgtccctcccccgctagggggcagcagcgagccgcccggggctccgctcc
ggtccggcgctcccccgcatcccgagccggcagcgtgcggggacagcccgggcacggggaaggtggcacgggatcgctttcc
tctgaacgcttctcgctgctctttgagcctgcagacacctgggggatacggggaaaaagctttaggctgaaagagagatttagaatg
acagaatcatagaacgcctgggttgcaaaggagcacagtgctcatccagatccaacccctgctatgtgcagggtcatcaaccag
cagcccaggctgcccagagccacatccagcctggccttgaatgcctgcagggatggggcatccacagcctccttgggcaacctgttc

```
agtgcgtcaccaccctctgggggaaaaactgcctcctcatatccaacccaaacctcccctgtctcagtgtaaagccattccccttgtcc
tatcaaggggagtttgctgtgacattgttggtctggggtgacacatgtttgccaattcagtgcatcacggagaggcagatcttggggat
aaggaagtgcaggacagcatggacgtgggacatgcaggtgttgagggctctgggacactctccaagtcacagcgttcagaacagc
cttaaggataagaagataggatagaaggacaaagagcaagttaaaacccagcatggagaggagcacaaaaaggccacagac
actgctggtccctgtgtctgagcctgcatgtttgatggtgtctggatgcaagcagaagggggtggaagagcttgcctggagacatacagc
tgggtcagtaggactgggacaggcagctggagaattgccatgtagatgttcatacaatcgtcaaatcatgaaggctggaaaagccct
ccaagatccccaagaccaaccccaacccaccaccgtgcccactggccatgtccctcagtgccacatccccacagttcttcatcacc
tccaggacggtgaccccccctccgtgggcagctgtgccactgcagcaccgctctttggagaaggtaaatcttgctaaatccagc
ccgacccctccctggcacaacgtaaggccattatctctcatccaactccaggacggagtcagtgagaatatt
```
gcggccgctgcattcta
gttgtggtttgtccaaactcatcaatgtatcttatcatgtctggatcccatcacaaagctctgacctcaatcctatagaaaggaggaatgag
ccaaaattcacccaacttattgtgggaagcttgtggaaggctactcgaaatgtttgacccaagttaaacaatttaaaggcaatgctacc
aaatactaattga▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
▓▓▓▓▓▓▓▓▓▓▓▓▓▓▓▓▓▓▓▓▓▓▓▓▓▓▓▓▓▓▓▓▓▓▓▓▓▓gacttcaactgtagggatcctctagagtcgacctgcaggcatgcaagc
ttggcgtaatcatggtcatagctgtttcctgtgtgaaattgttatccgctcacaattccacacaacatacgagccggaagcataaagtgta
aagcctggggtgcctaatgagtgagctaactcacattaattgcgttgcgctcactgcccgctttccagtcgggaaacctgtcgtgccagc
tgcattaatgaatcggccaacgcgcggggagaggcggtttgcgtattgggcgctcttccgcttcctcghctcactgactcgctgcgctcgg
tcgttcggctgcggcgagcggtatcagctcactcaaaggcggtaatacggttatccacagaatcaggggataacgcaggaaagaac
atgtgagcaaaaggccagcaaaaggccaggaaccgtaaaaaggccgcgttgctggcgtttttccataggctccgcccccctgacga
gcatcacaaaaatcgacgctcaagtcagaggtggcgaaacccgacaggactataaagataccaggcgtttccccctggaagctcc
ctcgtgcgctctcctgttccgaccctgccgcttaccggatacctgtccgcctttctcccttcgggaagcgtggcgctttctcaatgctcacgc
tgtaggtatctcagttcggtgtaggtcgttcgctccaagctgggctgtgtgcacgaaccccccgttcagcccgaccgctgcgccttatccg
gtaactatcgtcttgagtccaacccggtaagacacgacttatcgccactggcagcagccactggtaacaggattagcagagcgaggt
atgtaggcggtgctacagagttcttgaagtggtggcctaactacggctacactagaaggacagtatttggtatctgcgctctgctgaagc
cagttaccttcggaaaaagagttggtagctcttgatccggcaaacaaaccaccgctggtagcggtggtttttttgtttgcaagcagcaga
ttacgcgcagaaaaaaaggatctcaagaagatcctttgatcttttctacggggtctgacgctcagtggaacgaaaactcacgttaagg
gattttggtcatgagattatcaaaaaggatcttcacctagatccttttaaattaaaaatgaagttttaaatcaatctaaagtatatatgagtaa
acttggtctgacagttaccaatgcttaatcagtgaggcacctatctcagcgatctgtctatttcgttcatccatagttgcctgactccccgtcg
tgtagataactacgatacgggagggcttaccatctggccccagtgctgcaatgataccgcgagacccacgctcaccggctccagattt
atcagcaataaaccagccagccggaagggccgagcgcagaagtggtcctgcaactttatccgcctccatccagtctattaattgttgc
cgggaagctagagtaagtagttcgccagttaatagtttgcgcaacgttgttgccattgctacaggcatcgtggtgtcacgctcgttcgtttg
gtatggcttcattcagctccggttcccaacgatcaaggcgagttacatgatccccatgttgtgcaaaaaagcggttagctccttcggtcc
tccgatcgttgtcagaagtaagttggccgcagtgttatcactcatggttatggcagcactgcataattctcttactgtcatgccatccgtaag
atgcttttctgtgactggtgagtactcaaccaagtcattctgagaatagtgtatgcggcgaccgagttgctcttgcccggcgtcaatacgg
gataataccgcgccacatagcagaactttaaaagtgctcatcattggaaaacgttcttcggggcgaaaactctcaaggatcttaccgct
gttgagatccagttcgatgtaacccactcgtgcacccaactgatcttcagcatcttttactttcaccagcgtttctgggtgagcaaaaacag
gaaggcaaaatgccgcaaaaaagggaataagggcgacacggaaatgttgaatactcatactcttcctttttcaatattattgaagcattt
atcagggttattgtctcatgagcggatacatatttgaatgtatttagaaaaataaacaaataggggttccgcgcacatttccccgaaaagt
gccacctgacgtctaagaaaccattattatcatgacattaacctataaaaataggcgtatcacgaggccctttcgtc

REFERENCES (1) Hansson G K. Inflammation, atherosclerosis, and coronary artery disease. *N Engl J. Med.* 2005; 352:1685-1695.
(2) Mackay J, Mensah G A. The Atlas of Heart Disease and Stroke. WHO and CDC, http://www.who.inticardiovascular diseases/resources/atlas/en/; 2004.
(3) Law M R, Wald N J, Morris J K. The performance of blood pressure and other cardiovascular risk factors as screening tests for ischaemic heart disease and stroke. *J Med. Screen.* 2004; 11:3-7.
(4) Chu B, Ferguson M S, Underhill H, Takaya N, Cai J, Kliot M, Yuan C, Hatsukami T S. Images in cardiovascular medicine. Detection of carotid atherosclerotic plaque ulceration, calcification, and thrombosis by multicontrast weighted magnetic resonance imaging. *Circulation.* 2005; 112:e3-e4.
(5) Leber A W, Knez A, von Z F, Becker A, Nikolaou K, Paul S, Wintersperger B, Reiser M, Becker C R, Steinbeck G, Boekstegers P. Quantification of obstructive and nonobstructive coronary lesions by 64-slice computed tomography: a comparative study with quantitative coronary angiography and intravascular ultrasound. *J Am Coll Cardiol.* 2005; 46:147-154.
(6) Zhang S H, Reddick R L, Piedrahita J A, Maeda N. Spontaneous hypercholesterolemia and arterial lesions in mice lacking apolipoprotein E. *Science.* 1992; 258:468-471.
(7) Ishibashi S, Goldstein J L, Brown M S, Herz J, Burns D K. Massive xanthomatosis and atherosclerosis in cholesterol-fed low density lipoprotein receptor-negative mice. *J Clin Invest.* 1994; 93:1885-1893.
(8) Holvoet P, Theilmeier G, Shivalkar B, Flameng W, Collen D. LDL hypercholesterolemia is associated with accumulation of oxidized LDL, atherosclerotic plaque growth, and compensatory vessel enlargement in coronary arteries of miniature pigs. *Arterioscler Thromb Vasc Biol.* 1998; 18:415-422.
(9) Gerrity R G, Natarajan R, Nadler J L, Kimsey T. Diabetes-induced accelerated atherosclerosis in swine. *Diabetes.* 2001; 50:1654-1665.
(10) Panepinto L M, Phillips R W, Wheeler L R, Will D H. The Yucatan minature pig as a laboratory animal. *Lab Anim Sci.* 1978; 28:308-313.
(11) Hasler-Rapacz J, Ellegren H, Fridolfsson A K, Kirkpatrick B, Kirk S, Andersson L, Rapacz J. Identification of a mutation in the low density lipoprotein receptor gene associated with recessive familial hypercholesterolemia in swine. *Am J Med. Genet.* 1998; 76:379-386.
(12) Rapacz J, Hasler-Rapacz J. Animal Models: The Pig. In: Lusis A J, Sparkes R S, eds. *Genetic factors in atherosclerosis: Approaches and model systems.* Karger; 1989. p. 139-69.
(13) Greeve J, Altkemper I, Dieterich J H, Greten H, Windier E. Apolipoprotein B mRNA editing in 12 different mammalian species: hepatic expression is reflected in low concentrations of apoB-containing plasma lipoproteins. *J Lipid Res.* 1993; 34:1367-1383.
(14) Brown M S, Goldstein J L. Lipoprotein receptors in the liver. Control signals for plasma cholesterol traffic. *J Clin Invest.* 1983; 72:743-747.
(15) Rohlmann A, Gotthardt M, Hammer R E, Herz J. Inducible inactivation of hepatic LRP gene by cre-mediated recombination confirms role of LRP in clearance of chylomicron remnants. *J Clin Invest.* 1998; 101:689-695.
(16) Ramsoondar J J, Rucker E B, Vasquez J C, Gallagher D S, Grimm D R, Lunney J K, Schook L B, Piedrahita J A. Isolation and genetic characterization of the porcine apolipoprotein E gene. *Anim Genet.* 1998; 29:43-47.
17. Abifadel, M. et al. Mutations in PCSK9 cause autosomal dominant hypercholesterolemia. *Nat. Genet.* 34, 154-156 (2003).
18. Zhang, D. W. et al. Binding of proprotein convertase subtilisin/kexin type 9 to epidermal growth factor-like repeat A of low density lipoprotein receptor decreases receptor recycling and increases degradation. *J. Biol. Chem.* 282, 18602-18612 (2007).
19. Park, S. W., Moon, Y. A. & Horton, J. D. Post-transcriptional regulation of low density lipoprotein receptor protein by proprotein convertase subtilisin/kexin type 9a in mouse liver. *J. Biol. Chem.* 279, 50630-50638 (2004).

---

The invention claimed is:

1. A genetically modified pig as a model for studying atherosclerosis, wherein the genome of the modified pig comprises at least one modified gene or combination of modified genes selected from
   i) human PCSK9 gene, and
   ii) porcine PCSK9 gene,
   wherein the modified pig expresses at least one phenotype associated with atherosclerosis.

2. The modified pig according to claim 1, wherein the pig is a mini-pig.

3. The modified pig according to claim 2, wherein the mini-pig is selected from the group consisting of Goettingen, Yucatan, Bama Xiang Zhu, Wuzhishan and Xi Shuang Banna.

4. The modified pig according to claim 1, wherein the genome of the modified pig comprises at least one modified porcine PCSK9 gene comprising at least one mutation.

5. A genetically modified porcine blastocyst derived from the genetically modified pig defined in claim 1, wherein the genome of the modified porcine blastocyst comprises at least one modified gene or combination of modified genes selected from
   i) human PCSK9 gene, and
   ii) porcine PCSK9 gene.

6. A genetically modified porcine embryo derived from the genetically modified pig as defined in claim 1, wherein the genome of the modified porcine embryo comprises at least one modified gene or combination of modified genes selected from
   i) human PCSK9 gene, and
   ii) porcine PCSK9 gene.

7. A genetically modified porcine fetus derived from the genetically modified pig as defined in claim 1, wherein the genome of the modified porcine fetus comprises at least one modified gene or combination of modified genes selected from
   i) human PCSK9 gene, and
   ii) porcine PCSK9 gene.

8. A genetically modified porcine donor cell or cell nucleus derived from the genetically modified pig as defined in claim 1, wherein the genome of the modified porcine donor cell or cell nucleus comprises at least one modified gene or combination of modified genes selected from
   i) human PCSK9 gene, and
   ii) porcine PCSK9 gene.

9. The modified pig according to claim 1, wherein at least one phenotype associated with atherosclerosis is hypercholesterolemia.

10. The modified pig according to claim 9, wherein said hypercholesterolemia is characterized by an at least 10% increase in total cholesterol level in the plasma as compared to a standard level of the pig.

11. The genetically modified pig according to claim 1 obtainable by nuclear transfer comprising the steps of
   i) establishing at least one porcine oocyte having at least a part of a zona pellucida,
   ii) separating the porcine oocyte into at least two parts whereby an oocyte having a nucleus and at least one cytoplast is obtained,
   iii) establishing a porcine donor cell or membrane surrounded cell nucleus, wherein the genome of the cell or cell nucleus comprises at least one modified gene or combination of modified genes selected from
      a) human PCSK9 gene, and
      b) porcine PCSK9 gene,
   iv) fusing said at least one cytoplast with the donor cell or membrane surrounded cell nucleus,
   v) obtaining a reconstructed porcine embryo,
   vi) activating the reconstructed embryo to form an embryo,
   vii) culturing said embryo, and
   viii) transferring said cultured embryo to a host porcine mammal such that the embryo develops into a genetically modified fetus,
   wherein said genetically modified pig is obtained by nuclear transfer comprising steps i) to viii) and permitting term development of the fetus.

12. A method for evaluating the effect of a therapeutic treatment of atherosclerosis, said method comprising the steps of
   i) providing the modified pig according to claim 1,
   ii) treating said pig with a pharmaceutical composition, and
   iii) evaluating the modified pig for an effect of the composition on an atherosclerosis disease phenotype expressed by the pig.

13. The method of claim 12 comprising the further step of advising on medical treatment based on the afore-mentioned observed effects.

14. A method for screening the efficacy of a pharmaceutical composition for atherosclerosis, said method comprising the steps of
  i) providing the modified pig according to claim 1,
  ii) administering to said pig a pharmaceutical composition the efficacy of which is to be evaluated, and
  iii) evaluating the modified pig for an effect, if any, of the pharmaceutical composition on an atherosclerosis disease phenotype expressed by the modified pig.

15. A method for treatment of a human being suffering from atherosclerosis, said method comprising the initial steps of
  i) providing the modified pig according to claim 1,
  ii) administering to said pig a pharmaceutical composition the efficacy of which is to be evaluated,
  iii) evaluating the effect, if any, of the pharmaceutical composition on an atherosclerosis disease phenotype expressed by the modified pig, and
  iv) treating a human being suffering from atherosclerosis based on the effects observed in the pig.

16. The genetically modified porcine blastocyst according to claim 5 obtainable by nuclear transfer comprising the steps of
  i) establishing at least one porcine oocyte having at least a part of a zona pellucida,
  ii) separating the porcine oocyte into at least two parts whereby an oocyte having a nucleus and at least one cytoplast is obtained,
  iii) establishing a porcine donor cell or membrane surrounded cell nucleus, wherein the genome of the cell or cell nucleus comprises at least one modified gene or combination of modified genes selected from
    a) human PCSK9 gene, and
    b) porcine PCSK9 gene,
  iv) fusing said at least one cytoplast with the donor cell or membrane surrounded cell nucleus,
  v) obtaining a reconstructed porcine embryo,
  vi) activating the reconstructed embryo to form an embryo, and
  vii) culturing said embryo.

17. The genetically modified porcine embryo according to claim 6 obtainable by nuclear transfer comprising the steps of
  i) establishing at least one porcine oocyte having at least a part of a zona pellucida,
  ii) separating the porcine oocyte into at least two parts whereby an oocyte having a nucleus and at least one cytoplast is obtained,
  iii) establishing a porcine donor cell or membrane surrounded cell nucleus, wherein the genome of the cell or cell nucleus comprises at least one modified gene or combination of modified genes selected from
    a) human PCSK9 gene, and
    b) porcine PCSK9 gene,
  iv) fusing said at least one cytoplast with the donor cell or membrane surrounded cell nucleus,
  v) obtaining a reconstructed porcine embryo,
  vi) activating the reconstructed embryo to form an embryo, and optionally
  vii) culturing said embryo.

18. The genetically modified porcine fetus according to claim 7 obtainable by nuclear transfer comprising the steps of
  i) establishing at least one porcine oocyte having at least a part of a zona pellucida,
  ii) separating the porcine oocyte into at least two parts whereby an oocyte having a nucleus and at least one cytoplast is obtained,
  iii) establishing a porcine donor cell or membrane surrounded cell nucleus, wherein the genome of the cell or cell nucleus comprises at least one modified gene or combination of modified genes selected from
    a) human PCSK9 gene, and
    b) porcine PCSK9 gene,
  iv) fusing said at least one cytoplast with the donor cell or membrane surrounded cell nucleus,
  v) obtaining a reconstructed porcine embryo,
  vi) activating the reconstructed embryo to form an embryo,
  vii) culturing said embryo, and
  viii) transferring said cultured embryo to a host porcine mammal such that the embryo develops into a genetically modified fetus.

19. The genetically modified porcine donor cell according to claim 8 obtainable by nuclear transfer comprising the steps of
  i) establishing at least one porcine oocyte having at least a part of a zona pellucida,
  ii) separating the porcine oocyte into at least two parts whereby an oocyte having a nucleus and at least one cytoplast is obtained, and
  iii) establishing a porcine donor cell or membrane surrounded cell nucleus, wherein the genome of the cell or cell nucleus comprises at least one modified gene or combination of modified genes selected from
    a) human PCSK9 gene, and
    b) porcine PCSK9 gene.

* * * * *

SEQUENCE LISTING

```
<160> NUMBER OF SEQ ID NOS: 42

<210> SEQ ID NO 1
<211> LENGTH: 4267
<212> TYPE: DNA
<213> ORGANISM: Sus scrofa

<400> SEQUENCE: 1
ctcgagaggg agtgagggtt aaaactctgt ggtgcaacgg aaacgaatcc aactgggaaa      60
ccatgaggct gtgggttgga tccccggcct cgctcaatgg gttaaggatc cagcacggcg     120
ctgccgtgag ctgtggtgta ggtcgcagac gaagcttgga tcccacttgg ctgtggctgt     180
ggctgtggct gtggtgtagg cccgcagctg taactgtaat tcgaccccta gcctgggaac     240
ctccacaagc cacgggtgtg gccctaaaaa gcaaaaaaac gaaagcaaaa agaacactct     300
caaagcctaa actttgagca aaaagaacac tctcaaagcc taaactttga gcagatgcct     360
tacaccgccc ccacgcctct catcccctt ctgtctgggc ctccagctcc cttcccctt      420 aacccagaaa tcccagacct cagacccaag gatttcgaat ccccaggcct tggcccaatt     480
```

```
ctatcatccc agcacaggac aagaaaaaag cagggccggg ccttctggtc ctgctcctct    540
ccctgccagc ccaccccacc agtggcatgg aaaaagctcc ggaattactg ggtgaaaaaa    600
acctcttcca tgggggctgg aattaggggg ggggtgatgg ttgccaaccc caccccctccc   660 ctccctccct tcccccaccc tgctgtgtga aggggaggc cagcccactt cgtgacccga     720
cgggggctgg cccagctggc cccagttctg gaggagtggg cggggcgggg ggagccctat    780
aattggccga atctgggctc cctgaatcat actcagcccc ggaggaggaa ggaggaagga    840
ggaggaggaa gcaaccggtg aggagcagac ctggggcac agagatgggc tcggggcttc     900
ggtgtggggg ggtgggctgt cggggagga ggaaatgacc tggcccccg gggccaccac      960 cgaggcagga gttggggatg aggctagagc ccagggactg gacctagaag gagggtgggc   1020
agcaggagga ggttatccgc cttggctgga aggggaggtc agggaagcag cgggacctgt   1080
aggaagaacc agacgagcca gagccgacga attgtactgg caggtatggc gcatctactc   1140
aagttttgag cacactaaga gctccatcga ggagacccag gggtggcggc gaccagggt    1200 gacctcgacc gggctggcgg cagggtagct agagcgttgg tggaaggaca tgtaaatgag   1260
gattaaatta gggaatgagt ggaaaacagg gtttagatgt gaagttggag cttggaatgt   1320
gaaggtacca ggaagaacgt gagcttggag cccagaaagc aaggctgggg ctcacatggg   1380
actccagggt ggaaggggtg ggggggcgacg tgggtggaat ttgaaccctg ggaaaaaagg  1440
aaggcttttg ccgcacccg acctggggat ggggagatag gagaagacaa tgagggaatt    1500
acacggacaa tggaaaggat ctgctcggga aatatctgct tggattaggc tgatgcagat   1560
aagggggtgc aaggcttgga aggctgtgac tggacagggc tgggctctgg gtgagaggag   1620 cgagcccgc cgctgttgag tgacaatttc tccctcctgc aggttggcca atcgcaagcc    1680
agaagatgag ggttctgtgg gttgctttgg tggtaaccct cctcgcaggt atggggggtgg  1740 ggcttgctca ggttccctgc ccctccccca tccccggtgc cctccttca tccctgggtc    1800 tcttctgctg gtctctcttc cccttgagga gaggcctaga tgtgaggcct ctctggcact   1860
ccttgcttct gaacagctcg ttttactctc tgagcctcag tttccccatc tttaaaatgg   1920
gagttatgtt gagagattcc agctgtggct cagcaggtta agaacccgac tagtatccat   1980
gaggaagagg gttcaatccc ctggcttcgc tcagcgggtt aaggatccgg cgttgccatg   2040
agctgcggca taagtcgcag atgcagctcg aatcgggtgt tgctgtggct gtggtgcagg   2100
ctggcagcta tcgcttccat cggaccccts gcctgggaac ttccacgtat gccactggtg   2160
cagccctaaa agacaaacaa acaaaaacga aagaaagaga aaagaaagga aaggggggctt  2220 ctgtttctaa tgcgttgttg cctggcaggg cgtgagcatt agatacgtgt cagctgtgac   2280
tagcgtgcac ggagcacaca atccatgctt gtccagtaat tagacaggct gggtgtcctt   2340 ccacccctc cctgcccacc agtgctctag agaagcccac ccaccagggc tgggggagca    2400
cctgctctgt accaggtacc gtgtgctggg aggggcaga ggacctgatg gctgtgaact    2460
ggctcggtgc aggatgccgg acagaggacg agccggggcc gccgccggag gtgcacgtgt   2520
ggtgggagga gcccaagtgg cagggcagcc agccctggga gcaggccctg gccgcttct    2580 gggattacct gcgctgggtg cagtccctgt ctgaccaagt gcaggaggag ctgctcagca   2640
ccaaggtcac ccaggaactg acgtaagtgc ccacccgact cccgccgcgc gcgcgcgcgc   2700
gcgcgcgcgc gcctgaccct cctggcgaac cgtgtgttct ggaccctcag gctccacccg   2760
tccgggtttc cttctgtcct tgtcgccaac tcttggggt ctgggtctct gtttcttttt    2820
tttccttcct ccttttttgg ggggaaaaaa ctttttcttt tttctttcat ttgacttcat   2880
```

```
                                       -continued gtcttgcttt ctttccatct tgagctcctg ccttcgcctg tctctgggtc agtcttgccg   2940
tcccttgctg tctctgaatc tctggcacgt cctggccatc gccagctcag gagccctcct   3000
tctcccccct accgccccg ccctctctgc gcccagggag ctgatagagg agagcatgaa    3060
ggaggtgaag gcctaccgcg aggagctgga ggcgcagctg ggccccgtga cccaggagac   3120
gcaggcgcgc ctgtccaagg agctgcaggc ggcgcaggcc cgcgtgggcg ccgacatgga   3180
ggacgtgcgc aaccgcttgg tgctctaccg cagcgaggtg cacaacatgt ggggccagac   3240
caccgaggag ctgcggagcc gcctggcttc ccacctgcgc aagctgcgca gcggctgct    3300 ccgcgacacc gaggacctgc agaagcgcct ggccgtgtac caggcggggc tgcgcgaggg   3360
cgccgagcgc agcgtgagcg ccctccgcga gcgcctcggg cccctggtgg agcagggccg   3420
attgcgcgcc gccacccctga gtaccagggc cggccagccg ctgcgcgagc gcgcggaagc   3480
ctggggccag aagctgcgcg gacggctgga ggagatgggc agccggaccc gcgaccgcct   3540
ggatgagatg cgtgagcagc tggaggaggt gcgcaccaaa gtggaggagc agggcagcca   3600
gttgcgcctg caggccgagg gattccacgc cctcctcaaa ggctggttcg agcctctggt   3660
ggaagacata cggcgccagt gggccgggct ggtggagagg atgcagtcgg gcgtgagcat   3720
aagctcctcc acctctgcgc ccagtgataa tcagtgagtg ccctctcatc cgggcaccc    3780 cttcggggcc ccgttcctgc ccaactcccc cgcctccccc agccttagat gcctcttgg    3840 tgggcccctg cttaataaag attcatcaag cttcacagca gcttctgggt gtccccggtg   3900
tgatttctca gctccagcct cagtttccct ttccttccct gcactgacca cccagttctc   3960
tgtcctgccc tctgcctgtg tgtgtctatt tgtctcttct cccccttttc tttttttttg   4020
gccgagccca tggcatgcgg aagttccccc ggccagggat tgaacccatg ccacagccgc   4080
cacaacgaag gatccttaac tactaggcca ccagggaact ccatcctttc taactctgtc   4140
tttgctttcc cttttttagc gttttagggc tgcaccctca gcatgtggaa gtccccaggc   4200 tagggggtcaa attggcgcta cagctgccag cctacaccac agccccagca acgcaggatt   4260
cctcgag                                                              4267
```

<210> SEQ ID NO 2
<211> LENGTH: 317
<212> TYPE: PRT
<213> ORGANISM: Sus scrofa

<400> SEQUENCE: 2

```
Met Arg Val Leu Trp Val Ala Leu Val Val Thr Leu Leu Ala Gly Cys
 1               5                  10                  15

Arg Thr Glu Asp Glu Pro Gly Pro Pro Glu Val His Val Trp Trp
             20                  25                  30

Glu Glu Pro Lys Trp Gln Gly Ser Gln Pro Trp Glu Gln Ala Leu Gly
         35                  40                  45

Arg Phe Trp Asp Tyr Leu Arg Trp Val Gln Ser Leu Ser Asp Gln Val
     50                  55                  60

Gln Glu Glu Leu Leu Ser Thr Lys Val Thr Gln Glu Leu Thr Glu Leu
 65                  70                  75                  80

Ile Glu Glu Ser Met Lys Glu Val Lys Ala Tyr Arg Glu Glu Leu Glu
                 85                  90                  95

Ala Gln Leu Gly Pro Val Thr Gln Glu Thr Gln Ala Arg Leu Ser Lys
            100                 105                 110

Glu Leu Gln Ala Ala Gln Ala Arg Val Gly Ala Asp Met Glu Asp Val
        115                 120                 125
```

Arg Asn Arg Leu Val Leu Tyr Arg Ser Glu Val His Asn Met Leu Gly
            130                 135                 140

Gln Thr Thr Glu Glu Leu Arg Ser Arg Leu Ala Ser His Leu Arg Lys
145                 150                 155                 160

Leu Arg Lys Arg Leu Leu Arg Asp Thr Glu Asp Leu Gln Lys Arg Leu
                165                 170                 175

Ala Val Tyr Gln Ala Gly Leu Arg Glu Gly Ala Glu Arg Ser Val Ser
            180                 185                 190

Ala Leu Arg Glu Arg Leu Gly Pro Leu Val Glu Gln Gly Arg Leu Arg
            195                 200                 205

Ala Ala Thr Leu Ser Thr Arg Ala Gly Gln Pro Leu Arg Glu Arg Ala
            210                 215                 220

Glu Ala Trp Gly Gln Lys Leu Arg Gly Arg Leu Glu Glu Met Gly Ser
225                 230                 235                 240

Arg Thr Arg Asp Arg Leu Asp Glu Met Arg Glu Gln Leu Glu Glu Val
                245                 250                 255

Arg Thr Lys Val Glu Glu Gln Gly Ser Gln Leu Arg Leu Gln Ala Glu
                260                 265                 270

Gly Phe His Ala Leu Leu Lys Gly Trp Phe Glu Pro Leu Val Glu Asp
            275                 280                 285

Ile Arg Arg Gln Trp Ala Gly Leu Val Glu Arg Met Gln Ser Gly Val
            290                 295                 300

Ser Ile Ser Ser Ser Thr Ser Ala Pro Ser Asp Asn Gln
305                 310                 315

<210> SEQ ID NO 3
<211> LENGTH: 2403
<212> TYPE: DNA
<213> ORGANISM: Sus scrofa

<400> SEQUENCE: 3
ttccagtgcc aagacgggaa atgcatctcc tacaagtgga tttgtgatgg gaacaccgag      60
tgcaaggacg ggtccgatga gtccctggag acgtgcatgt ctgtcacctg caagataggg     120
gactttagct gtggggggccg tgtcaaccgc tgcattcctg agtcttggag gtgtgacggt     180
cagcaggact gcgagaatgg ctcagatgag aaggctgtt cccccaagac gtgctcccaa      240
gatgagttcc gctgccagga cggcaagtgc atcgccccaa agtttgtctg tgactcggac     300
cgggactgcc tggacggctc ggatgaagca tcctgcccca cacccacctg tggccccgcc     360
agcttccagt gcaacagctc cacctgcatc cctgagctgt gggcctgtga tggtgatcct     420
gactgcgagg acggctcaga cgagtggcca cagcactgca ggagccacag ctcatcactc     480
cccgagagga gcaacaaccc ctgctcagcc ctcgagttcc actgccacag tggcgagtgc     540
atccactcca gctggcgctg cgacggagac actgactgca aggacaagtc tgacgaggag     600
aactgcgatg tggccacgtg ccggcctgac gagttccagt gctcagacgg acctgcatc      660 catggtagcc ggcagtgcga cagggaatat gactgcaagg acatgagcga cgagcagggc     720
tgtgtcaatg cgactctgtg cgaggggccc aacaagttca gtgtcaaag cggcgagtgc      780 atctccttgg acaaagtgtg caactcagtc agggactgcc gggactggtc agacgagccc     840
ctcaaggagt gtgggaccaa cgagtgtctg acaacaagg gtggctgctc ccatatctgc      900
aatgacctca gatcggcta tgagtgcctc tgtcccgagg gcttccagct ggtggataag     960
cacagatgcg aagatatcga cgagtgtcag gacccagacg cctgcagcca gatctgcgtg    1020
aacctcgagg gcagctacaa gtgccagtgt gaggagggct ccagctgga gcctctcacc    1080

-continued

```
aaggcctgca aggccatagg caccatcgcc tacctcttct tcaccaaccg ccacgaggtg    1140
aggaagatga ccctggaccg tagtgagtac accagcctca tccccaacct gaagaacgtg    1200
gtcgctctgg acactgaggt ggccagcaat agaatctact ggtctgacct gtctcagagg    1260
aagatctaca gtacccagat cgacagggcc cccagctttt cctcctatga caccattatt    1320
ggcgaagatc tccaggcccc cgatgggctg cggtggact ggatccacag caacatatac     1380
tggactgact ccatcctggg cactgtctcc gtggctgaca ccaagggcgt gaagaggaag    1440
actctcttcc aagagaaagg ctccaagcca cgggccattg tggtggaccc tgtccatggc    1500
ttcatgtact ggactgattg ggaaccccc gccaagatca agaagggcgg cctgaacgga     1560
gtggacgtct actcgctggt gacggaggac atccagtggc caatggcat cacctggat      1620 ctttctggcg ccgccttta ctgggtcgac tccaagctcc actccatctc cagcatcgat     1680
gtcaacgggg ggaaccggaa gaccgtcctg gaggacaaga cgaagctggc gccccttc     1740 tccttggcca tttttgagga taaagtattt tggacagata taatcaacga agccattttc    1800
agtgccaacc gcctcacagg ctcggacata catttgatgg cagaaaacct gttgtctcca    1860
gaggacattg tccttttcca caacctcaca cagccgagag gggtgaactg gtgtgaaagg    1920
accgccctcc aaaacggtgg ctgccagtac ctgtgtctgc cagctccaca gatcaaccca    1980
cgctcgccga gttcacctg tgcctgcccg gatggcatgc tgttggccaa ggacatgagg    2040
agctgtctca cagagactga acctgcagga accacccagg gaccttccat ggtcaactcg    2100
acagctgtgg ggccaaagca caccgccagc tctgagctca ccacagccga gtcagtgacg    2160
atgtcccaac atgccctggg cgacgttgct ggccgaggag tcactgagaa gccccagagc    2220
gtgggtgctc tgtacattgt cctcccatt gcactgctca tcctcctctt cttcggaacc     2280
ttcctcctct ggaagaactg gaggcttaag agcatcaaca gcattaactt cgacaaccct    2340
gtgtaccaga gaccacgga agacgaggtc cacatctgcc gcagccagga cggctacacc    2400
tac                                                                  2403
```

<210> SEQ ID NO 4
<211> LENGTH: 801
<212> TYPE: PRT
<213> ORGANISM: Sus scrofa

<400> SEQUENCE: 4

```
Phe Gln Cys Gln Asp Gly Lys Cys Ile Ser Tyr Lys Trp Ile Cys Asp
  1               5                  10                  15

Gly Asn Thr Glu Cys Lys Asp Gly Ser Asp Glu Ser Leu Glu Thr Cys
             20                  25                  30

Met Ser Val Thr Cys Lys Ile Gly Asp Phe Ser Cys Gly Gly Arg Val
         35                  40                  45

Asn Arg Cys Ile Pro Glu Ser Trp Arg Cys Asp Gly Gln Gln Asp Cys
     50                  55                  60

Glu Asn Gly Ser Asp Glu Gly Cys Ser Pro Lys Thr Cys Ser Gln
 65                  70                  75                  80

Asp Glu Phe Arg Cys Gln Asp Gly Lys Cys Ile Ala Pro Lys Phe Val
                 85                  90                  95

Cys Asp Ser Asp Arg Asp Cys Leu Asp Gly Ser Asp Glu Ala Ser Cys
            100                 105                 110

Pro Thr Pro Thr Cys Gly Pro Ala Ser Phe Gln Cys Asn Ser Ser Thr
        115                 120                 125

Cys Ile Pro Glu Leu Trp Ala Cys Asp Gly Asp Pro Asp Cys Glu Asp
    130                 135                 140
```

```
Gly Ser Asp Glu Trp Pro Gln His Cys Arg Ser His Ser Ser Leu
145                 150                 155                 160

Pro Glu Arg Ser Asn Asn Pro Cys Ser Ala Leu Glu Phe His Cys His
                165                 170                 175

Ser Gly Glu Cys Ile His Ser Ser Trp Arg Cys Asp Gly Asp Thr Asp
                180                 185                 190

Cys Lys Asp Lys Ser Asp Glu Glu Asn Cys Asp Val Ala Thr Cys Arg
                195                 200                 205

Pro Asp Glu Phe Gln Cys Ser Asp Gly Thr Cys Ile His Gly Ser Arg
210                 215                 220

Gln Cys Asp Arg Glu Tyr Asp Cys Lys Asp Met Ser Asp Glu Gln Gly
225                 230                 235                 240

Cys Val Asn Ala Thr Leu Cys Glu Gly Pro Asn Lys Phe Lys Cys Gln
                245                 250                 255

Ser Gly Glu Cys Ile Ser Leu Asp Lys Val Cys Asn Ser Val Arg Asp
                260                 265                 270

Cys Arg Asp Trp Ser Asp Glu Pro Leu Lys Glu Cys Gly Thr Asn Glu
                275                 280                 285

Cys Leu Asp Asn Lys Gly Gly Cys Ser His Ile Cys Asn Asp Leu Lys
                290                 295                 300

Ile Gly Tyr Glu Cys Leu Cys Pro Glu Gly Phe Gln Leu Val Asp Lys
305                 310                 315                 320

His Arg Cys Glu Asp Ile Asp Glu Cys Gln Asp Pro Asp Ala Cys Ser
                325                 330                 335

Gln Ile Cys Val Asn Leu Glu Gly Ser Tyr Lys Cys Gln Cys Glu Glu
                340                 345                 350

Gly Phe Gln Leu Glu Pro Leu Thr Lys Ala Cys Lys Ala Ile Gly Thr
                355                 360                 365

Ile Ala Tyr Leu Phe Phe Thr Asn Arg His Glu Val Arg Lys Met Thr
370                 375                 380

Leu Asp Arg Ser Glu Tyr Thr Ser Leu Ile Pro Asn Leu Lys Asn Val
385                 390                 395                 400

Val Ala Leu Asp Thr Glu Val Ala Ser Asn Arg Ile Tyr Trp Ser Asp
                405                 410                 415

Leu Ser Gln Arg Lys Ile Tyr Ser Thr Gln Ile Asp Arg Ala Pro Ser
                420                 425                 430

Phe Ser Ser Tyr Asp Thr Ile Ile Gly Glu Asp Leu Gln Ala Pro Asp
                435                 440                 445

Gly Leu Ala Val Asp Trp Ile His Ser Asn Ile Tyr Trp Thr Asp Ser
450                 455                 460

Ile Leu Gly Thr Val Ser Val Ala Asp Thr Lys Gly Val Lys Arg Lys
465                 470                 475                 480

Thr Leu Phe Gln Glu Lys Gly Ser Lys Pro Arg Ala Ile Val Val Asp
                485                 490                 495

Pro Val His Gly Phe Met Tyr Trp Thr Asp Trp Gly Thr Pro Ala Lys
                500                 505                 510

Ile Lys Lys Gly Gly Leu Asn Gly Val Asp Val Tyr Ser Leu Val Thr
                515                 520                 525

Glu Asp Ile Gln Trp Pro Asn Gly Ile Thr Leu Asp Leu Ser Gly Gly
                530                 535                 540

Arg Leu Tyr Trp Val Asp Ser Lys Leu His Ser Ile Ser Ser Ile Asp
545                 550                 555                 560

Val Asn Gly Gly Asn Arg Lys Thr Val Leu Glu Asp Lys Thr Lys Leu
```

```
                        565                 570                 575
Ala His Pro Phe Ser Leu Ala Ile Phe Glu Asp Lys Val Phe Trp Thr
            580                 585                 590

Asp Ile Ile Asn Glu Ala Ile Phe Ser Ala Asn Arg Leu Thr Gly Ser
        595                 600                 605

Asp Ile His Leu Met Ala Glu Asn Leu Leu Ser Pro Glu Asp Ile Val
    610                 615                 620

Leu Phe His Asn Leu Thr Gln Pro Arg Gly Val Asn Trp Cys Glu Arg
625                 630                 635                 640

Thr Ala Leu Gln Asn Gly Gly Cys Gln Tyr Leu Cys Leu Pro Ala Pro
                645                 650                 655

Gln Ile Asn Pro Arg Ser Pro Lys Phe Thr Cys Ala Cys Pro Asp Gly
            660                 665                 670

Met Leu Leu Ala Lys Asp Met Arg Ser Cys Leu Thr Glu Thr Glu Pro
        675                 680                 685

Ala Gly Thr Thr Gln Gly Pro Ser Met Val Asn Ser Thr Ala Val Gly
    690                 695                 700

Pro Lys His Thr Ala Ser Ser Glu Leu Thr Thr Ala Glu Ser Val Thr
705                 710                 715                 720

Met Ser Gln His Ala Leu Gly Asp Val Ala Gly Arg Gly Val Thr Glu
                725                 730                 735

Lys Pro Gln Ser Val Gly Ala Leu Tyr Ile Val Leu Pro Ile Ala Leu
            740                 745                 750

Leu Ile Leu Leu Phe Phe Gly Thr Phe Leu Leu Trp Lys Asn Trp Arg
        755                 760                 765

Leu Lys Ser Ile Asn Ser Ile Asn Phe Asp Asn Pro Val Tyr Gln Lys
    770                 775                 780

Thr Thr Glu Asp Glu Val His Ile Cys Arg Ser Gln Asp Gly Tyr Thr
785                 790                 795                 800

Tyr

<210> SEQ ID NO 5
<211> LENGTH: 19
<212> TYPE: DNA
<213> ORGANISM: Sus scrofa

<400> SEQUENCE: 5
tgtcaaagcg gcgagtgca                                                       19

<210> SEQ ID NO 6
<211> LENGTH: 19
<212> TYPE: DNA
<213> ORGANISM: Sus scrofa

<400> SEQUENCE: 6
tcccatatct gcaatgacc                                                       19

<210> SEQ ID NO 7
<211> LENGTH: 19
<212> TYPE: DNA
<213> ORGANISM: Sus scrofa

<400> SEQUENCE: 7
accctggacc gtagtgagt                                                       19

<210> SEQ ID NO 8
<211> LENGTH: 19
<212> TYPE: DNA
```

<213> ORGANISM: Sus scrofa

<400> SEQUENCE: 8
tgacaccatt attggcgaa                                    19

<210> SEQ ID NO 9
<211> LENGTH: 19
<212> TYPE: DNA
<213> ORGANISM: Sus scrofa

<400> SEQUENCE: 9
gacaccatta ttggcgaag                                    19

<210> SEQ ID NO 10
<211> LENGTH: 19
<212> TYPE: DNA
<213> ORGANISM: Sus scrofa

<400> SEQUENCE: 10
agactctctt ccaagagaa                                    19

<210> SEQ ID NO 11
<211> LENGTH: 19
<212> TYPE: DNA
<213> ORGANISM: Sus scrofa

<400> SEQUENCE: 11
tgaacggagt ggacgtcta                                    19

<210> SEQ ID NO 12
<211> LENGTH: 19
<212> TYPE: DNA
<213> ORGANISM: Sus scrofa

<400> SEQUENCE: 12
tcacaggctc ggacataca                                    19

<210> SEQ ID NO 13
<211> LENGTH: 19
<212> TYPE: DNA
<213> ORGANISM: Sus scrofa

<400> SEQUENCE: 13
ccaacgagtg tctggacaa                                    19

<210> SEQ ID NO 14
<211> LENGTH: 19
<212> TYPE: DNA
<213> ORGANISM: Sus scrofa

<400> SEQUENCE: 14
cctacctctt cttcaccaa                                    19

<210> SEQ ID NO 15
<211> LENGTH: 1615
<212> TYPE: DNA
<213> ORGANISM: Sus scrofa

<400> SEQUENCE: 15
gcctgggaat gagtgccagc tcctccagtt ccacgtggcc tcaccacaca cctcaactct    60
gagtctggga gtcgtgtaac agggctgctg ggggatgggg gggtgcagtc agcgctcacc    120
aatctgtcac agaagttaac tggaactgtt ctttgttcta tccccggatg atggggttaa    180

```
atgcaaccat tttccccgtc ttagtggacc gagaaacaat gttcagagag gctaggtcat    240
ttgctcaagg tcacacagct gacaacccgc agagcctgga ttcaggcctg gaggctttgg    300
ttccagagtt cacagtccga accaggcgac gggacaggaa cactcccagg cctgtggaag    360
gcgcggtatg caggccgcga gctcctggaa tgcgcaaggc ttatgtgggg gcagagagct    420
gcatcctcat tgcacaaatc aggaaagcgg ctcagagaag cactcagatg tgcccaaggt    480
cacggccctc gagagggagt gagggttaaa actctgtggt gcaacggaaa cgaatccaac    540
tgggaaccat gaggctgtgg gttggatccc cggcctcgct caatgggtta aggatccagc    600
acggcgctgc cgtgagctgt ggtgtaggtc gcagacgagg cttggatccc acttggctgt    660
ggctgtggct gtggctgtgg tgtaggcccg cagctgtaac tgtaattcga ccctagcct    720 gggaacctcc acaagccacg ggtgtggccc taaaaagcaa aaaaacgaaa gcaaaagaa    780 cactctcaaa gcctaaactt tcagcaaaaa gaacactctc aaagcctaaa ctttgagcag    840
atgccttaca ccgccccac gcctctcatc cccttctgt ctgggcctcc agctcccttc    900 cccttaacc cagaaatccc agacctcaga cccaggattt cgagtcccca gccttgcccc    960
aattctattc atccaagcac aggacaagag agaggcaggg ccgggccttc tggtcctgct   1020
ccttctccct gcccagccca cccccaccag tggcatggag aaaggctcgg gagttactgg   1080
gtgagagaca cctctttcca tgggggctgg gagtaagggg gggggtgata ggctgccaag   1140 ccccaccct ccctccct ccctccccc tccctgctgt gtgaaagggg aggccagccc   1200
acctcgtgac ccgacggggg ctggcccagc tggccccagt tctggaggag tgggcggggc   1260 gggggagcc ctataattgg ccgaatctgg gctccctgaa tcctactcag ccccggagga   1320
ggaaggagga aggaggagga ggaagcaacc ggtgaggagc agacctgggg gcacagagat   1380
gggctcgggg cttcggtgtg ggagggtggg ctgtaggggg aggaggaaat gacctggccc   1440
cccggggcca ccaccgaggc aggagttggg gatgaggcta gagcccaggg actggaccta   1500
gaaggagggt gggcagcagg aggaggttat ccgccttggc tggaaggggga ggtcagggaa   1560 gcagcgggac ctgtaggaag aaccagacga gccagagccg acgaattgta ctggc       1615
```

<210> SEQ ID NO 16
<211> LENGTH: 3170
<212> TYPE: DNA
<213> ORGANISM: Sus scrofa

<400> SEQUENCE: 16

```
gcccagctgg ccccagttct ggaggagtgg gcggggcggg gggagcccta taattggccg     60
aatctgggct ccctgaatcc tactcagccc cggaggagga aggaggaagg aggaggagga    120
agcaaccggt gaggagcaga cctggggca cagagatggg ctcggggctt cggtgtgggg    180
gggtgggctg taggggagg aggaaatgac ctggcccccc ggggccacca ccgaggcagg    240 agttgggat gaggctagag cccagggact ggacctagaa ggaggtgggg cagcaggagg    300
aggttatccg ccttggctgg aaggggaggt cagggaagca gcgggacctg taggaagaac    360
cagacgagcc agagccgacg aattgtactg gcaggtatgg cgcatctact caagttttga    420
gcacactaag agctccatcg aggagaccca gggtggcgg cgaccagggg tgacctcgac    480
cgggctggcg gcagggtagc tagagcgttg gtggaaggac atgtaaatga ggattaaatt    540
agggaatgag tggaaaacag ggtttagatg tgaagttgga gcttggaatg tgaaggtacc    600
aggaagaacg tgagcttgga gcccagaaag caaggctggg gctcacatgg gactccaggg    660 tggaggggt gggggcgac gtgggtggaa tttgaaccct gggagagagg gaaggctttt    720
```

-continued

```
ggccgcagcc gacctgggga tggggagata ggagaagaca atgagggaat tacacggaca    780
atggaaagga tctgctcggg aaatatctgc ttggattagg ctgatgcaga taaggggtg     840
caaggcttgg aaggctgtga ctggacaggg ctgggctctg ggtgggagga gcgagccccg    900
ccgctgttga gtgacaattt ctccctcctg caggttggcc aatcgcaagc cagaagatga    960
gggttctgtg ggttgctttg gtggtaaccc tcctcgcagg tatggggtg gggcttgctc    1020
aggttccctg cccctccccc atcccggct gtacccggtg cccctccttc atccctgggt    1080
ctcttctgct ggtctctctt ccccttgagg agaggcctag atgtgaggcc tctctggcac    1140
tccttgcttc tgaacagctc gttttactct ctgagcctca gtttccccat ctttaaaatg    1200
ggagttatgt tgagagattc cagctgtggc tcagcaggtt aagaacccga ctagtatcca    1260
tgaggaagag ggttcaatcc ctggcttcgc tcagcgggtt aaggatccgg cgttgccatg    1320
agctgcggca taagtcgcag atgcagctcg aatcgggtgt tgctgtggct gtggtgcagg    1380
ctggcagcta tcgcttccat cggacccctc gcctgggaac ttccacgtat gccactggtg    1440
cagccctaaa agacaaacaa acaaaaacga aagaaagaga aagaaaagga aaggggcttt    1500
ctgtttctaa tgcgttgttg cctggcaggg cgtgagcatt agatacgtgt cagctgtgac    1560
tagcgtgcac ggagcacaca atccatgctt gtccagtaat tagacaggct gggtgtcctt    1620
ccacccctc cctgcccacc agtgctctag agaagcccac ccaccagggc tggggagca     1680
cctgctctgt accaggtacc gtgtgctggg aggggcaga ggacctgatg gctgtgaact    1740
ggctcggtgc aggatgccgg acagaggacg agccggggcc gccgccggag gtgcacgtgt    1800
ggtgggagga gcccaagtgg cagggcagcc agccctggga gcaggccctg ggccgcttct    1860
gggattacct gcgctgggtg cagtccctgt ctgaccaagt gcaggaggag ctgctcagca    1920
ccaaggtcac ccaggaactg acgtaagtgc ccacccgact cccgccgcgc gcgcgcgcgc    1980
gcgcgcgcgc ctgaccctcc tggcggaccg tgtgttctgg accctcaggc tccacccgtc    2040
cgggtttcct tctgtccttg tcgccaactc ttggggggtct gggtctctgt ttctttttt    2100
tccttcttcc ttttttgggg ggagtttact ttttctttt tctttcattt gacttcatgt    2160
cttgctttct ttccatcttg agctcctgcc ttcgcctgtc tctgggtcag tcttgccgtc    2220
cttgctgtct ctgaatctct ggcacgtcct ggccatcgcc agctcaggag ccctccttct    2280
ccccccccc gccccgccc tctctgcgcc caggagctg atagaggaga gcatgaagga    2340
ggtgaaggcc taccgcgagg agctggaggc gcagctgggc cccgtgaccc aggagacgca    2400
ggcgcgcctg tccaaggagc tgcaggcggc gcaggcccgc gtgggcgccg acatggagga    2460
cgtgcgcaac cgcttggtgc tctaccgcag cgaggtgcac aacatgttgg gccagaccac    2520
cgaggagctg cggagccgcc tggcttccca cctgcgcaag ctgcgcaagc ggctgctccg    2580
cgacaccgag gacctgcaga agcgcctggc cgtgtaccag gcggggctgc gcgagggcgc    2640
cgagcgcagc gtgagcgccc tccgcgacg cctcgggccc ctggtggagc agggccgatt    2700
gcgcgccgcc accctgagta ccagggccgg ccagccgctg cgcgagcgcg ccgaagcctg    2760
gggccagaag ctgcgcggac ggctggagga gatgggcagc cggacccgcg accgcctgga    2820
tgagatgcgt gagcagctgg aggaggtgcg caccaaagtg gaggagcagg gcagccagtt    2880
gcgcctgcag gccgaggcct tccaggcccg cctcaaaggc tggttcgagc ctctggtgga    2940
agacatgcgg cgccagtggg ccgggctggt ggagaggatg cagtcggccg tgagcatcag    3000
ctcctccacc tctgcgccca gtgataatca gtgagtgccc tctcatccgg gcacccctt     3060
cggggccccg ttcctgccca actcccccgc ctcccccagc cttagctgcc ctcttggtgg    3120
```

-continued

| | |
|---|---|
| gccccrgctt aataaagatt catcaagctt cacagcagct tctgggtgtc | 3170 |

<210> SEQ ID NO 17
<211> LENGTH: 6102
<212> TYPE: DNA
<213> ORGANISM: Sus scrofa

<400> SEQUENCE: 17

| | |
|---|---|
| attcatcaag cttcacagca gcttctgggt gtcccgtgt gatttctcag ctccagcctc | 60 |
| agtttccctt tccttccctg cactgaccac ccagttctct gtcctgccct ctgcctgtgt | 120 |
| gtgtctattt gtctcttctc cccctttct tttttttgg ccgagcccat ggcatgcgga | 180 |
| agttccccgg ccagggattg aacccatgcc acagccgcca caacgaagga tccttaacta | 240 |
| ctaggccacc agggaactcc atcctttcta actctgtctt tgctttccct tttttagcgt | 300 |
| tttagggctg caccctcagc atgtggaagt ccccaggcta ggggtcaaat tggcgctaca | 360 |
| gctgccagcc tacaccacag ccccagcaac gcaggatcca agccacatct ttgacctaca | 420 |
| ccacagctca tggtaacacc agatccttaa cccactgagc aagggattga acccacatcc | 480 |
| tcatggatac tagtcgggtt tgttaatcac tgagccacgg caggaacccc acccctgact | 540 |
| actgtgggca aaaagcaac ttcagagttc ctgttgtggc tcagtgggtt atgaacccaa | 600 |
| ctagtatcca tgagggtgcg ggttcgatcc ctgatcctgc tcagtgggtt aaggatctga | 660 |
| cattgccatg agctccagta taggtaacag aaatgtcttg catccacacc gctgtggctg | 720 |
| tgacgtaggc tggcagttta gctctgattc gaccccctagc ctgggaactt ccttatgccc | 780 |
| agggtttaac cctagaaaag aggggaaaa aaatcaacat ctgagcctcg gttggcccag | 840 |
| cttttaaaatg cctgcttcat ggccttgtta ctcaaaagac ctgaaaccac tgccatttgg | 900 |
| ttttttttt taagtgtctt ttttttttt taacgatttt tatttttcc attgtagttg | 960 |
| gtttacagcg ttctgtgagt tttctacgga cccagtcaca cacatatata cattctttt | 1020 |
| gtcacatcat cctccatcct gctccatccc cagtgactag atatagttcc cagtgctcta | 1080 |
| cagcaggatc tcattgctta tcctctccag atgcaatggt ttacgtctat taaacccaga | 1140 |
| ctcccagtcc atcccacgcc ctccccttcc ccccactgc catttttgtt gagccatttt | 1200 |
| cattttttt tcctcccctct ccctctctta cccgattctg cctccttcct gctcctggcc | 1260 |
| tctgttctca gtcctgctct ccctgagagg cttcatttct ctggcttcct cttttcctcc | 1320 |
| gcctctttct gtcctctccc cctctggttg ctcctgcccc tggccctgct tgtttctagt | 1380 |
| tgcccttcct ccaggtttgc cctcgccacc acgtgggccc tctcttttt ttttttttt | 1440 |
| tacttccccc gaccaggaat cgaaccctag ccatagaagt cacaatgcca gatccttagc | 1500 |
| tactagccca ccagggagtt ccatctcccc tcatccttct ctcctcccct ggatcactgg | 1560 |
| cctcttggct accttgacaa gctaccagg tgctgggtgc aggctggaga gaggggccag | 1620 |
| cctgtgaccc ttggtattaa gggcgggcc atcatgttgg gagctgacac gcagcatggc | 1680 |
| tggagcctgg agaagcagga gcttccctcc cacgccctca gttctcagga ggggagcagg | 1740 |
| attccatcca gagccagcgg acttgtgtct tccaggcggg cctctgcccc gcttggctct | 1800 |
| ggtaaactct gtgctcactc cgcgctttcc ctgccctgct tgccgctgtg gaatcaggct | 1860 |
| ccctccccc agccagatgt tccacccttg ggactgtgtg aggcggggct acatctgtgt | 1920 |
| gaggcagggc caagtttctg ctgattcact cactgtgtgt ccagggcctg ggcatctcat | 1980 |
| tccccagatg tcggggagtg gggctctcag ccatatctcc cattttaaaa gctggatctt | 2040 |
| ggagttccct tcatggctcg atggaagcaa atctggctag catccatgag gatgcgggtt | 2100 |

```
cgatccctgg cctcactcag taggttaagg atctggtgtt gccgagagct ggggtgtagg   2160
tagcagatgg ggctgtggct gtggtgcagg ccggcagctg cagctccagt ttgacccta    2220 acctgggaac ctccatgtgc actgggtgcg ccctaaaat aaataaatgc atacgtaact   2280
aaatacatac atacatacat acataataaa aataaaaaaa ttaaaagctg gatctcaaat   2340
tctgtttgaa gccagctagg cggagagggg cgctcaccac cacacccag cagcccaggt    2400 tcctctctca gtgaaaggag gctggcaggg ggggcagtgg ggtggcggct gaccccagca   2460
gggatccaga gagtcagcct gaagggggga agatgatgaa ggacagagaa ggggggcggca  2520 cgcagcctct cattgagcct ctgaaccttc ttagctgccc atcagttccc ccctccctaa   2580
acggaggtga cagtgacgat gagactggcc aaaccaagct gtcatccggg gtggggaggg   2640
gaggagagca gacattcggg tggatgtggg gagcgctggg ctcacagagg aagcagccct   2700
catcagaggg gcctgggggg ctggcggggg ctggatgcac tcggagggct gttgcaatcc   2760
ggccagggta gcatctgtgc ttgtctttca caaccatccc ctcctcgccc caaggctgac   2820
acgtggttgt tgggcacgag gccagccaac ctagcgtctg gggccagggc ctctctcccc   2880
cagctgccag ggatcacgag cagtcaaagg cagctggagg aagggggcag cctaggccgg   2940
cagccctgcc aaccaatgtg gaggaaggga cagggagagt gcgtggtggt aggagtggcc   3000 aagaggggc atgagagcag atggagtgtt tccaggacc tggaggcttg cagaggcagg    3060
gaacccagcg tcggggaaca gggtttctgg tggacccagt ggagggcaca gattaggagc   3120
cttgcagctg aggttctgcc tctttttta ttttagtgct gtacccgcgg catagggacg    3180
ttctcagcct aggagtcgaa tcagagctgc agctgctggc ctacaccaca gccacgccag   3240
atccaagctg cttctgcgac ctaaaccaca gcttacagca atgacggatc cttgacccac   3300
tgagtggggc cagggatgga actggcatcc tgagccacaa cagaaactca tctgcacttc   3360
tgacaggttc aggacaacct cctccaggag ttccccattg tggcgcagca gaaacgaatc   3420
caactaggaa ccacgatgtt gtaggttcga ccctggcct cgctcagtgg cttaaggatc    3480
tgacatgtga gctgtggtgt aggtcgcata catggcttgg atctagtgtt tctgcggctg   3540
tggagtagag cagcagccgt agctcccatg ggacccctaa cctgggaacc tccatgtgcc   3600
gcaggtacgg ccctaaaaag aaaaaaaaaa aaaaaaaaa gagaaagaga gagagaccct   3660
ccactgaagg aagattgggg gctgtgaaat taaggctcca gagagcgtcc agggaggcct   3720
gggagtctcc cagatgcaga gagagggag aatggaaggg ctagtcggac agtgatattg    3780
gagatggcat ggtgggcagg tgtgtggagg cagactatga gaccccagac tcctgaagag   3840
tcttgagctg aagagaccta ctaagaaggg gaggaggagt tgccatcctg gctcagtggt   3900
taacgaatcc gacgaggaac catgaggttg cgggttcgat ccccggcccc tgctcagtgg   3960
gttaaggatc cggcgttgcc atgagctgtg gtgtaggttg cagacgtggc tcggatcccg   4020
tgtggctgtg gctctggcgt aggccggcg ctacagctcc gattggaccc ctagcctggg    4080
aacctccata tgccatggga gcggcccaag aaatggcaaa aagacaaaaa aaaaaagact   4140
ccttccaaga acttgggtgc tatgcactat taaggccatg aggggtaata ccctcagagg   4200
gcccagagat gtaaagtcac acagccagca tgcggacaac tggatcgggg ccccccagcc   4260
tcaggcaatc actccactac cctcctcctg gctgggctg cccaagataa ggaacattat     4320
cttgggctga ttcaccacca ggcacacaga aggcatttat tacacttctt cttctttttt   4380
tttttttttt taattttgt cttttcagag ctgcacccac agcttataga ggtacccagg    4440
ctaggggtcg aatcagagca gcagctgcca ggcctgcacca cagccacagc aacgtgggat   4500
```

-continued

| | |
|---|---|
| ccgagctgca tcttaaacta ccccacagct cacagcaaca ccggatcctt aacccactga | 4560 |
| gtgaggccag ggatcgaacg aacctacgtc ctcatggatg ctactcaggt tcatttccgc | 4620 |
| tgagccacga tgggaactcc tgttgattac actttcaaag gataatgaag ggggatgtga | 4680 |
| gagaggtcaa aggtggacaa gggctagagc cctcaaacag accgaccaac ccccctctcc | 4740 |
| aagtctcagc tctgatgtcc cctcctccag gaagccctcc ttgacccccag gttgaatcga | 4800 |
| gcccctcat ctcagccctg tctactctgg gtcatcactc tctggggatg gatgggcctg | 4860 |
| tcccccgac cccaccccac cccactggac cgtgagccct ggggggacag gacagggct | 4920 |
| tcatcggcac catgctcagg cataacccag cacatgacta ggcctggcac gggcactcat | 4980 |
| tatttggtga aacgagtatg ctacctatgc aaagaaaata aataaacatg acattttcat | 5040 |
| aaaaccctct gaggtagatt tgtttccact gagccacgat gggagctcca tttaaaaatt | 5100 |
| ttttttaggag ttcccgtcat ggcgcagtgg ttaaccaatc cgactaggaa ccatgaggtt | 5160 |
| gcgggttcga tccctgccct tgctcagtgg gttaacgatc tggcgttgcc gtgagctgtg | 5220 |
| gtgcaggttg tagacgtggc tcagttgctg tggccctggt gtgtaggcca gcggcttcag | 5280 |
| ctccgattag accctagcc tgggaacctc catgtgacgc aggagaggcc caagaaatgg | 5340 |
| ctaggaatca tgaggttgca ggttcgatcc ctggccttgc tcaatgggtt aaggatccag | 5400 |
| tgttgtcgtg agctgtggtg taggttgcag atgaggctca gatcccacat tgctgtggct | 5460 |
| ctggcatggg ctggcggcta cagctccaat tcgaccccta gcctgggaac tccatatgc | 5520 |
| cgtgggagcg gctctagaaa tggcaaaaag accaaaagaa aagaaaaaa gaaaaaaaa | 5580 |
| gaaaaagtgg gcggggcca tagaggtggc ctggggacac agtgtaaatt gaattacttg | 5640 |
| tctggcttttt ttcttttcttt cttttttaggg ccgcaccggc ggcttatgga catatggagg | 5700 |
| ttcccaggct aggggtcgaa tcggagctgc acctgggttc tctcggggtt ccgctcaggc | 5760 |
| tctctcaggc tgccccccagg gggtggtgat ctgcccaggg gagccctggc agccaatgac | 5820 |
| gtagtcatgc ccattcctcc gggattggct gtcttgctttt tacagctaag aaagggtggg | 5880 |
| gtcctggtct agtgctgaga ggaaagcacg tcacagcctc ttgagcccca cctggtcgct | 5940 |
| ctagtaccct ctcctacatt ttaacaccat gaccccaag actcacattc aaggatctcc | 6000 |
| tttaccatcc ctggagtctc acccaagag ctcccaatac tgaatgtttt gcaccctgc | 6060 |
| cccttttctg ggtaggctca gccccagcct aggtgacccc ag | 6102 |

<210> SEQ ID NO 18
<211> LENGTH: 4054
<212> TYPE: DNA
<213> ORGANISM: Sus scrofa

<400> SEQUENCE: 18

| | |
|---|---|
| atacatacgc ggccgcggat ctgctcggga aatatctgct tggattaggc tgatgcagat | 60 |
| aaggggggtgc aaggcttgga aggctgtgac tggacagggc tgggctctgg gtgggaggag | 120 |
| cgagccccgc cgctgttgag tgacaatttc tccctcctgc aggttggcca atcgcaagcc | 180 |
| agaagatgag ggttctgtgg gttgctttgg tggtaaccct cctcgcaggt atgggggtgg | 240 |
| ggcttgctca ggttccctgc ccctccccca tcccggctg tacccggtgc cctccttca | 300 |
| tccctgggtc tcttctgctg gtctctcttc cccttgagga gaggcctaga tgtgaggcct | 360 |
| ctctggcact ccttgcttct gaacagctcg ttttactctc tgagcctcag tttccccatc | 420 |
| tttaaaatgg gagttatgtt gagagattcc agctgtggct cagcaggtta agaacccgac | 480 |
| tagtatccat gaggaagagg gttcaatccc tggcttcgct cagcggggtta aggatccggc | 540 |

-continued

```
gttgccatga gctgcggcat aagtcgcaga tgcagctcga atcgggtgtt gctgtggctg      600
tggtgcaggc tggcagctat cgcttccatc ggacccctcg cctgggaact tccacgtatg      660
ccactggtgc agccctaaaa gacaaacaaa caaaaacgaa agaaagagaa aagaaaggaa      720 aggggcttc tgtttctaat gcgttgttgc ctggcagggc gtgagcatta gatacgtgtc      780
agctgtgact agcgtgcacg gagcacacaa tccatgcttg tccagtaatt agacaggctg      840
ggtgtccttc caccccctcc ctgcccacca gtgctctaga gaagcccacc caccagggct      900 ggggagcac ctgctctgta ccaggtaccg tgtgctgcta aagggaacaa agctggagc       960 tccaccgcgg ataacttcgt atagcataca ttatacgaag ttatcgcgcc ctaccgggta     1020
ggggaggcgc ttttcccaag gcagtctgga gcatgcgctt tagcagcccc gctgggcact     1080
tggcgctaca caagtggcct ctggcctcgc acacattcca catccaccgg taggcgccaa     1140
ccggctccgt tctttggtgg cccttcgcg ccaccttcta ctcctcccct agtcaggaag      1200 ttccccccg ccccgcagct cgcgtcgtgc aggacgtgac aaatggaagt agcacgtctc     1260
actagtctcg tgcagatgga cagcaccgct gagcaatgga agcgggtagg cctttggggc     1320
agcggccaat agcagctttg gctccttcgc tttctgggct cagaggctgg gaaggggtgg     1380
gtccgggggc gggctcaggg gcgggctcag gggcggggcg ggcgcccgaa ggtcctccgg     1440
aagcccggca ttctgcacgc ttcaaaagcg cacgtctgcc gcgctgttct cctcttcctc     1500
atctccgggc ctttcgacct gcagccaata tgggatcggc cattgaacaa gatggattgc     1560
acgcaggttc tccggccgct tgggtggaga ggctattcgg ctatgactgg gcacaacaga     1620
caatcggctg ctctgatgcc gccgtgttcc ggctgtcagc gcaggggcgc ccggttcttt     1680
ttgtcaagac cgacctgtcc ggtgccctga atgaactgca ggacgaggca gcgcggctat     1740
cgtggctggc cacgacgggc gttccttgcg cagctgtgct cgacgttgtc actgaagcgg     1800
gaagggactg gctgctattg ggcgaagtgc cggggcagga tctcctgtca tctcaccttg     1860
ctcctgccga gaaagtatcc atcatggctg atgcaatgcg gcggctgcat acgcttgatc     1920
cggctacctg cccattcgac caccaagcga aacatcgcat cgagcgagca cgtactcgga     1980
tggaagccgg tcttgtcaat caggatgatc tggacgaaga gcatcagggg ctcgcgccag     2040
ccgaactgtt cgccaggctc aaggcgcgca tgcccgacgg cgaggatctc gtcgtgaccc     2100
atggcgatgc ctgcttgccg aatatcatgg tggaaaatgg ccgcttttct ggattcatcg     2160
actgtggccg ctgggtgtg gcggatcgct atcaggacat agcgttggct acccgtgata     2220
ttgctgaaga gcttggcggc gaatgggctg accgcttcct cgtgctttac ggtatcgccg     2280
ctcccgattc gcagcgcatc gccttctatc gccttcttga cgagttcttc tgaggggatc     2340
aattctctag agctcgctga tcagcctcga ctgtgccttc tagttgccag ccatctgttg     2400 tttgccctc ccccgtgcct tccttgaccc tggaaggtgc cactcccact gtcctttcct     2460
aataaaatga ggaaattgca tcgcattgtc tgagtaggtg tcattctatt ctggggggtg     2520
gggtggggca ggacagcaag ggggaggatt gggaagacaa tagcaggcat gctggggatg     2580
cggtgggctc tatggcttct gaggcggaaa gaaccagctg ggggctgcag cacgtgttga     2640
caattaatca tcggcatagt atatcggcat agtataatac gactcactat aggagggcca     2700
ccatggccaa gttgaccagt gccgttccgg tgctcaccgc gcgcgacgtc gccggagcgg     2760
tcgagttctg gaccgaccgg ctcgggttct cccgggactt cgtggaggac gacttcgccg     2820
gtgtggtccg ggacgacgtg accctgttca tcagcgcggt ccaggaccag gtggtgccgg     2880
acaacaccct ggcctgggtg tgggtgcgcg gcctggacga gctgtacgcc gagtggtcgg     2940
```

-continued

```
aggtcgtgtc cacgaacttc cgggacgcct ccgggccggc catgaccgag atcggcgagc    3000
agccgtgggg gcgggagttc gccctgcgcg acccggccgg caactgcgtg cacttcgtgg    3060
ccgaggagca ggactgaata acttcgtata gcatacatta tacgaagtta tggtacccaa    3120
ttcgccctat agtgagtcgt attaccgac cgtgtgttct ggaccctcag gctccaccct    3180
ccgggtttcc ttctgtcctt gtcgccaact cttgggggtc tgggtctctg ttttcttttt    3240
ttccttcttc cttttttggg gggagtttac tttttctttt ttctttcatt tgacttcatg    3300
tcttgctttc tttccatctt gagctcctgc cttcgcctgt ctctgggtca gtcttgccgt    3360
ccttgctgtc tctgaatctc tggcacgtcc tggccatcgc cagctcagga gccctccttc    3420
tccccccccc cgcccccgcc ctctctgcgc ccagggagct gatagaggag agcatgaagg    3480
aggtgaaggc ctaccgcgag gagctggagg cgcagctggg ccccgtgacc caggagacgc    3540
aggcgcgcct gtccaaggag ctgcaggcgg cgcaggcccg cgtgggcgcc gacatggagg    3600
acgtgcgcaa ccgcttggtg ctctaccgca gcgaggtgca caacatgttg ggccagacca    3660
ccgaggagct gcggagccgc ctggcttccc acctgcgcaa gctgcgcaag cggctgctcc    3720
gcgacaccga ggacctgcag aagcgcctgg ccgtgtacca ggcggggctg cgcgagggcg    3780
ccgagcgcag cgtgagcgcc ctccgcgagc gcctcgggcc cctggtggag cagggccgat    3840
tgcgcgccgc caccctgagt accagggccg ccagccgct gcgcgagcgc gccgaagcct    3900
ggggccagaa gctgcgcgga cggctggagg agatgggcag ccggaccgc gaccgcctgg    3960 atgagatgcg tgagcagctg gaggaggtgc gcaccaaagt ggaggagcag ggcagccagt    4020
tgcgcctgca ggccgagggc ggccgcgtat gtat                                4054
```

<210> SEQ ID NO 19
<211> LENGTH: 35
<212> TYPE: DNA
<213> ORGANISM: Artificial Sequence
<220> FEATURE:
<223> OTHER INFORMATION: Synthetic

<400> SEQUENCE: 19

```
aaaggcgcgc caccatgggc accgtcagct ccagg                               35
```

<210> SEQ ID NO 20
<211> LENGTH: 63
<212> TYPE: DNA
<213> ORGANISM: Artificial Sequence
<220> FEATURE:
<223> OTHER INFORMATION: Synthetic

<400> SEQUENCE: 20

```
aaaggccggc ctcactcact tgtcatcgtc gtccttgtag tcctggagct cctgggaggc    60
ctg                                                                   63
```

<210> SEQ ID NO 21
<211> LENGTH: 31
<212> TYPE: DNA
<213> ORGANISM: Artificial Sequence
<220> FEATURE:
<223> OTHER INFORMATION: Synthetic

<400> SEQUENCE: 21

```
aaattaatta actagtctgc aggctcagag g                                    31
```

<210> SEQ ID NO 22
<211> LENGTH: 44
<212> TYPE: DNA

```
<213> ORGANISM: Artificial Sequence
<220> FEATURE:
<223> OTHER INFORMATION: Synthetic

<400> SEQUENCE: 22
ggccggccgt ttaaacggcg cgccgcagat tgtgaaagtg gtcg                    44

<210> SEQ ID NO 23
<211> LENGTH: 44
<212> TYPE: DNA
<213> ORGANISM: Artificial Sequence
<220> FEATURE:
<223> OTHER INFORMATION: Synthetic

<400> SEQUENCE: 23
ggcgcgccgt ttaaacggcc ggcctcagcc tcgactgtgc cttc                    44

<210> SEQ ID NO 24
<211> LENGTH: 32
<212> TYPE: DNA
<213> ORGANISM: Artificial Sequence
<220> FEATURE:
<223> OTHER INFORMATION: Synthetic

<400> SEQUENCE: 24
gcgcttaatt aaagccccag ctggttccat ag                                 32

<210> SEQ ID NO 25
<211> LENGTH: 29
<212> TYPE: DNA
<213> ORGANISM: Artificial Sequence
<220> FEATURE:
<223> OTHER INFORMATION: Synthetic

<400> SEQUENCE: 25
aaaactagtg ccaagacggg aaatgcatc                                     29

<210> SEQ ID NO 26
<211> LENGTH: 29
<212> TYPE: DNA
<213> ORGANISM: Artificial Sequence
<220> FEATURE:
<223> OTHER INFORMATION: Synthetic

<400> SEQUENCE: 26
aaaacgggtg ctgttgatgc tcttaagcc                                     29

<210> SEQ ID NO 27
<211> LENGTH: 317
<212> TYPE: PRT
<213> ORGANISM: Homo sapiens

<400> SEQUENCE: 27

Met Lys Val Leu Trp Ala Ala Leu Leu Val Thr Phe Leu Ala Gly Cys
 1               5                  10                  15

Gln Ala Lys Val Glu Gln Ala Val Glu Thr Glu Pro Glu Pro Glu Leu
                20                  25                  30

Arg Gln Gln Thr Glu Trp Gln Ser Gly Gln Arg Trp Glu Leu Ala Leu
            35                  40                  45

Gly Arg Phe Trp Asp Tyr Leu Arg Trp Val Gln Thr Leu Ser Glu Gln
        50                  55                  60

Val Gln Glu Glu Leu Leu Ser Ser Gln Val Thr Gln Glu Leu Arg Ala
 65                  70                  75                  80

Leu Met Asp Glu Thr Met Lys Glu Leu Lys Ala Tyr Lys Ser Glu Leu
```

```
                    85                  90                  95
Glu Glu Gln Leu Thr Pro Val Ala Glu Thr Arg Ala Arg Leu Ser
            100                 105                 110
Lys Glu Leu Gln Ala Ala Gln Ala Arg Leu Gly Ala Asp Met Glu Asp
            115                 120                 125
Val Cys Gly Arg Leu Val Gln Tyr Arg Gly Glu Val Gln Ala Met Leu
            130                 135                 140
Gly Gln Ser Thr Glu Glu Leu Arg Val Arg Leu Ala Ser His Leu Arg
145                 150                 155                 160
Lys Leu Arg Lys Arg Leu Leu Arg Asp Ala Asp Asp Leu Gln Lys Arg
                165                 170                 175
Leu Ala Val Tyr Gln Ala Gly Ala Arg Glu Gly Ala Glu Arg Gly Leu
            180                 185                 190
Ser Ala Ile Arg Glu Arg Leu Gly Pro Leu Val Glu Gln Gly Arg Val
            195                 200                 205
Arg Ala Ala Thr Val Gly Ser Leu Ala Gly Gln Pro Leu Gln Glu Arg
            210                 215                 220
Ala Gln Ala Trp Gly Glu Arg Leu Arg Ala Arg Met Glu Glu Met Gly
225                 230                 235                 240
Ser Arg Thr Arg Asp Arg Leu Asp Glu Val Lys Glu Gln Val Ala Glu
                245                 250                 255
Val Arg Ala Lys Leu Glu Glu Gln Ala Gln Gln Ile Arg Leu Gln Ala
            260                 265                 270
Glu Ala Phe Gln Ala Arg Leu Lys Ser Trp Phe Glu Pro Leu Val Glu
            275                 280                 285
Asp Met Gln Arg Gln Trp Ala Gly Leu Val Glu Lys Val Gln Ala Ala
            290                 295                 300
Val Gly Thr Ser Ala Ala Pro Val Pro Ser Asp Asn His
305                 310                 315

<210> SEQ ID NO 28
<211> LENGTH: 5491
<212> TYPE: DNA
<213> ORGANISM: Homo sapiens

<400> SEQUENCE: 28
cttgatgctc agagaggaca agtcatttgc ccaaggtcac acagctggca actggcagag    60
ccaggattca cgccctggca atttgactcc agaatcctaa ccttaaccca gaagcacggc   120
ttcaagcccc tggaaaccac aatacctgtg cagccagggg ggaggtgctg gaatctcatt   180
tcacatgtgg gaggggggct cccctgtgct caaggtcaca accaaagagg aagctgtgat   240
taaaacccag gtcccatttg caaagcctcg acttttagca ggtgcatcat actgttccca   300
cccctcccat cccacttctg tccagccgcc tagccccact ttcttttttt tcttttttg    360
agacagtctc cctcttgctg aggctggagt gcagtggcga gatctcggct cactgtaacc   420
tccgcctccc gggttcaagc gattctcctg cctcagcctc ccaagtagct aggattacag   480
gcgcccgcca ccacgcctgg ctaactttg tattttagt agagatgggg tttcaccatg    540
ttggccaggc tggtctcaaa ctcctgacct taagtgattc gcccactgtg cctcccaaa    600
gtgctgggat tacaggcgtg agctaccgcc cccagcccct cccatcccac ttctgtccag   660
cccctagcc ctactttctt tctgggatcc aggagtccag atcccagcc cctctccag     720
attacattca tccaggcaca ggaaaggaca gggtcaggaa aggaggactc tgggcggcag   780
cctccacatt cccctctccac gcttggcccc cagaatggag gagggtgtct ggattactgg   840
```

```
gcgaggtgtc ctcccttcct ggggactgtg gggggtggtc aaaagacctc tatgccccac    900
ctccttcctc cctctgccct gctgtgcctg gggcagggg agaacagccc acctcgtgac    960
tgggggctgg cccagcccgc cctatccctg gggagggg cgggacaggg ggagccctat    1020
aattggacaa gtctgggatc cttgagtcct actcagcccc agcggaggtg aaggacgtcc    1080
ttccccagga gccggtgaga agcgcagtcg ggggcacggg gatgagctca ggggcctcta    1140
gaaagagctg ggaccctggg aagccctggc ctccaggtag tctcaggaga gctactcggg    1200
gtcgggcttg gggagaggag gagcgggggt gaggcaagca gcaggggact ggacctggga    1260
agggctgggc agcagagacg acccgacccg ctagaaggtg gggtggggag agcagctgga    1320
ctgggatgta agccatagca ggactccacg agttgtcact atcatttatc gagcacctac    1380
tgggtgtccc cagtgtcctc agatctccat aactggggag ccaggggcag cgacacggta    1440
gctagccgtc gattggagaa cttaaaatg aggactgaat tagctcataa atggaacacg    1500
gcgcttaact gtgaggttgg agcttagaat gtgaagggaa aatgaggaat gcgagactgg    1560
gactgagatg gaaccggcgg tggggagggg gtgggggat ggaattgaa ccccgggaga    1620 ggaagatgga attttctatg gaggccgacc tggggatggg gagataagag aagaccagga    1680
gggagttaaa tagggaatgg gttggggcg gcttggtaaa tgtgctggga ttaggctgtt    1740
gcagataatg caacaaggct tggaaggcta acctggggtg aggccgggtt ggggccgggc    1800
tgggggtggg aggagtcctc actggcggtt gattgacagt ttctccttcc ccagactggc    1860
caatcacagg caggaagatg aaggttctgt gggctgcgtt gctggtcaca ttcctggcag    1920 gtatggggc ggggcttgct cggttccccc cgctcctccc cctctcatcc tcacctcaac    1980
ctcctggccc cattcaggca gaccctgggc cccctcttct gaggcttctg tgctgcttcc    2040
tggctctgaa cagcgatttg acgctctctg ggcctcggtt tcccccatcc ttgagatagg    2100
agttagaagt tgttttgttg ttgttgtttg ttgttgttgt tttgttttt tgagatgaag    2160 tctcgctctg tcgcccaggc tggagtgcag tggcggatc tcggctcact gcaagctccg    2220
cctcccaggt ccacgccatt ctcctgcctc agcctcccaa gtagctggga ctacaggcac    2280
atgccaccac acccgactaa cttttttgta ttttcagtag agacggggtt tcaccatgtt    2340
ggccaggctg gtctggaact cctgacctca ggtgatctgc ccgtttcgat ctcccaaagt    2400
gctgggatta caggcgtgag ccaccgcacc tggctgggag ttagaggttt ctaatgcatt    2460
gcaggcagat agtgaatacc agacacgggg cagctgtgat ctttattctc catcaccccc    2520
acacagccct gcctggggca cacaaggaca ctcaatacat gcttttccgc tgggcgcggt    2580 ggctcaccc tgtaatccca gcactttggg aggccaaggt gggaggatca cttgagccca    2640
ggagttcaac accagcctgg gcaacatagt gagaccctgt ctctactaaa aatacaaaaa    2700
ttagccaggc atggtgccac acacctgtgc tctcagctac tcaggaggct gaggcaggag    2760
gatcgcttga gccagaaagg tcaaggttgc agtgaaccat gttcaggccg ctgcactcca    2820
gcctgggtga cagagcaaga ccctgtttat aaatacataa tgctttccaa gtgattaaac    2880
cgactccccc ctcaccctgc ccaccatggc tccaaagaag catttgtgga gcaccttctg    2940
tgtgccccta ggtactagat gcctggacgg ggtcagaagg accctgaccc accttgaact    3000
tgttccacac aggatgccag gccaaggtgg agcaagcggt ggagacagag ccggagcccg    3060
agctgcgcca gcagaccgag tggcagagcg gccagcgctg ggaactggca ctgggtcgct    3120
tttgggatta cctgcgctgg gtgcagacac tgtctgagca ggtgcaggag gagctgctca    3180
gctcccaggt cacccaggaa ctgaggtgag tgtccccatc ctggcccttg acctcctgg    3240
```

-continued

```
tgggcggcta tacctcccca ggtccaggtt tcattctgcc cctgtcgcta agtcttgggg    3300
ggcctgggtc tctgctggtt ctagcttcct cttcccattt ctgactcctg gctttagctc    3360
tctggaattc tctctctcag ctttgtctct ctctcttccc ttctgactca gtctctcaca    3420
ctcgtcctgg ctctgtctct gtccttccct agctctttta tatagagaca gagagatggg    3480
gtctcactgt gttgcccagg ctggtcttga acttctgggc tcaagcgatc ctcccgcctc    3540
ggcctcccaa agtgctggga ttagaggcat gagccacctt gcccggcctc ctagctcctt    3600
cttcgtctct gcctctgccc tctgcatctg ctctctgcat ctgtctctgt tccttctct    3660
cggcctctgc cccgttcctt ctctccctct tgggtctctc tggctcatcc ccatctcgcc    3720
cgccccatcc cagcccttct ccccgcctcc cactgtgcga caccctcccg ccctctcggc    3780
cgcagggcgt tgatggacga gaccatgaag gagttgaagg cctacaaatc ggaactggag    3840
gaacaactga ccccggtggc ggaggagacg cgggcacggc tgtccaagga gctgcaggcg    3900
gcgcaggccc ggctgggcgc ggacatggag gacgtgtgcg gccgcctggt gcagtaccgc    3960
ggcgaggtgc aggccatgct cggccagagc accgaggagc tgcgggtgcg cctcgcctcc    4020
cacctgcgca agctgcgtaa gcggctcctc cgcgatgccg atgacctgca gaagcgcctg    4080
gcagtgtacc aggccggggc ccgcgagggc gccgagcgcg gcctcagcgc catccgcgag    4140
cgcctggggc ccctggtgga cagggccgc gtgcgggccg ccactgtggg ctccctggcc    4200
ggccagccgc tacaggagcg ggcccaggcc tgggcgagc ggctgcgcgc gcggatggag    4260
gagatgggca gccggacccg cgaccgcctg gacgaggtga aggagcaggt ggcggaggtg    4320
cgcgccaagc tggaggagca ggcccagcag atacgcctgc aggccgaggc cttccaggcc    4380
cgcctcaaga gctggttcga gccctggtg gaagacatgc agcgcagtg ggccgggctg    4440
gtggagaagg tgcaggctgc cgtgggcacc agcgccgcc ctgtgcccag cgacaatcac    4500
tgaacgccga agcctgcagc catgcgaccc cacgccaccc cgtgcctcct gcctccgcgc    4560
agcctgcagc gggagaccct gtccccgccc cagccgtcct cctggggtgg accctagttt    4620
aataaagatt caccaagttt cacgcatctg ctggcctccc cctgtgattt cctctaagcc    4680
ccagcctcag tttctctttc tgcccacata ctggccacac aattctcagc cccctcctct    4740
ccatctgtgt ctgtgtgtat ctttctctct gccctttttt tttttttttag acggagtctg    4800
gctctgtcac ccaggctaga gtgcagtggc acgatcttgg ctcactgcaa cctctgcctc    4860
ttgggttcaa gcgattctgc tgcctcagta gctgggatta caggctcaca ccaccacacc    4920
cggctaattt ttgtattttt agtagagacg agctttcacc atgttggcca ggcaggtctc    4980
aaactcctga ccaagtgatc cacccgccgg cctcccaaag tgctgagatt acaggcctga    5040
gccaccatgc ccgccctg ccctctttc tttttaggg ggcagggaaa ggtctcaccc    5100
tgtcacccgc catcacagct cactgcagcc tccacctcct ggactcaagt gataagtgat    5160
cctcccgcct cagcctttcc agtagctgag actacaggcg cataccacta ggattaattt    5220
gggggggggg tggtgtgtgt ggagatgggg tctggctttg ttggccaggc tgatgtggaa    5280
ttcctgggct caagcgatac tcccaccttg gcctcctgag tagctgagac tactggctag    5340
caccaccaca cccagctttt tattattatt tgtagagaca aggtctcaat atgttgccca    5400
ggctagtctc aaaccctggg gctcaagaga tcctccgcca tcggcctccc aaagtgctgg    5460
gattccaggc atgggctccg agcggcctgc c                                   5491
```

<210> SEQ ID NO 29
<211> LENGTH: 1223
<212> TYPE: DNA

<213> ORGANISM: Homo sapiens

<400> SEQUENCE: 29

```
gggatccttg agtcctactc agccccagcg gaggtgaagg acgtccttcc ccaggagccg      60
actggccaat cacaggcagg aagatgaagg ttctgtgggc tgcgttgctg gtcacattcc     120
tggcaggatg ccaggccaag gtggagcaag cggtggagac agagccggag cccgagctgc     180
gccagcagac cgagtggcag agcggccagc gctgggaact ggcactgggt cgcttttggg     240
attacctgcg ctgggtgcag acactgtctg agcaggtgca ggaggagctg ctcagctccc     300
aggtcaccca ggaactgagg gcgctgatgg acgagaccat gaaggagttg aaggcctaca     360
aatcggaact ggaggaacaa ctgaccccgg tggcggagga gacgcgggca cggctgtcca     420
aggagctgca ggcggcgcag gcccggctgg gcgcggacat ggaggacgtg tgcggccgcc     480
tggtgcagta ccgcggcgag gtgcaggcca tgctcggcca gagcaccgag gagctgcggg     540
tgcgcctcgc ctcccacctg cgcaagctgc gtaagcggct cctccgcgat gccgatgacc     600
tgcagaagcg cctggcagtg taccaggccg gggcccgcga gggcgccgag cgcggcctca     660
gcgccatccg cgagcgcctg gggccctggt ggaacagggg ccgcgtgcgg gccgccactg     720
tgggctccct ggccggccag ccgctacagg agcgggccca ggcctggggc gagcggctgc     780
gcgcgcggat ggaggagatg ggcagccgga cccgcgaccg cctggacgag gtgaaggagc     840
aggtggcgga ggtgcgcgcc aagctggagg agcaggccca gcagatacgc ctgcaggccg     900
aggccttcca ggcccgcctc aagagctggt tcgagcccct ggtggaagac atgcagcgcc     960
agtgggccgg gctggtggag aaggtgcagg ctgccgtggg caccagcgcc gcccctgtgc    1020
ccagcgacaa tcactgaacg ccgaagcctg cagccatgcg accccacgcc accccgtgcc    1080
tcctgcctcc gcgcagcctg cagcgggaga ccctgtcccc gccccagccg tcctcctggg    1140
gtggacccta gtttaataaa gattcaccaa gtttcacgca aaaaaaaaaa aaaaaaaaa     1200
aaaaaaaaaa aaaaaaaaaa aaa                                            1223
```

<210> SEQ ID NO 30
<211> LENGTH: 44359
<212> TYPE: DNA
<213> ORGANISM: Homo sapiens

<400> SEQUENCE: 30

```
gccccgagtg caatcgcggg aagccagggt ttccagctag acacagcag gtcgtgatcc       60
gggtcgggac actgcctggc agaggctgcg agcatgggc cctggggctg gaaattgcgc      120
tggaccgtcg ccttgctcct cgccgcggcg gggactgcag gtaaggcttg ctccaggcgc     180
cagaataggt tgagagggag ccccggggg gcccttggga atttattttt ttgggtacaa     240
ataatcactc catccctggg agacttgtgg ggtaatggca cggggtcctt cccaaacggc     300
tggagggggc gctggagggg ggcgctgagg ggagcgcgag ggtcgggagg agtctgaggg     360
atttaaggga aacgggcac cgctgtcccc caagtctcca cagggtgagg gaccgcatct     420
tctttgagac ggagtctagc tctgtcgccc aggatggagt gcagtggcac gatctcagct     480
cactgcaacc tccgcctccc gggtttaagc gagtctcctc tctcagcctc ccgaatagct     540
gggattacag gcgcccaacc accacgcccg cctaattttt gtattttag tagagacggg     600
ttttcaccat tttggccagg ctggtctcga acccgacct caggtgatct gcccaaagt      660
gctgggatta caggcgtcag ccaccgcgcc cggccgggac cctctcttct aactcggagc     720
tgggtgtggg gacctccagt cctaaaacaa gggatcactc ccaccccgc cttaagtcct     780
```

```
tctgggggcg agggcgactg gagacccgga tgtccagcct ggaggtcacc gcgggctcag    840
gggtcccgat ccgctttgcg cgaccccagg gcgccactgc catcctgagt tgggtgcagt    900
cccgggattc cgccgcgtgc tccgggacgg gggccacccc ctcccgcccc tgccccgcc     960 cctttggccc gcccccgaa ttccattggg tgtagtccaa caggccaccc tcgagccact    1020 cccccttgtcc aatgtgaggc ggtggaggcg gaggcgggcg tcgggaggac ggggcttgtg   1080
tacgagcggg gcggggctgg cgcggaagtc tgagcctcac cttgtccggg gcgaggcgga   1140
tgcaggggag gcctggcgtt cctccgcggt tcctgtcaca aaggcgacga caagtcccgg   1200
gtccccggag ccgcctccgc gacatacacg agtcgccctc cgttatcctg ggccctcctg   1260
gcgaagtccc cggtttccgc tgtgctctgt ggcgacacct ccgtcccac cttgtcctgg    1320 ggggcgccct cgccccacca gccccgatca agttcacaga ggggcccccg gccaccctca   1380
aggcctcggt tccttacgag gttgaaacgt tgcctcagaa tctcccgcc cctccttggt    1440 ctgcagccga gatcttcagc cacggtgggg cagctatccc ccgggaccga cccctgggg    1500 tggcctcgct tcttcagagg ctgtgaatgg cttcggttca gctgtccaag cggcgatttt   1560
tcctctgggt gaaatggatt agattttaga ttttccacaag aggctggtta gtgcatgatc   1620
ctgagttaga gcttttttagg tggctttaaa ttagttgcag agagacagcc tcgccctaga   1680
caacagctac atggcccttt ccctcctgag aaccagccta gcctagaaaa ggattgggat   1740
tgcctgatga acacaaggat tgcaggaaac ttttttttta attggcaagg gggttggctt   1800
tgactggatg gagagctttg aactgccttg aaattcacgc tgtaactaac acaccagttt   1860
cctctgggag gccagagagg gagggagggt gtaatgaaat acggatgatt gttcttttat   1920
ttttatttac ttatttattt tttaactttt tgtagagatg aggtctcgct tggttgctca   1980
ggctggtctt gaactcctgg cctcaagcga tcctcctacc tcagcctccc aaagtgttgg   2040
gattacagga gtgagccacc gcgcccacc ggggatgatg atgattgcaa acattctgcc    2100
actcagtttt acaaaagaaa gagaggcact ggattaatgt gtatctcact caccaatcaa   2160
cctcttcctt aagagaaat gttaaggaag tcttaggcaa ggccttgttt gttcatcact    2220
ttagtttctc tctcccggga tggctgagaa tgtgatgttt cctctgttgt caaggagact   2280
acacccctga tgttttcctc cagacttctg agagctggtg tgtgtttcta gcactttcta   2340
gctgcaccac ctcacgctgt agctggcttc aaggcatatc caggggggag tttcttgtcc   2400 atttcctta caaagggaag ttgttggaat ctgaaccgca agccttcact tagaccaaaa    2460
tcaggcaaca gcggtgagcg cagctccaaa cgtgtcaatg actcacccaa atttgagtaa   2520
gggagttggc tgctttaacg agccgcaggg tgattcccctt gtcatttccg gaaatacctta  2580 tcttccaggg aacactggga aaaacaggg agacctttgt tgagacagaa aacctgtagg    2640
ggaattctgt tcctcattcc tgctcttatc tgtagacttc ctccctgata agatccaatt   2700
ctagatgggt cggttgctcc ttgctttgat gggtgctttg atgggcttta ttattattat   2760
tattattatt attattattt tgatgggctt tttgatgtcc cttttccttc cacactctgt   2820
cccaactgtc aagcaaatag ccttttgttg ctaagagact gcagatgtaa ccgaccagca   2880
gcaaacagtg agtcaggctc tctcttccgg aagcaaaatc aattgctgag atcactctgg   2940
ggaaaatacc caccttattt ggaaagaagc actgatcaat tgatgtctat ttttttttt   3000 tttgagttgg agtctcgccc tgtcacccag gctggagtgc aatggcataa tctcgcctca   3060
ctgcaatccc cgcctccgg gttccagcaa ttcctgcc tcagcctcct gagtagctgg     3120
aattataggc gcctgccaca acacccggct aattttgta tttgtagtag agatgggtt    3180
```

```
tcaccacgtt ggccaggctg gtctcgaact cctgacctcg tgatccaccc gcctcagcct    3240
cccaaagtcc aaggattgca ggcgtgaccc actgtgccag ccaatcaatt gatttctcat    3300
tcattttcag ctggctctgt tcccttaagc caggggattt tcgtttgttt gtttccccct    3360
caaggaaatg attctagcta cagttttgat ttccttgtac aactgttttc agtagcacag    3420
ggaaagaaaa catcgaaagc attcaccacc tcatttgtgt gctgggggaa aaagcagaaa    3480
tgtgtattct cttttttttgt ttcgatgacc ttgttcctga cttgttactc gtgacttgag    3540
agatcagagg gctagaggac tagaatttat agaggtgttt tttttgtttg tttatttttg    3600
ttcgagttgc ccaggctgga gtgcagtggc gcaatctcgg ctcactgcaa cctctgcctc    3660
ccaggttcaa gcgattcttc ggcctcagcc tcctgagtag ctggaactac aggcgcccgc    3720
caccacaccc agctaatttt tgtattttc agtagagatg ggatttcacc atattggtca    3780
agctggcctc gaactcctga cctcgtgatc cacccgcctc agtttcccaa agtgctggga    3840
gtacaggcgt gagccgccgt gcccggcctt tttgtgtttt tgtgtttttg agaggagctc    3900
attgcttttt aggcttccct agcgtgagaa aatctgggga tccatgctct agtttacttc    3960
cttttttttt tttttttga gatggagtct cgcttagatt gccaatctc agctcattgc    4020 aacttctgcc tccggggttc aagggattct cgtgtctcag cctcctgggt agctaggata    4080
cgggcacccg ctaccatgcc tggctaattt tgtacttta gtagagacag ggtttcgcca    4140
cgttggccag gctggtctcg aactcctgac ctcaggtgag ccgcctgcct tggcctccca    4200
aagtgctgag attacaggcg tgagccaccg cgcttggcct aatttgcttt tcctgaaatt    4260
caaatggtct aatatgaaaa acgccaacct tgcttgaaag aataagaaag aggtgcggtt    4320
tcgttgggcc gttgatgttt ggaacaggac tggttttgtc cccttgctcg gaaagggcag    4380
caactgtgag gacagctccc tgacgtgctc tcactcagca ctgttccgtt cctgagcact    4440
gtccccacta gctaggccaa gggagctcat ttggcaggca actgctgtct ggctgcgcct    4500
gtggcagtaa aatctgcctt tattttttgg aggcagggtc ttgccctgtc gctcaggctg    4560
aagtgtgcag ttatagctca ctgcagcctc cagcttctgt actcaactga tcctcctctc    4620
tcagcctcct gagtagctgg gactatacgc acgtgttacc actcccacct cagtttgttt    4680
gtttatttat ttatttattt atttattgag atggagtttt gctcttgctg cccaggctgg    4740
agtgcaatgg cgcgatctcg gctcaccgca acctccacct cctggttcaa gcgattctcc    4800
tgcctcagcc tcctgagtag ctgggattac aggcatgcac caccacgccc ggctaatttt    4860 gtattttcg tagagatggg gtttctccac attggttcag gctgttctcg aactcccaac    4920
ctcaggtgat ccaccgcct cagcctccca aagtgctggg attataggcg tgagccccg    4980 aacccggcca ctcccagcta gtttaaatt ttttgtttgt ttgttcgttt gttttattt    5040 tttgagacag agtctcccgc ccaggctgga gcgcagatca ctgcatcctt gacctcccag    5100
gcttaagcca tcctccccac tcagcctccc aagtagctgg gattacaggt gtgtgccact    5160
atgcttggct aagttgtgta ttttttgtag agatggggtt caaggattc tcgctttgtt    5220 gcctcggttg gtctcaaact cctgggctca agcagtcctc cctcctcagc ctcccaaggt    5280
gctggggaaa tccactttg aaacattgtc tggagagttg cccaggtggt agatcacaga    5340
aataggtcat cgtggggtcc ttcccatggg tgcagtcttg agccacctgt ggccagcaaa    5400
tatttggaga ataatagtca ggggagagct tgaggtccag ggaaaggttt tgttttctt    5460 cagggaaagg tttttattgt tctttatccc tccttaaagg accttcaggt gttactgaca    5520
ttcccggtct acccagtggc acatttagtt tgtaagctgg gccctcgtac agaggtaggg    5580
```

```
aggtgagagc attggattag tggtcaccaa agctgcggtc acctagtggg gtgatcagag    5640
gctcctccct taagatcttg attgccaacg cctctggccc aactttcctt tttatttatc    5700
gcaagcctcc tggaatctca attgcttttt gcccacccgg tgtgtcagca caagaaatga    5760
gtcatttcct cctttaagca cagttgaaat tgagctgtga gtcagtgagg tgtgtacgat    5820
attgtcaaag cggggtgtgt acagtattga cagatctgta gttgggcaag agaattatca    5880
gagtttgtga ccacagcaga ttccaaagct cgactcattt tcttctctct tccttccctt    5940
ttttcttttc tttttttttt tttttttgac agagtctcgc tctgttgccc aggctggagt    6000
gcagtggcac aatctgggct cactgcagcc cctgcctcct gggttcaaat gattctcatg    6060
tttcagcctc ccgagtagct gcaattacag gcattcgggt tcaagtgatt ctcctgcctc    6120
agccacctga gcagctggga ttacaggcgc ccgccaccac gcccggctaa tttttgtatt    6180
tttagtagag acggggtttc accatgttgg ccaggctggt ctcgaactcc tgaactcagg    6240
tgatccgccc acttcggcct cccaaagtgc tgagattaca gacgtgagtc accgcgccca    6300
gcctgttctg ttctttaatt ctcaaaacac cctctaggaa gtagagactg ccattctccc    6360
ccattttaca gatcaggaaa ctgagtccca gaaggattta gtcagttacc caagttgttc    6420
tagttaaatg gcctggaaag ccagtgaagc ccaggattgt ctatctaacc cccttactac    6480
tctaactttc agggaatcca catgaatgtg ctgggtcaac catcaaagtt gaaatggata    6540
aaggggggctg gatgcggtgg ctgatgcctg taatcctagc actttgggag gccgagatgg    6600
gtgggtggat tgcttgagcc caagagtttg agaccagcct gggcaacata gtgagacacc    6660
tgtctctgca aaaaataaat aaaagttag ctgagtgtga tggtgcaccc ctctagtcac    6720
agctgttgag ttaggcttag gcaggaggat cgcatgaacc tgggaggtgg aggcggccgt    6780
gagcctcagt catgccactg cactccaacc tgggcaacag agtgaaagcc ggtgtccgaa    6840
agagaaagaa aaaagacat agatacatct tttaaagtta ggttgtatgt taattaccta    6900
caactcagtt tcaactgtgc ttaaaggagg aaatgactca tttcttgcta catatcaaat    6960
tagcccaaaa tgtagtggct taaaacaaca catttatgat ttctcagttt ttgcgtgtca    7020
ggaatttgga agcagcacag ctagacggtt ccagctcagg gtctctcatg aagttgcaat    7080
caaaatattg gcaggagaga aaaacatatt ttcagaagct gcaggcatag gaagacttgg    7140
ctggggttga aggatccact tccaagatgg cgcactcagt ggctcttggc tggaggcctc    7200
agttccctgc tgcgtggagc tctccctcca gctgcttgag tggactcatg acatgcagct    7260
ggcctcccct ggagcagtcg atccaacaat gagcatggcc atgaactagg ctcagaagcc    7320
actccctgtc gtctctacat tttcctatca gaagcaagtc attaaaagtc cagtgccact    7380
ccaggggaga cgaattaggc tctgccttct gaaaggatta tcacagaaga tgcggtccta    7440
tattctttt ttaaaattat tctttttttt attttgtaga gatgggtct tggtatgttg    7500
cctaggccag tctggaattc ctgggctcaa acaatcctgt ctctgcctcc caaagtgttg    7560
ggattacagg catgagccac tgcacctggt catgtggtca tatttctttt tctttttttt    7620
tttttttttg agacagagtc tctgtcgccc aggctggagt atggtggcgt gatctcagtt    7680
cactgcagcc tccgcctccc gggttcaagc gattctcctg cctcagcctc ctgagtagct    7740
gggattacag gcgcccgcca acatgcccag ctaatttttt tagtagagat ggggtttcac    7800
catgttagcc aggatggtct cgatctcctg atttggtgat ccgcccacct ggcctccca    7860
aagtttcaac catcgatcag aacttattga tgtacttatg tagctaggca cggtggcgcg    7920
tgcctgtaat cccagctact tggaagggtt aaggcaggag aatcgcttga acctgggagg    7980
```

```
cagaggttac agtgagtcaa gatcatacca ttgcactcca gtctgggcaa cagaatgaga    8040
ctctgtctca aaaacaaaaa acaaacccct gtatgtgatt ttcctggata gcatctgtta    8100
catcttcaca aagataaaaa gtcagacttg gctgggcatg gtggctcaca cctgtaatcc    8160
cagcactgag aggctgaggc aggcagatca cttgaggtca ggaatttgag accaggctgg    8220
gcagcatggt gaaacccgt ctctacaaaa aatacaaaaa ttagccgggt gtggtgtcac    8280
gcacctgtat tcccaagcta ctcaggaagc taaggcagga gaatcacttg aacccagagg    8340
tggaggtttg cagtgagttg agattgtgcc attgcactcc agcctgggcg acagagtgag    8400
actctgtgtc aaaaataaaa taaaataaaa ttttaaaaaa ggcagatttt tttttcttct    8460
tggtattgtt accttattat agtaataata agtgcatagt gcatgctgag ataagcaatc    8520
ataatttgtt attgcggccg ggcatggtgg ctccagccta taatcccagc actttggtca    8580
ggagttcaag gccagcctgg ccaatatagt gaaactccat ctctactaaa atacaagaaa    8640
ttacctgggc atggtggcag ttgctggtga tccccagcta cttgggaggc tgaggcagga    8700
gaatcgcttg aacctgggaa gcagaggttg cagtgagcca agattgcacc actgcactcc    8760
agcctgggtg acagagtgag actctgtctg aaaataataa taataataat ttgttattgc    8820
ttttattgcc ttagtttaca tagggaatca aagtttatac tttgatttat aaaagttgct    8880
ttgattctag ttcacagaac cagaatcttt catataaagg tattgagggg cccagtgtgg    8940
tggctcatgc ctgtaatccc agcatattgg gaggctgagg agggaggatc actttaggag    9000
tttgaggcca gcctaggcaa catagtgaga ccttgtctct acaaaaaatt ccaacattag    9060
ctgggcatgg tggcatgtgc ctgtagtccc atttatttgg ggggctgagg caggaggatc    9120
acttgagccc acgaggttca atccaggttg cagtaagcca tgatcctgcc actgcactcc    9180
agtttgggta acagagcgaa gctatgtctc aaaaaagaa aaaaaagta ttctaaatcc    9240
aaatttaata tataaaacta aatgcaggcc aagtgtggtg gcatatacct ataatcacaa    9300
cactttggga ggctgaggtg ggaggattgc ttgagcccaa gagttcaaga ccagcctagg    9360
taacacagta agaccccatc tctacaaaaa gtagaaaaat tagcctggca tggtggtgag    9420
tgcttttaat cccaactact taggggggctg agatgggaag attgcttgag cctcagagtt    9480
tgaggctgca gtgggccgtg atcgctccac tgatcgctct aaagtgagac cctgtctcaa    9540
aaaaaagaa aatagaagaa aactaaatac attcaataag actttgatct cttttccaag    9600
gtgtaaatat attttgggaa attttccagt tactttgttc tcattttaat gtaataatct    9660
aagtcttggt tttctaagga aaagttttct cttattatat cttttgttaa tgtttctctc    9720
ccatttcttt tgatctgatc ttcagataca tgattatctt cactgctaaa tttgtgttct    9780
ctggcctcta catttataat ttctcataat tctttatcta agtatttctt ccctacctac    9840
tgaagaaaac tcaagttttc ttccaccta atgattatgc tgtgtctgtg agttttcttc    9900
atgactcttt acagtacaag ttttttgttt ttgttttttt aatggtcaga tggatagaac    9960
aacacaggtt ttgtttgttt tgtttttaact tttaaaaaaa ttataataga taaagggtct   10020
cactacgttg tccaggctga tctcatactc ctgggctcaa gcaatccacc cacctctgcc   10080
tcccaaagtg ctgggattac agtcatgagc caacatgcct gggcagtaca ggttttttt   10140
gagacggagt tttgttcttg ttgccgaggc tggagtgcaa tggcacaatc ttggctcacc   10200
acaaagtctg cctcccaggt tcaagtgatt ctcctgcctc agcctcctga gtagctggga   10260
ttacaggcat gtgccaccac gcccagctaa ttttgtattt ttagtagaga cggggtttca   10320
ccatgttggc caggctggtt tcgaactgct gacctcaggt gatctgccca cctcggcctc   10380
```

```
ccaaagtgct gggattacag gcatgagcca ccatgcccag ctgtagtaca ggttttaata   10440
tgctaaatac tcttcctttc tttattaatg tgcatggaag ttctaatatt tttttcccat   10500
accccagaga gtccatattt tggaatcaac aacactagcc tttgttgaca agtgtctctc   10560
ttgggttcct tctttgtgtc ctccactgaa ttttggggtt cataaaattt catttgttgt   10620
gcttgcttaa ttccctggga atcagactgt tcctgatcgg atgacatttc tggttaattc   10680
tttagttggc aggaaataga cacaggaaac gtggtcagtt tctgattctg gcgttgagag   10740
acccttctc cttttcctct ctctcagtgg gcgacagatg cgaaagaaac gagttccagt   10800
gccaagacgg gaaatgcatc tcctacaagt gggtctgcga tggcagcgct gagtgccagg   10860
atggctctga tgagtcccag gagacgtgct gtgagtcccc tttgggcatg atatgcattt   10920
attttgtaa tagagacagg gtctcgccat gttggccagg ctggtcttga atttctggtc   10980
tcaagtgatc cgctggcctc ggcctcccaa agtgctggga ttacaggcac cacgcctggc   11040
ctgtgacacg attcttaacc ccttttgat gatggcggct ggaaaagtgg ccagtggatt   11100
ttgatgtatt caatcatgaa ttaggaggtg gggagagaat gaattattgg agctttcctt   11160
aaagccatta aatggctcta ttgttttttc aattgatgtg aatttcacat aacatgaaat   11220
taaccagctc agtggcatta atacatctgc aatgctgtgt ggccaccacc tctatcttgt   11280
tccaaaactt tgcataacct aatgtctttt tttttttttt ttttgagac ggagtctcgt   11340
tccatcaccc aggctggagt gcagtggtgt gatctcagct cactgcaacc tccgcctccc   11400
aggttcacgc catcctcctg cctcagcctc ccgagtagct gggactacag gcaccctcca   11460
ccacatccgg ctaattttttt gtatctttag tagagatggg gtttcaccat gttagccggg   11520
atggtctcga tctcctgacc tcgtgatcca cctgcctcg cctcccaaag tgctggcatt   11580
acaggcgtga gccaccatgc ccggcctatt ttttttttta agagatggag tctaattctg   11640
ttgcccaggc tggagtccag tggtaccatc atacttcact gcagccttga cctcttgggc   11700
tcaagtgatt ctcttgcctc gaactcccaa agtattggga ttacaggtgt gagccaccgc   11760
actcagccta atgtccagtt tttaacaagc tccatttaaa tgccctccgt tttgacccat   11820
aaaggggtag gcttggccgg gcacaatggc ttgtgtctgt agtcccagct acttgggagg   11880
ctgaggcaga aaggcagaaa gattgcttta taaagcccag gagtttgagg gccacctggg   11940
tggcatagct agacctcatc tctaaaaaat agtaataaa taaatatttg ttttttgtttt   12000
tttcttttttc ttttctttt tttttttttt tgagacggag tcttgctctg ttgcccaggc   12060
tggagtgcag tggcgcgatc tcagctcact gcaagctgtg cctcctgggt tcatgccatt   12120
ctcctgcctc agcctcccga gtagctggga ctacaggcgc ccactaccac gcccagctaa   12180
tttttttgtat tttagtagga gatggggttt caccacgtta gccaggatgg tctcaatctc   12240
ctgacctcgt gatccgccag ctttggcctc ccaaagtgtt gggattacag gcgtgagcca   12300
ctgagcccgc cccatatgta tgtatatata tattttttta aaatgggaga ccaggcatgg   12360
tggctcatgc ctagaatccc agcactttgg gaagctgagg taggcggatc acttgaggcc   12420
atgagtttga accagcctg ctcaacatga tgaaacttct atctctacta aaaaaaaag   12480
tgggattagg tcaggcacgg tggctcacac ctgtaatccc agcactttca gaggccgagg   12540
caggaggatc atgaggtcag gagatcgaga ccatcctggc taacacggtg aaaccccgtc   12600
tctactaaaa aaatacaaaa aattagccag gcgtggtggc gggtgcctgt agtcccagct   12660
actcaggagg ctgaggcagg agaatggcgt gaacccggga ggcggagctt gcagtgagcc   12720
aagatcgtgc cactgtactc cagcctgggc gacagagcaa gactctgtct caaaaaaaaa   12780
```

```
aaaaaaagtg ggattgacat tctcttcaaa gttctggggt tttcctttgc aaagacagga   12840
ttggcaaggc cagtgggtct ttttttgtgtg tgtgtgtgtg acggagtctc actctgccac  12900
ccaggctgga gtgcaatggc aggatctcgg ctcaccgcaa cctcctcctc ccaggttaaa   12960
gtgattctcc tgcctcagcc tcccgagtag ctgggactac aggtgcccgc caccacaccc   13020
aactaatttt tgtattttta gtagagacag ggtttcacta tattggccag gctggtcttg   13080
aaccctgac ctcacgtgat ccacccgcct tggcctccca aagtgctggg attacaggcg    13140
tgagccactg tgctcggcct cagtgggtct ttcctttgag tgacagttca atcctgtctc   13200
ttctgtagtg tctgtcacct gcaaatccgg ggacttcagc tgtggggcc gtgtcaaccg    13260
ctgcattcct cagttctgga ggtgcgatgg ccaagtggac tgcgacaacg gctcagacga   13320
gcaaggctgt cgtaagtgtg gccctgcctt tgctattgag cctatctgag tcctggggag   13380
tggtctgact ttgtctctac ggggtcctgc tcgagctgca aggcagctgc cccgaactgg   13440
gctccatctc ttgggggctc ataccaagcc tcttccgccc ttcaaatccc cccttgacca   13500
ggaggcatta caaagtgggg atggtgctac ctcttcgggt ttgtcacgca cagtcaggga   13560
ggctgtccct gccgagggct agccacctgg cacacacact ggcaagccgc tgtgattccc   13620
gctggtcgtg atccccgtga tcctgtgatc cccgccccgt gaggctgaac acatagtgac   13680
gcttgctagc caagcctcaa tgacccacgt aacatgaagg gggaaaagcc agaaagttct   13740
gccaaggagc aaggccaaga atcccgaagg gaaatggact ttgaagctgg gcgtcttctt   13800
ggctgtctta atacaagtgg cacatccaaa tccaaaaccc cgaaattcaa agtcttgagc   13860
acccgaaatt ctgaaacgtc ttgagcactg acctttagaa ggaaatgctt attggagcat   13920
tttggatttc ggattttttac cactgagtgt ggagtcctaa ttaggaaaaa aaccaggctg   13980
accgaaccaa aggaaagcaa taaagaagg cagatagggt caggcacggt ggctcacccc    14040
tgtaatccca gccttttgag aggctgaggc gggtggatca cttgaggtca ggagttcgag   14100
agcagcctgg ccaacacggt gaaaccccat ctctactgaa aatacaaaaa ctagccaggt   14160
atggtggcgt ctgcctgtaa tcccagctac tcgggaggct gagacaggag aatcacttga   14220
acctgggagg cagaggttgc agtgagccaa tatcacgcca ttgcactcca gcctggggga   14280
caagagcgaa attctgtctc aaaaaaaaag aagaagaagg ccgacaaact atgtaactct   14340
gcctttctcc atggtccaga acacacagcc ctcctgcgta ataactcct tatcttcctg    14400
ctcccagcta tcatcagaca cctcggctga tagaaaattg caagttagct cactgcaacc   14460
tcggcattat aagtactgca caaagcccct ttcagcgcac agcacaagca ccattctata   14520
aaatctccag caagcggcca ggtgcagtgg ctcatacctg taatcccagc attttgggag   14580
actgaggcgg gcggatcacc tgaggtcagg agtttgagac cagcctggcc aacatggtga   14640
aaccccgtct ctattaaaaa tacaaaaaa ttagccaggc gtggtggcag gtgcctgtaa    14700
tcccagctac ttgaaggct gaggcaggag aatcgcttga acccgggagg tggaagttgc    14760
agtgagccga gatcttgcca tcgcactcca gcctggggga caagagtgag acttcgtctc   14820
aaaaaaaaaa aaaaaaattc ccagcaagcc tttgtcttct ggcagtcagc tcctctcttg   14880
ctgacctgct cattgctttc ttgcaaggta ttttcctacc tactttctgg aataaatctg   14940
tcttctgta cttacaacta cctttttttaa aatttcttc ttttttgaga tggagtctca    15000
ctctgtttgc ccaggctgga gttcagtggt gcaatctcag ctcactgcaa cctctaccta   15060
ctgggttcaa gcgattctcc tgcctcagct tcccgagtag ctgggattac aggcgtgcac   15120
cagcacgcag gctaatttttt gtatttttag tagagacggg gtttcaccat gttggccaag   15180
```

```
gtggtcttga actcctgacc tcaagtgatc ctcccacctc agcctcccaa agcgctagga    15240
ttacggccat gagccactga ggccggctgc acctacaact gtcttgataa attcttaccc    15300
ccacaccact ggtccagata gtcagtgctc acccacaaca ttaaggatat tccaaatttg    15360
aaacattcca aaatcagaaa aatattccaa ctctgaaaat attccaaaat ccaaaaaaat    15420
tcaaaatcca aaacacttct ggtcccaagc attttagaga agggatactc aacccaaaat    15480
aaggacagca attctataaa ttgtgctacc atcttgcagg tctcagttta acagctttac    15540
acctattagc gcaccagtgc tcatagcagt gctgggaaat gtgtacagat gaggaaactg    15600
aggcaccgag agggcagtgg ttcagagtcc atggcccctg actgctcccc agcccgcctt    15660
tccaggggcc tggcctcact gcggcagcgt ccccggctat agaatgggct ggtgttggga    15720
gacttcacac ggtgatggtg gtctcggccc atccatccct gcagccccca agacgtgctc    15780
ccaggacgag tttcgctgcc acgatgggaa gtgcatctct cggcagttcg tctgtgactc    15840
agaccgggac tgcttggacg gctcagacga ggcctcctgc ccggtgctca cctgtggtcc    15900
cgccagcttc cagtgcaaca gctccacctg catcccccag ctgtgggcct gcgacaacga    15960
ccccgactgc gaagatggct cggatgagtg gccgcagcgc tgtagggggtc tttacgtgtt    16020 ccaaggggac agtagcccct gctcggcctt cgagttccac tgcctaagtg gcgagtgcat    16080
ccactccagc tggcgctgtg atggtggccc cgactgcaag gacaaatctg acgaggaaaa    16140
ctgcggtatg ggcggggcca gggtgggggc ggggcgtcct atcacctgtc cctgggctcc    16200
cccaggtgtg ggacatgcag tgatttaggt gccgaagtgg atttccaaca acatgccaag    16260
aaagtattcc catttcatgt ttgtttcttt ttttctttt ctttctttat tttgttttg    16320 agatggagtc tcactctgtg attttttttca tctctaaatt tcctacatcc atatggccac    16380
catgaggccc caggctggcc gatggttgct gttagcttat tgggaaatca ctgtttggaa    16440
ggtgctggtt gttttttgtt gtttgttgtt tttgttttttg ttttttgtttt gagacgggagt    16500 ctcgctctgt cgccagggtg gagtgcagtg gcgcgatcag ctcactgcaa cctccgcttc    16560
ctgggttcaa gccattctcc tgcctcagcc tcccaagtag cgcggattac aggcatgtgc    16620
caccacctcc ggctattttt ttttctattt agtagagatg gggtttcacc atgttagtca    16680
ggctggtcat gaactcttga cctcaggtga tccacccgcc tcggcctccc aaagtgctgg    16740
gattacaggc gtgcactgct gcacccagcc tttttttgtt tttttgagac agggtcttgc    16800
tgtcacccag gttgaagtaa ggtggcacga ttatggctca ctgcggcctt gatctccttg    16860
gctcaagcga tcctctcact tcagcctctc aagcagttgg aaccacaggc tgtaccacca    16920
agcctggcca attttttttgt acagacacag gctggtcttg aactcctggg ctcaagcaat    16980
cctcctgcct tggcctccca aagtgctggg attccaggca tgagccgctg cacccggcaa    17040
aaggccctgc ttctttttct ctggttgtct cttcttgaga aaatcaacac actctgtcct    17100
gttttccagc tgtggccacc tgtcgccctg acgaattcca gtgctctgat ggaaactgca    17160
tccatggcag ccggcagtgt gaccgggaat atgactgcaa ggacatgagc gatgaagttg    17220
gctgcgttaa tggtgagcgc tggccatctg gttttccatc ccccattctc tgtgccttgc    17280
tgcttgcaaa tgatttgtga agccagaggg cgcttccctg gtcagctctg caccagctgt    17340
gcgtctgtgg gcaagtgact tgacttctca gagcctcact tccttttgtt ttgagacgga    17400
gtctcgctct gacacccagg ctggagtgct gtggcacaat cacagctcac ggcagcctct    17460
gcctctgatg tccagtgatt ctcctgcctc agcctcccga gtagctgaga ttaaaggcgt    17520
ataccaccac gcccggctaa tttttttgtat ttttattaga gacagggttt ctccatgttg    17580
```

```
gccaggctgg tcttgaactc ctggtctcag gtgatccacc cgcctcggcc tcccaaagtg   17640
ctaggattac aggtgtgagc cactgcgcca ggcctaattt ttttgtattt ttagtagaga   17700
tgcggttttg ccatattgcc caggctggtc tcgaactcct gggctcaagc gatctgcctg   17760
ccttggcctc ccaaagtgct gggattacag gcacaaacca ccgtgcccga cgcgttttct   17820
taatgaatcc atttgcatgc gttcttatgt gaataaacta ttatatgaat gagtgccaag   17880
caaactgagg ctcagacaca cctgaccttc ctccttcctc tctctggctc tcacagtgac   17940
actctgcgag ggacccaaca agttcaagtg tcacagcggc gaatgcatca ccctggacaa   18000
agtctgcaac atggctagag actgccggga ctggtcagat gaacccatca agagtgcgg    18060 tgagtctcgg tgcaggcggc ttgcagagtt tgtggggagc caggaaaggg actgagacat   18120
gagtgctgta gggttttggg aactccactc tgcccaccct gtgcaaaggg ctcctttttt   18180
cattttgaga cagtctcgca cggtcgccca ggctggagcg caatggcgcg atctcggctc   18240
actgcaacct ctgcctccca ggttcaagtg attctcctgc ctcagcctcc tgagtagctg   18300
ggattacagg cgcccaccac caagcccggg taattttttg tatgtttagt agagatgggg   18360
tttcactatg ttggccaggc tggtgttgaa ctcctgacct catgatccgc ccacctcggc   18420
ctcccaaagt gctgggatta caggcgtgac ccaccccatg aaaaaaaatt aaaaaatgaa   18480
gcgatgctgg gcgcggtgga tcacgcctgt aatcccagca ctttgggaag ctgaggcagg   18540
cagatcacga gggcaggaga ttgagaccat cctggctaat acggtgaaac cccatctcta   18600
ctaaaactac aaaaaattag ccgggtgtgg tggcaggcac ctgtgatccc agctactcag   18660
gaggctgagg caggagaatc gcttgaaccc aggaggtgga ggttgcagtg agccgggatc   18720
acaccattgc actccagcct gggtgacaga gtgagactct gtctcaaaaa aaaaaaaaa    18780 aaaaaagcg aattctgaaa tacatgaatt cttttcctta gatgcctgct tctgtcttga    18840
ggtttgttgt tgttatttcg aaacagagtc ttgctctgtc gctcaggctg gagtgcagtg   18900
gcatgatctt ggctcaccac aacctccggc tcccaggttc aagcgattct tctgcctcag   18960
cctcctgagt agctgggatt acagctgaat gccaccttgc tgggctaatt tttgtatttt   19020
tagtagagat ggggtttcac catgttggcc aggctggcct cgaactcctg acctcgagtg   19080
atctgcccgc ctcctgaagt gctgggatta caggcgtgag ccacctcgtc ctggtgaggg   19140
tttttttttt tccccaaccc tctgtggtgg atactgaaag accatattag gataactgta   19200
cagtatagag aaggcagtgg caagttttct ctgtcatata ccagagtggg cttgggcatg   19260
gtggcatact cctgtagtct cagctaatca ggaggctgag gaaggaggat cgcttgggcc   19320
caggagttgg agactgtagt gagctgtgat cacaccacca cacttcaatc tgggcaacag   19380
agcaagagac cctatctcta aaaaaagta agtatttcgg acactgtggg ccatacggtc   19440
tctggtgcag tttctcaaca tggctgttgg gtgaacacaa ccacgcacag aacgcaaacc   19500
aatacacgtg gctgtgggcc cagaaaatgt tatttatgga cacaaaaatt ggaatttcat   19560
ataactgttt tgtgtcatga aaatgatttc ccttttttatt tttattttc ttctcaagta   19620 tttaaatatg taaaagccat ttttaggcct ggcaggatgg ttcacagctg taatcccagc   19680
actttgggag gtcgaggcgg gaggatcacg aggtcaggag atcgagacca tcctggccaa   19740
cacagtgaaa ccccgtctct actaaaaata caaaaaatta accaggcttg gtggcgcgcg   19800
tctgtagtcc cagctgctca ggaggctgag gcaggagaat cgcttgaatg caggaggcgg   19860
aggttgtagt gagccgaggt tgcaccactg cactccagcc tgagcgacag agtgagagtc   19920
cgcctcaaac aaaaaaatgt ttgcccatgc tggtcttgaa ctcctgggct caagctatct   19980
```

```
gcctgccttg gtctcccaaa gttctgggat tacaggcatg agctacagcg cccggacttt      20040
tgttgtttta tatctatata tctatatata acttgtttta tgtatatata taacttgttt      20100
tatatatata cataaactgc agtaaaaaac atgtaacata aaatttacct tctcaaacct      20160
tattaagtgc acagttctgt gccattagca aattcacact gttgtacaac atcacaacca      20220
ccatctccag aactttttt ttttttttta ttcttttga cagagtct cactcgtcgc          20280 acgggctgga gtgcagtggt gcgatctcgg ttcactgcaa cctccaccta ccaggttcaa      20340
gcaattctcc tgcctcagcc ccctcagtag ctgggattac aggtgcccgt cctaccacgc      20400
ccagctaatt tttgtatttt cagtagagac tgactgggtt tcaccatgtt ggccaggctg      20460
gtctcgaact cctgacctca agtgatcctc ccacctcagc ctcccaaagt gctgggaata      20520
caggcatgag ccactgcgcc cggcccccaga actcttttat cttcccaaac tgaagctctg     20580
tccccatgaa acactcactc tccatcccct ccccaactcc tggcacccac cattctactt      20640
tctgtcccta tgaatgtgat ggctctaggg acctcctctg agtggaatca gacagcattt      20700 tcctttttg actggcttat ttcactgagc caagtgcggt ggcacacgcc tgtaatccca      20760
aaactttggg agaccgaggc gggcgcatca cctgaggtca ggagttcgag accagcccgg      20820
ccaacatggt gaaacccat ctctagtaaa aatacaaaaa attagcctgt catggtcgtg       20880
ggtgcctgta atcccagcta gtgggaggc tgaggcagga gaatcgcttg tacccaggag       20940
gcggaggtcg cagtgagccg agatcgtgcc attacactcc agcctgggca caagagtga      21000 aactccgtct ctcctaaaaa tacaaaaaaa ttagctgggc atggtggcac atgcctgtag      21060
tcccagctac ttgggaggct gaggcaggag aatcacttga acccgggagg tggaggttgt      21120
aatgagccaa ggttggcggc gaaggatgg gtaggggccc gagagtgacc agtctgcatc      21180
ccctggccct gcgcagggac caacgaatgc ttggacaaca acggcggctg ttcccacgtc      21240
tgcaatgacc ttaagatcgg ctacgagtgc ctgtgcccg acggcttcca gctggtggcc      21300
cagcgaagat gcgaaggtga tttccgggtg ggactgagcc ctgggccccc tctgcgcttc      21360
ctgacatggc aaccaaaccc ctcatgcctc agtttcccca tctgttaagt gtgcttgaaa      21420
gcagttagga gggtttcatg agattccacc tgcatgaaaa actatcattg gctggccaga      21480
gtttcttgcc tctggggatt agtaattaag aaatttcagg ccgggtgcgt aatccctgta      21540
atcccaacac cttgggacgc cgaggcgggc agatcacctg aggtcgggag ttccagacca      21600
gcctgaccaa catggagaaa ccccgtctct actaaaaata caaaattagc cgggcttggt      21660
ggtgcatgcc tataatccca gctactcagg aggctgaggc aggagaatca cttgaacctg      21720
ggaggtggag gttgtggtga gccaagatcg tgccattgca ctccagcctg gcaacaaga      21780 gtgaaactcc atccaaaaaa aaagaaaag aaagaaaaa aagaaaaga aatttcagct        21840 gacacagctt cacactcttg gttgggttcc cgtggtgaat gatgaggtca ggtgatgact      21900
ggggatgaca cctggctgtt tccttgatta catctcccga gaggctgggc tgtctcctgg      21960
ctgccttcga aggtgtgggt tttggcctgg gccccatcgc tccgtctcta gccattgggg     22020
aagagcctcc ccaccaagcc tctttctctc tcttccagat atcgatgagt gtcaggatcc      22080
cgacacctgc agccagctct gcgtgaacct ggagggtggc tacaagtgcc agtgtgagga      22140
aggcttccag ctggaccccc acacgaaggc ctgcaaggct gtgggtgagc acggaaggc      22200 ggcgggtggg ggcggcctca ccccttgcag gcagcagtgg tggggagtt tcatcctctg      22260 aactttgcac agactcatat cccctgaccg ggaggctgtt tgctcctgag gctctggca      22320 ggggagtctg ccgccctgtt aggacttggg cttgccaggg ggatgcctgc atatgtccta     22380
```

```
gtttttggga atatccagtt aacggaaccc tcagccctac tggtggaaca ggaaccggct    22440
ttcctttcag ggacaacctg gggagtgact tcaaggggtt aaagaaaaaa aattagctgg    22500
gcatggtgcc acacacctgt ggtcccagct actcagaagg ctgaggcggg aggattgctt    22560
gagggcagga ggattggttg atcctcccac ctcagcctcc ggagtagctg ggacctcagg    22620
tgcatgccac tatgcctggc taattttctt ttttctttt ttttttttt cgagacggag    22680 tctcgctctg ttgcccaggc tggagtgcag tggcaggatc tcggctcact gcaagctccg    22740
cctcccgggt tcacgccatt ctcctgcctc agcctcccca gtagctggga ctacaggagc    22800
ccgccactgc accaggccaa ttttttttgta ttttagtag agacgggtt tcactgtgtt    22860 agccaggatg gtctcgatct cctgacttcg tgatccgccc acctcggcct tccaaagtgc    22920
tcggattaca ggcgtgagcc actgcgccca gccgctaatt ttcatatttt tagtaaaaac    22980
agggtttcac catgttggcc aggctagtct tgaactcctg aacccaagtg atcctcctgc    23040
cttggcctcc caaagtgctg ggattacaga caccacacct ggctattatt attttttaga    23100
gacagggtgc tgctctatct tccagcctgt agtgcagtgc agcctccatc atagctcgct    23160
gcagccttga cctcctgggt tcacgtgatc gtcccgccta agcctctgga ggagctggga    23220
gtactggcat gtgccaccat gcctggttaa tttttttttt ttttttttg agacagagtc    23280 tcattctgtc acccaggctg gagtgcggtg gtgcgatctt ggcttactga aacctccacc    23340
tcccaggttc cagcaattct cctgcctcac ccttctgagt agctgggatt acaggttccg    23400
gctaccaaac ctggctagtt tttgtatgtt tagtagagac agggtttcac catgttggtg    23460
aggctggtct cgattctccc gcctcagcct cccaaagtgc tgggattaca ggcttgagcc    23520
accgtgcctg gctttttttt tttttttttt ttttgtggca ataaggtctc attgtcttgc    23580
ccaggctagc cttatgctcc tagcctcaag tgatcctcct ccctcagcct cccaaagtgc    23640
tgggattaca ggtgggcgcc actgtgcctg ttcccgttgg gaggtctttt ccaccctctt    23700
tttctgggtg cctcctctgg ctcagccgca ccctgcagga tgacacaagg ggatggggag    23760
gcactcttgg ttccatcgac gggtcccctc tgacccccctg acctcgctcc ccggaccccc    23820
aggctccatc gcctacctct tcttcaccaa ccggcacgag gtcaggaaga tgacgctgga    23880
ccggagcgag tacaccagcc tcatccccaa cctgaggaac gtggtcgctc tggacacgga    23940
ggtggccagc aatagaatct actggtctga cctgtcccag agaatgatct gcaggtgagc    24000
gtcgcccctg cctgcagcct tggcccgcag gtgagatgag ggctcctggc gctgatgccc    24060
ttctctcctc ctgcctcagc acccagcttg acagagccca cggcgtctct tcctatgaca    24120
ccgtcatcag cagagacatc caggcccccg acgggctggc tgtggactgg atccacagca    24180
acatctactg gaccgactct gtcctgggca ctgtctctgt tgcggatacc aagggcgtga    24240
agaggaaaac gttattcagg gagaacggct ccaagccaag ggccatcgtg gtggatcctg    24300 ttcatggggtg cgtatccacg acgctgaggg ctgcagaggg aatggaggga gcaggaagga    24360
gcttcaggaa ctggttagtg ggctgggcat ggtggctcaa agcacctgta atcccagcac    24420
tttgggaggc caaggtgggt ggatcatcaa gaccagcctg accaacatgg tgaaacctcg    24480
tctctactaa aaatacaaaa attagccggg tgtggtggtg ggcacctgta atcccagctg    24540
ctcgggaggc tgaggcagga gaatcacttg aacctgggag atggaggttg cagtgagcca    24600
agacagcccc actgcactcc agcctgggtg acagagtgag actccgtctc aaaaaaaaaa    24660
aaaaaaacta acaaaaaaac tggttagtgg ctagacaaca ggatggtatc ttccaagccc    24720
atggctgact cagcagctcc tgggtcaaga cactgtgacc tgtgtcccct ggcaggaagc    24780
```

```
atcgcccctg ccacctgccc ggtgtactct gtacctgtca ggtgacatct gctacctaag    24840
cacgtgagag gtggcatttc acagtttcag tgtggtgctg acaacccggg acgcacactg    24900
tccttgcagc tacaatcagg aggtgaatgt tgggtttcca gcagagaaca ctggagaagg    24960
cacacttggt gtctggaagg gaaaagcagg gaagagagca tcatcagatg cctgcgggtg    25020
aaggtgggcc cgctatggcc agcgtccctt tttatttta tttatttatt tatttgagat     25080
ggaatctcgc tctgtcgccc agactgtagt gcagtggtgc gatcacggct cactgcaagc    25140
tccgcctcac aggttcacgc cattctcctg cctcagcctc ccgagtagct gggactacag    25200
gcacccgcca ccacgcccgg ttaattttt gcatttttat tagagacggg gtttcaccgc     25260
gttagccagg atggtctaaa tctcctgacc ctgtgatcca cccgcctcgg cctccctaag    25320
tgcttggatt acaagcgtga gccaccacgc ccggccccct tttatttt tattttttga      25380
gacggagtct cgctctgtcg cccaggctag attgcagtgg cgtgatctcg gctcactgca    25440
gcctccgcct cccaggttca agtgattctc ctgcctcaac ctcccaacta attaggatta    25500
caagcatgta ccaccatgcc tgactaattt tttgtatttt tagtagagac tgggtttcac    25560
catgttggct aggctggtct cgaacccta gcctcaagta atctgcctgc ctcagcctcc     25620
caaacagcgg ggattacagg catgagccac tgtgcccaac ccaaccctgg atctctttta    25680
aacaagacaa tgctcgctgt tgccacagaa caatgggtgg ggtacatgtg cccagtgtg     25740
tttggccaca taactgccag gccagaggga aagagactct cagactgtct ccactcagat    25800
acaaatgtgt gtgttgtgtg cgtgtgttct ggtctcatat ttgtttgttt tgagacaggg    25860
tgtcgctctg tcactgagtc tggagtgcag tggcgcaatc agagttcact gcagcctcaa    25920
actcttgggc tcagttgatt ctcccacttc agcctcccaa gtagctggaa ctacaggtga    25980
acaccactgt gcccagctaa tttatttat ttttagtaga gatgaggtct cactatgttg     26040
cccaggctgg tcttgacctc ctagcctcaa gcaatcctcc tgccttggtc tcccaaagtg    26100
ctgggattac acgtgcgagc cattgcgcat ggcttgtgtt cttgtgtttc ttcctttttc    26160
tttcgagatg gcgtctcagt ctgccaccca ggctggagtg cagtggtgtg atcatagctc    26220
actgtagcct caacttcctg ggctcaagca atcctcttga tttcagcctc ccgggcctgg    26280
ccagcatggt gaaaccccgt ctctactaaa aatacaaaaa tgtagccagg cgtggtggtg    26340
ggcgcctgta atcccagcta caccagaggc tgaggcagga aatcgcttg agcctggaag     26400
gtggaggttg cagcaagcca agatcgtgcc actgcactcc agcctgggca acagagacag    26460
actctgtctc aaaaaaaaaa aaaaaaaacc caaacaagcc acatttggag tttgggggttc   26520
ccagcaggac tatttcccaa gcctgagcct ggctgtttct tccagaattc gttgcacgca    26580
ttggctggga tcctccccg ccctccagcc tcacagctat tctctgtcct cccaccagct     26640
tcatgtactg gactgactgg ggaactcccg ccaagatcaa gaaaggggc ctgaatggtg      26700
tggacatcta ctcgctggtg actgaaaaca ttcagtggcc caatggcatc accctaggta    26760
tgttcgcagg acagccgtcc cagccagggc cgggcacagg ctggaggaca gacgggggtt    26820
gccaggtggc tctgggacaa gcccaagctg ctccctgaag gtttccctct ttcttttctt    26880
tgttttttct ttttttgaga tgaggtcttg gtctgtcacc caggctggag tgcactggcg    26940
caatcgtagc tcactgcagc ctccacctcc caggctcaag tgatcctcct gcctcaccct    27000
cctgagtagc tgagattaca gacacgtgcc accacggcag actaattttta ttttattttt   27060
gggaagagac aaagtcttgt tatgttggcc tggctggtct caaactcagg gtgcaagcga    27120
tcctcccgcc tcagccttcc aaaactgctgg gattacaggc gtgggccacc gtacccagcc   27180
```

```
tccttgaagt ttttctgacc tgcaactccc ctacctgccc attggagagg gcgtcacagg    27240
ggaggggttc aggctcacat gtggttggag ctgcctctcc aggtgctttt ctgctaggtc    27300
cctggcaggg ggtcttcctg cccggagcag cgtggccagg ccctcaggac cctctgggac    27360
tggcatcagc acgtgacctc tccttatcca cttgtgtgtc tagatctcct cagtggccgc    27420
ctctactggg ttgactccaa acttcactcc atctcaagca tcgatgtcaa cggggcaac    27480
cggaagacca tcttggagga tgaaaagagg ctggcccacc ccttctcctt ggccgtcttt    27540
gaggtgtggc ttacgtacga gatgcaagca cttaggtggc ggatagacac agactataga    27600
tcactcaagc caagatgaac gcagaaaact ggttgtgact aggaggaggt cttagacctg    27660
agttatttct attttcttct ttctttttt tttttttttt gagacagagt tttgctctcg    27720
tttcccaggc tggagggcaa tggcatgatc tcggctcacc gcaacctcca cctcccaggt    27780
tcaagtgatt ctcctgtctc aggctcccca gtagctggga ttacaggcat gcaccaccac    27840
catgcccggc taattttgta ttttagtag agacggagtt tctccatgtt ggtcaggctg    27900
gtctcgaact cccgacctca ggtgatctgc ctgcctcggc ctcccaaagt gctgggatta    27960
cagacttgag ccaccgcgcc cagctatttc tgttttcttt ctttcttctt cttcttttt    28020
tttttctaag agacaggatc tcactctgtc cccaggcagg agtgcagtgc tgtgatcata    28080
gctcactgca gccttaacct cctgggctca agtgatcttc ccacctcagc ctcccaagta    28140
gctggaacta caggtgcaca ccaccatgcc cagctcattt ttgtattttt ttttttttg    28200
agacagtctc gttctgtcac cccggctgga gtgcagtggt acaatcttgg ctcactgcaa    28260
cctctgcctc ccaggttcaa gcgattctcc tgcctcagcc tcctgagtag ttgagattac    28320
aggcatgtgt gccatcatac ctggctgatt tttgtatttt ttttagaga tggggtctca    28380
gtatgttgac caggcttgtc ttaaactccc ggcctcaagt gatcctccca cttcagtctc    28440
ccaaagtgct gggattacag gcatgagcca ctgcggccgg tttgttttct tttttttttc    28500
gttttttgga gacggaattt cacctttgtt gcccaggatg gagtgcaatg gcacgatatc    28560
gcctcaccac aacctctgcc tcctgggttc aaaccatttt cctgcctcag ccttcttagt    28620
agctgggatt acaagcatgt gccaccacgc ccggctgatt ttgtattttt agtagagatg    28680
gggtttctcc atgttggcca ggctggtctc gaactcctga cctcaggtca ttcgcccacc    28740
tctgcctccc aaagtgctgg gattacaggc gtgagccacc gtgcccggtg tttgtattc    28800
ttttttactga gagtcgtgaa aggcagtgat cctctgtcac atgtgatctt ggctctcagg    28860
ggacatttgg caatttctag attttttg gttgtcacaa gtcaatgggg aagactgttg    28920
gcatttagtg ggtagaggct ggtgacgctg ctgaacaccc agaacaggga agtagcaggc    28980
cctagataga gccatcgtgg ggaaaccctg ctctaaggaa atggcgctat tttataaccc    29040
cacgttcctg gcatgattac caacagccaa aagtggagtc cccccaagtg tgttcgtcca    29100
tttgcattgc agtaaaggaa tagctgaggc cgggtaattt ataaagaaaa gagatttaaa    29160
ctgggtatgg cagtttatgc ctataatccc agaactttgg gaggctgagg caggaggatc    29220
gcttgagtcc aggagtgtga gaccgagacc agcctggcca acatgacgaa actctgtctc    29280
tacaaaaaat acaaaaagta ggccaggcac ggtggttcac gcctgtaatc ccagcacttt    29340
gggaggccga ggcgggcgga tcacgaggtc aggagatcga gaccatcctg gctaacacgg    29400
tgaaacccccg tctctactaa aaatacaaaa acaaaattag ccgggtgtgg tggcaggcgc    29460
ctgtagtccc agctactcgg gaggctgagg cgggagaatg gcgtgaaccc gggaggcgga    29520
gcttgcagtg agccaagatc gcgccactgc actccagcct gggtgaccga gttgagactc    29580
```

```
cgtctcaaaa aaaaaaaaaa aaaaaaaaat acaaaaagta gccaggtgtg gtggcaggca   29640
cctgtaatcc tgggttctcg agaccgaggc atgagaattg cctgaccca ggaggtggag    29700 gctgcagtga gccaagatca tgccactgca ctccagcctg ggcgacagag tgggactctg   29760
tctcaaaaaa caacaaaaaa aaagttctgg aaatggatgg tggtgatggt gatacttcca   29820
caacagcgtg aatctgctta aggccaccga actgtgcact cacaaatagt cgagatggta   29880
cattttatgt tatgtgtatt tcaccacaat taaaaactag ttgtgggcca ggtgtggtgg   29940
ttcatgcctg taatcccagc actttgggag gtcagaggga ggtggatcat gaggtcagca   30000
gttcgagacc agccaggcca catggtgaaa ccccatctc tactaaaaat acaaaaatta    30060
gccaggcgtg gtggcacatg cctgtagtcc cagctacttg agaggctgaa gcaggagaat   30120
cgcttgaacc tgggaggcta agattgcagt gagccgagat cgtgccactg cactccagcc   30180
tggacgacag agtgagactt cgtctcaaaa aaaaaccaa aaaaaaatt agctgtgggt      30240 caggcactgt ggctcacgcc tgtaatccca gcactttggg agaccgaggt aggtggatgg   30300
cctgaggtca ggagttcgaa tccagcctgg ccaacatggt gaaagcccgt ctctactaaa   30360
aatacaaaaa attagtcagg tatgttggca cacctgtaat cccagctact cgggaggctg   30420
aagcaagaga atcgtttgaa cccaggaggt ggacgttgca gtgagccgag attgggccac   30480
tgtactccag cctgggcaac aaaagtgaaa ctctgtctga acaaacaaa caaacaaaca    30540 aacagacaaa caaaaaaact agttgtggag agagggtggc ctgtgtctca tcccagtgtt   30600
taacgggatt tgtcatcttc cttgctgcct gtttaggaca aagtattttg gacagatatc   30660
atcaacgaag ccattttcag tgccaaccgc ctcacaggtt ccgatgtcaa cttgttggct   30720
gaaaacctac tgtccccaga ggatatggtt ctcttccaca acctcaccca gccaagaggt   30780
aagggtgggt cagccccacc cccccaacct tgaaacctcc ttgtggaaac tctggaatgt   30840 tctgaaatt tctggaatct tctggtatag ctgatgatct cgttcctgcc ctgactccgc      30900
ttcttctgcc ccaggagtga actggtgtga gaggaccacc ctgagcaatg gcggctgcca   30960
gtatctgtgc ctccctgccc cgcagatcaa ccccactcg cccaagttta cctgcgcctg     31020 cccgacggc atgctgctgg ccaggacat gaggagctgc ctcacaggtg tggcacacgc     31080
cttgtttctg cgtcctgtgt cctccaactg cccctcctg agcctctctc tgctcatctg     31140
tcaaatgggt acctcaaggt cgttgtaagg actcatgagt cgggataacc atactttct    31200 tggatggaca catcagcacc gggcttgaca tttacccagt tcccctttga tgcctggttt    31260
cctctttccc ggcccctga agaggtgatc tgatttctga caggagccct gagggaggaa    31320
atggtcccct tgttgactt ttcttttct ttatttttt cttttgagat ttgctgtcac       31380
ccagcctgga atgcagtggt gccatcttgg ctcactgcta cctctcccac tgggttcaag    31440
caattctcct gcctcagcct cccaagtagc tgggattaca agcatgcgcc accatgcctg    31500
gctaagtttt gtatttttag tacagacagg gtttctccat ggtggccagg ctggtcttga   31560
actcctgacc tcaggtgatc ctcccacctc tgcctcccga agtgctacga ttacaggcat   31620
gagccaccgc gcccatcccc ctttgttgac ttttctcatc ctctgagaaa gtctcagttg   31680
aggccagcac ctccctcaag tgaattgaat ctccctttg aacaacaaca aataacaata    31740
tgacccagac gtggtggctc acacctgtgg tcccagctac tcgggaggct gaggtgtgag   31800
gattgcttga gccaggagg tcaaggctac agagagctat aatcacacca cttcactcca    31860
gcctggggga caaagtgaaa ccctgtctga aaaaacaaa aaagaaaaa ggaaaagaa      31920 acaatacgat cacaaagtag atattcatag tgtttatttt cagtactctt ttttttttt    31980
```

```
tttttttttt ttgagacgga gtcttgctct gttgcccagg ctggagtgca gtggcacgat    32040
cttggctcac tgcagcctct gcctcccagg ttcaagcgct tggctcactg caacctccgc    32100
ctcctgggtt caagcgcttc ttctgcctca gcctcccag tagctgggac tataggcacg     32160
tcccactacg cccagctaat ttttgtatt tttagtaga gatggggttt cactatgtta      32220
gccaggatgg tctcgatctc ctgacctcgt gatctgcctg ccttgggctc ccaaagtgtt    32280
gggattatgg gcatgagcca ctgcacctgg ccttttttt ttttttttt gagatggagt      32340
ttcgctcttg ttgcccaggc tggagtgcaa tggtgtgatc tcggctcact gcaacctctg    32400
cctcctgggt tcaagcaatt ctcctgcctc agcctcccga gtagctggga ttacaggcac    32460
ctgccaccac gcctggctaa ttttgtact tttagtagag acggggtttc tccatgttgg     32520
tcaggctggt ctcaaactcc tgacctcagg tgatccaccc acctcggcct cccaaagttc    32580
tgggattaca gacatgagcc accgcgcctg gccgtgtctg gccttttta gttatttctt     32640
tttttttttt tttttttttt gagacagagt cttactccgt cgcccaggct ggagtgcagc    32700
ggtgcgatgt ctcgcactg caagctccgc cccctgggtt catgccattc tcctgcctca     32760
gccttctgag tagctgggac tgcaggcgcc tgccactacg cccggctact tttttgtata    32820
tttagtagag atggagtttc actgtgttag ccaggatggt ctcgatctcc tgactttgtg    32880
atccgcccgc ctcggcctcc caaagtgctg ggattacagg cgtgagccac catgccaggc    32940
tttttttttt tttttttttt ttgagacgga gtcttgctct gtcgcccagg ctggagtgca    33000
gtgccatgat ctcagctcac tgcaagctcc acttcccagg ctcacgccat tctccagcct    33060
cagcctccca gtagctgag actacagggg cccgccacca cactcggcta attttttgt     33120
attttagta gagacggggt ttcaccatgt tagccaggct ggtcttgaac tcctaacctc     33180
aggcgattca cctgcctcgg cctcccaaag tgctgggatt aaaggtatga gccacctcgc    33240
ctggtgtgag ccacctcgcc cagcctgagc cacctcaccc agcctaagcc actgtgcctg    33300
gcctgatttt ggactttta aaatttat taataattat tttgggttt cttttttg          33360
agacagggtc ttactctgtc atccaggcca tcctgtctgt ctgtcatccc agtgatggga    33420
tcataccttg ctgcagcctc tacctcctgg gctcaagcga tcctcccccc tcagcctcct    33480
gagtagctgg gagtacaggt gtgcaccacc acacctggct aatttttttt tttttttttg    33540
tatatagaga tggtattttg ccatgttgac caggctagtc ttaaactcct ggactcactc    33600
aagagatcct cctgccttgg cctcccaagg tcatttgaga ctttcgtcat taggcgcaca    33660
cctatgagaa gggcctgcag gcacgtgca ctcagaagac gtttatttat tctttcagag     33720
gctgaggctg cagtggccac ccaggagaca tccaccgtca ggctaaaggt cagctccaca    33780
gccgtaagga cacagcacac aaccacccga cctgttcccg acacctcccg gctgcctggg    33840
gccacccctg ggctcaccac ggtggagata tgacaatgt ctcaccaagg taaagactgg     33900
gccctcccta ggcccctctt cacccagaga cgggtccctt cagtggccac gaacattttg    33960
gtcacgagat ggagtccagg tgtcgtcctc actcccttgc tgaccttctc tcacttgggc    34020
cgtgtgtctc tgggccctca gtttcccttat ctgtaaagtg ggtctaataa cagttcttgc   34080
cctctttgca aggattaaat gggccaaatc atatgagggg ccaggtcctt caggctcctg    34140
gttcccaaag tcagccacgc accgtgtggg tcccaaaatt ttatcaaggc acattcgttg    34200
cctcagcttc aggcatctgc ccaaaaaggc caggactaag gcaaggagag ggagggattc    34260
ctcagtactc agcttttcac agaggctcca aaaggctaag gaatccagta acgttttaac    34320
acaattttac aattttttt tttgagacgg agttttgctc ttgttgccca ggctggagtg     34380
```

```
cagtggcacg atctcggctc actgcaacct ctggctcccg ggttcaagcg attctcctgc   34440
ctcagtctcc cgagtagctg ggattacagg catgcgccac cacgctcggc taattttgta   34500
tttttagtac agaaggggct tctctgttgg tcaggctggt cgtgaactct caacctcagg   34560
tgagccaccc gcctgagcct cccaaagtgc tgggattaca ggtgtgagcc accacgcctg   34620
gccttttttt tgagacagag tctcgctctc gcccatgctg tactgcagtg acgcagtctg   34680
ggctcactgt aacctccgct tcccaggttc aagtgattct tctgccgcag cctcccatgt   34740
agagtagctg ggattacagg cacccgccac catgcctggc taattcttgc attttttagta  34800 gagatggggt ttcacagtgt tggccaggct ggtctcaaac ttctgacctc aagtcatctg   34860
cctgccttgg ccctgccaaa gtgctgggat tatagatgtg agccaccgcg cctggcctac   34920
agtttattct ttggtggctc acacctgtaa tctcagcact tgggaggcc aaggtgggag    34980 aatggcttga gcccaggagt tcaagtccag cctgggcaac atagcaagac cctatctcta   35040
ctacaaaata aataataaat aaactaattt ttttcttttt aaaacccaac tattcaacat   35100
ggcaatgcaa tatattaaaa aaattttttt tttctttgaa acggagtctc tcactgtcac   35160
ccgggctgga gtgcagtgtc gccatcttgg ctcactgcaa cctccgcctc ccaggtccaa   35220
gtgattctcc tgcttcagcc tcccgagtag ctgggattac aggcacccac caccataccc   35280
agctaatatt tttgtatttt tagtagagat ggggtttcac tatgttgggc aggctggtct   35340
ggaactcctg acctcgtgat ctgcccgagg atcggcggcc tcccaaagtg ctggggattg   35400
caggcatgag ccaccgtgcc cagccaaaac ttttttattt ttattttttt gggacacggt   35460
ctcactgtgt accccagact ggagtgatag agtgctgtca tggctcactg cagcctcaac   35520
ctccctgggc tcaggtgatc ttcctgcttc agtctcccag gtagctggga ctacaggcat   35580
gagccaccac acccagctaa ttttttgaatt ttttgtaga cagggttt caccttgtgg      35640 cccagacttg tctctaactc cagggctcaa gcgatctgcc cacccttggcc tcccaaagtg  35700 ctgagattaa tgcaatttaa aaaatttttt ggccaggcct ggtggctcat gcctgtattc   35760
acaacacctt gggaggcaaa ggtgggcaga tcacttgagg tcaggagttc gagactagcc   35820
tggccaacat ggtgaaaccc cctgtctact aaaaaatac aaaaattacc tgggcacagt    35880
ggtgggtgcc tgtaatccca gctacttggg atgctgaggg tggagaattg cttgaacctg   35940
ggaggcagaa gttgcagtaa gccaagatca tgccactgga ctccagcctc agtgacagag   36000
caaaactctg tctccaaaaa aattgttttt tttttttttt tttcaaatca tcacactaca   36060
gccaaggcct ggccacttac ttttgtaaat aaagttttat tggagccagt ggaccagtga   36120
ggccgaatct tgcaggtgta agatcacagt ctatccttga aaattttgat attttgttca   36180
ttgggtggtt tttcattaat ttaaatttta aaaataaca tattaaaggc tggtgtggag    36240
gtgcacgcct gcagtcctag ctactcccag aggctgaggc gggagacttg cttgagccca   36300
agagttgaag tccagcctgg gcaacatagc gagaccccca tctctaaaaa taaaaataat   36360
gcattagaat attattggat tcctgggcag ggcacagtgg ctcacacctg taatcccagc   36420
actttgggag gctgaggtgg gtggatcacc tgaggtcagg agtttgagac cagcctggcc   36480
aacatggtga aaccccgtct ctactaaaaa tacaaaaatt agccaggcgt ggtggcaggt   36540
gcctgtaatc ccagctactc gggaggctga agcacgagaa tcgcttgaat ccaggaggcg   36600
gaggttgcag tgagctgaga ttgcgccatt gcactccagc ctggaggaca agagtgaaac   36660
tccattcccc tctgcaaaga aaaggaatat tatcagattc ctaagctttt tggctccccc   36720
tttagtttgg gggctggggt ggtgagtgtc tgacctggcc tcactgtcct ccctggatgt   36780
```

```
gatgagaccc aggtgtgggt caggatgtca ttcgtttgtc caccagaggg cgcccaaact   36840
gctttgagct gctgggaaat ggtgctccta gactttagc aaacaaacaa aaaaaaatgg   36900
cacatcggca aatttcagac cattcttttt ttttttttt ttggttccag agtagctgaa   36960
atctttgttc agttacaagc aggataaaat ggaaactgcc tgggagaggc tgagaaacct   37020
tcttgcttgg gggaggtggg gcactgctag aattaatcgc ttcacagacc agcccatcca   37080
ggactcctca aatttggcaa aaagccatt cattcattca ttcatttatg tagagacgag   37140
ggggatctgg ctatattgcc tagattggtc tcaaattcct ggcctcaagt gatcctcctg   37200
ccttggtcta ctaatgtgct gcgattacag gcatgagcca ccgtgcctag ctctagtgga   37260
cttgaaatgt tgccttgccc agggccctta tgttgaatgg cccaggtcca cttgtatggt   37320
tctgtaccaa ggttaacccc atcccataat gcctgggaca gttgatgcag acaatcagc   37380 ttctgtgcca ttcaacctca ggactgagca tgctgggcat tgtgggtcc gaaggtggct   37440 cccctgtccc cttcaaaata ccctcttttt cttttcttct ttttttttt tttttttttt   37500 tgagacgaag tcttgctctg ttgccccagc tagagtgcag tggtgcgatc tcagctcccc   37560
gcaacctctg cttcccgggt tcaggcgatt ctcctgcctc agcctcctga gtagctggga   37620
ttacaggtgc ccaccgccac agctggctaa ttttttgtatt tttagtagag acagggtttc   37680
accgtgttgg ccaggctggt cttgaactcc tgacctcagg caacctgccc acctcagcct   37740
cccaaagtgc tgggattaca ggtttgagcc actgggcctg gccttttttt ttttttttg   37800 agagggagtc tcactctgtt gcccaggctg gagtgcaatg gcgcgatctt gactcactgc   37860
aactccattt cccgggttca agtgattctc ctccctcagc ctcccaagta gctgggatta   37920
caggtgcatg ccaccacggc cagctaattt tgtatttta gtagagacag ggtttcacta   37980
tgttgatcat gctggtctca aactcctgac cttaggtgat ctgcccgcct tagcctccca   38040
aagtgttggg attacaggtg tgagccaccg cgcccagacc aaaatatgct cattttaata   38100
aaatgcacaa gtaggttgac aagaatttca cctgcaacct tgtcaaccac ctagaataaa   38160
agcctctgca gccctcccct aaagactcat caatgtgagg ctcaagaacc ttcttaggct   38220
gggctcggtg gctcatttct gtaatccctg cactttggaa ggctgaggca ggaggatctc   38280
ttgaggccag gagttcaaga caagcctggg caacatagcc agacctctgt ttctatcccc   38340
cacaaaaaga accttcttaa accggaattg agtcctacaa cctcgataac tcacaaataa   38400
gcccgtgtgg cctctcacag acttgggaag ttctccaagt gtccagggag atgtgccagg   38460
cgctttcctg ccgtgaccac cgtcctctgc ctgctccatt tcttggtggc cttcctttag   38520
acctgggcct cactcttgct tctctcctgc agctctgggc gacgttgctg gcagaggaaa   38580
tgagaagaag cccagtagcg tgagggctct gtccattgtc ctccccatcg gtaagcgcgg   38640
gccggtcccc cagcgtcccc caggtcacag cctcccgcta tgtgacctcg tgcctggctg   38700
gttgggcctg ttcacttttt ctcctggaca gggaacagcc ccactggtgt cctttatcac   38760
ccccacggcc tctcctggct tggggctgac agtgacaaga tcagacagct aaggggtcag   38820
atggaggatg tggagctggg tcccgtgctg tggaatagcc tcaccgagat ttgagtgcct   38880
tctggggaac tggttcccct gcagggggct gtgtggagag gcgcgctctc cctgcctcac   38940
ccatgctcat cctaactcgg ttaccatcac atctctttt tctttttttc ttaaattta   39000 agaaaaaaga aatttaattt ttttgagaga cagagtcttg ctctgtcacc caggctggag   39060
tgcagtggca ccatcatgcc tcgctgcagc ctcaatgtct gggctcaagc gatcctccca   39120
cctcagcctc ctgagtagct ggtgcaagcc actataccc acttcctatt tcttaaaaag   39180
```

```
tcacagccct gtgtgtggct aatcctggac agaaatctag aagaagtcag ctacttctgg    39240
ggcgtggctc acccagtggg cttcaggtta gatatttctt atacttatga ggctgggtgt    39300
ggtggcttat gcctgtaatc ccagcacttt gggaggctga agtgggtgga ttgcttgggc    39360
tcaggagttc gagaccaacc tgggcaacat ggcgaaaccc tgtttctaga aaggtacaa     39420
aaattagctg ggcaggtggc acgtgcctgt ggtaccagct acttgagggc ctgaggcagg    39480
aggatcgctt gaacctggga ggtcgaggtt gcagtgaact gagatcatgt cactgcactc    39540
cagcctggtg acagagcaag accccgtctc aaaaaaaaaa aagaaagaa aaaaattctt     39600
atgcatagat ttgcctcttt tctgtttgtt tgttttgaga tggagtctcg ctctgtcgcc    39660
caggctggag tacagtggct caacctcggc tcactgcaac ctctgcctcc cgggttcaag    39720
caattctcct gcctcagcct cctgagtagc tgggactaca ggcgcccgcc accatgccca    39780
gctaattttt gtattttttag tagagactga ctgggtttca tcatgttggc caggctggtc    39840
tcgaactctt gacctcatga tccgcccgcc tcagcctccc aaaatgctgg gattacaggc    39900
gtgagccacc aggcccaggc cgcaaggcga tctctaaaca aacataaaag accaggagtc    39960
aaggttatgg tacgatgccc gtgttttcac tccagccacg gagctgggtc tctggtctcg    40020
ggggcagctg tgtgacagag cgtgcctctc cctacagtgc tcctcgtctt cctttgcctg    40080
ggggtcttcc ttctatggaa gaactggcgg cttaagaaca tcaacagcat caactttgac    40140
aaccccgtct atcagaagac cacagaggat gaggtccaca tttgccacaa ccaggacggc    40200
tacagctacc cctcggtgag tgaccctctc tagaaagcca gagcccatgg cggccccctc    40260
ccagctggag gcatatgatc ctcaagggac caggccgagg cttccccagc cctccagatc    40320
gaggacagca ttaggtgaat gcttctgtgc gctcattcag aatgtcagcg acaatggcc     40380
ttggtggtgt agaggaatgt tggataagca aatagagagc tccatcagat ggtgacaggg    40440
caaagaaagt caaaaggagt tcagaggccg ggcgcggtgg ctcatgcctg taatcccagg    40500
actttgggag gccgaggctg gcggatcacc tgaagtcagg agtttgagac cagcttggcc    40560
atcatgacaa accccgtctc tattaaaaa tacaaaaaat tagccaggcg tgggagtggg     40620
cgcctgtaat cccagctact cgggaggccg aggtagaaaa atcgcttgaa cctaggaggc    40680
agaggttgca gtgagccgag atcgcgccac tgcattccag cccgggaggc aagagcaaaa    40740
ctccatctca aaaaaaaaa aaaaaggagt tcagaggccc ggcatggtgg ttcacacatg     40800
tgatcccaga acttggggag gttgaggcag gagaatcacc tgagctcaga gttcaagacc    40860
agcctgggca gcacagcaag accccatctc tgcaaaaaat aaaaatttag cccagtgtgg    40920
tgatgagcgc ctagttccag ctactaggga ggctaaggca ggaggattgc ttgaggctaa    40980
ggtaggagat tgagactgca gtgacttgtg attgcgtcac tgcgctccag cctgggtgac    41040
agagcaagcc cttgtctctt aaaaaaaaa aaaaattcaa agaagggttt ccagagggcc     41100
aggagggagg aagggagagg aggtgtttta ttttttttgct tttatttttt attttgagac    41160
agagtctctc tctgtcaccc aggttggagt gcagtgctgt gatcttggct cactgcaact    41220
tctgcctcct gggttcaagc aattcttatg cctcagcctc agcctcctga gtagctggga    41280
ttacaacact atgcccgggt aattttttgta tttttagtag acgaggtt tcgccatgtt      41340
gcccagactg tctcgaact cctgacctca agtgatccac ccgccttggc ctccccacgt     41400
gctgggattg caggcgtgag ccactgcgcc cgccttgatc tttacacaag gggtttaggg    41460
taggtagcct tctctgaacc aggagaacag cctgtgcgaa ggccctgagg ctggaccgtg    41520
cctgttgggt ttgaggccgt tgtagctgga gcaaacagag agagggtaa aaaggcagga     41580
```

```
ggctaccagg caggttgtgc agagccttgt gggccactgg ggaggacttt ggcttttgcc   41640
ctgagagcgg tgggaagtga ctgaatccgg tactcaccgt ctccctctgg cggctcctgg   41700
gggaacatgc ttggggatca ggctggggga ggctgccagg cccaggaggt gagaagtagg   41760
tggcctccag ccgtgtttcc tgaatgctgg actgatagtt tccgctgttt accatttgtt   41820
ggcagagaca gatggtcagt ctggaggatg acgtggcgtg aacatctgcc tggagtcccg   41880
tccctgccca gaacccttcc tgagacctcg ccggccttgt tttattcaaa gacagagaag   41940
accaaagcat tgcctgccag agctttgttt tatatattta ttcatctggg aggcagaaca   42000
ggcttcggac agtgcccatg caatggcttg ggttgggatt ttggtttctt cctttcctcg   42060
tgaaggataa gagaaacagg cccgggggga ccaggatgac acctccattt ctctccagga   42120
agttttgagt ttctctccac cgtgacacaa tcctcaaaca tggaagatga aggggaggg   42180
gatgtcaggc ccagagaagc aagtggcttt caacacacaa cagcagatgg caccaacggg   42240
accccctggc cctgcctcat ccaccaatct ctaagccaaa cccctaaact caggagtcaa   42300
cgtgtttacc tcttctatgc aagccttgct agacagccag gttagccttt gccctgtcac   42360
ccccgaatca tgacccaccc agtgtctttc gaggtgggtt tgtaccttcc ttaagccagg   42420
aaagggattc atggcgtcgg aaatgatctg gctgaatccg tggtggcacc gagaccaaac   42480
tcattcacca aatgatgcca cttcccagag gcagagcctg agtcactggt cacccttaat   42540
atttattaag tgcctgagac acccggttac cttggccgtg aggacacgtg gcctgcaccc   42600
aggtgtggct gtcaggacac cagcctggtg cccatcctcc cgaccccctac ccacttccat   42660
tcccgtggtc tccttgcact ttctcagttc agagttgtac actgtgtaca tttggcattt   42720
gtgttattat tttgcactgt tttctgtcgt gtgtgttggg atgggatccc aggccaggga   42780
aagcccgtgt caatgaatgc cggggacaga gaggggcagg ttgaccggga cttcaaagcc   42840
gtgatcgtga atatcgagaa ctgccattgt cgtctttatg tccgcccacc tagtgcttcc   42900
acttctatgc aaatgcctcc aagccattca cttccccaat cttgtcgttg atgggtatgt   42960
gtttaaaaca tgcacggtga ggccgggcgc agtggctcac gcctgtaatc ccagcacttt   43020
gggaggccga ggcgggtgga tcatgaggtc aggagatcga gaccatcctg gctaacacgt   43080
gaaaccccgt ctctactaaa aatacaaaaa attagccggg cgtggtggcg ggcacctgta   43140
gtcccagcta ctcgggaggc tgaggcagga gaatggtgtg aacccgggaa gcggagcttg   43200
cagtgagccg agattgcgcc actgcagtcc gcagtctggc ctgggcgaca gagcgagact   43260
ccgtctcaaa aaaaaaaaac aaaaaaaaac catgcatggt gcatcagcag cccatggcct   43320
ctggccaggc atggcgaggc tgaggtggga ggatggtttg agctcaggca tttgaggctg   43380
tcgtgagcta tgattatgcc actgcttccc agcctgggca acatagtaag accccatctc   43440
ttaaaaaatg aatttggcca gacacaggtg cctcacgcct gtaatcccag cactttggga   43500
ggctgagctg atcacttgga gttcaggagt tggagaccag gctgagcaa caaagcgaga   43560
tcccatctct acaaaaacca aaaagttaaa aatcagctgg gtacggtggc acgtgcctgt   43620
gatcccagct acttgggagg ctgaggcagg aggatcgcct gagcccagga ggtgaggtt   43680
gcagtgagcc atgatcgagc cactgcactc cagcctgggc aacagatgaa gaccctattt   43740
cagaaataca actataaaaa aataaataaa tcctccagtc tggatcgttt gacgggactt   43800
caggttcttt ctgaaatcgc cgtgttactg ttgcactgat gtccggagag acagtgacag   43860
cctccgtcag actcccgcgt gaagatgtca caagggattg gcaattgtcc ccagggacaa   43920
aacactgtgt cccccccagt gcagggaacc gtgataagcc tttctggttt cggagcacgt   43980
```

```
aaatgcgtcc ctgtacagat agtggggatt ttttgttatg tttgcactt  gtatattggt   44040 tgaaactgtt atcacttata tatatatata tacacacata tatataaaat ctattttattt  44100 ttgcaaaccc tggttgctgt atttgttcag tgactattct cggggccctg tgtaggggggt  44160 tattgcctct gaaatgcctc ttctttatgt acaaagatta tttgcacgaa ctggactgtg   44220
tgcaacgctt tttgggagaa tgatgtcccc gttgtatgta tgagtggctt ctgggagatg   44280
ggtgtcactt tttaaaccac tgtatagaag gttttttgtag cctgaatgtc ttactgtgat  44340
caattaaatt tcttaaatg                                                44359

<210> SEQ ID NO 31
<211> LENGTH: 5175
<212> TYPE: DNA
<213> ORGANISM: Homo sapiens

<400> SEQUENCE: 31
gccccgagtg caatcgcggg aagccagggt ttccagctag gacacagcag gtcgtgatcc      60
gggtcgggac actgcctggc agaggctgcg agcatggggc cctggggctg gaaattgcgc    120
tggaccgtcg ccttgctcct cgccgcgcg gggactgcag tgggcgacag atgtgaaaga     180
aacgagttcc agtgccaaga cgggaaatgc atctcctaca gtgggtctg cgatggcagc    240 gctgagtgcc aggatggctc tgatgagtcc caggagacgt gcttgtctgt cacctgcaaa   300
tccggggact tcagctgtgg gggccgtgtc aaccgctgca ttcctcagtt ctggaggtgc   360
gatggccaag tggactgcga caacggctca gacgagcaag gctgtccccc caagacgtgc   420
tcccaggacg agtttcgctg ccacgatggg aagtgcatct ctcggcagtt cgtctgtgac   480
tcagaccggg actgcttgga cggctcagac gaggcctcct gcccggtgct cacctgtggt   540
cccgccagct tccagtgcaa cagctccacc tgcatccccc agctgtgggc ctgcgacaac   600
gaccccgact gcgaagatgg ctcggatgag tggccgcagc gctgtagggg tctttacgtg    660
ttccaagggg acagtagccc ctgctcggcc ttcgagttcc actgcctaag tggcgagtgc    720
atccactcca gctggcgctg tgatggtggc cccgactgca aggacaaatc tgacgaggaa   780
aactgcgctg tggccacctg tcgccctgac gaattccagt gctctgatgg aaactgcatc   840
catggcagcc ggcagtgtga ccgggaatat gactgcaagg acatgagcga tgaagttggc   900
tgcgttaatg tgcacactctg cgagggaccc aacaagttca gtgtcacag cggcgaatgc   960 atcacctgg acaaagtctg caacatggct agagactgcc gggactggtc agatgaaccc   1020
atcaaagagt gcgggaccaa cgaatgcttg gacaacaacg gcggctgttc ccacgtctgc   1080
aatgacctta agatcggcta cgagtgcctg tgccccgacg gcttccagct ggtggcccag   1140
cgaagatgcg aagatatcga tgagtgtcag gatcccgaca cctgcagcca gctctgcgtg   1200
aacctggagg gtggctacaa gtgccagtgt gaggaaggct tccagctgga ccccacacg   1260 aaggcctgca aggctgtggg ctccatcgcc tacctcttct tcaccaaccg gcacgaggtc   1320
aggaagatga cgctggaccg gagcgagtac accagcctca tccccaacct gaggaacgtg   1380
gtcgctctgg acacggaggt ggccagcaat agaatctact ggtctgacct gtcccagaga   1440
atgatctgca gcacccagct tgacagagcc cacggcgtct cttcctatga caccgtcatc   1500
agcagggaca tccaggcccc cgacgggctg gctgtggact ggatccacag caacatctac   1560
tggaccgact ctgtcctggg cactgtctct gttgcggata ccaagggcgt gaagaggaaa   1620
acgttattca gggagaacgg ctccaagcca agggccatcg tggtggatcc tgttcatggc   1680
ttcatgtact ggactgactg ggaaactccc gccaagatca agaaaggggg cctgaatggt   1740
```

```
gtggacatct actcgctggt gactgaaaac attcagtggc ccaatggcat caccctagat    1800
ctcctcagtg gccgcctcta ctgggttgac tccaaacttc actccatctc aagcatcgat    1860
gtcaatgggg gcaaccggaa gaccatcttg gaggatgaaa agaggctggc ccacccttc     1920 tccttggccg tctttgagga caaagtattt tggacagata tcatcaacga agccattttc    1980
agtgccaacc gcctcacagg ttccgatgtc aacttgttgg ctgaaaacct actgtcccca    2040
gaggatatgg tcctcttcca caacctcacc cagccaagag gagtgaactg gtgtgagagg    2100
accaccctga gcaatggcgg ctgccagtat ctgtgcctcc ctgccccgca gatcaacccc    2160
cactcgccca gtttacctg cgcctgcccg gacggcatgc tgctggccag ggacatgagg     2220
agctgcctca cagaggctga ggctgcagtg gccacccagg agacatccac cgtcaggcta    2280
aaggtcagct ccacagccgt aaggacacag cacacaacca cccggcctgt tcccgacacc    2340
tcccggctgc ctggggccac ccctgggctc accacggtgg agatagtgac aatgtctcac    2400
caagctctgg gcgacgttgc tggcagagga aatgagaaga agcccagtag cgtgagggct    2460
ctgtccattg tcctccccat cgtgctcctc gtcttccttt gcctgggggt cttccttcta    2520
tggaagaact ggcggcttaa gaacatcaac agcatcaact ttgacaaccc cgtctatcag    2580
aagaccacag aggatgaggt ccacatttgc cacaaccagg acggctacag ctacccctcg    2640
agacagatgg tcagtctgga ggatgacgtg gcgtgaacat ctgcctggag tcccgccct    2700 gcccagaacc cttcctgaga cctcgccggc cttgttttat tcaaagacag agaagaccaa    2760
agcattgcct gccagagctt tgttttatat atttattcat ctgggaggca gaacaggctt    2820
cggacagtgc ccatgcaatg gcttgggttg ggattttggt ttcttccttt cctgtgaagg    2880
ataagagaaa caggcccggg gggaccagga tgacacctcc atttctctcc aggaagtttt    2940
gagtttctct ccaccgtgac acaatcctca aacatggaag atgaaagggc aggggatgtc    3000
aggcccagag aagcaagtgg ctttcaacac acaacagcag atggcaccaa cgggacccc    3060 tggccctgcc tcatccacca atctctaagc caaacccta aactcaggag tcaacgtgtt   3120
tacctcttct atgcaagcct tgctagacag ccaggttagc cttttgccctg tcacccccga   3180 atcatgaccc acccagtgtc tttcgaggtg ggtttgtacc ttccttaagc caggaaaggg   3240
attcatggcg tcggaaatga tctggctgaa tccgtggtgg caccgagacc aaactcattc   3300
accaaatgat gccacttccc agaggcagag cctgagtcac cggtcaccct taatatttat   3360
taagtgcctg agacacccgg ttaccttggc cgtgaggaca cgtggcctgc acccaggtgt   3420
ggctgtcagg acaccagcct ggtgcccatc ctcccgaccc ctacccactt ccattcccgt    3480
ggtctccttg cactttctca gttcagagtt gtacactgtg tacatttggc atttgtgtta    3540
ttattttgca ctgttttctg tcgtgtgtgt tgggatggga tcccaggcca gggaaagccc    3600
gtgtcaatga atgccgggga cagagagggg caggttgacc gggacttcaa agccgtgatc    3660
gtgaatatcg agaactgcca ttgtcgtctt tatgtccgcc cacctagtgc ttccacttct    3720
atgcaaatgc ctccaagcca ttcacttccc caatcttgtc gttgatgggt atgtgtttaa    3780
aacatgcacg gtgaggccgg gcgcagtggc tcacgcctg taatcccagc actttgggag     3840
gccgaggcgg gtggatcatg aggtcaggag atcgagacca tcctggctaa caaggtgaaa    3900
ccccgtctct actaaaaata caaaaaatta gccgggcgcg tggtgggca cctgtagtcc     3960 cagctactcg ggaggctgag gcaggagaat ggtgtgaacc cgggaagcgg agcttgcagt    4020
gagccgagat tgcgccactg cagtccgcag tctggcctgg gcgacagagc gagactccgt    4080
ctcaaaaaaa acaaaacaaa aaaaaaccat gcatggtgca tcagcagccc atggcctctg    4140
```

-continued

```
gccaggcatg gcgaggctga ggtgggagga tggtttgagc tcaggcattt gaggctgtcg    4200
tgagctatga ttatgccact gctttccagc ctgggcaaca tagtaagacc ccatctctta    4260
aaaaatgaat ttggccagac acaggtgcct cacgcctgta atcccagcac tttgggaggc    4320
tgagctggat cacttgagtt caggagttgg agaccaggcc tgagcaacaa agcgagatcc    4380
catctctaca aaaccaaaa agttaaaaat cagctgggta tggtggcacg tgcctgtgat    4440
cccagctact gggaggctg aggcaggagg atcgcctgag cccaggaggt ggaggttgca    4500
gtgagccatg atcgagccac tgcactccag cctgggcaac agatgaagac cctatttcag    4560
aaatacaact ataaaaaaaa taaataaatc ctccagtctg gatcgtttga cgggacttca    4620
ggttctttct gaaatcgccg tgttactgtt gcactgatgt ccggagagac agtgacagcc    4680
tccgtcagac tccgcgtga agatgtcaca agggattggc aattgtcccc agggacaaaa    4740
cactgtgtcc cccccagtgc agggaaccgt gataagcctt tctggtttcg gagcacgtaa    4800
atgcgtccct gtacagatag tggggatttt ttgttatgtt tgcactttgt atattggttg    4860
aaactgttat cacttatata tatatataca cacatatata taaaatctat ttattttgc     4920 aaaccctggt tgctgtatt gttcagtgac tattctcggg gccctgtgta gggggttatt    4980
gcctctgaaa tgcctcttct ttatgtacaa agattatttg cacgaactgg actgtgtgca    5040 acgcttttg ggagaatgat gtccccgttg tatgtatgag tggcttctgg gagatgggtg    5100 tcactttta aaccactgta tagaaggttt ttgtagcctg aatgtcttac tgtgatcaat    5160
taaatttctt aaatg                                                    5175
```

<210> SEQ ID NO 32
<211> LENGTH: 860
<212> TYPE: PRT
<213> ORGANISM: Homo sapiens

<400> SEQUENCE: 32

```
Met Gly Pro Trp Gly Trp Lys Leu Arg Trp Thr Val Ala Leu Leu Leu
 1               5                  10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190
```

```
Asp Ser Ser Pro Cys Ser Ala Phe Glu Phe His Cys Leu Ser Gly Glu
    195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
            245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
        290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
            355                 360                 365

Val Asn Leu Glu Gly Gly Tyr Lys Cys Gln Cys Glu Glu Gly Phe Gln
        370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
        450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
        530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
        610                 615                 620
```

```
Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
            645                 650                 655

Asn Leu Thr Gln Pro Arg Gly Val Asn Trp Cys Glu Arg Thr Thr Leu
        660                 665                 670

Ser Asn Gly Gly Cys Gln Tyr Leu Cys Leu Pro Ala Pro Gln Ile Asn
    675                 680                 685

Pro His Ser Pro Lys Phe Thr Cys Ala Cys Pro Asp Gly Met Leu Leu
690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
                820                 825                 830

Glu Asp Glu Val His Ile Cys His Asn Gln Asp Gly Tyr Ser Tyr Pro
            835                 840                 845

Ser Arg Gln Met Val Ser Leu Glu Asp Asp Val Ala
    850                 855                 860

<210> SEQ ID NO 33
<211> LENGTH: 1420
<212> TYPE: DNA
<213> ORGANISM: Artificial Sequence
<220> FEATURE:
<223> OTHER INFORMATION: Synthetic Sequence

<400> SEQUENCE: 33
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc ccaaggacct gaaatgaccc tgtgccttat ttgaactaac caatcagttc     300
gcttctcgct tctgttcgcg cgcttctgct ccccgagctc aataaaagag cccacaaccc     360
ctcactcggc gcgccagtcc tccgatagac tgcgtcgccc gggtaccgt attcccaata     420 aagcctcttg ctgtttgcat ccgaatcgtg gactcgctga tccttgggag ggtctcctca     480
gattgattga ctgcccacct cggggggtctt tcatttggag gttccaccga gatttggaga     540
cccctgccca gggaccaccg accccccgc cgggaggtaa gctggccagc ggtcgtttcg     600
tgtctgtctc tgtctttgtg cgtgtttgtg ccggcatcta atgtttgcgc ctgcgtctgt     660
actagttagc taactagctc tgtatctggc ggacccgtgg tggaactgac gagttctgaa     720
```

```
cacccggccg caaccctggg agacgtccca gggactttgg gggccgtttt tgtggcccga    780
cctgaggaag ggagtcgatg tggaatccga ccccgtcagg atatgtggtt ctggtaggag    840
acgagaacct aaaacagttc ccgcctccgt ctgaattttt gctttcggtt tggaaccgaa    900
gccgcgcgtc ttgtctgctg cagcgctgca gcatcgttct gtgttgtctc tgtctgactg    960
tgtttctgta tttgtctgaa aattagggcc agactgttac cactcccttca agtttgacct   1020 taggtcactg gaaagatgtc gagcggatcg ctcacaacca gtcggtagat gtcaagaaga   1080
gacgttgggt taccttctgc tctgcagaat ggccaacctt taacgtcgga tggccgcgag   1140
acggcacctt taaccgagac ctcatcaccc aggttaagat caaggtcttt tcacctggcc   1200
cgcatggaca cccagaccag gtcccctaca tcgtgacctg ggaagccttg gcttttgacc   1260 ccctcctg ggtcaagccc tttgtacacc ctaagcctcc gcctcctctt cctccatccg      1320
ccccgtctct ccccccttgaa cctcctcgtt cgaccccgcc tcgatcctcc ctttatccag   1380
ccctcactcc ttctctaggc gccggaatta gatcgatctc                         1420

<210> SEQ ID NO 34
<211> LENGTH: 27
<212> TYPE: DNA
<213> ORGANISM: Artificial Sequence
<220> FEATURE:
<223> OTHER INFORMATION: Vector Region

<400> SEQUENCE: 34
tcgaggtcga cggtatcgat aagctta                                         27

<210> SEQ ID NO 35
<211> LENGTH: 60
<212> TYPE: DNA
<213> ORGANISM: Artificial Sequence
<220> FEATURE:
<223> OTHER INFORMATION: siRNA Region

<400> SEQUENCE: 35
tcgagaaaaa tgtcaaagcg gcgagtgcat tcaagagatg cactcgccgc tttgacaggg    60

<210> SEQ ID NO 36
<211> LENGTH: 4902
<212> TYPE: DNA
<213> ORGANISM: Artificial Sequence
<220> FEATURE:
<223> OTHER INFORMATION: Synthetic Sequence

<400> SEQUENCE: 36
gatctgtggt ctcatacaga acttataaga ttcccaaatc caaagacatt tcacgtttat    60
ggtgatttcc cagaacacat agcgacatgc aaatattgca gggcgccact cccctgtccc   120
tcacagccat cttcctgcca gggcgcacgc gcgctgggtg ttcccgccta gtgacactgg   180
gcccgcgatt ccttggagcg ggttgatgac gtcagcgttc gaattctacc gggtagggga   240
ggcgcttttc ccaaggcagt ctggagcatg cgctttagca gccccgctgg gcacttggcg   300
ctacacaagt ggcctctggc ctcgcacaca ttccacatcc accggtaggc gccaaccggc   360
tccgttcttt ggtggcccct tcgcgccacc ttctactcct cccctagtca ggaagttccc   420
ccccgccccg cagctcgcgt cgtgcaggac gtgacaaatg gaagtagcac gtctcactag   480
tctcgtgcag atggacagca ccgctgagca atggaagcgg gtaggccttt ggggcagcgg   540
ccaatagcag ctttgctcct tcgctttctg ggctcagagg ctgggaaggg gtgggtccgg   600
gggcgggctc aggggcgggc tcaggggcgg ggcgggcgcc cgaaggtcct ccggaggccc   660
```

-continued

```
ggcattctgc acgcttcaaa agcgcacgtc tgccgcgctg ttctcctctt cctcatctcc      720
gggcctttcg acctgcagcc caagctagct taccatgacc gagtacaagc ccacggtgcg      780
cctcgccacc cgcgacgacg tccccagggc cgtacgcacc ctcgccgccg cgttcgccga      840
ctaccccgcc acgcgccaca ccgtcgatcc ggaccgccac atcgagcggg tcaccgagct      900
gcaagaactc ttcctcacgc gcgtcgggct cgacatcggc aaggtgtggg tcgcggacga      960
cggcgccgcg gtggcggtct ggaccacgcc ggagagcgtc gaagcggggg cggtgttcgc     1020
cgagatcggc ccgcgcatgg ccgagttgag cggttcccgg ctggccgcgc agcaacagat     1080
ggaaggcctc ctggcgccgc accggcccaa ggagcccgcg tggttcctgg ccaccgtcgg     1140
cgtctcgccc gaccaccagg gcaagggtct gggcagcgcc gtcgtgctcc ccggagtgga     1200
ggcggccgag cgcgccgggg tgcccgcctt cctggagacc tccgcgcccc gcaacctccc     1260
cttctacgag cggctcggct tcaccgtcac cgccgacgtc gaggtgcccg aaggaccgcg     1320
cacctggtgc atgaccccgca agcccggtgc ctgacgcccg ccccacgacc cgcagcgccc     1380
gaccgaaagg agcgcacgac cccatgcatc gataaaataa agatttttat ttagtctcca     1440
gaaaaagggg ggaatgaaag accccacctg taggtttggc aagctagaga accatcagat     1500
gtttccaggg tgccccaagg acctgaaatg accctgtgcc ttatttgaac taaccaatca     1560
gttcgcttct cgcttctgtt cgcgcgcttc tgctccccga gctcaataaa agagcccaca     1620 accccctcact cggcgcgcca gtcctccgat agactgcgtc gcccgggtac ccgtgtatcc     1680
aataaaccct cttgcagttg catccgactt gtggtctcgc tgttccttgg gagggtctcc     1740
tctgagtgat tgactacccg tcagcggggg tctttcatgg gtaacagttt cttgaagttg     1800
gagaacaaca ttctgagggt aggagtcgaa tattaagtaa tcctgactca attagccact     1860
gttttgaatc cacatactcc aatactcctg aaatagttca ttatggacag cgcagaagag     1920
ctggggagaa ttaattcgta atcatggtca tagctgtttc ctgtgtgaaa ttgttatccg     1980
ctcacaattc cacacaacat acgagccgga agcataaagt gtaaagcctg gggtgcctaa     2040
tgagtgagct aactcacatt aattgcgttg cgctcactgc ccgctttcca gtcgggaaac     2100
ctgtcgtgcc agctgcatta atgaatcggc caacgcgcgg ggagaggcgg tttgcgtatt     2160
gggcgctctt ccgcttcctc gctcactgac tcgctgcgct cggtcgttcg gctgcggcga     2220
gcggtatcag ctcactcaaa ggcggtaata cggttatcca cagaatcagg ggataacgca     2280
ggaaagaaca tgtgagcaaa aggccagcaa aaggccagga accgtaaaaa ggccgcgttg     2340
ctggcgtttt tccataggct ccgcccccct gacgagcatc acaaaaatcg acgctcaagt     2400
cagaggtggc gaaacccgac aggactataa agataccagg cgtttccccc tggaagctcc     2460
ctcgtgcgct ctcctgttcc gaccctgccg cttaccggat acctgtccgc ctttctccct     2520
tcgggaagcg tggcgctttc tcatagctca cgctgtaggt atctcagttc ggtgtaggtc     2580
gttcgctcca agctgggctg tgtgcacgaa ccccccgttc agcccgaccg ctgcgcctta     2640
tccggtaact atcgtcttga gtccaacccg gtaagacacg acttatcgcc actggcagca     2700
gccactggta acaggattag cagagcgagg tatgtaggcg gtgctacaga gttcttgaag     2760
tggtggccta actacggcta cactagaagg acagtatttg gtatctgcgc tctgctgaag     2820
ccagttacct tcggaaaaag agttggtagc tcttgatccg gcaaacaaac caccgctggt     2880
agcggtggtt ttttgtttg caagcagcag attacgcgca gaaaaaagg atctcaagaa     2940 gatcctttga tcttttctac ggggtctgac gctcagtgga acgaaaactc acgttaaggg     3000
attttggtca tgagattatc aaaaaggatc ttcacctaga tccttttaaa ttaaaaatga     3060
```

-continued

| | | |
|---|---|---|
| agtttttaaat caatctaaag tatatatgag taaacttggt ctgacagtta ccaatgctta | 3120 | |
| atcagtgagg cacctatctc agcgatctgt ctatttcgtt catccatagt tgcctgactc | 3180 | |
| cccgtcgtgt agataactac gatacgggag ggcttaccat ctggcccag tgctgcaatg | 3240 | |
| ataccgcgag acccacgctc accggctcca gatttatcag caataaacca gccagccgga | 3300 | |
| agggccgagc gcagaagtgg tcctgcaact ttatccgcct ccatccagtc tattaattgt | 3360 | |
| tgccgggaag ctagagtaag tagttcgcca gttaatagtt tgcgcaacgt tgttgccatt | 3420 | |
| gctacaggca tcgtggtgtc acgctcgtcg tttggtatgg cttcattcag ctccggttcc | 3480 | |
| caacgatcaa ggcgagttac atgatccccc atgttgtgca aaaagcggt tagctccttc | 3540 | |
| ggtcctccga tcgttgtcag aagtaagttg gccgcagtgt tatcactcat ggttatggca | 3600 | |
| gcactgcata attctcttac tgtcatgcca tccgtaagat gcttttctgt gactggtgag | 3660 | |
| tactcaacca agtcattctg agaatagtgt atgcggcgac cgagttgctc ttgcccggcg | 3720 | |
| tcaatacggg ataataccgc gccacatagc agaactttaa aagtgctcat cattggaaaa | 3780 | |
| cgttcttcgg ggcgaaaact ctcaaggatc ttaccgctgt tgagatccag ttcgatgtaa | 3840 | |
| cccactcgtg cacccaactg atcttcagca tcttttactt tcaccagcgt ttctgggtga | 3900 | |
| gcaaaaacag gaaggcaaaa tgccgcaaaa aagggaataa gggcgacacg aaatgttga | 3960 | |
| atactcatac tcttcctttt tcaatattat tgaagcattt atcagggtta ttgtctcatg | 4020 | |
| agcggataca tatttgaatg tatttagaaa aataaacaaa taggggttcc gcgcacattt | 4080 | |
| ccccgaaaag tgccacctga cgtctaagaa accattatta tcatgacatt aacctataaa | 4140 | |
| aataggcgta tcacgaggcc ctttcgtctc gcgcgtttcg gtgatgacgg tgaaaacctc | 4200 | |
| tgacacatgc agctcccgga gacggtcaca gcttgtctgt aagcggatgc cgggagcaga | 4260 | |
| caagcccgtc agggcgcgtc agcgggtgtt ggcgggtgtc ggggctggct taactatgcg | 4320 | |
| gcatcagagc agattgtact gagagtgcac catatgcggt gtgaaatacc gcacagatgc | 4380 | |
| gtaaggagaa aataccgcat caggcgccat tcgccattca ggctgcgcaa ctgttgggaa | 4440 | |
| gggcgatcgg tgcgggcctc ttcgctatta cgccagctgg cgaaaggggg atgtgctgca | 4500 | |
| aggcgattaa gttgggtaac gccagggttt tcccagtcac gacgttgtaa aacgacggcg | 4560 | |
| caaggaatgg tgcatgcaag gagatggcgc ccaacagtcc cccggccacg gggcctgcca | 4620 | |
| ccatacccac gccgaaacaa gcgctcatga gcccgaagtg gcgagccga tcttccccat | 4680 | |
| cggtgatgtc ggcgatatag gcgccagcaa ccgcacctgt ggcgccggtg atgccggcca | 4740 | |
| cgatgcgtcc ggcgtagagg cgattagtcc aatttgttaa agacaggata tcagtggtcc | 4800 | |
| aggctctagt tttgactcaa caatatcacc agctgaagcc tatagagtac gagccataga | 4860 | |
| taaaataaaa gatttatttt agtctccaga aaagggggg aa | 4902 | |

<210> SEQ ID NO 37
<211> LENGTH: 6307
<212> TYPE: DNA
<213> ORGANISM: Artificial Sequence
<220> FEATURE:
<223> OTHER INFORMATION: Synthetic Sequence

<400> SEQUENCE: 37

| | | |
|---|---|---|
| tcgcgcgttt cggtgatgac ggtgaaaacc tctgacacat gcagctcccg gagacggtca | 60 | |
| cagcttgtct gtaagcggat gccgggagca gacaagcccg tcagggcgcg tcagcgggtg | 120 | |
| ttggcgggtg tcggggctgg cttaactatg cggcatcaga gcagattgta ctgagagtgc | 180 | |
| accatatgcg gtgtgaaata ccgcacagat gcgtaaggag aaaataccgc atcaggcgcc | 240 | |

-continued

```
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt accctacagt    420
tgaagtcgga agtttacata cacttaagtt ggagtcatta aaactcgttt ttcaactact    480
ccacaaattt cttgttaaca acaatagtt ttggcaagtc agttaggaca tctactttgt    540
gcatgacaca agtcattttt ccaacaattg tttacagaca gattatttca cttataattc    600
actgtatcac aattccagtg ggtcagaagt ttacatacac taagttgact gtgcctttaa    660
acagcttgga aaattccaga aaatgatgtc atggctttag aagcttctga tagactaatt    720
gacatcattt gagtcaattg gaggtgtacc tgtggatgta tttcaaggga attctgtgga    780
atgtgtgtca gttagggtgt ggaaagtccc caggctcccc aggcaggcag aagtatgcaa    840
agcatcgagg atgtacgggc cagatatacg cgataacttc gtataatgta tgctatacga    900
agttatcgcg tgaggttttc accgtcatca ccgaaacgcg cgaggcagct gtggaatgtg    960
tgtcagttag ggtgtggaaa gtccccaggc tccccagcag gcagaagtat gcaaagcatg   1020
catctcaatt agtcagcaac caggtgtgga aagtccccag gctccccagc aggcagaagt   1080
atgcaaagca tgcatctcaa ttagtcagca accatagtcc cgcccctaac tccgcccatc   1140
ccgcccctaa ctccgcccag ttccgcccat tctccgcccc atggctgact aattttttttt  1200
atttatgcag aggccgaggc cgcctcggcc tctgagctat tccagaagta gtgaggaggc   1260
ttttttggag ctaccatgg agaagttact attccgaagt tcctattctc tagaaagtat    1320
aggaacttca agcttggcac tggtgagcaa gggcgaggag ctgttcaccg gggtggtgcc   1380
catcctggtc gagctggacg gcgacgtaaa cggccacaag ttcagcgtgt ccggcgaggg   1440
cgagggcgat gccacctacg gcaagctgac cctgaagttc atctgcacca ccggcaagct   1500
gcccgtgccc tggcccaccc tcgtgaccac cctgacctac ggcgtgcagt gcttcagccg   1560
ctaccccgac cacatgaagc agcacgactt cttcaagtcc gccatgcccg aaggctacgt   1620
ccaggagcgc accatcttct tcaaggacga cggcaactac aagacccgcg ccgaggtgaa   1680
gttcgagggc gacaccctgg tgaaccgcat cgagctgaag ggcatcgact tcaaggagga   1740
cggcaacatc ctggggcaca agctggagta caactacaac agccacaacg tctatatcat   1800
ggccgacaag cagaagaacg gcatcaaggt gaacttcaag atccgccaca acatcgagga   1860
cggcagcgtg cagctcgccg accactacca gcagaacacc cccatcggcg acggccccgt   1920
gctgctgccc gacaaccact acctgagcac ccagtccgcc ctgagcaaag accccaacga   1980
gaagcgcgat cacatggtcc tgctggagtt cgtgaccgcc gccgggatca ctctcggcat   2040
ggacgagctg tacaagtaaa gcggccgcgg ccaattgggc caccggtgct agccccctaa   2100
cgttactggc cgaagccgct tggaataagg ccggtgtgcg tttgtctata tgttattttc   2160
caccatattg ccgtcttttg gcaatgtgag ggcccggaaa cctggccctg tcttcttgac   2220
gagcattcct aggggtcttt cccctctcgc caaaggaatg caaggtctgt tgaatgtcgt   2280
gaaggaagca gttcctctgg aagcttcttg aagacaaaca acgtctgtag cgacccttg    2340
caggcagcgg aaccccccac ctggcgacag gtgcctctgc ggccaaaagc cacgtgtata   2400
agatacacct gcaaaggcgg cacaaccccca gtgccacgtt gtgagttgga tagttgtgga   2460
aagagtcaaa tggctctcct caagcgtatt caacaagggg ctgaaggatg cccagaaggt   2520
acccattgt atgggatctg atctggggcc tcggtgcaca tgctttacat gtgtttagtc    2580
gaggttaaaa aacgtctagg cccccgaac cacggggacg tggttttcct ttgaaaaaca    2640
```

```
cgataatacc atgaccgagt acaagcccac ggtgcgcctc gccacccgcg acgacgtccc    2700
ccgggccgta cgcaccctcg ccgccgcgtt cgccgactac cccgccacgc gccacaccgt    2760
cgatccggac cgccacatcg agcgggtcac cgagctgcaa gaactcttcc tcacgcgcgt    2820
cgggctcgac atcggcaagg tgtgggtcgc ggacgacggc gccgcggtgg cggtctggac    2880
cacgccggag agcgtcgaag cggggcggt gttcgccgag atcggcccgc gcatggccga    2940
gttgagcggt tcccgctggg ccgcgcagca acagatggaa ggcctcctgg cgccgcaccg    3000
gcccaaggag cccgcgtggt tcctggccac cgtcggcgtc tcgcccgacc accagggcaa    3060
gggtctgggc agcgccgtcg tgctccccgg agtggaggcg gccgagcgcg ccggggtgcc    3120
cgccttcctg gagacctccg cgccccgcaa cctcccttc tacgagcggc tcggcttcac    3180
cgtcaccgcc gacgtcgagg tgcccgaagg accgcgcacc tggtgcatga cccgcaagcc    3240
cggtgcctga cgcccgccca aagacccgc agcgcccgac cgaaaggagc gcacgacccc    3300
atgcatcgaa tcgatatcgc ggccgcgact ctagatcata atcagcccgg gggtgatcag    3360
cctcgactgt gccttctagt tgccagccat ctgttgtttg ccctccccc gtgccttcct    3420 tgaccctgga aggtgccact cccactgtcc tttcctaata aaatgaggaa attgcatcgc    3480
attgtctgag taggtgtcat tctattctgg ggggtggggt ggggcaggac agcaagggg    3540 aggattggga agacaatagc aggcatgctg gggatgcggt gggctctatg gaaccagctg    3600
gggctcgaca ttctagttgt ggtttgtcca aactcatcaa tgtatcttat catgtctgga    3660
tcccatcaca aagctctgac ctcaatccta tagaaaggag gaatgagcca aaattcaccc    3720
aacttattgt gggaagcttg tggaaggcta ctcgaaatgt ttgacccaag ttaaacaatt    3780
taaaggcaat gctaccaaat actaattgag tgtatgttaa cttctgaccc actgggaatg    3840
tgatgaaaga aataaaagct gaaatgaatc attctctcta ctattattct gatatttcac    3900
attcttaaaa taaagtggtg atcctaactg accttaagac agggaatctt tactcggatt    3960
aaatgtcagg aattgtgaaa aagtgagttt aaatgtattt ggctaaggtg tatgtaaact    4020
tccgacttca actgtaggga tcctctagag tcgacctgca ggcatgcaag cttggcgtaa    4080
tcatggtcat agctgtttcc tgtgtgaaat tgttatccgc tcacaattcc acacaacata    4140
cgagccggaa gcataaagtg taaagcctgg ggtgcctaat gagtgagcta actcacatta    4200
attgcgttgc gctcactgcc cgcttcccag tcgggaaacc tgtcgtgcca gctgcattaa    4260
tgaatcggcc aacgcgcggg gagaggcggt ttgcgtattg ggcgctcttc cgcttcctcg    4320
ctcactgact cgctgcgctc ggtcgttcgg ctgcggcgag cggtatcagc tcactcaaag    4380
gcggtaatac ggttatccac agaatcaggg gataacgcag gaaagaacat gtgagcaaaa    4440
ggccagcaaa aggccaggaa ccgtaaaaag gccgcgttgc tggcgttttt ccataggctc    4500 cgccccctg acgagcatca aaaaatcga cgctcaagtc agaggtggcg aaacccgaca    4560
ggactataaa gataccaggc gtttccccct ggaagctccc tcgtgcgctc tcctgttccg    4620
accctgccgc ttaccggata cctgtccgcc tttctccctt cgggaagcgt ggcgctttct    4680
caatgctcac gctgtaggta tctcagttcg gtgtaggtcg ttcgctccaa gctgggctgt    4740
gtgcacgaac cccccgttca gcccgaccgc tgcgccttat ccggtaacta tcgtcttgag    4800
tccaacccgg taagacacga cttatcgcca ctggcagcag ccactggtaa caggattagc    4860
agagcgaggt atgtaggcgg tgctacagag ttcttgaagt ggtggcctaa ctacggctac    4920
actagaagga cagtatttgg tatctgcgct ctgctgaagc cagttacctt cggaaaaaga    4980
gttggtagct cttgatccgg caaacaaacc accgctggta gcggtggttt ttttgtttgc    5040
```

| | |
|---|---|
| aagcagcaga ttacgcgcag aaaaaaagga tctcaagaag atcctttgat cttttctacg | 5100 |
| gggtctgacg ctcagtggaa cgaaaactca cgttaaggga ttttggtcat gagattatca | 5160 |
| aaaaggatct tcacctagat ccttttaaat taaaaatgaa gttttaaatc aatctaaagt | 5220 |
| atatatgagt aaacttggtc tgacagttac caatgcttaa tcagtgaggc acctatctca | 5280 |
| gcgatctgtc tatttcgttc atccatagtt gcctgactcc ccgtcgtgta gataactacg | 5340 |
| atacgggagg gcttaccatc tggccccagt gctgcaatga taccgcgaga cccacgctca | 5400 |
| ccggctccag atttatcagc aataaaccag ccagccggaa gggccgagcg cagaagtggt | 5460 |
| cctgcaactt tatccgcctc catccagtct attaattgtt gccgggaagc tagagtaagt | 5520 |
| agttcgccag ttaatagttt gcgcaacgtt gttgccattg ctacaggcat cgtggtgtca | 5580 |
| cgctcgtcgt ttggtatggc ttcattcagc tccggttccc aacgatcaag gcgagttaca | 5640 |
| tgatccccca tgttgtgcaa aaaagcggtt agctccttcg gtcctccgat cgttgtcaga | 5700 |
| agtaagttgg ccgcagtgtt atcactcatg gttatggcag cactgcataa ttctcttact | 5760 |
| gtcatgccat ccgtaagatg cttttctgtg actggtgagt actcaaccaa gtcattctga | 5820 |
| gaatagtgta tgcggcgacc gagttgctct tgcccggcgt caatacggga taataccgcg | 5880 |
| ccacatagca gaactttaaa agtgctcatc attggaaaac gttcttcggg gcgaaaactc | 5940 |
| tcaaggatct taccgctgtt gagatccagt tcgatgtaac ccactcgtgc acccaactga | 6000 |
| tcttcagcat cttttacttt caccagcgtt tctgggtgag caaaaacagg aaggcaaaat | 6060 |
| gccgcaaaaa agggaataag ggcgacacgg aaatgttgaa tactcatact cttcctttt | 6120 |
| caatattatt gaagcattta tcagggttat tgtctcatga gcggatacat atttgaatgt | 6180 |
| atttagaaaa ataaacaaat aggggttccg cgcacatttc cccgaaaagt gccacctgac | 6240 |
| gtctaagaaa ccattattat catgacatta acctataaaa ataggcgtat cacgaggccc | 6300 |
| tttcgtc | 6307 |

<210> SEQ ID NO 38
<211> LENGTH: 6221
<212> TYPE: DNA
<213> ORGANISM: Artificial Sequence
<220> FEATURE:
<223> OTHER INFORMATION: Synthetic Sequence

<400> SEQUENCE: 38

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt accctacagt | 420 |
| tgaagtcgga gtttacata cacttaagtt ggagtcatta aaactcgttt ttcaactact | 480 |
| ccacaaattt cttgttaaca acaatagttt ttggcaagtc agttaggaca tctactttgt | 540 |
| gcatgacaca agtcattttt ccaacaattg tttacagaca gattatttca cttataattc | 600 |
| actgtatcac aattccagtg ggtcagaagt ttacatacac taagttgact gtgcctttaa | 660 |
| acagcttgga aaattccaga aaatgatgtc atggctttag aagcttctga tagactaatt | 720 |
| gacatcattt gagtcaattg gaggtgtacc tgtggatgta tttcaaggga attctgtgga | 780 |

```
atgtgtgtca gttagggtgt ggaaagtccc caggctcccc aggcaggcag aagtatgcaa    840
agcatcgagg atgtacgggc cagatatacg cgtatctgag gggactaggg tgtgtttagg    900
cgaaaagcgg ggcttcggtt gtacgcggtt aggagtcccc tcaggatata gtagtttcgc    960
ttttgcatag ggaggggaa atgtagtctt atgcaataca cttgtagtct tgcaacatgg   1020
taacgatgag ttagcaacat gccttacaag gagagaaaaa gcaccgtgca tgccgattgg   1080
tggaagtaag gtggtacgat cgtgccttat taggaaggca acagacaggt ctgacatgga   1140
ttggacgaac cactgaattc cgcattgcag agataattgt atttaagtgc ctagctcgat   1200
acaataaacg ccatttgacc attcaccaca ttggtgtgca cctccaaagc ttgatatcta   1260
ccatggagaa gttactattc cgaagttcct attctctaga aagtatagga acttcaagct   1320
tggcactggt gagcaagggc gaggagctgt tcaccggggt ggtgcccatc ctggtcgagc   1380
tggacggcga cgtaaacggc cacaagttca gcgtgtccgg cgagggcgag ggcgatgcca   1440
cctacggcaa gctgaccctg aagttcatct gcaccaccgg caagctgccc gtgccctggc   1500
ccaccctcgt gaccaccctg acctacggcg tgcagtgctt cagccgctac cccgaccaca   1560
tgaagcagca cgacttcttc aagtccgcca tgcccgaagg ctacgtccag gagcgcacca   1620
tcttcttcaa ggacgacggc aactacaaga cccgcgccga ggtgaagttc gagggcgaca   1680
ccctggtgaa ccgcatcgag ctgaagggca tcgacttcaa ggaggacggc aacatcctgg   1740
ggcacaagct ggagtacaac tacaacagcc acaacgtcta tatcatggcc gacaagcaga   1800
agaacggcat caaggtgaac ttcaagatcc gccacaacat cgaggacggc agcgtgcagc   1860
tcgccgacca ctaccagcag aacacccca tcggcgacgg ccccgtgctg ctgcccgaca   1920
accactacct gagcacccag tccgccctga gcaaagaccc caacgagaag cgcgatcaca   1980
tggtcctgct ggagttcgtg accgccgccg ggatcactct cggcatggac gagctgtaca   2040
agtaaagcat agcggccgta aattccgccc ctctctccct cccccccccc taacgttact   2100
ggccgaagcc gcttggaata aggccggtgt gcgtttgtct atatgttatt ttccaccata   2160
ttgccgtctt ttggcaatgt gagggcccgg aaacctggcc ctgtcttctt gacgagcatt   2220
cctaggggtc tttcccctct cgccaaagga atgcaaggtc tgttgaatgt cgtgaaggaa   2280
gcagttcctc tggaagcttc ttgaagacaa acaacgtctg tagcgaccct ttgcaggcag   2340
cggaaccccc cacctggcga caggtgcctc tgcggccaaa agccacgtgt ataagataca   2400
cctgcaaagg cggcacaacc ccagtgccac gttgtgagtt ggatagttgt ggaaagagtc   2460
aaatggctct cctcaagcgt attcaacaag ggctgaagg atgcccagaa ggtaccccat   2520
tgtatgggat ctgatctggg gcctcggtgc acatgcttta catgtgttta gtcgaggtta   2580
aaaaacgtct aggccccccg aaccacgggg acgtggtttt cctttgaaaa acacgatgat   2640
aagcttgcca caaccatgac cgagtacaag cccacggtgc gcctcgccac ccgcgacgac   2700
gtccccgggg ccgtacgcac cctcgccgcc gcgttcgccg actacccgc cacgcgccac   2760
accgtcgatc cggaccgcca catcgagcgg gtcaccgagc tgcaagaact cttcctcacg   2820
cgcgtcgggc tcgacatcgg caaggtgtgg gtcgcggacg acggcgccgc ggtggcggtc   2880
tggaccacgc cggagagcgt cgaagcgggg gcggtgttcg ccgagatcgg cccgcgcatg   2940
gccgagttga gcggttcccg gctggccgcg cagcaacaga tggaaggcct cctggcgccg   3000
caccggccca aggagcccgc gtggttcctg gccaccgtcg gcgtctcgcc cgaccaccag   3060
ggcaagggtc tgggcagcgc cgtcgtgctc cccgagtgg aggcggccga gcgcgccggg   3120
gtgcccgcct tcctggagac ctccgcgccc cgcaacctcc ccttctacga gcggctcggc   3180
```

```
ttcaccgtca ccgccgacgt cgaggtgccc gaaggaccgc gcacctggtg catgacccgc   3240
aagcccggtg cctgaagatc ccccggggga tcagcctcga ctgtgccttc tagttgccag   3300
ccatctgttg tttgcccctc ccccgtgcct tccttgaccc tggaaggtgc cactcccact   3360
gtcctttcct aataaaatga ggaaattgca tcgcattgtc tgagtaggtg tcattctatt   3420 ctgggggtg gggtggggca ggacagcaag ggggaggatt gggaagacaa tagcaggcat   3480 gctgggatg cggtgggctc tatggaacca gctgggctc gacattctag ttgtggtttg   3540
tccaaactca tcaatgtatc ttatcatgtc tggatcccat cacaaagctc tgacctcaat   3600
cctatagaaa ggaggaatga gccaaaattc acccaactta ttgtgggaag cttgtggaag   3660
gctactcgaa atgtttgacc caagttaaac aatttaaagg caatgctacc aaatactaat   3720
tgagtgtatg ttaacttctg acccactggg aatgtgatga agaaataaa agctgaaatg   3780 aatcattctc tctactatta ttctgatatt tcacattctt aaaataaagt ggtgatccta   3840
actgacctta agacagggaa tctttactcg gattaaatgt caggaattgt gaaaaagtga   3900
gtttaaatgt atttggctaa ggtgtatgta aacttccgac ttcaactgta gggatcctct   3960
agagtcgacc tgcaggcatg caagcttggc gtaatcatgg tcatagctgt ttcctgtgtg   4020
aaattgttat ccgctcacaa ttccacacaa catacgagcc ggaagcataa agtgtaaagc   4080
ctggggtgcc taatgagtga gctaactcac attaattgcg ttgcgctcac tgcccgcttt   4140
ccagtcggga aacctgtcgt gccagctgca ttaatgaatc ggccaacgcg cggggagagg   4200
cggtttgcgt attgggcgct cttccgcttc ctcgctcact gactcgctgc gctcggtcgt   4260
tcggctgcgg cgagcggtat cagctcactc aaaggcggta atacggttat ccacagaatc   4320
aggggataac gcaggaaaga acatgtgagc aaaaggccag caaaaggcca ggaaccgtaa   4380
aaaggccgcg ttgctggcgt ttttccatag gctccgcccc cctgacgagc atcacaaaaa   4440
tcgacgctca gtcagaggt ggcgaaaccc gacaggacta taaagatacc aggcgtttcc   4500
ccctggaagc tccctcgtgc gctctcctgt tccgaccctg ccgcttaccg gatacctgtc   4560
cgcctttctc ccttcgggaa gcgtggcgct ttctcaatgc tcacgctgta ggtatctcag   4620
ttcggtgtag tcgttcgct ccaagctggg ctgtgtgcac gaaccccccg ttcagcccga   4680
ccgctgcgcc ttatccggta actatcgtct tgagtccaac ccggtaagac acgacttatc   4740
gccactggca gcagccactg gtaacaggat tagcagagcg aggtatgtag gcggtgctac   4800
agagttcttg aagtggtggc ctaactacgg ctacactaga aggacagtat tggtatctg   4860 cgctctgctg aagccagtta ccttcggaaa aagagttggt agctcttgat ccggcaaaca   4920
aaccaccgct ggtagcggtg gtttttttgt ttgcaagcag cagattacgc gcagaaaaaa   4980
aggatctcaa gaagatcctt tgatctttc tacgggtct gacgctcagt ggaacgaaaa   5040
ctcacgttaa gggattttgg tcatgagatt atcaaaaagg atcttcacct agatcctttt   5100
aaattaaaaa tgaagtttta aatcaatcta agtatatat gagtaaactt ggtctgacag   5160
ttaccaatgc ttaatcagtg aggcacctat ctcagcgatc tgtctatttc gttcatccat   5220
agttgcctga ctccccgtcg tgtagataac tacgatacgg gagggcttac catctggccc   5280
cagtgctgca atgataccgc gagacccacg ctcaccggct ccagatttat cagcaataaa   5340
ccagccagcc ggaagggccg agcgcagaag tggtcctgca actttatccg cctccatcca   5400
gtctattaat tgttgccggg aagctagagt aagtagttcg ccagttaata gtttgcgcaa   5460
cgttgttgcc attgctacag gcatcgtggt gtcacgctcg tcgtttggta tggcttcatt   5520
cagctccggt tcccaacgat caaggcgagt tacatgatcc cccatgttgt gcaaaaaagc   5580
```

```
ggttagctcc ttcggtcctc cgatcgttgt cagaagtaag ttggccgcag tgttatcact    5640
catggttatg gcagcactgc ataattctct tactgtcatg ccatccgtaa gatgcttttc    5700
tgtgactggt gagtactcaa ccaagtcatt ctgagaatag tgtatgcggc gaccgagttg    5760
ctcttgcccg cgtcaatac gggataatac cgcgccacat agcagaactt aaaagtgct     5820 catcattgga aaacgttctt cggggcgaaa actctcaagg atcttaccgc tgttgagatc    5880
cagttcgatg taacccactc gtgcacccaa ctgatcttca gcatcttta ctttcaccag    5940 cgtttctggg tgagcaaaaa caggaaggca aaatgccgca aaaagggaa taagggcgac    6000 acggaaatgt tgaatactca tactcttcct ttttcaatat tattgaagca tttatcaggg   6060
ttattgtctc atgagcggat acatatttga atgtatttag aaaaataaac aataggggt     6120 tccgcgcaca tttccccgaa aagtgccacc tgacgtctaa gaaaccatta ttatcatgac   6180
attaacctat aaaaataggc gtatcacgag gccctttcgt c                        6221
```

<210> SEQ ID NO 39
<211> LENGTH: 6268
<212> TYPE: DNA
<213> ORGANISM: Artificial Sequence
<220> FEATURE:
<223> OTHER INFORMATION: Synthetic Sequence

<400> SEQUENCE: 39

```
cgcgcgtttc ggtgatgacg gtgaaaacct ctgacacatg cagctcccgg agacggtcac      60
agcttgtctg taagcggatg ccgggagcag acaagcccgt cagggcgcgt cagcgggtgt     120
tggcgggtgt cggggctggc ttaactatgc ggcatcagag cagattgtac tgagagtgca     180
ccatatgcgg tgtgaaatac cgcacagatg cgtaaggaga aaataccgca tcaggcgcca     240
ttcgccattc aggctgcgca actgttggga agggcgatcg gtgcgggcct cttcgctatt     300
acgccagctg gcgaaagggg gatgtgctgc aaggcgatta agttgggtaa cgccagggtt     360
ttcccagtca cgacgttgta aaacgacggc cagtgaattc gagctcggta ccctacagtt     420
gaagtcggaa gtttacatac acttaagttg gagtcattaa aactcgtttt tcaactactc     480
cacaaatttc ttgttaacaa acaatagttt tggcaagtca gttaggacat ctactttgtg    540
catgacacaa gtcatttttc caacaattgt ttacagacag attatttcac ttataattca     600
ctgtatcaca attccagtgg gtcagaagtt tacatacact aagttgactg tgcctttaaa    660
cagcttggaa aattccagaa aatgatgtca tggctttaga agcttctgat agactaattg     720
acatcatttg agtcaattgg aggtgtacct gtggatgtat tcaagggaa ttctgtggaa     780 tgtgtgtcag ttagggtgtg aaagtcccc aggctcccca ggcaggcaga agtatgcaaa    840
gcatcgagga tgtacgggcc agatatacgc gtgaggtttt caccgtcatc accgaaacgc     900
gcgaggcagc tgtggaatgt gtgtcagtta gggtgtggaa agtccccagg ctccccagca     960
ggcagaagta tgcaaagcat gcatctcaat tagtcagcaa ccaggtgtgg aaagtcccca   1020
ggctccccag caggcagaag tatgcaaagc atgcatctca attagtcagc aaccatagtc   1080
ccgcccctaa ctccgcccat cccgcccta actccgccca gttccgccca ttctccgccc    1140
catggctgac taatttttttt tatttatgca gaggccgagg ccgcctcggc ctctgagcta   1200
ttccagaagt agtgaggagg cttttttgga ggctaccatg agaagttac tattccgaag    1260 ttcctattct ctagaaagta taggaacttc aagcttggca ctggtgagca agggcgagga    1320
gctgttcacc ggggtggtgc ccatcctggt cgagctggac ggcgacgtaa acggccacaa   1380
gttcagcgtg tccggcgagg gcgagggcga tgccacctac ggcaagctga ccctgaagtt   1440
```

| | |
|---|---|
| catctgcacc accggcaagc tgcccgtgcc ctggcccacc ctcgtgacca ccctgaccta | 1500 |
| cggcgtgcag tgcttcagcc gctacccccga ccacatgaag cagcacgact tcttcaagtc | 1560 |
| cgccatgccc gaaggctacg tccaggagcg caccatcttc ttcaaggacg acggcaacta | 1620 |
| caagacccgc gccgaggtga agttcgaggg cgacaccctg gtgaaccgca tcgagctgaa | 1680 |
| gggcatcgac ttcaaggagg acggcaacat cctggggcac aagctggagt acaactacaa | 1740 |
| cagccacaac gtctatatca tggccgacaa gcagaagaac ggcatcaagg tgaacttcaa | 1800 |
| gatccgccac aacatcgagg acggcagcgt gcagctcgcc gaccactacc agcagaacac | 1860 |
| ccccatcggc gacggccccg tgctgctgcc cgacaaccac tacctgagca cccagtccgc | 1920 |
| cctgagcaaa gaccccaacg agaagcgcga tcacatggtc ctgctggagt tcgtgaccgc | 1980 |
| cgccgggatc actctcggca tggacgagct gtacaagtaa agcggccgcg ccaattggg | 2040 |
| ccaccggtgc tagccccta acgttactgg ccgaagccgc ttggaataag gccggtgtgc | 2100 |
| gtttgtctat atgttatttt ccaccatatt gccgtctttt ggcaatgtga gggcccggaa | 2160 |
| acctggccct gtcttcttga cgagcattcc taggggtctt tcccctctcg ccaaaggaat | 2220 |
| gcaaggtctt ttgaatgtcg tgaaggaagc agttcctctg gaagcttctt gaagacaaac | 2280 |
| aacgtctgta gcgacccttt gcaggcagcg gaacccccca cctggcgaca ggtgcctctg | 2340 |
| cggccaaaag ccacgtgtat aagatacacc tgcaaaggcg gcacaacccc agtgccacgt | 2400 |
| tgtgagttgg atagttgtgg aaagagtcaa atggctctcc tcaagcgtat tcaacaaggg | 2460 |
| gctgaaggat gcccagaagg tacccccattg tatgggatct gatctggggc ctcggtgcac | 2520 |
| atgctttaca tgtgtttagt cgaggttaaa aaacgtctag gccccccgaa ccacggggac | 2580 |
| gtggttttcc tttgaaaaac acgataatac catgaccgag tacaagccca cggtgcgcct | 2640 |
| cgccacccgc gacgacgtcc cccgggccgt acgcacccte gccgccgcgt tcgccgacta | 2700 |
| ccccgccacg cgccacaccg tcgatccgga ccgccacatc gagcgggtca ccgagctgca | 2760 |
| agaactcttc ctcacgcgcg tcgggctcga catcggcaag gtgtgggtcg cggacgacgg | 2820 |
| cgccgcggtg gcggtctgga ccacgccgga gagcgtcgaa gcggggggcgg tgttcgccga | 2880 |
| gatcggcccg cgcatggccg agttgagcgg ttcccggctg gccgcgcagc aacagatgga | 2940 |
| aggcctcctg gcgccgcacc ggcccaagga gcccgcgtgg ttcctggcca ccgtcggcgt | 3000 |
| ctcgcccgac caccagggca agggtctggg cagcgccgtc gtgctccccg gagtggaggc | 3060 |
| ggccgagcgc gccggggtgc ccgccttcct ggagacctcc gcgccccgca acctccccttt | 3120 |
| ctacgagcgg ctcggcttca ccgtcaccgc cgacgtcgag gtgcccgaag gaccgcgcac | 3180 |
| ctggtgcatg acccgcaagc ccggtgcctg acgcccgccc acaagacccg cagcgcccga | 3240 |
| ccgaaaggag cgcacgaccc catgcatcga atcgatatcg cggccgcgac tctagatcat | 3300 |
| aatcagcccg ggggtgatca gcctcgactg tgccttctag ttgccagcca tctgttgttt | 3360 |
| gcccctcccc cgtgccttcc ttgaccctgg aaggtgccac tcccactgtc ctttcctaat | 3420 |
| aaaatgagga aattgcatcg cattgtctga gtaggtgtca ttctattctg gggggtgggg | 3480 |
| tggggcagga cagcaagggg gaggattggg aagacaatag caggcatgct ggggatgcgg | 3540 |
| tgggctctat ggaaccagct ggggctcgac attctagttg tggtttgtcc aaactcatca | 3600 |
| atgtatctta tcatgtctgg atcccatcac aaagctctga cctcaatcct atagaaagga | 3660 |
| ggaatgagcc aaaattcacc caacttattg tgggaagctt gtggaaggct actcgaaatg | 3720 |
| tttgacccaa gttaaacaat ttaaaggcaa tgctaccaaa tactaattga gtgtatgtta | 3780 |
| acttctgacc cactgggaat gtgatgaaag aaataaaagc tgaaatgaat cattctctct | 3840 |

```
actattattc tgatatttca cattcttaaa ataaagtggt gatcctaact gaccttaaga    3900
cagggaatct ttactcggat taaatgtcag gaattgtgaa aaagtgagtt taaatgtatt    3960
tggctaaggt gtatgtaaac ttccgacttc aactgtaggg atcctctaga gtcgacctgc    4020
aggcatgcaa gcttggcgta atcatggtca tagctgtttc ctgtgtgaaa ttgttatccg    4080
ctcacaattc cacacaacat acgagccgga agcataaagt gtaaagcctg gggtgcctaa    4140
tgagtgagct aactcacatt aattgcgttg cgctcactgc ccgctttcca gtcgggaaac    4200
ctgtcgtgcc agctgcatta atgaatcggc caacgcgcgg ggagaggcgg tttgcgtatt    4260
gggcgctctt ccgcttcctc gctcactgac tcgctgcgct cggtcgttcg gctgcggcga    4320
gcggtatcag ctcactcaaa ggcggtaata cggttatcca cagaatcagg ggataacgca    4380
ggaaagaaca tgtgagcaaa aggccagcaa aaggccagga accgtaaaaa ggccgcgttg    4440
ctggcgtttt tccataggct ccgcccccct gacgagcatc acaaaaatcg acgctcaagt    4500
cagaggtggc gaaacccgac aggactataa agataccagg cgtttccccc tggaagctcc    4560
ctcgtgcgct ctcctgttcc gaccctgccg cttaccggat acctgtccgc ctttctccct    4620
tcgggaagcg tggcgctttc tcaatgctca cgctgtaggt atctcagttc ggtgtaggtc    4680
gttcgctcca agctgggctg tgtgcacgaa ccccccgttc agcccgaccg ctgcgcctta    4740
tccggtaact atcgtcttga gtccaacccg gtaagacacg acttatcgcc actggcagca    4800
gccactggta acaggattag cagagcgagg tatgtaggcg gtgctacaga gttcttgaag    4860
tggtggccta actacggcta cactagaagg acagtatttg gtatctgcgc tctgctgaag    4920
ccagttacct tcggaaaaag agttggtagc tcttgatccg gcaaacaaac caccgctggt    4980
agcggtggtt tttttgtttg caagcagcag attacgcgca gaaaaaaagg atctcaagaa    5040
gatcctttga tcttttctac ggggtctgac gctcagtgga acgaaaactc acgttaaggg    5100
attttggtca tgagattatc aaaaaggatc ttcacctaga tccttttaaa ttaaaaatga    5160
agttttaaat caatctaaag tatatatgag taaacttggt ctgacagtta ccaatgctta    5220
atcagtgagg cacctatctc agcgatctgt ctatttcgtt catccatagt tgcctgactc    5280
cccgtcgtgt agataactac gatacgggag ggcttaccat ctggccccag tgctgcaatg    5340
ataccgcgag acccacgctc accggctcca gatttatcag caataaacca gccagccgga    5400
agggccgagc gcagaagtgg tcctgcaact ttatccgcct ccatccagtc tattaattgt    5460
tgccgggaag ctagagtaag tagttcgcca gttaatagtt tgcgcaacgt tgttgccatt    5520
gctacaggca tcgtggtgtc acgctcgtcg tttggtatgg cttcattcag ctccggttcc    5580
caacgatcaa ggcgagttac atgatccccc atgttgtgca aaaaagcggt tagctccttc    5640
ggtcctccga tcgttgtcag aagtaagttg gccgcagtgt tatcactcat ggttatggca    5700
gcactgcata attctcttac tgtcatgcca tccgtaagat gcttttctgt gactggtgag    5760
tactcaacca agtcattctg agaatagtgt atgcggcgac cgagttgctc ttgcccggcg    5820
tcaatacggg ataataccgc gccacatagc agaactttaa aagtgctcat cattggaaaa    5880
cgttcttcgg ggcgaaaact ctcaaggatc ttaccgctgt tgagatccag ttcgatgtaa    5940
cccactcgtg cacccaactg atcttcagca tcttttactt tcaccagcgt ttctgggtga    6000
gcaaaaacag gaaggcaaaa tgccgcaaaa aagggaataa gggcgacacg gaaatgttga    6060
atactcatac tcttcctttt tcaatattat tgaagcattt atcagggtta ttgtctcatg    6120
agcggataca tatttgaatg tatttagaaa aataaacaaa taggggttcc gcgcacattt    6180
ccccgaaaag tgccacctga cgtctaagaa accattatta tcatgacatt aacctataaa    6240
```
aataggcgta tcacgaggcc ctttcgtc    6268

<210> SEQ ID NO 40
<211> LENGTH: 6346
<212> TYPE: DNA
<213> ORGANISM: Artificial Sequence
<220> FEATURE:
<223> OTHER INFORMATION: Synthetic Sequence

<400> SEQUENCE: 40

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt accctacagt | 420 |
| tgaagtcgga agtttacata cacttaagtt ggagtcatta aaactcgttt ttcaactact | 480 |
| ccacaaattt cttgttaaca acaatagtt ttggcaagtc agttaggaca tctactttgt | 540 |
| gcatgacaca agtcattttt ccaacaattg tttacagaca gattatttca cttataattc | 600 |
| actgtatcac aattccagtg ggtcagaagt ttacatacac taagttgact gtgcctttaa | 660 |
| acagcttgga aaattccaga aaatgatgtc atggctttag aagcttctga tagactaatt | 720 |
| gacatcattt gagtcaattg gaggtgtacc tgtggatgta tttcaaggga attctgtgga | 780 |
| atgtgtgtca gttagggtgt ggaaagtccc caggctcccc aggcaggcag aagtatgcaa | 840 |
| agcatcgagg atgtacgggc cagatatacg cgataacttc gtataatgta tgctatacga | 900 |
| agttatcgcg tgaggttttc accgtcatca ccgaaacgcg cgaggcagct gtggaatgtg | 960 |
| tgtcagttag ggtgtggaaa gtccccaggc tccccagcag gcagaagtat gcaaagcatg | 1020 |
| catctcaatt agtcagcaac caggtgtgga agtccccag gctccccagc aggcagaagt | 1080 |
| atgcaaagca tgcatctcaa ttagtcagca accatagtcc cgcccctaac tccgcccatc | 1140 |
| ccgcccctaa ctccgcccag ttccgcccat tctccgcccc atggctgact aattttttt | 1200 |
| atttatgcag aggccgaggc cgcctcggcc tctgagctat tccagaagta gtgaggaggc | 1260 |
| ttttttggag gctaccatgg agaagttact attccgaagt tcctattctc tagaaagtat | 1320 |
| aggaacttca gcttggcac tggtgagcaa gggcgaggag ctgttcaccg gggtggtgcc | 1380 |
| catcctggtc gagctggacg gcgacgtaaa cggccacaag ttcagcgtgt ccggcgaggg | 1440 |
| cgagggcgat gccacctacg gcaagctgac cctgaagttc atctgcacca ccggcaagct | 1500 |
| gcccgtgccc tggcccaccc tcgtgaccac cctgacctac ggcgtgcagt gcttcagccg | 1560 |
| ctaccccgac cacatgaagc agcacgactt cttcaagtcc gccatgcccg aaggctacgt | 1620 |
| ccaggagcgc accatcttct tcaaggacga cggcaactac aagacccgcg ccgaggtgaa | 1680 |
| gttcgagggc gacaccctgg tgaaccgcat cgagctgaag ggcatcgact tcaaggagga | 1740 |
| cggcaacatc ctggggcaca gctggagta caactacaac agccacaacg tctatatcat | 1800 |
| ggccgacaag cagaagaacg gcatcaaggt gaacttcaag atccgccaca acatcgagga | 1860 |
| cggcagcgtg cagctcgccg accactacca gcagaacacc cccatcggcg acggccccgt | 1920 |
| gctgctgccc gacaaccact acctgagcac ccagtccgcc ctgagcaaag ccccaacga | 1980 |
| gaagcgcgat cacatggtcc tgctggagtt cgtgaccgcc gccgggatca ctctcggcat | 2040 |

```
ggacgagctg tacaagtaaa gcggccgcgg ccaattgggc caccggtgct agccccctaa    2100
cgttactggc cgaagccgct tggaataagg ccggtgtgcg tttgtctata tgttattttc    2160
caccatattg ccgtcttttg gcaatgtgag ggcccggaaa cctggccctg tcttcttgac    2220
gagcattcct aggggtcttt cccctctcgc caaaggaatg caaggtctgt tgaatgtcgt    2280
gaaggaagca gttcctctgg aagcttcttg aagacaaaca acgtctgtag cgacccttttg   2340
caggcagcgg aaccccccac ctggcgacag gtgcctctgc ggccaaaagc cacgtgtata    2400
agatacacct gcaaaggcgg cacaacccca gtgccacgtt gtgagttgga tagttgtgga    2460
aagagtcaaa tggctctcct caagcgtatt caacaagggg ctgaaggatg cccagaaggt    2520
accccattgt atgggatctg atctggggcc tcggtgcaca tgctttacat gtgtttagtc    2580
gaggttaaaa aacgtctagg ccccccgaac cacggggacg tggttttcct ttgaaaaaca    2640
cgataatacc atgaccgagt acaagcccac ggtgcgcctc gccacccgcg acgacgtccc    2700
ccgggccgta cgcacccctcg ccgccgcgtt cgccgactac cccgccacgc gccacaccgt    2760
cgatccggac cgccacatcg agcgggtcac cgagctgcaa gaactcttcc tcacgcgcgt    2820
cgggctcgac atcggcaagg tgtgggtcgc ggacgacggc gccgcggtgg cggtctggac    2880
cacgccggag agcgtcgaag cggggggcggt gttcgccgag atcggcccgc gcatggccga    2940
gttgagcggg tcccggctgg ccgcgcagca acagatggaa ggcctcctgg cgccgcaccg    3000
gcccaaggag cccgcgtggt tcctggccac cgtcggcgtc tcgcccgacc accagggcaa    3060
gggtctgggc agcgccgtcg tgctccccgg agtggaggcg gccgagcgcg ccggggtgcc    3120
cgccttcctg gagacctccg cgccccgcaa cctccccttc tacgagcggc tcggcttcac    3180
cgtcaccgcc gacgtcgagg tgcccgaagg accgcgcacc tggtgcatga cccgcaagcc    3240
cggtgcctga cgcccgccca aagacccgc agcgcccgac cgaaaggagc gcacgacccc    3300
atgcatcgaa tcgatatcgc ggccgcgact ctagatcata atcagcccgg gggtgatcag    3360
cctcgactgt gccttctagt tgccagccat ctgttgtttg cccctccccc gtgccttcct    3420
tgaccctgga aggtgccact cccactgtcc tttcctaata aaatgaggaa attgcatcgc    3480
attgtctgag taggtgtcat tctattctgg ggggtggggt ggggcaggac agcaagggg    3540
aggattggga agacaatagc aggcatgctg gggatgcggt gggctctatg gaaccagctg    3600
gggcgcgatt aacttcgtat aaagtctcct atacgaagtt atcgcgccat tctagttgtg    3660
gtttgtccaa actcatcaat gtatcttatc atgtctggat cccatcacaa agctctgacc    3720
tcaatcctat agaaaggagg aatgagccaa aattcaccca acttattgtg ggaagcttgt    3780
ggaaggctac tcgaaatgtt tgacccaagt taaacaattt aaaggcaatg ctaccaaata    3840
ctaattgagt gtatgttaac ttctgaccca ctgggaatgt gatgaaagaa ataaagctg     3900
aaatgaatca ttctctctac tattattctg atatttcaca ttcttaaaat aaagtggtga    3960
tcctaactga ccttaagaca gggaatcttt actcggatta aatgtcagga attgtgaaaa    4020
agtgagttta aatgtatttg gctaaggtgt atgtaaactt ccgacttcaa ctgtagggat    4080
cctctagagt cgacctgcag gcatgcaagc ttggcgtaat catggtcata gctgtttcct    4140
gtgtgaaatt gttatccgct cacaattcca cacaacatac gagccggaag cataaagtgt    4200
aaagcctggg gtgcctaatg agtgagctaa ctcacattaa ttgcgttgcg ctcactgccc    4260
gctttccagt cgggaaacct gtcgtgccag ctgcattaat gaatcggcca acgcgcgggg    4320
agaggcggtt tgcgtattgg gcgctcttcc gcttcctcgc tcactgactc gctgcgctcg    4380
gtcgttcggc tgcggcgagc ggtatcagct cactcaaagg cggtaatacg ttatccaca    4440
```

```
gaatcagggg ataacgcagg aaagaacatg tgagcaaaag gccagcaaaa ggccaggaac      4500
cgtaaaaagg ccgcgttgct ggcgttttc cataggctcc gccccctga cgagcatcac       4560 aaaaatcgac gctcaagtca gaggtggcga acccgacag gactataaag ataccaggcg      4620
tttccccctg gaagctccct cgtgcgctct cctgttccga ccctgccgct taccggatac    4680
ctgtccgcct ttctcccttc gggaagcgtg cgctttctc aatgctcacg ctgtaggtat     4740
ctcagttcgg tgtaggtcgt tcgctccaag ctgggctgtg tgcacgaacc ccccgttcag    4800
cccgaccgct gcgccttatc cggtaactat cgtcttgagt ccaacccggt aagacacgac    4860
ttatcgccac tggcagcagc cactggtaac aggattagca gagcgaggta tgtaggcggt    4920
gctacagagt tcttgaagtg gtggcctaac tacggctaca ctagaaggac agtatttggt    4980
atctgcgctc tgctgaagcc agttaccttc ggaaaaagag ttggtagctc ttgatccggc    5040
aaacaaacca ccgctggtag cggtggtttt tttgtttgca agcagcagat tacgcgcaga    5100
aaaaaaggat ctcaagaaga tcctttgatc ttttctacgg ggtctgacgc tcagtggaac    5160
gaaaactcac gttaagggat tttggtcatg agattatcaa aaaggatctt cacctagatc    5220
cttttaaatt aaaaatgaag ttttaaatca atctaaagta tatatgagta aacttggtct    5280
gacagttacc aatgcttaat cagtgaggca cctatctcag cgatctgtct atttcgttca    5340
tccatagttg cctgactccc cgtcgtgtag ataactacga tacggagggg cttaccatct    5400
ggccccagtg ctgcaatgat accgcgagac ccacgctcac cggctccaga tttatcagca    5460
ataaaccagc cagccggaag ggccgagcgc agaagtggtc ctgcaacttt atccgcctcc    5520
atccagtcta ttaattgttg ccgggaagct agagtaagta gttcgccagt taatagtttg    5580
cgcaacgttg ttgccattgc tacaggcatc gtggtgtcac gctcgtcgtt tggtatggct    5640
tcattcagct ccggttccca acgatcaagg cgagttacat gatccccat gttgtgcaaa     5700 aaagcggtta gctccttcgg tcctccgatc gttgtcagaa gtaagttggc cgcagtgtta    5760
tcactcatgg ttatggcagc actgcataat tctcttactg tcatgccatc cgtaagatgc    5820
ttttctgtga ctggtgagta ctcaaccaag tcattctgag aatagtgtat gcggcgaccg    5880
agttgctctt gcccggcgtc aatacgggat aataccgcgc cacatagcag aactttaaaa    5940
gtgctcatca ttggaaaacg ttcttcgggg cgaaaactct caaggatctt accgctgttg    6000
agatccagtt cgatgtaacc cactcgtgca cccaactgat cttcagcatc ttttactttc    6060
accagcgttt ctgggtgagc aaaaacagga aggcaaaatg ccgcaaaaaa gggaataagg    6120
gcgacacgga aatgttgaat actcatactc ttcctttttc aatattattg aagcatttat    6180
cagggttatt gtctcatgag cggatacata tttgaatgta tttagaaaaa taaacaaata    6240
ggggttccgc gcacatttcc ccgaaaagtg ccacctgacg tctaagaaac cattattatc    6300
atgacattaa cctataaaaa taggcgtatc acgaggccct ttcgtc                   6346

<210> SEQ ID NO 41
<211> LENGTH: 8958
<212> TYPE: DNA
<213> ORGANISM: Artificial Sequence
<220> FEATURE:
<223> OTHER INFORMATION: Synthetic Sequence

<400> SEQUENCE: 41
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
```

-continued

```
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt accctacagt    420
tgaagtcgga agtttacata cacttaagtt ggagtcatta aaactcgttt ttcaactact    480
ccacaaattt cttgttaaca aacaatagtt ttggcaagtc agttaggaca tctactttgt    540
gcatgacaca agtcattttt ccaacaattg tttacagaca gattatttca cttataattc    600
actgtatcac aattccagtg ggtcagaagt ttacatacac taagttgact gtgcctttaa    660
acagcttgga aaattccaga aaatgatgtc atggctttag aagcttctga tagactaatt    720
gacatcattt gagtcaattg gaggtgtacc tgtggatgta tttcaaggga attctgtgga    780
atgtgtgtca gttagggtgt ggaaagtccc caggctcccc aggcaggcag aagtatgcaa    840
agcatgcata tcgatactag tttaattaac tagtctgcag gctcagaggc acacaggagt    900
ttctgggctc accctgcccc cttccaaccc ctcagttccc atcctccagc agctgtttgt    960
gtgctgcctc tgaagtccac actgaacaaa cttcagccta ctcatgtccc taaaatgggc   1020
aaacattgca agcagcaaac agcaaacaca cagccctccc tgcctgctga ccttggagct   1080
ggggcagagg tcagagacct ctctgggccc atgccacctc caacatccac tcgaccccctt  1140 ggaatttcgg tggagaggag cagaggttgt cctggcgtgg tttaggtagt gtgagagggt   1200
ccgggttcaa aaccacttgc tgggtgggga gtcgtcagta agtggctatg ccccgacccc   1260
gaagcctgtt tccccatctg tacaatggaa atgataaaga cgcccatctg atagggtttt   1320
tgtggcaaat aaacatttgg tttttttgtt ttgttttgtt ttgttttttg agatggaggt   1380
ttgctctgtc gcccaggctg gagtgcagtg acacaatctc atctcaccac aaccttcccc   1440
tgcctcagcc tcccaagtag ctgggattac aagcatgtgc caccacacct ggctaatttt   1500
ctatttttag tagagacggg tttctccatg ttggtcagcc tcagcctccc aagtaactgg   1560
gattacaggc ctgtgccacc acacccggct aattttttct attttttgaca gggacggggt   1620 ttcaccatgt tggtcaggct ggtctagagg taccggatct tgctaccagt ggaacagcca   1680
ctaaggattc tgcagtgaga gcagagggcc agctaagtgg tactctccca gagactgtct   1740
gactcacgcc acccctcca  ccttggacac aggacgctgt ggtttctgag ccaggtacaa   1800
tgactccttt cggtaagtgc agtggaagct gtacactgcc caggcaaagc gtccgggcag   1860
cgtaggcggg cgactcagat cccagccagt ggacttagcc cctgtttgct cctccgataa   1920
ctggggtgac cttggttaat attcaccagc agcctccccc gttgcccctc tggatccact   1980
gcttaaatac ggacgaggac agggcccgtgt ctcctcagct tcaggcacca ccactgacct   2040
gggacagtcc cagatccgcg gcctcgacgg tatcgataag cttgatatcg aattctagtc   2100
gtcgaccact ttcacaatct gcggcgcgcc accatgggca ccgtcagctc caggcggtcc   2160
tggtggccgc tgccactgct gctgctgctg ctgctgctcc tgggtccggc gggcgcccgt   2220
gcgcaggagg acgaggacgg cgactacgag gagctggtgc tagccttgcg ttccgaggag   2280
gacggcctgg ccgaagcacc cgagcacgga accacagcca ccttccaccg ctgcgccaag   2340
gatccgtgga ggttgcctgg cacctacgtg gtggtgctga aggaggagac ccacctctcg   2400
cagtcagagc gcactgcccg ccgcctgcag gcccaggctg cccgccgggg atacctcacc   2460
aagatcctgc atgtcttcca tggccttctt cctggcttcc tggtgaagat gagtggcgac   2520
ctgctggagc tggccttgaa gttgccccat gtcgactaca tcgaggagga ctcctctgtc   2580
```

```
tttgcccaga gcatcccgtg gaacctggag cggattaccc ctccacggta ccgggcggat      2640
gaataccagc cccccgacgg aggcagcctg gtggaggtgt atctcctaga caccagcata      2700
cagagtgacc accgggaaat cgagggcagg gtcatggtca ccgacttcga gaatgtgccc      2760
gaggaggacg ggacccgctt ccacagacag gccagcaagt gtgacagtca tggcacccac      2820
ctggcagggg tggtcagcgg ccgggatgcc ggcgtggcca aggtgccag catgcgcagc       2880 ctgcgcgtgc tcaactgcca agggaagggc acggttagcg gcaccctcat aggcctggag      2940
tttattcgga aaagccagct ggtccagcct gtggggccac tggtggtgct gctgcccctg      3000
gcgggtgggt acagccgcgt cctcaacgcc gcctgccagc cctggcgag gctggggtc        3060 gtgctggtca ccgctaccgg caacttccgg gacgatgcct gcctctactc cccagcctca      3120
gctcccgagt catcacagt tggggccacc aatgccagg accagccggt gaccctgggg        3180
actttgggga ccaactttgg ccgctgtgtg gacctctttg ccccagggga ggacatcatt      3240
ggtgcctcca gcgactgcag cacctgcttt gtgtcacaga gtgggacatc acaggctgct      3300
gcccacgtgg ctggcattgc agccatgatg ctgtctgccg agccggagct caccctggcc      3360
gagttgaggc agagactgat ccacttctct gccaaagatg tcatcaatga ggcctggttc      3420
cctgaggacc agcgggtact gaccccccaac ctggtggccg ccctgccccc cagcacccat     3480
ggggcaggtt ggcagctgtt ttgcaggact gtgtggtcag cacactcggg gcctacacgg      3540
atggccacag ccatcgcccg ctgcgcccca gatgaggagc tgctgagctg ctccagtttc      3600
tccaggagtg ggaagcggcg gggcgagcgc atggaggccc aaggggcaa gctggtctgc       3660 cgggcccaca acgcttttgg gggtgagggt gtctacgcca ttgccaggtg ctgcctgcta      3720
ccccaggcca actgcagcgt ccacacagct ccaccagctg aggccagcat ggggacccgt      3780
gtccactgcc accaacaggg ccacgtcctc acaggctgca gctcccactg ggaggtggag      3840
gaccttggca cccacaagcc gcctgtgctg aggccacgag gtcagcccaa ccagtgcgtg      3900
ggccacaggg aggccagcat ccacgcttcc tgctgccatg cccaggtct ggaatgcaaa       3960 gtcaaggagc atggaatccc ggcccctcag gagcaggtga ccgtggcctg cgaggagggc      4020
tggaccctga ctggctgcag tgccctccct gggacctccc acgtcctggg ggcctacgcc      4080
gtagacaaca cgtgtgtagt caggagccgg gacgtcagca ctacaggcag caccagcgaa      4140
gaggccgtga cagccgttgc catctgctgc cggagccggc acctggcgca ggcctcccag      4200
gagctccagc tggcgcaggc ctcccaggag ctccaggact acaaggacga cgatgacaag      4260
tgactgaggc cggcctcagc ctcgactgtg ccttctagtt gccagccatc tgttgtttgc      4320
ccctcccccg tgccttcctt gaccctggaa ggtgccactc ccactgtcct ttcctaataa      4380
aatgaggaaa ttgcatcgca ttgtctgagt aggtgtcatt ctattctggg gggtggggtg      4440
gggcaggaca gcaaggggga ggattgggaa gacaatagca ggcatgctgg ggatgcggtg      4500
ggctctatgg aaccagctgg ggctttaatt aagatctcga cctcgaaatt ctaccgggta      4560
ggggaggcgc ttttcccaag gcagtctgga gcatgcgctt tagcggcccc gctgggcact      4620
tggcgctaca caagtggcct ctggcctcgc acacattcca catccaccgg taggcgccaa      4680
ccggctccgt tctttggtgg ccccttcgcg ccaccttcta ctcctcccct agtcaggaag      4740
ttcccccccg ccccgcagct cgcgtcgtgc aggacgtgac aaatgaagt agcacgtctc       4800 actagtctcg tgcagatgga cagcaccgct gagcaatgga agcgggtagg cctttgggc       4860 agcggccaat agcagctttg gctccttcgc tttctgggct cagaggctgg gaaggggtgg      4920
gtccgggggc gggctcaggg gcgggctcag gggcggggcg ggcgcccgaa ggtcctccgg      4980
```

-continued

```
aggcccggca ttctgcacgc ttcaaaagcg cacgtctgcc gcgctgttct cctcttcctc    5040
atctccgggc ctttcgacct gcatccatct agatctcgag cagctgaagc ttaccatgac    5100
cgagtacaag cccacggtgc gcctcgccac ccgcgacgac gtcccccggg ccgtacgcac    5160
cctcgccgcc gcgttcgccg actaccccgc cacgcgccac accgtcgatc cggaccgcca    5220
catcgagcgg gtcaccgagc tgcaagaact cttcctcacg cgcgtcgggc tcgacatcgg    5280
caaggtgtgg gtcgcggacg acggcgccgc ggtggcggtc tggaccacgc cggagagcgt    5340
cgaagcgggg gcggtgttcg ccgagatcgg cccgcgcatg gccgagttga gcggttcccg    5400
gctggccgcg cagcaacaga tggaaggcct cctggcgccg caccggccca aggagcccgc    5460
gtggttcctg gccaccgtcg gcgtctcgcc cgaccaccag ggcaagggtc tgggcagcgc    5520
cgtcgtgctc cccggagtgg aggcggccga gcgcgccggg gtgcccgcct tcctggagac    5580
ctccgcgccc cgcaacctcc ccttctacga gcggctcggc ttcaccgtca ccgccgacgt    5640
cgaggtgccc gaaggaccgc gcacctggtg catgacccgc aagcccggtg cctgacgccc    5700
gcccacaaga cccgcagcgc ccgaccgaaa ggagcgcacg accccatgca tcgaatcgat    5760
atccccgggc cgtcctgtaa gtctgcagaa attgatgatc tattaaacaa taaagatgtc    5820
cactaaaatg gaagttttc ctgtcatact ttgttaagaa gggtgagaac agagtaccta    5880
cattttgaat ggaaggattg gagctacggg ggtggggtg gggtgggatt agataaatgc    5940
ctgctctta ctgaaggctc tttactattg ctttatgata atgtttcata gttggatatc    6000
ataatttaaa caagcaaaac caaattaagg gccagctcat tcctcccact catgatctat    6060
agatctatag atctctcgtg ggatcattgt tttctcttg attcccactt tgtggttcta    6120
agtactgtgg tttccaaatg tgtcagtttc atagcctgaa gaacgagatc agcagcctct    6180
gttccacata cacttcattc tcagtattgt tttgccaagt tctaattcca tcagaagctg    6240
gtcgagctag cggccgctgc attctagttg tggtttgtcc aaactcatca atgtatctta    6300
tcatgtctgg atcccatcac aaagctctga cctcaatcct atagaaagga ggaatgagcc    6360
aaaattcacc caacttattg tgggaagctt gtggaaggct actcgaaatg tttgacccaa    6420
gttaaacaat ttaaaggcaa tgctaccaaa tactaattga gtgtatgtta acttctgacc    6480
cactgggaat gtgatgaaag aaataaaagc tgaaatgaat cattctctct actattattc    6540
tgatatttca cattcttaaa ataaagtggt gatcctaact gaccttaaga cagggaatct    6600
ttactcggat taaatgtcag gaattgtgaa aaagtgagtt taaatgtatt tggctaaggt    6660
gtatgtaaac ttccgacttc aactgtaggg atcctctaga gtcgacctgc aggcatgcaa    6720
gcttggcgta atcatggtca tagctgtttc ctgtgtgaaa ttgttatccg ctcacaattc    6780
cacacaacat acgagccgga agcataaagt gtaaagcctg gggtgcctaa tgagtgagct    6840
aactcacatt aattgcgttg cgctcactgc ccgctttcca gtcgggaaac ctgtcgtgcc    6900
agctgcatta atgaatcggc caacgcgcgg ggagaggcgg tttgcgtatt gggcgctctt    6960
ccgcttcctc gctcactgac tcgctgcgct cggtcgttcg gctgcggcga gcggtatcag    7020
ctcactcaaa ggcggtaata cggttatcca cagaatcagg ggataacgca ggaaagaaca    7080
tgtgagcaaa aggccagcaa aaggccagga accgtaaaaa ggccgcgttg ctggcgtttt    7140
tccataggct ccgcccccct gacgagcatc acaaaaatcg acgctcaagt cagaggtggc    7200
gaaacccgac aggactataa agataccagg cgtttccccc tggaagctcc ctcgtgcgct    7260
ctcctgttcc gaccctgccg cttaccggat acctgtccgc ctttctccct tcgggaagcg    7320
tggcgctttc tcaatgctca cgctgtaggt atctcagttc ggtgtaggtc gttcgctcca    7380
```

-continued

| | |
|---|---|
| agctgggctg tgtgcacgaa ccccccgttc agcccgaccg ctgcgcctta tccggtaact | 7440 |
| atcgtcttga gtccaacccg gtaagacacg acttatcgcc actggcagca gccactggta | 7500 |
| acaggattag cagagcgagg tatgtaggcg gtgctacaga gttcttgaag tggtggccta | 7560 |
| actacggcta cactagaagg acagtatttg gtatctgcgc tctgctgaag ccagttacct | 7620 |
| tcggaaaaag agttggtagc tcttgatccg gcaaacaaac caccgctggt agcggtggtt | 7680 |
| tttttgtttg caagcagcag attacgcgca gaaaaaagg atctcaagaa gatcctttga | 7740 |
| tcttttctac ggggtctgac gctcagtgga acgaaaactc acgttaaggg attttggtca | 7800 |
| tgagattatc aaaaaggatc ttcacctaga tccttttaaa ttaaaaatga gttttaaat | 7860 |
| caatctaaag tatatatgag taaacttggt ctgacagtta ccaatgctta atcagtgagg | 7920 |
| cacctatctc agcgatctgt ctatttcgtt catccatagt tgcctgactc cccgtcgtgt | 7980 |
| agataactac gatacgggag ggcttaccat ctggccccag tgctgcaatg ataccgcgag | 8040 |
| acccacgctc accggctcca gatttatcag caataaacca gccagccgga agggccgagc | 8100 |
| gcagaagtgg tcctgcaact ttatccgcct ccatccagtc tattaattgt tgccgggaag | 8160 |
| ctagagtaag tagttcgcca gttaatagtt tgcgcaacgt tgttgccatt gctacaggca | 8220 |
| tcgtggtgtc acgctcgtcg tttggtatgg cttcattcag ctccggttcc caacgatcaa | 8280 |
| ggcgagttac atgatccccc atgttgtgca aaaaagcggt tagctccttc ggtcctccga | 8340 |
| tcgttgtcag aagtaagttg gccgcagtgt tatcactcat ggttatggca gcactgcata | 8400 |
| attctcttac tgtcatgcca tccgtaagat gcttttctgt gactggtgag tactcaacca | 8460 |
| agtcattctg agaatagtgt atgcggcgac cgagttgctc ttgcccggcg tcaatacggg | 8520 |
| ataataccgc gccacatagc agaactttaa aagtgctcat cattggaaaa cgttcttcgg | 8580 |
| ggcgaaaact ctcaaggatc ttaccgctgt tgagatccag ttcgatgtaa cccactcgtg | 8640 |
| cacccaactg atcttcagca tcttttactt tcaccagcgt ttctgggtga gcaaaaacag | 8700 |
| gaaggcaaaa tgccgcaaaa aagggaataa gggcgacacg gaaatgttga atactcatac | 8760 |
| tcttcctttt tcaatattat tgaagcattt atcagggtta ttgtctcatg agcggataca | 8820 |
| tatttgaatg tatttagaaa aataaacaaa taggggttcc gcgcacattt ccccgaaaag | 8880 |
| tgccacctga cgtctaagaa accattatta tcatgacatt aacctataaa aataggcgta | 8940 |
| tcacgaggcc ctttcgtc | 8958 |

<210> SEQ ID NO 42
<211> LENGTH: 8320
<212> TYPE: DNA
<213> ORGANISM: Artificial Sequence
<220> FEATURE:
<223> OTHER INFORMATION: Synthetic Sequence

<400> SEQUENCE: 42

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt accctacagt | 420 |
| tgaagtcgga agtttacata cacttaagtt ggagtcatta aaactcgttt ttcaactact | 480 |

```
ccacaaattt cttgttaaca aacaatagtt ttggcaagtc agttaggaca tctactttgt    540
gcatgacaca agtcattttt ccaacaattg tttacagaca gattatttca cttataattc    600
actgtatcac aattccagtg ggtcagaagt ttacatacac taagttgact gtgcctttaa    660
acagcttgga aaattccaga aaatgatgtc atggctttag aagcttctga tagactaatt    720
gacatcattt gagtcaattg gaggtgtacc tgtggatgta tttcaaggga attctgtgga    780
atgtgtgtca gttagggtgt ggaaagtccc caggctcccc aggcaggcag aagtatgcaa    840
agcatgcata tcgatactag tgagctcacg gggacagccc cccccaaag ccccagggga    900
tgtaattacg tccctccccc gctagggggc agcagcgagc cgcccgggc tccgctccgg    960
tccggcgctc ccccgcatc cccgagccgg cagcgtgcgg ggacagcccg ggcacgggga   1020
aggtggcacg ggatcgcttt cctctgaacg cttctcgctg ctctttgagc ctgcagacac   1080
ctgggggat acgggaaaa agctttaggc tgaaagagag atttagaatg acagaatcat    1140
agaacggcct gggttgcaaa ggagcacagt gctcatccag atccaacccc ctgctatgtg   1200
cagggtcatc aaccagcagc ccaggctgcc cagagccaca tccagcctgg ccttgaatgc   1260
ctgcagggat ggggcatcca cagcctcctt gggcaacctg ttcagtgcgt caccaccctc   1320
tgggggaaaa actgcctcct catatccaac ccaaacctcc cctgtctcag tgtaaagcca   1380
ttccccttg tcctatcaag ggggagtttg ctgtgacatt gttggtctgg ggtgacacat    1440
gtttgccaat tcagtgcatc acggagaggc agatcttggg gataaggaag tgcaggacag   1500
catggacgtg ggacatgcag gtgttgaggg ctctgggaca ctctccaagt cacagcgttc   1560
agaacagcct taaggataag aagataggat agaaggacaa agagcaagtt aaaacccagc   1620
atggagagga gcacaaaaag gccacagaca ctgctggtcc ctgtgtctga gcctgcatgt   1680
ttgatggtgt ctggatgcaa gcagaagggg tggaagagct tgcctggaga gatacagctg   1740
ggtcagtagg actgggacag gcagctggag aattgccatg tagatgttca tacaatcgtc   1800
aaatcatgaa ggctggaaaa gccctccaag atccccaaga ccaaccccaa cccacccacc   1860
gtgcccactg gccatgtccc tcagtgccac atccccacag ttcttcatca cctccaggga   1920
cggtgacccc cccacctccg tgggcagctg tgccactgca gcaccgctct ttggagaagg   1980
taaatcttgc taaatccagc ccgaccctcc cctggcacaa cgtaaggcca ttatctctca   2040
tccaactcca ggacggagtc agtgagaata ttttaattaa cctaggtgta caggcgcgcc   2100
aagcttagat ctgtggtctc atacagaact tataagattc ccaaatccaa agacatttca   2160
cgtttatggt gatttcccag aacacatagc gacatgcaaa tattgcaggg cgccactccc   2220
ctgtccctca cagccatctt cctgccaggg cgcacgcgcg ctgggtgttc ccgcctagtg   2280
acactgggcc cgcgattcct tggagcgggt tgatgacgtc agcgttcgaa ttcttaatta   2340
agatctcgac ctcgaaattc taccgggtag gggaggcgct tttcccaagg cagtctggag   2400
catgcgcttt agcggccccg ctgggcactt ggcgctacac aagtggcctc tggcctcgca   2460
cacattccac atccaccggt aggcgccaac cggctccgtt ctttggtggc ccttcgcgc    2520
cacctttctac tcctcccta gtcaggaagt tcccccccgc ccgcagctc gcgtcgtgca    2580
ggacgtgaca aatggaagta gcacgtctca ctagtctcgt gcagatggac agcaccgctg   2640
agcaatggaa gcgggtaggc ctttggggca gcggccaata gcagctttgg ctccttcgct   2700
ttctgggctc agaggctggg aagggtgggt tccggggcg gctcagggg cgggctcagg    2760
ggcggggcgg gcgcccgaag gtcctccgga ggccggcat tctgcacgct tcaaaagcgc    2820
acgtctgccg cgctgttctc ctcttcctca tctccgggcc tttcgacctg catccatcta   2880
```

| | |
|---|---|
| gatctcgagc agctgaagct taccatgacc gagtacaagc ccacggtgcg cctcgccacc | 2940 |
| cgcgacgacg tcccccgggc cgtacgcacc ctcgccgccg cgttcgccga ctaccccgcc | 3000 |
| acgcgccaca ccgtcgatcc ggaccgccac atcgagcggg tcaccgagct gcaagaactc | 3060 |
| ttcctcacgc gcgtcgggct cgacatcggc aaggtgtggg tcgcggacga cggcgccgcg | 3120 |
| gtggcggtct ggaccacgcc ggagagcgtc gaagcggggg cggtgttcgc cgagatcggc | 3180 |
| ccgcgcatgg ccgagttgag cggttcccgg ctggccgcgc agcaacagat ggaaggcctc | 3240 |
| ctggcgccgc accggcccaa ggagcccgcg tggttcctgg ccaccgtcgg cgtctcgccc | 3300 |
| gaccaccagg gcaagggtct gggcagcgcc gtcgtgctcc ccggagtgga ggcggccgag | 3360 |
| cgcgccgggg tgcccgcctt cctggagacc tccgcgcccc gcaacctccc cttctacgag | 3420 |
| cggctcggct tcaccgtcac cgccgacgtc gaggtgcccg aaggaccgcg cacctggtgc | 3480 |
| atgacccgca agcccggtgc ctgacgcccg cccacaagac ccgcagcgcc cgaccgaaag | 3540 |
| gagcgcacga ccccatgcat cgaatcgata tccccgggcc gtcctgtaag tctgcagaaa | 3600 |
| ttgatgatct attaaacaat aaagatgtcc actaaaatgg aagttttttcc tgtcatactt | 3660 |
| tgttaagaag ggtgagaaca gagtacctac attttgaatg aaggattgg agctacgggg | 3720 |
| gtgggggtgg ggtgggatta gataaatgcc tgctctttac tgaaggctct ttactattgc | 3780 |
| tttatgataa tgtttcatag ttggatatca taatttaaac aagcaaaacc aaattaaggg | 3840 |
| ccagctcatt cctcccactc atgatctata gatctataga tctctcgtgg gatcattgtt | 3900 |
| tttctcttga ttcccacttt gtggttctaa gtactgtggt ttccaaatgt gtcagtttca | 3960 |
| tagcctgaag aacgagatca gcagcctctg ttccacatac acttcattct cagtattgtt | 4020 |
| ttgccaagtt ctaattccat cagaagctgg tcgagctagc ggatccgacg ccgccatctc | 4080 |
| taggcccgcg ccggcccct cgcacagact tgtgggagaa gctcggctac tcccctgccc | 4140 |
| cggttaattt gcatataata tttcctagta actatagagg cttaatgtgc gataaaagac | 4200 |
| agataatctg ttcttttaa tactagctac attttacatg ataggcttgg atttctataa | 4260 |
| gagatacaaa tactaaatta ttattttaaa aaacagcaca aaaggaaact caccctaact | 4320 |
| gtaaagtaat tgtgtgtttt gagactataa atatcccttg gagaaaagcc ttgtttacgc | 4380 |
| gtgggccccc atgggctagc gagctcacgg ggacagcccc cccccaaagc ccccagggat | 4440 |
| gtaattacgt ccctcccccg ctaggggggca gcagcgagcc gccggggct ccgctccggt | 4500 |
| ccggcgctcc ccccgcatcc ccgagccggc agcgtgcggg gacagcccgg gcacggggaa | 4560 |
| ggtggcacgg gatcgctttc ctctgaacgc ttctcgctgc tctttgagcc tgcagacacc | 4620 |
| tgggggggata cggggaaaaa gctttaggct gaaagagaga tttagaatga cagaatcata | 4680 |
| gaacggcctg ggttgcaaag gagcacagtg ctcatccaga tccaaccccc tgctatgtgc | 4740 |
| agggtcatca accagcagcc caggctgccc agagccacat ccagcctggc cttgaatgcc | 4800 |
| tgcagggatg gggcatccac agcctccttg ggcaacctgt tcagtgcgtc accaccctct | 4860 |
| gggggaaaaa ctgcctcctc atatccaacc caaacctccc ctgtctcagt gtaaagccat | 4920 |
| tccccccttgt cctatcaagg gggagttttgc tgtgacattg ttggtctggg gtgacacatg | 4980 |
| tttgccaatt cagtgcatca cggagaggca gatcttgggg ataaggaagt gcaggacagc | 5040 |
| atggacgtgg gacatgcagg tgttgagggc tctgggacac tctccaagtc acagcgttca | 5100 |
| gaacagcctt aaggataaga agataggata gaaggacaaa gagcaagtta aaacccagca | 5160 |
| tggagaggag cacaaaaagg ccacagacac tgctggtccc tgtgtctgag cctgcatgtt | 5220 |
| tgatggtgtc tggatgcaag cagaagggt ggaagagctt gcctggagag atacagctgg | 5280 |

```
gtcagtagga ctgggacagg cagctggaga attgccatgt agatgttcat acaatcgtca   5340
aatcatgaag gctggaaaag ccctccaaga tccccaagac caaccccaac ccacccaccg   5400
tgcccactgg ccatgtccct cagtgccaca tccccacagt tcttcatcac ctccagggac   5460
ggtgacccc  ccacctccgt gggcagctgt gccactgcag caccgctctt tggagaaggt   5520
aaatcttgct aaatccagcc cgaccctccc ctggcacaac gtaaggccat tatctctcat   5580
ccaactccag gacggagtca gtgagaatat tgcggccgct gcattctagt tgtggtttgt   5640
ccaaactcat caatgtatct tatcatgtct ggatcccatc acaaagctct gacctcaatc   5700
ctatagaaag gaggaatgag ccaaaattca cccaacttat tgtgggaagc ttgtggaagg   5760
ctactcgaaa tgtttgaccc aagttaaaca atttaaaggc aatgctacca aatactaatt   5820
gagtgtatgt taacttctga cccactggga atgtgatgaa agaaataaaa gctgaaatga   5880
atcattctct ctactattat tctgatattt cacattctta aaataaagtg gtgatcctaa   5940
ctgaccttaa gacagggaat ctttactcgg attaaatgtc aggaattgtg aaaaagtgag   6000
tttaaatgta tttggctaag gtgtatgtaa acttccgact tcaactgtag ggatcctcta   6060
gagtcgacct gcaggcatgc aagcttggcg taatcatggt catagctgtt tcctgtgtga   6120
aattgttatc cgctcacaat tccacacaac atacgagccg gaagcataaa gtgtaaagcc   6180
tggggtgcct aatgagtgag ctaactcaca ttaattgcgt tgcgctcact gcccgctttc   6240
cagtcgggaa acctgtcgtg ccagctgcat taatgaatcg gccaacgcgc ggggagaggc   6300
ggtttgcgta ttgggcgctc ttccgcttcc tcgctcactg actcgctgcg ctcggtcgtt   6360
cggctgcggc gagcggtatc agctcactca aaggcggtaa tacggttatc cacagaatca   6420
ggggataacg caggaaagaa catgtgagca aaaggccagc aaaaggccag gaaccgtaaa   6480
aaggccgcgt tgctggcgtt tttccatagg ctccgccccc ctgacgagca tcacaaaaat   6540
cgacgctcaa gtcagaggtg gcgaaacccg acaggactat aaagatacca ggcgtttccc   6600
cctggaagct ccctcgtgcg ctctcctgtt ccgaccctgc cgcttaccgg atacctgtcc   6660
gcctttctcc cttcgggaag cgtggcgctt tctcaatgct cacgctgtag gtatctcagt   6720
tcggtgtagg tcgttcgctc caagctgggc tgtgtgcacg aaccccccgt tcagcccgac   6780
cgctgcgcct tatccggtaa ctatcgtctt gagtccaacc cggtaagaca cgacttatcg   6840
ccactggcag cagccactgg taacaggatt agcagagcga ggtatgtagg cggtgctaca   6900
gagttcttga agtggtggcc taactacggc tacactagaa ggacagtatt tggtatctgc   6960
gctctgctga agccagttac cttcggaaaa agagttggta gctcttgatc cggcaaacaa   7020
accaccgctg gtagcggtgg tttttttgtt tgcaagcagc agattacgcg cagaaaaaaa   7080
ggatctcaag aagatccttt gatcttttct acggggtctg acgctcagtg gaacgaaaac   7140
tcacgttaag ggattttggt catgagatta tcaaaaagga tcttcaccta gatcctttta   7200
aattaaaaat gaagttttaa atcaatctaa agtatatatg agtaaacttg gtctgacagt   7260
taccaatgct taatcagtga ggcacctatc tcagcgatct gtctatttcg ttcatccata   7320
gttgcctgac tccccgtcgt gtagataact acgatacggg agggcttacc atctggcccc   7380
agtgctgcaa tgataccgcg agacccacgc tcaccggctc cagatttatc agcaataaac   7440
cagccagccg gaagggccga gcgcagaagt ggtcctgcaa cttatcccgc ctccatccag   7500
tctattaatt gttgccggga agctagagta agtagttcgc cagttaatag tttgcgcaac   7560
gttgttgcca ttgctacagg catcgtggtg tcacgctcgt cgtttggtat ggcttcattc   7620
agctccggtt cccaacgatc aaggcgagtt acatgatccc ccatgttgtg caaaaaagcg   7680
```

```
gttagctcct tcggtcctcc gatcgttgtc agaagtaagt tggccgcagt gttatcactc      7740
atggttatgg cagcactgca taattctctt actgtcatgc catccgtaag atgcttttct      7800
gtgactggtg agtactcaac caagtcattc tgagaatagt gtatgcggcg accgagttgc      7860
tcttgcccgg cgtcaatacg ggataatacc gcgccacata gcagaacttt aaaagtgctc      7920
atcattggaa aacgttcttc ggggcgaaaa ctctcaagga tcttaccgct gttgagatcc      7980
agttcgatgt aacccactcg tgcacccaac tgatcttcag catcttttac tttcaccagc      8040
gtttctgggt gagcaaaaac aggaaggcaa aatgccgcaa aaaagggaat aagggcgaca      8100
cggaaatgtt gaatactcat actcttcctt tttcaatatt attgaagcat ttatcagggt      8160
tattgtctca tgagcggata catatttgaa tgtatttaga aaaataaaca aatagggggtt     8220 ccgcgcacat ttccccgaaa agtgccacct gacgtctaag aaaccattat tatcatgaca      8280
ttaacctata aaataggcg tatcacgagg ccctttcgtc                             8320
```